US006440656B1

(12) United States Patent
Bolognesi et al.

(10) Patent No.: US 6,440,656 B1
(45) Date of Patent: Aug. 27, 2002

(54) METHODS FOR THE INHIBITION OF RESPIRATORY SYNCYTIAL VIRUS TRANSMISSION

(75) Inventors: Dani Paul Bolognesi; Thomas James Matthews; Carl T. Wild, all of Durham; Shawn O'Lin Barney, Cary; Dennis Michael Lambert, Cary; Stephen Robert Petteway, Jr., Cary, all of NC (US)

(73) Assignee: Trimeris, Inc., Durham, NC (US)

( * ) Notice: Subject to any disclaimer, the term of this patent is extended or adjusted under 35 U.S.C. 154(b) by 0 days.

(21) Appl. No.: 08/255,208

(22) Filed: Jun. 7, 1994

Related U.S. Application Data

(63) Continuation-in-part of application No. 08/073,028, filed on Jun. 7, 1993, now Pat. No. 5,464,933.

(51) Int. Cl.$^7$ .................................................. C12Q 1/70

(52) U.S. Cl. ........................... 435/5; 435/7.1; 530/300; 530/324; 530/325; 530/326; 424/211.1

(58) Field of Search ........................... 435/5; 424/211.1

(56) References Cited

PUBLICATIONS

Wild et al., "A synthetic peptide inhibitor of human immunodeficiency virus replication: Correlation between solution structure and viral inhibition," Proc. Natl. Acad. Sci. USA 89:10537–10541 1992.*
Bousse et al., "A single amino acid change enhances the fusion promotion activity of human parainfluenza virus type 1 hemagglutinin–neuraminidase glycoprotein," Virol. 209:654–657, 1995.*
Geysen et al., "Cognitive features of continuous antigenic determinants," J. Molec. Recog. 1:33–41, 1988.*
Wildner et al., "Database screening for molecular mimicry," Immunol. Today18(5):251–252, 1997.*
Roudier, J., "Response to Wildner et al. and Burns et al.," Immunol. Today 18(5):252, 1997.*
Hall, C., "Prospects for a respiratory syncytial virus vaccine," Science 265:1393–1394, 1994.*
Toms, G., "Respiratory syncytial virus– how soon will we have a vaccine?" Arch. Dis. Child. 72:1–3, 1995.*
Benet et al., "Pharmacokinetics: the dynamics of drug absorption, distribution, and elimination," in The Pharmacological Basis of Therapeutics, Goodman et al., eds., Pergammon Press, New York, pp. 3–32, 1990.*
Flexner, C. and C. Hendrix, 1997, "Pharmacology of antiretroviral agents", in *AIDS: Biology, Diagnosis, Treatment and Prevention*, fourth edition, DeVita, V.T., et al., eds., Lippincott–Raven Publishers, pp. 479–493.*
Yarchoan, R. and S. Broder, 1992 "Correlations between the in vitro and in vivo activity of anti–HIV agents: implications for future drug development", J. Enzyme Inhib. 6:99–111.*

Gait, M.J. and J. Karn, 1995, "Progress in anti–HIV structure–based design", TIBTECH 13:430–438.*
Suzuki et al., 1995, "Viral Interleukin 10 (IL–10), the human Herpes Virus 4 Cellular IL–10 Homologue, Induces Local Anergy to Allogenic and Syngeneic Tumors", J of Experimental Medicine 182:477–486.
Wild et al., 1994, "Propensity for a Leucine Zipper–Like Domain of Human Immunodeficiency Virus Type 1 gp41 to Form Oligomers Correlates With a Role in Virus–Induced Fusion Rather Than Assembly of the Glycoprotein Complex", Proc. Natl. Acad. Sci. USA 91:12676–80.
Bousse et al., 1994, "Regions on the Hemagglutinin–Neuraminidase Proteins of Human Parainfluenza Virus Type–1 and Sendai Virus Important for Membrane Fusion", Virology 204:506–514.
Wang et al., "Ion Channel Activity of Influenza A Virus M2 Protein: Characteriztion of the Amantidine Block", J of Virology 67:5585–94.
Lazinski et al., 1983, "Relating Structure to Function in the Hepatitis Delta Virus Antigen", J of Virology 67:2672–80.
White, J.M., 1992, "Membrane Fusion", Science 258:917–924.
Daar et al., 1990, "High concentrations of recombinant soluble CD4 are required to neutralize primary human immunodeficiency virus type 1 isolates", Proc. Natl. Acad. Sci. USA 87:6574–6579.
Erickson et al., 1990, "Design, Activity, and 2.8 Å Crystal Structure of a $C_2$ Symmetric Inhibitor Complexed to HIV–1 Protease", Science 249:527–533.
Smith et al., 1987, "Blocking of HIV–1 Infectivity by a Soluble, Secreted Form of the CD4 Antigen", Science 238:1704–1707.

(List continued on next page.)

*Primary Examiner*—Laurie Scheiner
*Assistant Examiner*—Jeffrey S. Parkin
(74) *Attorney, Agent, or Firm*—Pennie & Edmonds LLP; M. Bud Nelson

(57) ABSTRACT

Fusion of the viral envelope, or infected cell membranes with uninfected cell membranes, is an essential step in the viral life cycle. Recent studies involving the human immunodeficiency virus type 1 (HIV-1) demonstrated that synthetic peptides (designated DP-107 and DP-178) derived from potential helical regions of the transmembrane (TM) protein, gp41, were potent inhibitors of viral fusion and infection. A computerized antiviral searching technology (C.A.S.T.) that detects related structural motifs (e.g., ALLMOTI5, 107×178×4, and PLZIP) in other viral proteins was employed to identify similar regions in the respiratory syncytial virus (RSV). Several conserved heptad repeat domains that are predicted to form coiled-coil structures with antiviral activity were identified in the RSV genome. Synthetic peptides of 16 to 39 amino acids derived from these regions were prepared and their antiviral activities assessed in a suitable in vitro screening assay. These peptides proved to be potent inhibitors of RSV fusion. Based upon their structural and functional equivalence to the known HIV-1 inhibitors DP-107 and DP-178, these peptides should provide a novel approach to the development of targeted therapies for the treatment of RSV infections.

13 Claims, 31 Drawing Sheets

OTHER PUBLICATIONS

Figure 2:
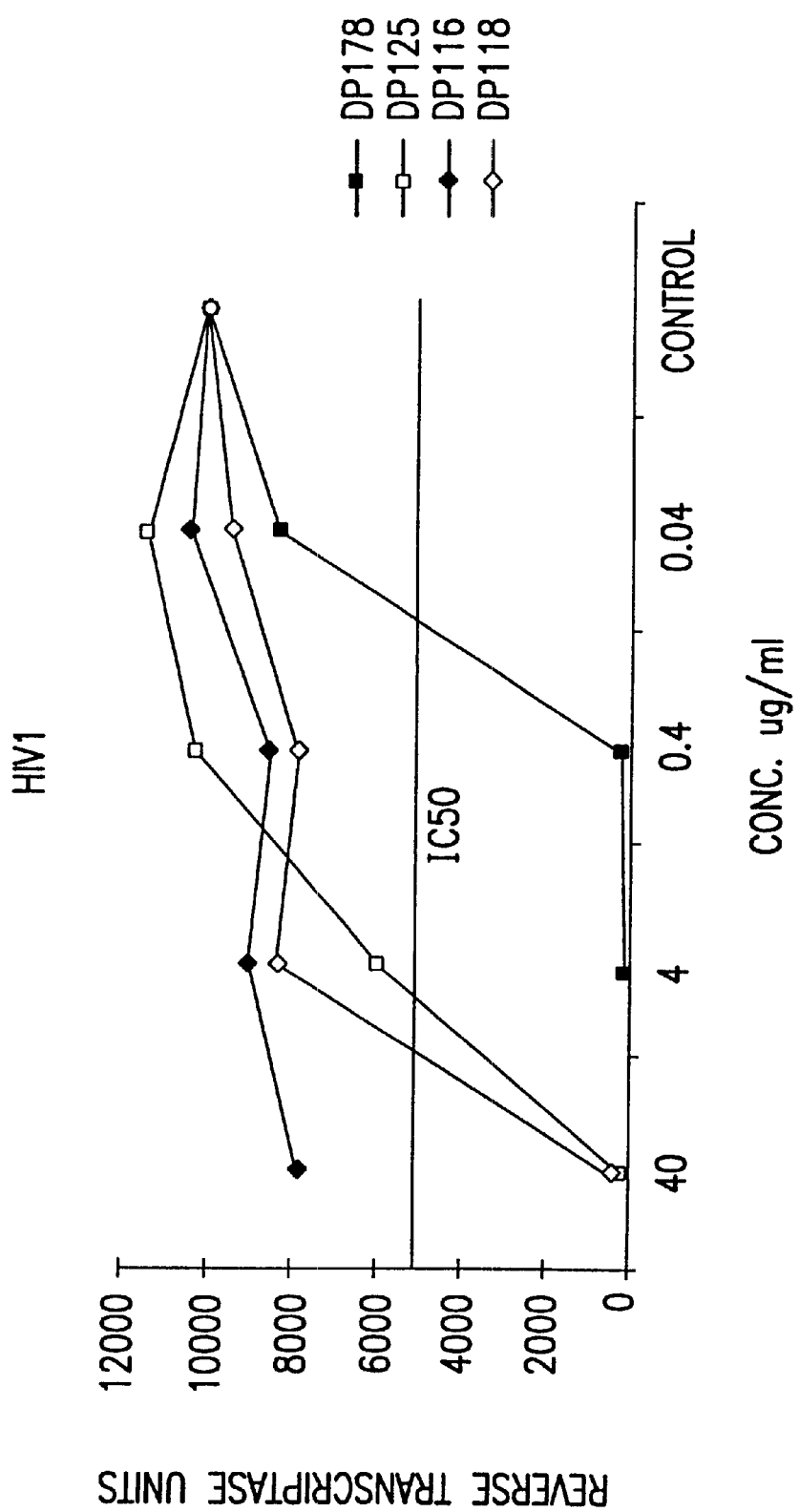

Collins et al., 1984, "Nucleotide Sequence of the Gene Encoding the Fusion (F) Glycoprotein of Human Respiratory Syncytial Virus", Proc. Natl. Acad. Sci. USA 81:7683–87.

Staden, 1994, "Searching for Motifs in Protein Sequences", Chapter 12 in: *Methods in Molecular Biology,* vol. 25, Griffin et al., eds., Humana Press, Inc., Totowa, NJ, p. 131–139.

Staden, 1994, "Using Patterns to Analyze Protein Sequences", Chapter 13 in: *Methods in Molecular Biology,* vol. 25, Griffin et al., eds., Humana Press, Inc., Totowa, NJ, p. 141–154.

Staden, 1990, "Searching for Patterns in Protein and Nucleic Acid Sequences", Meth. Enzymol. 183:193–211.

* cited by examiner

HIV1LAI (DP-178; SEQ ID:1)    YTSLIHSLIEESQNQQEKNEQELLELDKWASLWNWF
HIV1SF2 (DP-185; SEQ ID:3)    YTNTIYTLLEESQNQQEKNEQELLELDKWASLWNWF
HIV1RF  (SEQ ID:4)            YTGIIYNLLEESQNQQEKNEQELLELDKWANLWNWF
HIV1MN  (SEQ ID:5)            YTSLIYSLLEKSQIQQEKNEQELLELDKWASLWNWF
HIV2ROD (SEQ ID:6)            LEANISKSLEQAQIQQEKNMYELQKLNSWDIFGNWF
HIV2NIHZ (SEQ ID:7)           LEANISQSLEQAQIQQEKNMYELQKLNSWDVFTNWL
DP180   (SEQ ID:2)            SSESFTLLEQWNNWKLQLAEQWLEQINEKHYLEDIS
DP118   (SEQ ID:10)           QQLLDVVKRQQEMLRLTVWGTKNLQARVTAIEKYLKDQ
DP125   (SEQ ID:8)            CGGNNLLRAIEAQQHLLQLTVWGIKQLQARILAVERYLKDQ
DP116   (SEQ ID:9)            LQARILAVERYLKDQQQ

FIG.1

| Number of Syncytia/well: concentration in μg/ml (micrograms/ml) | | | | | | | | | |
|---|---|---|---|---|---|---|---|---|---|
| DP178 | 10 | 5 | 1 | 0.2 | 0.1 | 0.05 | 0.025 | 0.0125 | Control |
| *Syncytia* | | | | | | | | | |
| HIV1LAI | 0 | 0 | 0 | 0 | 0 | 0 | 0 | 0 | 67 |
| HIV1MN | 0 | 0 | 0 | 0 | 0 | ND | ND | ND | 34 |
| HIV1RF | 0 | 0 | 0 | 0 | 0 | ND | ND | ND | 65 |
| HIV1SF2 | 0 | 0 | 0 | 0 | 0 | ND | ND | ND | 58 |
| | | | | | | | | | |
| DP125 | 10 | 5 | 1 | 0.2 | 0.1 | 0.05 | 0.025 | 0.0125 | Control |
| *Syncytia* | | | | | | | | | |
| HIV1LAI | 0 | 0 | 54 | 69 | 80 | 75 | 79 | 82 | 67 |
| HIV1MN | 0 | 0 | 30 | 36 | ND | ND | ND | ND | 34 |
| HIV1RF | 0 | 0 | 67 | 63 | ND | ND | ND | ND | 65 |
| HIV1SF2 | 0 | 0 | 9 | 66 | ND | ND | ND | ND | 58 |
| | | | | | | | | | |
| DP116 | 10 | 5 | 1 | 0.2 | 0.1 | 0.05 | 0.025 | 0.0125 | Control |
| *Syncytia* | | | | | | | | | |
| HIV1LAI | 75 | ND | ND | ND | ND | ND | ND | ND | 67 |
| HIV1MN | 35 | ND | ND | ND | ND | ND | ND | ND | 34 |
| HIV1RF | 81 | ND | ND | ND | ND | ND | ND | ND | 65 |
| HIV1SF2 | 81 | ND | ND | ND | ND | ND | ND | ND | 58 |

FIG.4A

| DP180 | 40 | 20 | 10 | 5 | 2.5 | 1.25 | 0.625 | 0.3125 | Control |
|---|---|---|---|---|---|---|---|---|---|
| *Syncytia* | | | | | | | | | |
| HIV1LAI | 50 | >45 | >45 | >45 | >45 | >45 | >45 | >45 | 58 |
| | | | | | | | | | |
| DP185 | 40 | 20 | 10 | 5 | 2.5 | 1.25 | 0.625 | 0.3125 | Control |
| *Syncytia* | | | | | | | | | |
| HIV1LAI | 0 | 0 | 0 | 0 | 0 | 0 | 0 | ND | 60 |

FIG.4B

HIV1

Number of Syncytia/well: concentration in ng/ml (nanograms/ml)

| DP178 Syncytia | 20 | 10 | 5 | 2.5 | 1.25 | 0.625 | 0.3125 | Control |
|---|---|---|---|---|---|---|---|---|
| HIV1 | 0 | 0 | 0 | 0 | 0 | 14 | 20 | 48 |
| DP116 Syncytia | 20 | 10 | 5 | 2.5 | 1.25 | 0.625 | 0.3125 | Control |
| HIV1 | ND | 48 | ND | ND | ND | ND | ND | ND |

HIV2

Number of Syncytia/well: concentration in µg/ml (micrograms/ml)

| DP178 Syncytia | 20 | 10 | 5 | 2.5 | 1.25 | 0.625 | 0.3125 | Control |
|---|---|---|---|---|---|---|---|---|
| HIV2 | 50 | 54 | 55 | 57 | 63 | 77 | 78 | 76 |
| DP116 Syncytia | 20 | 10 | 5 | 2.5 | 1.25 | 0.625 | 0.3125 | Control |
| HIV2 | ND | 58 | ND | ND | ND | ND | ND | ND |

FIG.5

FIG. 12

| Sequence | A | D | A | D | A | D | A | D | A | D | Motifs |
|---|---|---|---|---|---|---|---|---|---|---|---|
| GCN4 (gcn4_yeast) | M K Q | L E D | K V E | E L L | S K N | Y H L | E N E | V A R | L K K | L | [LMNV] {CFGIMPTW} |
| C-FOS (fos_human) | T D T | L Q A | E T D | Q L E | D E K | S A L | Q T E | I A N | L L K | E | [IKLT] {CFGHIMPRVWY} |
| C-JUN (tap1_human) | I A R | L E E | K V K | T L K | A Q N | S E L | A S T | A N M | L R E | Q | [AILNV] {CDFGHILPVWY} |
| C-MYC (myo_human) | E Q K | L I S | E E D | L L R | K R R | E Q L | K H K | L E Q | L R N | S | [ELR] {ACFGMPVWY} |
| FLU LOOP 36 | I E K | T N E | K F H | Q I E | K E F | S E V | E G R | I Q D | L E K | Y | [FILTV] {

FIG. 13

| Sequence | | | | | | | | | | | | | | | Positions | | | | | | | | | | | | | | | | Motifs |
|---|---|---|---|---|---|---|---|---|---|---|---|---|---|---|---|---|---|---|---|---|---|---|---|---|---|---|---|---|---|---|---|
| | A | D | A | D | A | D | A | D | A | D | A | D | A | D | A | D | A | D | A | D | A | D | A | D | A | D | A | D | A | D | |
| DP-107 (env_hv1bru)L1=D | N | N | L | L | R | A | I | E | A | Q | Q | H | L | L | Q | L | T | V | W | G | I | K | Q | L | Q | A | R | I | | | [ILQT] {CFIMPSTY} |
| DP-107 (env_hv1bru)L1=D | N | N | L | L | R | A | I | E | A | Q | Q | H | L | L | Q | L | T | V | W | G | I | K | Q | L | Q | A | R | I | | | [ILQTV] {CDFIMPST} |
| DP-107 (env_hv1bru)L1=D | N | N | L | L | R | A | I | E | A | Q | Q | H | L | L | Q | L | T | V | W | G | I | K | Q | L | Q | A | R | I | | | [ILQTV] {CDFIMPST} |
| DP-107 (env_hv1bru)L2=D | | | N | N | L | L | R | A | I | E | A | Q | Q | H | L | L | T | V | W | G | I | K | Q | L | Q | A | R | I | L | A | [EKLNQV] {CDFKMPSVY} |
| DP-107 (env_hv1bru)L2=D | | | N | N | L | L | R | A | I | E | A | Q | Q | H | L | L | T | V | W | G | I | K | Q | L | Q | A | R | I | L | A | [EKLNQV] {CFKMPS} |
| DP-107 (env_hv1bru)L2=D | | | N | N | L | L | R | A | I | E | A | Q | Q | H | L | L | T | V | W | G | I | K | Q | L | Q | A | R | I | L | A | [EKLNQV] {CFKMPS} |
| DP-178 (env_hv1bru)Y1=A | Y | T | S | L | I | H | S | L | I | E | E | S | Q | N | Q | Q | E | K | N | E | Q | E | L | L | E | L | D | K | W | A | [EKLQY] {ACFGMPRWY} |
| DP-178 (env_hv1bru)Y1=A | Y | T | S | L | I | H | S | L | I | E | E | S | Q | N | Q | Q | E | K | N | E | Q | E | L | L | E | L | D | K | W | A | [EKLQWY] {CFGMPRVY} |
| DP-178 (env_hv1bru)Y1=A | Y | T | S | L | I | H | S | L | I | E | E | S | Q | N | Q | Q | E | K | N | E | Q | E | L | L | E | L | D | K | W | A | [EFKL

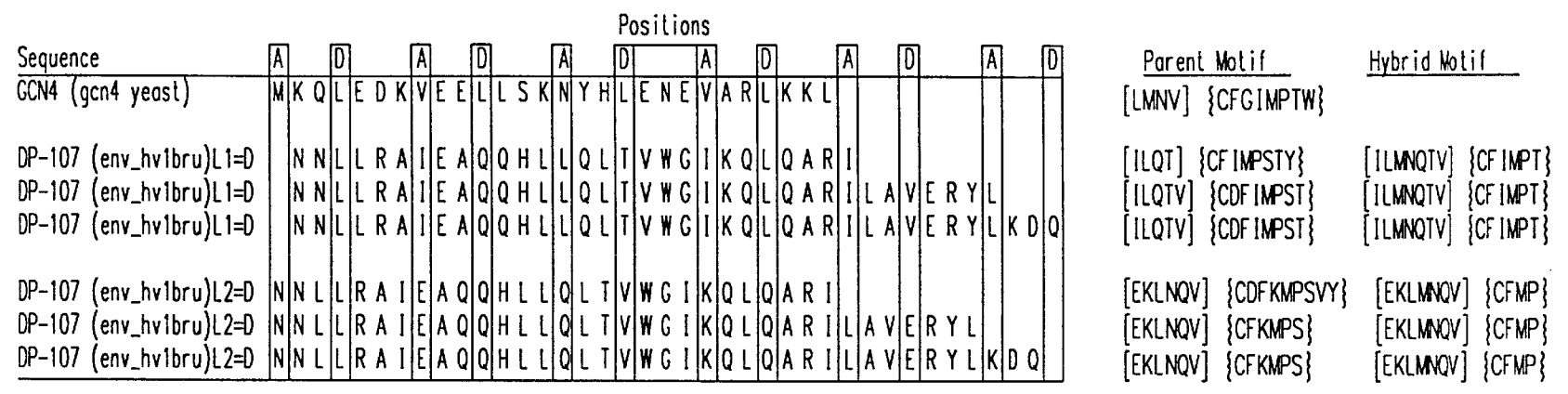

| Sequence | Positions | | | | | | | | | | | | | | | | | | | | | | | | | | | | | | | Parent Motif | Hybrid Motif |
|---|---|---|---|---|---|---|---|---|---|---|---|---|---|---|---|---|---|---|---|---|---|---|---|---|---|---|---|---|---|---|---|---|---|
| | A | D | | A | D | | A | D | | A | D | | A | D | | A | D | | A | D | | A | D | | A |

FIG. 15

| Sequence | Positions | | | | | | | | | | | | | | | | | | | Parent Motif | Hybrid Motif |
|---|---|---|---|---|---|---|---|---|---|---|---|---|---|---|---|---|---|---|---|---|---|
| | A | D | A | D | A | D | A | D | A | D | A | D | A | D | A | | | | | | |
| GCN4 (gcn4 yeast) | M | K Q | L E D | K V E | E L L | S K N | Y H L | E N E | V A R | L K K L | | | | | | | | | [LMNV] {CFGIMPTW} | |
| DP-178 (env_hv1bru)Y1=A | Y | T S | L I H | S L I | E E S | Q N Q | Q E K | N E Q | E L L | E L D K | W A S | L W N W | | | | | | | [EKLQY] {ACFGMPRVWY} | [EKLMNQVY] {CFGMPW} |
| DP-178 (env_hv1bru)Y1=A | Y | T S | L I H | S L I | E E S | Q N Q | Q E K | N E Q | E L L | E L D K | W A S | L W N W | | | | | | | [EKLQNY] {CFGMPRVY} | [EKLMNQVWY] {CFGMP} |
| DP-178 (env_hv1bru)Y1=A | Y | T S | L I H | S L I | E E S | Q N Q | Q E K | N E

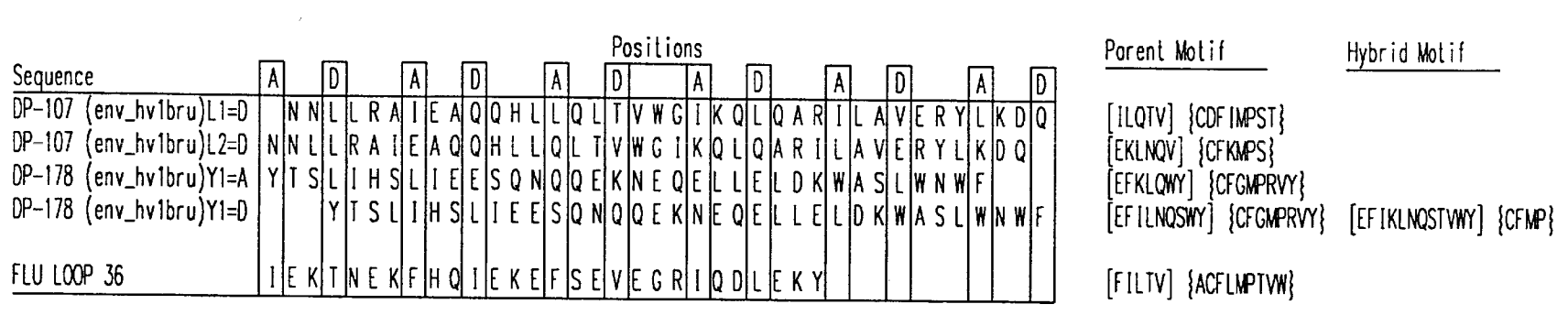

| Sequence | Positions | | | | | | | | | | | | | | Parent Motif | Hybrid Motif |
|---|---|---|---|---|---|---|---|---|---|---|---|---|---|---|---|---|
| | A | D | A | D | A | D | A | D | A | D | A | | | | | |
| DP-107 (env_hv1b

| Sequence | Positions | | | | | | | | | | | | | | | | | | | | | | | | | | | | | | | | | Parent Motif | Hybrid Motif |
|---|---|---|---|---|---|---|---|---|---|---|---|---|---|---|---|---|---|---|---|---|---|---|---|---|---|---|---|---|---|---|---|---|---|---|---|
| | a | d | a | d | a | d | a | d | a | d | a | d | a | d | a | d | a | d | a | d | a | d | a | d | a | d | a | d | a | d | a | d | | |
| GCN4 (gcn4 yeast) | M | K | Q | L | E | D | K | V | E | E | L | L | S | K | N | Y | H | L | E | N | E | V | A | R | L | K | K | L | V | G | E | R | [LMNV] {CFGIMPTW} | |
| DP-107 (env_hv1bru)L1=D | | N | N | L | L | R | A | I | E | A | Q | Q | H | L | L | Q | L

FIG. 18

| Sequence | Positions | | | | | | | | | | | | | | | | | | | | | | | | | | | | Parent Motif | Hybrid Motif |
|---|---|---|---|---|---|---|---|---|---|---|---|---|---|---|---|---|---|---|---|---|---|---|---|---|---|---|---|---|---|---|
| | A | D | A | D | A | D | A | D | A | D | A | D | A | D | A | D | A | D | A | D | A | D | A | D | A | D | A | D | | |
| GCN4 (gcn4 yeast) | M | K | Q | L | E | D | K | V | E | E | L | L | S | K | N | Y | H | L | E | N | E | V | A | R | L | K | K | L | [LMNV] {CFGIMPTW} | |
| DP-107 (env_hv1bru)L1=D | | | N | N | L | L | R | A | I | E | A | Q | Q | H | L | L | Q | L | T | V | W | G | I | K | Q | L | Q | A | [ILQTV] {CDFIMPST} | |
| DP-107 (env_hv1bru)L2=D | | | N | N | L | L | R | A | I | E | A | Q | Q | H | L | L | Q | L | T | V | W | G | I | K | Q | L | Q | A | [EKLNQV] {CFKMPS} | |
| DP-178 (env_hv1bru)Y1=A | Y | T | S | L | I | H | S | L | I | E | E | S | Q | N | Q | Q | E | K | N | E | Q | E | L | L | E | L | D | K | [EFKLQWY] {CFGMPRVY} | |
| DP-178 (env_hv1bru)Y1=D | | | Y | T | S | L | I | H | S | L | I | E | E | S | Q | N | Q | Q | E | K | N | E | Q | E | L | L | E | L | [EFILNQSWY] {CFGMPRVY} | |
| C-FOS (fos_human) | T | D | T | L | Q | A | E | T | D | Q | L | E | D | E | K | S | A | L | Q | T | E | I | A | N | L | L | K | E | [IKLT] {CFGHIMPRVWY} | |
| C-JUN (jun_human) | I | A | R | L | E | E | K | V | K | T | L | K | A | Q | N | S | E | L | A | S | T | A | N | M | L | R | E | Q | [AILNV] {CDFGHILPVWY} | |
| C-MYC (myc_human) | E | Q | K | L | I | S | E | E | D | L | L | R | K | R | R | E | Q | L | K | H | K | L | E | Q | L | R | N | S | [ELR] {ACFGMPVWY} | |
| FLU LOOP 36 | I | E | K | T | N | E | K | F | H | Q | I | E | K | E | F | S | E | V | E | G | R | I | I | Q | D | L | E | K | [FILTV] {ACFLMPTVW} | |

Hybrid Motif:
= [AEFIKLMNQ

P-[LIV]-{P}(6)-[LIV]-{P}(6)-[LIV]
P-{P}(1)-[LIV]-{P}(6)-[LIV]-{P}(6)-[LIV]
P-{P}(2)-[LIV]-{P}(6)-[LIV]-{P}(6)-[LIV]
P-{P}(3)-[LIV]-{P}(6)-[LIV]-{P}(6)-[LIV]
P-{P}(4)-[LIV]-{P}(6)-[LIV]-{P}(6)-[LIV]
P-{P}(5)-[LIV]-{P}(6)-[LIV]-{P}(6)-[LIV]
P-{P}(6)-[LIV]-{P}(6)-[LIV]-{P}(6)-[LIV]
P-{P}(7)-[LIV]-{P}(6)-[LIV]-{P}(6)-[LIV]
P-{P}(8)-[LIV]-{P}(6)-[LIV]-{P}(6)-[LIV]
P-{P}(9)-[LIV]-{P}(6)-[LIV]-{P}(6)-[LIV]
P-{P}(10)-[LIV]-{P}(6)-[LIV]-{P}(6)-[LIV]
P-X(1,12)-[LIV]-{P}(6)-[LIV]-{P}(6)-[LIV]
P-X(13,23)-[LIV]-{P}(6)-[LIV]-{P}(6)-[LIV]

FIG. 19

```
     Fusion         ♥ALLMOTI5♥
     Peptide                                    ▲107x178x4▲
♥.......FLGFLG    A AGSTMGARSM TLTVQARQ   ▲LL SGIVQQQ   DP107-NNL
```

*LRAIEAQQHL LQLTVWGIKQ LQARILAVER YLKDQ-DP107* QLLG▲♥ I WGC

```
                                              ▲107x178x4▲
                   ♥ALLMOTI5♥                 *LVS Coiled-Coil*
SGKLICT TAVP  ♥WNASWS NKSLEQIWNN MTWM  *E  ▲WDREINN  DP178-
```

*YTSLIHSL IEESQNQQEK NEQELLELDK*  *WASLWNWF-DP178*   NI

```
              ♦Transmembrane Region♦
TNWLWYIK▲  ♦IF IMIVGGLVGL RIVFAVLSIV  NRVRQGYS♥  PL
```

```
                ♣P23LZIPC♣
SFQTHLPTPR GPDR   ♣PEGIEE EGGERDRDRS IRLVNGSLAL IWDDLRSL♣  CL
```

```
     ♥ALLMOTI5♥              ▲107x178x4▲
 F  ♥SYHRLRDLL LIVTRIVELL GRRGW  ▲EALKY WWNLLQYWSQ
```

*ELKNSAVSLL NAT*▲ AIAVAEG TDRVIEVVQG A♥ CRAIRHIPR

RIRQGLERIL L

FIG. 20

```
        Fusion        ♥ALLMOTI5♥
        Peptide                  ♠107x178x4♠
♥.......FLGFL    LGVGSAIAS GVA   ♠VSKVLHL EGEVNKIKSA
```

```
                                                  ♣P1&12LZIPC♣
LLSTNKAVVS LSNGVSVLTS KVLDLKNYID KQ♠♥ LL   ♣PIVNKQ
```

```
     ♠107x178x4♠
SC   ♠SISNIETV I♣ EFQQKNNRLLEITREFSVNAG♠ VTTPVSTMLTNSELLSL
```

```
          ♣P1&12LZIPC♣
          ♥ALLMOTI5♥
INDM ♣PI ♥TNDQ KKLMSNNVQI V♣ RQQSYSI♣ MS IIKEEVLAYV
```

VQ♥ LPLYGVID TPCWKLHTSP LCTTNTKEGS NICLTRTDRG WYCDNAGSVS

FFPQAETCKV QSNRVFCDTM NSLTLPSEIN LCNVDIFNPK

YDCKIMTSKT DVSSSVITSL GAIVSCYGKT KCTASNKNRG

IIKTFSNGCDYVSNKGMDTV SVGNTLYYVN KQEGKSLYVK G

```
          ♣P7, 12, & 23LZIPC♣
               ♠107x178x4♠              ♥ALLMOTI5♥
EPIINFYDPLVF ♣PSDE ♠FDASISQVNEKINQSLAF ♥I♣ RKSDELL♣
```

```
                    ♦Transmembrane Region♦
HNVNA♠   GK STTN  ♦IMITTI IIVIIVILLS LIAVGLLLY♥  C♦
```

KARSTPVTLS KDQLSGINNI AFSN

FIG. 21

Fusion
Peptide ♥ALLMOTI5♥ ♠107x178x4♠
.......FLGFLG ♥AAGTA MGAAA ♠TALTVQSQHLLAGILQQQKNLLAAV ♠107x178x4♠
EAQ♠ QQM ♠LKLTIWGVKNLNARVTALEKYLEDQARLN♠ AWG♥ CA

*LVS Coiled-Coil*
♥ALLMOTI5♥ ♠107x178x4♠
WKQVCHTTVP WQWNNRTPDW ♥NNMT *WLE ♠WERQISYLEGNIT ♠107x178x4♠
TQLEEARAQEEKNLD♠ AYQKLSS* WSDFWSW♥ FDF ♠SKWLN ♦ILK ♦Transmembrane Region♦
IGFLDVLGIIGLRLLYTV♦ YS♠ CIARVRQGYS PLSPQIHIHP WKGQPDNAEG

PGEGGDKRKN SSEPWQKESG TAEWKSNWCK RLTNWCSISS IWLYNS

♥ALLMOTI5♥
♥CLTL LVHLRSAFQY IQYGLGELKA AAQEAVVALA RLAQNAGYQIWL♥

ACRSAYRA IINSPRRVRQ GLEGILN

FIG. 22

Fusion                                             ♠107x178x4♠
Peptide    ♥ALLMOTI5♥                              *LVS Coiled-Coil*
.......FAG    ♥VVL    AGVALGVATA AQITAGIALHQ    ♠*SNLNAQAIQ

SLRTSLEQSNKAIEEIREATQETVIA*    VQGVQDY♠    VNNEL♥    VP

♥ALLMOTI5♥
                                                  ♠107x178x4♠
                                             ♣P6 & 12LZIPC♣
AMQHMSCELVGQRLGLRLLRYYTELLSIFGPSLRD    ♣PISA    ♠♥EISIQALIYAL

GGEIHKILEKLGYSGSD♠    MIAILESRGIKTKI♥    THVDLPGKF ILSISY

♣P1 & 12LZIPC♣
♣PTLSEVKGVIVHRLEAV♣    SYNIGSQEWYTTVPRYIATNGYLISNFDESSCVFVS

ESAICSQNSL YPMSPLLQQC IRGDTSSCAR TLVSGTMGNK FILSKGNIVA

NCASILCKCY STSTIINQSP DKLLTFIASD TCPLVEIDGA TIQVGGRQYP

*LVS Coiled-Coil*
                    ♥ALLMOTI5♥
                ♣P12 & 23LZIPC♣
DMVYEGKVAL G    ♣PAISLD    ♥RL*DVGTNLGNALKKLDDAKVLI♣

♦Transmembrane Region♦
DSS♣    NQILETVR RS♥*    SFN    ♦FGSLL SVPILSCTAL ALLLLIYCC♦

K RRYQQTLKQH TKVDPAFKPD LTGTSKSYVR SL

FIG. 23

Fusion ♥ALLMOTI5♥
Peptide ♦107x178x4♦
♥.......FIGAI IGSVALGVA TAAQITAASA LIQANQNAAN ♦ILRLKESITA

TIEAVHEVTDGLSQLAVA♦ VG KM♥ QQFVNDQFNNTAQELDCIKITQQV

♥ALLMOTI5♥
GVELNLYLTELTTV FGPQITSPAL ♥TQLTIQALYNAGGNMDYLLTKLGVG

♣P1 & 12LZIPC♣
NNQLSSLIGSGLIT GN♥ ♣PILYDSQT QLLGIQVTLP SVGNLNNMRATYLET

LSVST TKGFASALVP KVVTQVGSVI EELDTSYCIE TDLDLYCTRI VTFPMSPGIY

SCLNGNTSAC MYSKTEGALT TPYMTLKGSV IANCKMTTCR CADPPGIISQ

♥ALLMOTI5♥
♦107x178x4♦
NYGEAVSLID RHSCN ♦♥VLSLD GITLRLSGEF DATYQKNISI LDSQVIVTG

*LVS Coiled-Coil* ♦Trans-
*N LDISTELGNV NNSISNALDK LEESNSKLDK VNVKLTSTSA ♦LIT* YIA membrane Region♦
LTAISLVCGILSLV♥♦ LACYLMY♦ KQKAQQKTLLWLGNNTLGQMRATTKM

FIG. 24

Fusion　　　　　▼ALLMOTI5▼
Peptide　　　　♠107x178x4♠　　*LVS Coiled-Coil*
.......FFGGV　　♠IG　▼TIALG　　*VATSAQITAAVALVEAKQARSDIEKLKE

AIRDTNKAVQSVQSSIGNLIVAIKSVQ*　DYVNKE▼♠　IVPSIARLGCEAAG

▼ALLMOTI5▼
　　　　　　　♠107x178x4♠
LQLGIALTQH　♠▼YSELTNIFGDNIGSLQEKGIKLQGIASLYRTNITE▼♠

♣P5 & 12LZIPC♣
IFTTSTVDKYDIYDLLFTESIKVRVIDVDLNDYSITLQVRL　♣PLLTRLLNTQIYR

VDSISYNI♣　QNREWYI♣　PLPSHIMTKGAFLGGADVKECIEAFSSYIC

PSDPGFVLNHEMESCLSGNISQCPRTVVKSDIVPRYAFVNGGVVANCITT

TCTCNGIGNRINQPPDQGVKIITHKECNTIGINGMLFNTNKEGTLAFYTP

▼ALLMOTI5▼
　　　　　　　　　　　　　♠107x178x4♠
　　　　　　　　♣P6 & 23LZIPC♣
NDITLNNSVALD　♣PIDI　♠SIELN　▼KAKSDLEESKEWI♣　RRSNQKL♣

◆Transmembrane Region◆
DSIGNWHQSSTT　◆IIIV♠　LIM IIILFIINVT II◆　　IIAVKYY▼　R

IQKRNRVDQN DKPYVLTNK

FIG. 25

Fusion
Peptide
.......GLFGAI AGFIENGWEGMIDGWYGFRHQNSEGTG

♦107x178x4♦
♥ALLMOTI5♥
*LVS Coiled-Coil*
*Q ♥AADLKST ♦QAAIDQINGKLNRVIEKTNEKFHQIEKEFSEVEGRIQ

DLEKYVEDTKIDL* WSYNAELLVALENQHTI♦ DLT♥ DSEMNKLFEKTR

RQLRENAEEMGNGCF

| AV | CD | RSV F2 | YTSVITIELSNIKENKCNGTDAKVKLIKQELDKYKNAVTELQLLMQST |
|---|---|---|---|
| + | +/++ | T-142 | YTSVITIELSNIKENKCNGTDAKVKLIKQELDKYK |
| ++ | +/+++ | T-143 | TSVITIELSNIKENKCNGTDAKVKLIKQELDKYKN |
| + | +/++ | T-144 | SVITIELSNIKENKCNGTDAKVKLIKQELDKYKNA |
| - | +/+ | T-145 | VITIELSNIKENKCNGTDAKVKLIKQELDKYKNAV |
| - | +/- | T-146 | ITIELSNIKENKCNGTDAKVKLIKQELDKYKNAVT |
| - | | T-147 | TIELSNIKENKCNGTDAKVKLIKQELDKYKNAVTE |
| - | - | T-148 | IELSNIKENKCNGTDAKVKLIKQELDKYKNAVTEL |
| - | +/- | T-149 | ELSNIKENKCNGTDAKVKLIKQELDKYKNAVTELQ |
| - | - | T-150 | LSNIKENKCNGTDAKVKLIKQELDKYKNAVTELQL |
| - | +/+ | T-151 | SNIKENKCNGTDAKVKLIKQELDKYKNAVTELQLL |
| - | +/++ | T-152 | NIKENKCNGTDAKVKLIKQELDKYKNAVTELQLLM |
| - | +/+ | T-153 | IKENKCNGTDAKVKLIKQELDKYKNAVTELQLLMQ |
| - | +/++ | T-154 | KENKCNGTDAKVKLIKQELDKYKNAVTELQLLMQS |
| - | +/+ | T-155 | ENKCNGTDAKVKLIKQELDKYKNAVTELQLLMQST |

FIG.27

| AV | CD | RSV | Sequence |
|---|---|---|---|
| +++ | +/− | T-67 | DEFDASISQVNEKINQSLAFIRKSDELL |
|  |  | F1-178 | GEPIINFYDPLVFPSDEFDASISQVNEKINQSLAFIRKSDELLHNVNAGKSTT |
| +/− |  | T-104 | IINFYDPLVFPSDEFDASISQVNEKINQSLAFIRK |
| +/− |  | T-105 | INFYDPLVFPSDEFDASISQVNEKINQSLAFIRKS |
| +/− |  | T-106 | NFYDPLVFPSDEFDASISQVNEKINQSLAFIRKSD |
| + |  | T-107 | FYDPLVFPSDEFDASISQVNEKINQSLAFIRKSDE |
| ++ |  | T-108 | YDPLVFPSDEFDASISQVNEKINQSLAFIRKSDEL |
| ++ |  | T-109 | DPLVFPSDEFDASISQVNEKINQSLAFIRKSDELL |
| + |  | T-110 | PLVFPSDEFDASISQVNEKINQSLAFIRKSDELLH |
| +++ | +/− | T-111 | LVFPSDEFDASISQVNEKINQSLAFIRKSDELLHN |
| ++ | +/− | T-112 | VFPSDEFDASISQVNEKINQSLAFIRKSDELLHNV |
| +++ | +/− | T-113 | FPSDEFDASISQVNEKINQSLAFIRKSDELLHNVN |
| +++ | +/− | T-114 | PSDEFDASISQVNEKINQSLAFIRKSDELLHNVNA |
| +++ | +/− | T-115 | SDEFDASISQVNEKINQSLAFIRKSDELLHNVNAG |
| ++ | +/− | T-116 (T-67 LIKE) | DEFDASISQVNEKINQSLAFIRKSDELLHNVNAGK |
| ++ | +/− | T-117 | EFDASISQVNEKINQSLAFIRKSDELLHNVNAGKS |
| ++ |  | T-118 | FDASISQVNEKINQSLAFIRKSDELLHNVNAGKST |
| +++ | +/− | T-119 | DASISQVNEKINQSLAFIRKSDELLHNVNAGKSTT |

FIG. 28

| AV | CD | HPF3 | Sequence |
|---|---|---|---|
| – | – | 178 | YTPNDITLNNSVALDPIDISIELNKAKSDLEESKEWIRRSNQKLDSIGNWHQSSTT |
| – | – | 189 | YTPNDITLNNSVALDPIDISIELNKAKSDLEESKE |
| – | – | 190 | TPNDITLNNSVALDPIDISIELNKAKSDLEESKEW |
| – | – | 191 | PNDITLNNSVALDPIDISIELNKAKSDLEESKEWI |
| –/+ | +/– | 192 | NDITLNNSVALDPIDISIELNKAKSDLEESKEWIR |
| +/– | +/– | 193 | DITLNNSVALDPIDISIELNKAKSDLEESKEWIRR |
| + | +/+ | 194 | ITLNNSVALDPIDISIELNKAKSDLEESKEWIRRS |
| +++ | +/+ | 195 | TLNNSVALDPIDISIELNKAKSDLEESKEWIRRSN |
| ++ | +/+ | 196 | LNNSVALDPIDISIELNKAKSDLEESKEWIRRSNQ |
| – | +/+ | 197 | NNSVALDPIDISIELNKAKSDLEESKEWIRRSNQK |
| +++ |  | 198 | NSVALDPIDISIELNKAKSDLEESKEWIRRSNQKL |
| +++ |  | 199 | SVALDPIDISIELNKAKSDLEESKEWIRRSNQKLD |
| +++ |  | 200 | VALDPIDISIELNKAKSDLEESKEWIRRSNQKLDS |
| +++ |  | 201 | ALDPIDISIELNKAKSDLEESKEWIRRSNQKLDSI |
| + |  | 202 | LDPIDISIELNKAKSDLEESKEWIRRSNQKLDSIG |
| + |  | 203 | DPIDISIELNKAKSDLEESKEWIRRSNQKLDSIGN |
| ++ |  | 204 | PIDISIELNKAKSDLEESKEWIRRSNQKLDSIGNW |
| ++ |  | 205 | IDISIELNKAKSDLEESKEWIRRSNQKLDSIGNWH |
|  |  | 206 | DISIELNKAKSDLEESKEWIRRSNQKLDSIGNWHQ |
|  |  | 207 | ISIELNKAKSDLEESKEWIRRSNQKLDSIGNWHQS |
|  |  | 208 | SIELNKAKSDLEESKEWIRRSNQKLDSIGNWHQSS |
|  |  | 209 | IELNKAKSDLEESKEWIRRSNQKLDSIGNWHQSST |
|  |  | 210 | ELNKAKSDLEESKEWIRRSNQKLDSIGNWHQSSTT |

FIG.29

| CD | HPF3 | 107 | GTIALGVATSAQITAAVALVEAKQARSDIEKLKEAIRDTNKAVQSVQSSIGNLIVAIKSVQDYVNKEIVP |
|---|---|---|---|
| +/+ | | 157 | ALGVATSAQITAAVALVEAKQARSDIEKLKEAIRD |
| +/+ | | 158 | LGVATSAQITAAVALVEAKQARSDIEKLKEAIRDT |
| +/− | | 159 | GVATSAQITAAVALVEAKQARSDIEKLKEAIRDTN |
| +/+ | | 160 | VATSAQITAAVALVEAKQARSDIEKLKEAIRDTNK |
| +/+ | | 161 | ATSAQITAAVALVEAKQARSDIEKLKEAIRDTNKA |
| +/− | | 162 | TSAQITAAVALVEAKQARSDIEKLKEAIRDTNKAV |
| +/+ | | 163 | SAQITAAVALVEAKQARSDIEKLKEAIRDTNKAVQ |
| +/+++ | | 164 | AQITAAVALVEAKQARSDIEKLKEAIRDTNKAVQS |
| +/+ | | 165 | QITAAVALVEAKQARSDIEKLKEAIRDTNKAVQSV |
| +/− | | 166 | ITAAVALVEAKQARSDIEKLKEAIRDTNKAVQSVQ |
| +/− | | 167 | TAAVALVEAKQARSDIEKLKEAIRDTNKAVQSVQS |
| +/− | | 168 | AAVALVEAKQARSDIEKLKEAIRDTNKAVQSVQSS |
| +/− | | 169 | AVALVEAKQARSDIEKLKEAIRDTNKAVQSVQSSI |
| +/− | | 170 | VALVEAKQARSDIEKLKEAIRDTNKAVQSVQSSIG |
| +/− | | 171 | ALVEAKQARSDIEKLKEAIRDTNKAVQSVQSSIGN |
| +/− | | 172 | LVEAKQARSDIEKLKEAIRDTNKAVQSVQSSIGNL |
| +/− | | 173 | VEAKQARSDIEKLKEAIRDTNKAVQSVQSSIGNLI |
| +/++ | | 174 | EAKQARSDIEKLKEAIRDTNKAVQSVQSSIGNLIV |
| | | T-40 | AKQARSDIEKLKEAIRDTNKAVQSVQSSIGNLIVA |
| +/++ | | 175 | KQARSDIEKLKEAIRDTNKAVQSVQSSIGNLIVAI |
| +/+++ | | 176 | QARSDIEKLKEAIRDTNKAVQSVQSSIGNLIVAIK |
| +/− | | 177 | ARSDIEKLKEAIRDTNKAVQSVQSSIGNLIVAIKS |
| +/− | | 178 | RSDIEKLKEAIRDTNKAVQSVQSSIGNLIVAIKSV |
| − | | 179 | SDIEKLKEAIRDTNKAVQSVQSSIGNLIVAIKSVQ |
| − | | 180 | DIEKLKEAIRDTNKAVQSVQSSIGNLIVAIKSVQD |
| − | | 181 | IEKLKEAIRDTNKAVQSVQSSIGNLIVAIKSVQDY |
| − | | 182 | EKLKEAIRDTNKAVQSVQSSIGNLIVAIKSVQDYV |
| +/++ | | 183 | KLKEAIRDTNKAVQSVQSSIGNLIVAIKSVQDYVN |
| +/+++ | | 184 | LKEAIRDTNKAVQSVQSSIGNLIVAIKSVQDYVNK |
| − | | 185 | KEAIRDTNKAVQSVQSSIGNLIVAIKSVQDYVNKE |
| − | | 186 | EAIRDTNKAVQSVQSSIGNLIVAIKSVQDYVNKEI |
| − | | 187 | AIRDTNKAVQSVQSSIGNLIVAIKSVQDYVNKEIV |
| − | | 188 | IRDTNKAVQSVQSSIGNLIVAIKSVQDYVNKEIVP |

FIG.30

```
                         SEQUENCE LISTING (1) GENERAL INFORMATION:

(iii) NUMBER OF SEQUENCES: 111

(2) INFORMATION FOR SEQ ID NO:1:

(i) SEQUENCE CHARACTERISTICS:
          (A) LENGTH: 36 amino acids
          (B) TYPE: amino acid
          (D) TOPOLOGY: unknown (ii) MOLECULE TYPE: peptide (xi) SEQUENCE DESCRIPTION: SEQ ID NO:1:

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

(2) INFORMATION FOR SEQ ID NO:2:

(i) SEQUENCE CHARACTERISTICS:
          (A) LENGTH: 36 amino acids
          (B) TYPE: amino acid
          (D) TOPOLOGY: unknown (ii) MOLECULE TYPE: peptide (xi) SEQUENCE DESCRIPTION: SEQ ID NO:2:

Ser Ser Glu Ser Phe Thr Leu Leu Glu Gln Trp Asn Asn Trp Lys Leu
1               5                   10                  15

Gln Leu Ala Glu Gln Trp Leu Glu Gln Ile Asn Glu Lys His Tyr Leu
            20                  25                  30

Glu Asp Ile Ser
        35

(2) INFORMATION FOR SEQ ID NO:3:

(i) SEQUENCE CHARACTERISTICS:
          (A) LENGTH: 36 amino acids
          (B) TYPE: amino acid
          (D) TOPOLOGY: unknown
```

(ii) MOLECULE TYPE: peptide (xi) SEQUENCE DESCRIPTION: SEQ ID NO:3:

Tyr Thr Asn Thr Ile Tyr Thr Leu Leu Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

(2) INFORMATION FOR SEQ ID NO:4:

(i) SEQUENCE CHARACTERISTICS:
        (A) LENGTH: 36 amino acids
        (B) TYPE: amino acid
        (D) TOPOLOGY: unknown (ii) MOLECULE TYPE: peptide (xi) SEQUENCE DESCRIPTION: SEQ ID NO:4:

Tyr Thr Gly Ile Ile Tyr Asn Leu Leu Glu Glu Ser Gln Asn Gln Gln
1               5                   10                  15

Glu Lys Asn Glu Gln Glu Leu Leu Glu Leu Asp Lys Trp Ala Asn Leu
            20                  25                  30

Trp Asn Trp Phe
        35

(2) INFORMATION FOR SEQ ID NO:5:

(i) SEQUENCE CHARACTERISTICS:
        (A) LENGTH: 36 amino acids
        (B) TYPE: amino acid
        (D) TOPOLOGY: unknown (ii) MOLECULE TYPE: peptide (xi) SEQUENCE DESCRIPTION: SEQ ID NO:5:

Tyr Thr Ser Leu Ile Tyr Ser Leu Leu Glu Lys Ser Gln Thr Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

(2) INFORMATION FOR SEQ ID NO:6:

(i) SEQUENCE CHARACTERISTICS:
        (A) LENGTH: 36 amino acids
        (B) TYPE: amino acid
        (D) TOPOLOGY: unknown (ii) MOLECULE TYPE: peptide (xi) SEQUENCE DESCRIPTION: SEQ ID NO:6:

Leu Glu Ala Asn Ile Ser Lys Ser Leu Glu Gln Ala Gln Ile Gln Gln
1               5                   10                  15

Glu Lys Asn Met Tyr Glu Leu Gln Lys Leu Asn Ser Trp Asp Ile Phe
            20                  25                  30

Gly Asn Trp Phe
        35

(2) INFORMATION FOR SEQ ID NO:7:

(i) SEQUENCE CHARACTERISTICS:
            (A) LENGTH: 36 amino acids
            (B) TYPE: amino acid
            (D) TOPOLOGY: unknown (ii) MOLECULE TYPE: peptide (xi) SEQUENCE DESCRIPTION: SEQ ID NO:7:

Leu Glu Ala Asn Ile Ser Gln Ser Leu Glu Gln Ala Gln Ile Gln Gln
 1               5                  10                  15

Glu Lys Asn Met Tyr Glu Leu Gln Lys Leu Asn Ser Trp Asp Val Phe
                20                  25                  30

Thr Asn Trp Leu
             35

(2) INFORMATION FOR SEQ ID NO:8:

(i) SEQUENCE CHARACTERISTICS:
            (A) LENGTH: 41 amino acids
            (B) TYPE: amino acid
            (D) TOPOLOGY: unknown (ii) MOLECULE TYPE: peptide (xi) SEQUENCE DESCRIPTION: SEQ ID NO:8:

Cys Gly Gly Asn Asn Leu Leu Arg Ala Ile Glu Ala Gln Gln His Leu
 1               5                  10                  15

Leu Gln Leu Thr Val Trp Gly Ile Lys Gln Leu Gln Ala Arg Ile Leu
                20                  25                  30

Ala Val Glu Arg Tyr Leu Lys Asp Gln
             35                  40

(2) INFORMATION FOR SEQ ID NO:9:

(i) SEQUENCE CHARACTERISTICS:
            (A) LENGTH: 17 amino acids
            (B) TYPE: amino acid
            (D) TOPOLOGY: unknown (ii) MOLECULE TYPE: peptide (xi) SEQUENCE DESCRIPTION: SEQ ID NO:9:

Leu Gln Ala Arg Ile Leu Ala Val Glu Arg Tyr Leu Lys Asp Gln Gln
 1               5                  10                  15

Gln (2) INFORMATION FOR SEQ ID NO:10:

(i) SEQUENCE CHARACTERISTICS:
            (A) LENGTH: 38 amino acids
            (B) TYPE: amino acid
            (D) TOPOLOGY: unknown (ii) MOLECULE TYPE: peptide (xi) SEQUENCE DESCRIPTION: SEQ ID NO:10:

Gln Gln Leu Leu Asp Val Val Lys Arg Gln Gln Glu Met Leu Arg Leu
 1               5                  10                  15

Thr Val Trp Gly Thr Lys Asn Leu Gln Ala Arg Val Thr Ala Ile Glu
                20                  25                  30

Lys Tyr Leu Lys Asp Gln
             35

(2) INFORMATION FOR SEQ ID NO:11:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:11:

ATGACGCTGA CGGTACAGGC C                                         21

(2) INFORMATION FOR SEQ ID NO:12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

TGACTAAGCT TAATACCACA GCCAATTTGT TAT                             33

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GGAGCTGCTT GGGGCCCCAG AC                                        22

(2) INFORMATION FOR SEQ ID NO:14:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CCAAATCCCC AGGAGCTGCT CGAGCTGCAC TATACCAGAC                      40

(2) INFORMATION FOR SEQ ID NO:15:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

ATAGCTTCTA GATTAATTGT TAATTTCTCT GTCCC                           35

(2) INFORMATION FOR SEQ ID NO:16:

(i) SEQUENCE CHARACTERISTICS:
        (A) LENGTH: 50 amino acids
        (B) TYPE: amino acid (D) TOPOLOGY: unknown (ii) MOLECULE TYPE: peptide (ix) FEATURE:
        (A) NAME/KEY: Peptide
        (B) LOCATION: 1
        (D) OTHER INFORMATION: /label= A
            /note= "x comprises an amino group, an acetyl
            group, a 9-fluoromethyoxymethyl-carbonyl group, a
            hydrophobic group, or a macromolecule carrier (ix) FEATURE:
        (A) NAME/KEY: Peptide
        (B) LOCATION: 50
        (D) OTHER INFORMATION: /label= B
            /note= " x comprises a carboxyl group, an amido
            group, a hydrophobic group, or a macromolecular
            carrier group."

(xi) SEQUENCE DESCRIPTION: SEQ ID NO:16:

Xaa Tyr Thr Ser Val Ile Thr Ile Glu Leu Ser Asn Ile Lys Glu Asn
1               5                   10                  15

Lys Cys Asn Gly Thr Asp Ala Lys Val Lys Leu Ile Lys Gln Glu Leu
            20                  25                  30

Asp Lys Tyr Lys Asn Ala Val Thr Glu Leu Gln Leu Leu Met Gln Ser
        35                  40                  45

Thr Xaa
    50

(2) INFORMATION FOR SEQ ID NO:17:

(i) SEQUENCE CHARACTERISTICS:
        (A) LENGTH: 39 amino acids
        (B) TYPE: amino acid
        (D) TOPOLOGY: unknown (ii) MOLECULE TYPE: peptide (ix) FEATURE:
        (A) NAME/KEY: Peptide
        (B) LOCATION: 1
        (D) OTHER INFORMATION: /label= A
            /note= "x comprises an amino group, an acetyl
            group, a 9-fluoromethyoxymethyl-carbonyl group, or
            a macromolecule carrier group."

(ix) FEATURE:
        (A) NAME/KEY: Peptide
        (B) LOCATION: 39
        (D) OTHER INFORMATION: /label= B
            /note= "x comprises a carboxyl group, an amido
            group, a hydrophobic group, or a macromolecular
            carrier group."

(xi) SEQUENCE DESCRIPTION: SEQ ID NO:17:

Xaa Phe Tyr Asp Pro Leu Val Phe Pro Ser Asp Glu Phe Asp Ala Ser
1               5                   10                  15

Ile Ser Gln Val Asn Glu Lys Ile Asn Gln Ser Leu Ala Phe Ile Arg
            20                  25                  30

Lys Ser Asp Glu Leu Leu Xaa
        35

(2) INFORMATION FOR SEQ ID NO:18:

(i) SEQUENCE CHARACTERISTICS:
        (A) LENGTH: 37 amino acids
        (B) TYPE: amino acid
        (D) TOPOLOGY: unknown

```
        (ii) MOLECULE TYPE: peptide (ix) FEATURE:
             (A) NAME/KEY: Peptide
             (B) LOCATION: 1
             (D) OTHER INFORMATION: /label= A
                 /note= "x comprises an amino group, an acetly
                 group, a 9-fluoromethyoxymethyl-carbonyl group, a
                 hydrophobic group, or a macromolecule carrier (ix) FEATURE:
             (A) NAME/KEY: Peptide
             (B) LOCATION: 37
             (D) OTHER INFORMATION: /label= B
                 /note= "x comprises a carboxyl group, an amido
                 group, a hydrophobic group, or a macromolecular
                 carrier group."

(xi) SEQUENCE DESCRIPTION: SEQ ID NO:18:

Xaa Ile Thr Leu Asn Asn Ser Val Ala Leu Asp Pro Ile Asp Ile Ser
1               5                   10                  15

Ile Glu Leu Asn Lys Ala Lys Ser Asp Leu Glu Glu Ser Lys Glu Trp
            20                  25                  30

Ile Arg Arg Ser Xaa
            35

(2) INFORMATION FOR SEQ ID NO:19:

(i) SEQUENCE CHARACTERISTICS:
            (A) LENGTH: 37 amino acids
            (B) TYPE: amino acid
            (D) TOPOLOGY: unknown (ii) MOLECULE TYPE: peptide (ix) FEATURE:
             (A) NAME/KEY: Peptide
             (B) LOCATION: 1
             (D) OTHER INFORMATION: /label= A
                 /note= "x comprises an amino group, an acetly
                 group, a 9-fluoromethyoxymethyl-carbonyl group, a
                 hydrophobic group, or a macromolecule carrier (ix) FEATURE:
             (A) NAME/KEY: Peptide
             (B) LOCATION: 37
             (D) OTHER INFORMATION: /label= B
                 /note= "x comprises a carboxyl group, an amido
                 group, a hydrophobic group, or a macromolecular
                 carrier group."

(xi) SEQUENCE DESCRIPTION: SEQ ID NO:19:

Xaa Ala Leu Gly Val Ala Thr Ser Ala Gln Ile Thr Ala Ala Val Ala
1               5                   10                  15

Leu Val Glu Ala Lys Gln Ala Arg Ser Asp Ile Glu Lys Leu Lys Glu
            20                  25                  30

Ala Ile Arg Asp Xaa
            35

(2) INFORMATION FOR SEQ ID NO:20:

(i) SEQUENCE CHARACTERISTICS:
            (A) LENGTH: 28 amino acids
            (B) TYPE: amino acid
            (D) TOPOLOGY: unknown (ii) MOLECULE TYPE: peptide (xi) SEQUENCE DESCRIPTION: SEQ ID NO:20:

Met Lys Gln Leu Glu Asp Lys Val Glu Glu Leu Leu Ser Lys Asn Tyr
```

```
                  1               5              10              15
His Leu Glu Asn Glu Val Ala Arg Leu Lys Lys Leu
                 20              25
```

(2) INFORMATION FOR SEQ ID NO:21:

(i) SEQUENCE CHARACTERISTICS:
        (A) LENGTH: 28 amino acids
        (B) TYPE: amino acid
        (D) TOPOLOGY: unknown (ii) MOLECULE TYPE: peptide (xi) SEQUENCE DESCRIPTION: SEQ ID NO:21:

```
Thr Asp Thr Leu Gln Ala Glu Thr Asp Gln Leu Glu Asp Glu Lys Ser
 1               5              10                          15
Ala Leu Gln Thr Glu Ile Ala Asn Leu Leu Lys Glu
                20              25
```

(2) INFORMATION FOR SEQ ID NO:22:

(i) SEQUENCE CHARACTERISTICS:
        (A) LENGTH: 28 amino acids
        (B) TYPE: amino acid
        (D) TOPOLOGY: unknown (ii) MOLECULE TYPE: peptide (xi) SEQUENCE DESCRIPTION: SEQ ID NO:22:

```
Ile Ala Arg Leu Glu Glu Lys Val Lys Thr Leu Lys Ala Gln Asn Ser
 1               5              10                          15
Glu Leu Ala Ser Thr Ala Asn Met Leu Arg Glu Gln
                20              25
```

(2) INFORMATION FOR SEQ ID NO:23:

(i) SEQUENCE CHARACTERISTICS:
        (A) LENGTH: 28 amino acids
        (B) TYPE: amino acid
        (D) TOPOLOGY: unknown (ii) MOLECULE TYPE: peptide (xi) SEQUENCE DESCRIPTION: SEQ ID NO:23:

```
Glu Gln Lys Leu Ile Ser Glu Glu Asp Leu Leu Glu Lys Arg Arg Glu
 1               5              10                          15
Gln Leu Lys His Lys Leu Glu Gln Leu Arg Asn Ser
                20              25
```

(2) INFORMATION FOR SEQ ID NO:24:

(i) SEQUENCE CHARACTERISTICS:
        (A) LENGTH: 28 amino acids
        (B) TYPE: amino acid
        (D) TOPOLOGY: unknown (ii) MOLECULE TYPE: peptide (xi) SEQUENCE DESCRIPTION: SEQ ID NO:24:

```
Ile Glu Lys Thr Asn Glu Lys Phe His Gln Ile Glu Lys Glu Phe Ser
 1               5              10                          15
Glu Val Glu Gly Arg Ile Gln Asp Leu Glu Lys Tyr
                20              25
```

(2) INFORMATION FOR SEQ ID NO:25:

(i) SEQUENCE CHARACTERISTICS:
        (A) LENGTH: 38 amino acids
        (B) TYPE: amino acid
        (D) TOPOLOGY: unknown (ii) MOLECULE TYPE: peptide (xi) SEQUENCE DESCRIPTION: SEQ ID NO:25:

Asn Asn Leu Leu Arg Ala Ile Glu Ala Gln Gln His Leu Leu Gln Leu
1               5                  10                  15

Thr Val Trp Gly Ile Lys Gln Leu Gln Ala Arg Ile Leu Ala Val Glu
            20                  25                  30

Arg Tyr Leu Lys Asp Gln
            35

(2) INFORMATION FOR SEQ ID NO:26:

(i) SEQUENCE CHARACTERISTICS:
        (A) LENGTH: 338 amino acids
        (B) TYPE: amino acid
        (D) TOPOLOGY: unknown (ii) MOLECULE TYPE: protein (xi) SEQUENCE DESCRIPTION: SEQ ID NO:26:

Phe Leu Gly Phe Leu Gly Ala Ala Gly Ser Thr Met Gly Ala Arg Ser
1               5                  10                  15

Met Thr Leu Thr Val Gln Ala Arg Gln Leu Leu Ser Gly Ile Val Gln
            20                  25                  30

Gln Gln Asn Asn Leu Leu Arg Ala Ile Glu Ala Gln Gln His Leu Leu
        35                  40                  45

Gln Leu Thr Val Trp Gly Ile Lys Gln Leu Gln Ala Arg Ile Leu Ala
    50                  55                  60

Val Glu Arg Tyr Leu Lys Asp Gln Gln Leu Leu Gly Ile Trp Gly Cys
65                  70                  75                  80

Ser Gly Lys Leu Ile Cys Thr Thr Ala Val Pro Trp Asn Ala Ser Trp
                85                  90                  95

Ser Asn Lys Ser Leu Glu Gln Ile Trp Asn Asn Met Thr Trp Met Glu
            100                 105                 110

Trp Asp Arg Glu Ile Asn Asn Tyr Thr Ser Leu Ile His Ser Leu Ile
        115                 120                 125

Glu Glu Ser Gln Asn Gln Gln Glu Lys Asn Glu Gln Glu Leu Leu Glu
    130                 135                 140

Leu Asp Lys Trp Ala Ser Leu Trp Asn Trp Phe Asn Ile Thr Asn Trp
145                 150                 155                 160

Leu Trp Tyr Ile Lys Ile Phe Ile Met Ile Val Gly Gly Leu Val Gly
                165                 170                 175

Leu Arg Ile Val Phe Ala Val Leu Ser Ile Val Asn Arg Val Arg Gln
            180                 185                 190

Gly Tyr Ser Pro Leu Ser Phe Gln Thr His Leu Pro Thr Pro Arg Gly
        195                 200                 205

Pro Asp Arg Pro Glu Gly Ile Glu Glu Glu Gly Gly Glu Arg Asp Arg
    210                 215                 220

Asp Arg Ser Ile Arg Leu Val Asn Gly Ser Leu Ala Leu Ile Trp Asp
225                 230                 235                 240

Asp Leu Arg Ser Leu Cys Leu Phe Ser Tyr His Arg Leu Arg Asp Leu
                245                 250                 255

```
Leu Leu Ile Val Thr Arg Ile Val Glu Leu Leu Gly Arg Arg Gly Trp
            260                 265                 270

Glu Ala Leu Lys Tyr Trp Trp Asn Leu Leu Gln Tyr Trp Ser Gln Glu
        275                 280                 285

Leu Lys Asn Ser Ala Val Ser Leu Leu Asn Ala Thr Ala Ile Ala Val
    290                 295                 300

Ala Glu Gly Thr Asp Arg Val Ile Glu Val Val Gln Gly Ala Cys Arg
305                 310                 315                 320

Ala Ile Arg His Ile Pro Arg Arg Ile Arg Gln Gly Leu Glu Arg Ile
                325                 330                 335

Leu Leu (2) INFORMATION FOR SEQ ID NO:27:

(i) SEQUENCE CHARACTERISTICS:
        (A) LENGTH: 437 amino acids
        (B) TYPE: amino acid
        (D) TOPOLOGY: unknown (ii) MOLECULE TYPE: protein (xi) SEQUENCE DESCRIPTION: SEQ ID NO:27:

Phe Leu Gly Phe Leu Leu Gly Val Gly Ser Ala Ile Ala Ser Gly Val
1               5                   10                  15

Ala Val Ser Lys Val Leu His Leu Glu Gly Glu Val Asn Lys Ile Lys
            20                  25                  30

Ser Ala Leu Leu Ser Thr Asn Lys Ala Val Val Ser Leu Ser Asn Gly
        35                  40                  45

Val Ser Val Leu Thr Ser Lys Val Leu Asp Leu Lys Asn Tyr Ile Asp
    50                  55                  60

Lys Gln Leu Leu Pro Ile Val Asn Lys Gln Ser Cys Ser Ile Ser Asn
65                  70                  75                  80

Ile Glu Thr Val Ile Glu Phe Gln Gln Lys Asn Asn Arg Leu Leu Glu
                85                  90                  95

Ile Thr Arg Glu Phe Ser Val Asn Ala Gly Val Thr Thr Pro Val Ser
            100                 105                 110

Thr Met Leu Thr Asn Ser Glu Leu Leu Ser Leu Ile Asn Asp Met Pro
        115                 120                 125

Ile Thr Asn Asp Gln Lys Lys Leu Met Ser Asn Asn Val Gln Ile Val
    130                 135                 140

Arg Gln Gln Ser Tyr Ser Ile Met Ser Ile Ile Lys Glu Glu Val Leu
145                 150                 155                 160

Ala Tyr Val Val Gln Leu Pro Leu Tyr Gly Val Ile Asp Thr Pro Cys
                165                 170                 175

Trp Lys Leu His Thr Ser Pro Leu Cys Thr Thr Asn Thr Lys Glu Gly
            180                 185                 190

Ser Asn Ile Cys Leu Thr Arg Thr Asp Arg Gly Trp Tyr Cys Asp Asn
        195                 200                 205

Ala Gly Ser Val Ser Phe Phe Pro Gln Ala Glu Thr Cys Lys Val Gln
    210                 215                 220

Ser Asn Arg Val Phe Cys Asp Thr Met Asn Ser Leu Thr Leu Pro Ser
225                 230                 235                 240

Glu Ile Asn Leu Cys Asn Val Asp Ile Phe Asn Pro Lys Tyr Asp Cys
                245                 250                 255

Lys Ile Met Thr Ser Lys Thr Asp Val Ser Ser Ser Val Ile Thr Ser
            260                 265                 270
```

```
Leu Gly Ala Ile Val Ser Cys Tyr Gly Lys Thr Lys Cys Thr Ala Ser
            275                 280                 285

Asn Lys Asn Arg Gly Ile Ile Lys Thr Phe Ser Asn Gly Cys Asp Tyr
        290                 295                 300

Val Ser Asn Lys Gly Met Asp Thr Val Ser Val Gly Asn Thr Leu Tyr
305                 310                 315                 320

Tyr Val Asn Lys Gln Glu Gly Lys Ser Leu Tyr Val Lys Gly Glu Pro
                325                 330                 335

Ile Ile Asn Phe Tyr Asp Pro Leu Val Phe Pro Ser Asp Glu Phe Asp
            340                 345                 350

Ala Ser Ile Ser Gln Val Asn Glu Lys Ile Asn Gln Ser Leu Ala Phe
        355                 360                 365

Ile Arg Lys Ser Asp Glu Leu Leu His Asn Val Asn Ala Gly Lys Ser
370                 375                 380

Thr Thr Asn Ile Met Ile Thr Thr Ile Ile Val Ile Ile Val Ile
385                 390                 395                 400

Leu Leu Ser Leu Ile Ala Val Gly Leu Leu Leu Tyr Cys Lys Ala Arg
                405                 410                 415

Ser Thr Pro Val Thr Leu Ser Lys Asp Gln Leu Ser Gly Ile Asn Asn
            420                 425                 430

Ile Ala Phe Ser Asn
            435

(2) INFORMATION FOR SEQ ID NO:28:

(i) SEQUENCE CHARACTERISTICS:
        (A) LENGTH: 328 amino acids
        (B) TYPE: amino acid
        (D) TOPOLOGY: unknown (ii) MOLECULE TYPE: protein (xi) SEQUENCE DESCRIPTION: SEQ ID NO:28:

Phe Leu Gly Phe Leu Gly Ala Ala Gly Thr Ala Met Gly Ala Ala Ala
1               5                   10                  15

Thr Ala Leu Thr Val Gln Ser Gln His Leu Leu Ala Gly Ile Leu Gln
            20                  25                  30

Gln Gln Lys Asn Leu Leu Ala Ala Val Glu Ala Gln Gln Gln Met Leu
        35                  40                  45

Lys Leu Thr Ile Trp Gly Val Lys Asn Leu Asn Ala Arg Val Thr Ala
50                  55                  60

Leu Glu Lys Tyr Leu Glu Asp Gln Ala Arg Leu Asn Ala Trp Gly Cys
65                  70                  75                  80

Ala Trp Lys Gln Val Cys His Thr Thr Val Pro Trp Gln Trp Asn Asn
                85                  90                  95

Arg Thr Pro Asp Trp Asn Asn Met Thr Trp Leu Glu Trp Glu Arg Gln
            100                 105                 110

Ile Ser Tyr Leu Glu Gly Asn Ile Thr Thr Gln Leu Glu Glu Ala Arg
        115                 120                 125

Ala Gln Glu Glu Lys Asn Leu Asp Ala Tyr Gln Lys Leu Ser Ser Trp
130                 135                 140

Ser Asp Phe Trp Ser Trp Phe Asp Phe Ser Lys Trp Leu Asn Ile Leu
145                 150                 155                 160

Lys Ile Gly Phe Leu Asp Val Leu Gly Ile Ile Gly Leu Arg Leu Leu
                165                 170                 175
```

```
Tyr Thr Val Tyr Ser Cys Ile Ala Arg Val Arg Gln Gly Tyr Ser Pro
            180                 185                 190

Leu Ser Pro Gln Ile His Ile His Pro Trp Lys Gly Gln Pro Asp Asn
        195                 200                 205

Ala Glu Gly Pro Gly Glu Gly Asp Lys Arg Lys Asn Ser Ser Glu
        210                 215                 220

Pro Trp Gln Lys Glu Ser Gly Thr Ala Glu Trp Lys Ser Asn Trp Cys
225                 230                 235                 240

Lys Arg Leu Thr Asn Trp Cys Ser Ile Ser Ile Trp Leu Tyr Asn
                245                 250                 255

Ser Cys Leu Thr Leu Leu Val His Leu Arg Ser Ala Phe Gln Tyr Ile
            260                 265                 270

Gln Tyr Gly Leu Gly Glu Leu Lys Ala Ala Ala Gln Glu Ala Val Val
            275                 280                 285

Ala Leu Ala Arg Leu Ala Gln Asn Ala Gly Tyr Gln Ile Trp Leu Ala
            290                 295                 300

Cys Arg Ser Ala Tyr Arg Ala Ile Ile Asn Ser Pro Arg Arg Val Arg
305                 310                 315                 320

Gln Gly Leu Glu Gly Ile Leu Asn
                325
```

(2) INFORMATION FOR SEQ ID NO:29:

(i) SEQUENCE CHARACTERISTICS:
        (A) LENGTH: 438 amino acids
        (B) TYPE: amino acid
        (D) TOPOLOGY: unknown (ii) MOLECULE TYPE: protein (xi) SEQUENCE DESCRIPTION: SEQ ID NO:29:

```
Phe Ala Gly Val Val Leu Ala Gly Val Ala Leu Gly Val Ala Thr Ala
1               5                   10                  15

Ala Gln Ile Thr Ala Gly Ile Ala Leu His Gln Ser Asn Leu Asn Ala
            20                  25                  30

Gln Ala Ile Gln Ser Leu Arg Thr Ser Leu Glu Gln Ser Asn Lys Ala
            35                  40                  45

Ile Glu Glu Ile Arg Glu Ala Thr Gln Glu Thr Val Ile Ala Val Gln
        50                  55                  60

Gly Val Gln Asp Tyr Val Asn Asn Glu Leu Val Pro Ala Met Gln His
65                  70                  75                  80

Met Ser Cys Glu Leu Val Gly Gln Arg Leu Gly Leu Arg Leu Leu Arg
                85                  90                  95

Tyr Tyr Thr Glu Leu Leu Ser Ile Phe Gly Pro Ser Leu Arg Asp Pro
            100                 105                 110

Ile Ser Ala Glu Ile Ser Ile Gln Ala Leu Ile Tyr Ala Leu Gly Gly
            115                 120                 125

Glu Ile His Lys Ile Leu Glu Lys Leu Gly Tyr Ser Gly Ser Asp Met
        130                 135                 140

Ile Ala Ile Leu Glu Ser Arg Gly Ile Lys Thr Lys Ile Thr His Val
145                 150                 155                 160

Asp Leu Pro Gly Lys Phe Ile Ile Leu Ser Ile Ser Tyr Pro Thr Leu
                165                 170                 175

Ser Glu Val Lys Gly Val Ile Val His Arg Leu Glu Ala Val Ser Tyr
            180                 185                 190

Asn Ile Gly Ser Gln Glu Trp Tyr Thr Thr Val Pro Arg Tyr Ile Ala
```

-continued

```
                195                 200                 205
Thr Asn Gly Tyr Leu Ile Ser Asn Phe Asp Glu Ser Ser Cys Val Phe
        210                 215                 220

Val Ser Glu Ser Ala Ile Cys Ser Gln Asn Ser Leu Tyr Pro Met Ser
225                 230                 235                 240

Pro Leu Leu Gln Gln Cys Ile Arg Gly Asp Thr Ser Ser Cys Ala Arg
                245                 250                 255

Thr Leu Val Ser Gly Thr Met Gly Asn Lys Phe Ile Leu Ser Lys Gly
        260                 265                 270

Asn Ile Val Ala Asn Cys Ala Ser Ile Leu Cys Lys Cys Tyr Ser Thr
            275                 280                 285

Ser Thr Ile Ile Asn Gln Ser Pro Asp Lys Leu Leu Thr Phe Ile Ala
    290                 295                 300

Ser Asp Thr Cys Pro Leu Val Glu Ile Asp Gly Ala Thr Ile Gln Val
305                 310                 315                 320

Gly Gly Arg Gln Tyr Pro Asp Met Val Tyr Glu Gly Lys Val Ala Leu
                325                 330                 335

Gly Pro Ala Ile Ser Leu Asp Arg Leu Asp Val Gly Thr Asn Leu Gly
        340                 345                 350

Asn Ala Leu Lys Lys Leu Asp Asp Ala Lys Val Leu Ile Asp Ser Ser
            355                 360                 365

Asn Gln Ile Leu Glu Thr Val Arg Arg Ser Ser Phe Asn Phe Gly Ser
    370                 375                 380

Leu Leu Ser Val Pro Ile Leu Ser Cys Thr Ala Leu Ala Leu Leu Leu
385                 390                 395                 400

Leu Ile Tyr Cys Cys Lys Arg Arg Tyr Gln Gln Thr Leu Lys Gln His
                405                 410                 415

Thr Lys Val Asp Pro Ala Phe Lys Pro Asp Leu Thr Gly Thr Ser Lys
                420                 425                 430

Ser Tyr Val Arg Ser Leu
        435
```

(2) INFORMATION FOR SEQ ID NO:30:

(i) SEQUENCE CHARACTERISTICS:
        (A) LENGTH: 436 amino acids
        (B) TYPE: amino acid
        (D) TOPOLOGY: unknown (ii) MOLECULE TYPE: protein (xi) SEQUENCE DESCRIPTION: SEQ ID NO:30:

```
Phe Ile Gly Ala Ile Ile Gly Ser Val Ala Leu Gly Val Ala Thr Ala
1               5                   10                  15

Ala Gln Ile Thr Ala Ala Ser Ala Leu Ile Gln Ala Asn Gln Asn Ala
            20                  25                  30

Ala Asn Ile Leu Arg Leu Lys Glu Ser Ile Thr Ala Thr Ile Glu Ala
        35                  40                  45

Val His Glu Val Thr Asp Gly Leu Ser Gln Leu Ala Val Ala Val Gly
    50                  55                  60

Lys Met Gln Gln Phe Val Asn Asp Gln Phe Asn Asn Thr Ala Gln Glu
65                  70                  75                  80

Leu Asp Cys Ile Lys Ile Thr Gln Gln Val Gly Val Glu Leu Asn Leu
                85                  90                  95

Tyr Leu Thr Glu Leu Thr Thr Val Phe Gly Pro Gln Ile Thr Ser Pro
                100                 105                 110
```

```
Ala Leu Thr Gln Leu Thr Ile Gln Ala Leu Tyr Asn Ala Gly Gly Asn
        115                 120                 125

Met Asp Tyr Leu Leu Thr Lys Leu Gly Val Gly Asn Asn Gln Leu Ser
130                 135                 140

Ser Leu Ile Gly Ser Gly Leu Ile Thr Gly Asn Pro Ile Leu Tyr Asp
145                 150                 155                 160

Ser Gln Thr Gln Leu Leu Gly Ile Gln Val Thr Leu Pro Ser Val Gly
                165                 170                 175

Asn Leu Asn Asn Met Arg Ala Thr Tyr Leu Glu Thr Leu Ser Val Ser
            180                 185                 190

Thr Thr Lys Gly Phe Ala Ser Ala Leu Val Pro Lys Val Val Thr Gln
        195                 200                 205

Val Gly Ser Val Ile Glu Glu Leu Asp Thr Ser Tyr Cys Ile Glu Thr
    210                 215                 220

Asp Leu Asp Leu Tyr Cys Thr Arg Ile Val Thr Phe Pro Met Ser Pro
225                 230                 235                 240

Gly Ile Tyr Ser Cys Leu Asn Gly Asn Thr Ser Ala Cys Met Tyr Ser
                245                 250                 255

Lys Thr Glu Gly Ala Leu Thr Thr Pro Tyr Met Thr Leu Lys Gly Ser
            260                 265                 270

Val Ile Ala Asn Cys Lys Met Thr Thr Cys Arg Cys Ala Asp Pro Pro
        275                 280                 285

Gly Ile Ile Ser Gln Asn Tyr Gly Glu Ala Val Ser Leu Ile Asp Arg
    290                 295                 300

His Ser Cys Asn Val Leu Ser Leu Asp Gly Ile Thr Leu Arg Leu Ser
305                 310                 315                 320

Gly Glu Phe Asp Ala Thr Tyr Gln Lys Asn Ile Ser Ile Leu Asp Ser
                325                 330                 335

Gln Val Ile Val Thr Gly Asn Leu Asp Ile Ser Thr Glu Leu Gly Asn
            340                 345                 350

Val Asn Asn Ser Ile Ser Asn Ala Leu Asp Lys Leu Glu Glu Ser Asn
        355                 360                 365

Ser Lys Leu Asp Lys Val Asn Val Lys Leu Thr Ser Thr Ser Ala Leu
370                 375                 380

Ile Thr Tyr Ile Ala Leu Thr Ala Ile Ser Leu Val Cys Gly Ile Leu
385                 390                 395                 400

Ser Leu Val Leu Ala Cys Tyr Leu Met Tyr Lys Gln Lys Ala Gln Gln
                405                 410                 415

Lys Thr Leu Leu Trp Leu Gly Asn Asn Thr Leu Gly Gln Met Arg Ala
            420                 425                 430

Thr Thr Lys Met
        435

(2) INFORMATION FOR SEQ ID NO:31:

(i) SEQUENCE CHARACTERISTICS:
        (A) LENGTH: 430 amino acids
        (B) TYPE: amino acid
        (D) TOPOLOGY: unknown (ii) MOLECULE TYPE: protein (xi) SEQUENCE DESCRIPTION: SEQ ID NO:31:

Phe Phe Gly Gly Val Ile Gly Thr Ile Ala Leu Gly Val Ala Thr Ser
1               5                   10                  15
```

```
Ala Gln Ile Thr Ala Ala Val Ala Leu Val Glu Ala Lys Gln Ala Arg
             20                  25                  30

Ser Asp Ile Glu Lys Leu Lys Glu Ala Ile Arg Asp Thr Asn Lys Ala
             35                  40                  45

Val Gln Ser Val Gln Ser Ser Ile Gly Asn Leu Ile Val Ala Ile Lys
 50                  55                  60

Ser Val Gln Asp Tyr Val Asn Lys Glu Ile Val Pro Ser Ile Ala Arg
 65                  70                  75                  80

Leu Gly Cys Glu Ala Ala Gly Leu Gln Leu Gly Ile Ala Leu Thr Gln
             85                  90                  95

His Tyr Ser Glu Leu Thr Asn Ile Phe Gly Asp Asn Ile Gly Ser Leu
            100                 105                 110

Gln Glu Lys Gly Ile Lys Leu Gln Gly Ile Ala Ser Leu Tyr Arg Thr
            115                 120                 125

Asn Ile Thr Glu Ile Phe Thr Thr Ser Thr Val Asp Lys Tyr Asp Ile
            130                 135                 140

Tyr Asp Leu Leu Phe Thr Glu Ser Ile Lys Val Arg Val Ile Asp Val
145                 150                 155                 160

Asp Leu Asn Asp Tyr Ser Ile Thr Leu Gln Val Arg Leu Pro Leu Leu
            165                 170                 175

Thr Arg Leu Leu Asn Thr Gln Ile Tyr Arg Val Asp Ser Ile Ser Tyr
            180                 185                 190

Asn Ile Gln Asn Arg Glu Trp Tyr Ile Pro Leu Pro Ser His Ile Met
            195                 200                 205

Thr Lys Gly Ala Phe Leu Gly Gly Ala Asp Val Lys Glu Cys Ile Glu
            210                 215                 220

Ala Phe Ser Ser Tyr Ile Cys Pro Ser Asp Pro Gly Phe Val Leu Asn
225                 230                 235                 240

His Glu Met Glu Ser Cys Leu Ser Gly Asn Ile Ser Gln Cys Pro Arg
            245                 250                 255

Thr Val Val Lys Ser Asp Ile Val Pro Arg Tyr Ala Phe Val Asn Gly
            260                 265                 270

Gly Val Val Ala Asn Cys Ile Thr Thr Thr Cys Thr Cys Asn Gly Ile
            275                 280                 285

Gly Asn Arg Ile Asn Gln Pro Pro Asp Gln Gly Val Lys Ile Ile Thr
            290                 295                 300

His Lys Glu Cys Asn Thr Ile Gly Ile Asn Gly Met Leu Phe Asn Thr
305                 310                 315                 320

Asn Lys Glu Gly Thr Leu Ala Phe Tyr Thr Pro Asn Asp Ile Thr Leu
            325                 330                 335

Asn Asn Ser Val Ala Leu Asp Pro Ile Asp Ile Ser Ile Glu Leu Asn
            340                 345                 350

Lys Ala Lys Ser Asp Leu Glu Glu Ser Lys Glu Trp Ile Arg Arg Ser
            355                 360                 365

Asn Gln Lys Leu Asp Ser Ile Gly Asn Trp His Gln Ser Ser Thr Thr
            370                 375                 380

Ile Ile Ile Val Leu Ile Met Ile Ile Ile Leu Phe Ile Ile Asn Val
385                 390                 395                 400

Thr Ile Ile Ile Ile Ala Val Lys Tyr Tyr Arg Ile Gln Lys Arg Asn
            405                 410                 415

Arg Val Asp Gln Asn Asp Lys Pro Tyr Val Leu Thr Asn Lys
            420                 425                 430
```

(2) INFORMATION FOR SEQ ID NO:32:

(i) SEQUENCE CHARACTERISTICS:
        (A) LENGTH: 221 amino acids
        (B) TYPE: amino acid
        (D) TOPOLOGY: unknown (ii) MOLECULE TYPE: protein (xi) SEQUENCE DESCRIPTION: SEQ ID NO:32:

```
Gly Leu Phe Gly Ala Ile Ala Gly Phe Ile Glu Asn Gly Trp Glu Gly
 1               5                  10                  15
Met Ile Asp Gly Trp Tyr Gly Phe Arg His Gln Asn Ser Glu Gly Thr
                20                  25                  30
Gly Gln Ala Ala Asp Leu Lys Ser Thr Gln Ala Ala Ile Asp Gln Ile
            35                  40                  45
Asn Gly Lys Leu Asn Arg Val Ile Glu Lys Thr Asn Glu Lys Phe His
        50                  55                  60
Gln Ile Glu Lys Glu Phe Ser Glu Val Glu Gly Arg Ile Gln Asp Leu
 65                 70                  75                  80
Glu Lys Tyr Val Glu Asp Thr Lys Ile Asp Leu Trp Ser Tyr Asn Ala
                85                  90                  95
Glu Leu Leu Val Ala Leu Glu Asn Gln His Thr Ile Asp Leu Thr Asp
            100                 105                 110
Ser Glu Met Asn Lys Leu Phe Glu Lys Thr Arg Arg Gln Leu Arg Glu
        115                 120                 125
Asn Ala Glu Glu Met Gly Asn Gly Cys Phe Lys Ile Tyr His Lys Cys
130                 135                 140
Asp Asn Ala Cys Ile Glu Ser Ile Arg Asn Gly Thr Tyr Asp His Asp
145                 150                 155                 160
Val Tyr Arg Asp Glu Ala Leu Asn Asn Arg Phe Gln Ile Lys Gly Val
                165                 170                 175
Glu Leu Lys Ser Gly Tyr Lys Asp Trp Ile Leu Trp Ile Ser Phe Ala
            180                 185                 190
Ile Ser Cys Phe Leu Leu Cys Val Val Leu Leu Gly Phe Ile Met Trp
        195                 200                 205
Ala Cys Gln Arg Gly Asn Ile Arg Cys Asn Ile Cys Ile
210                 215                 220
```

(2) INFORMATION FOR SEQ ID NO:33:

(i) SEQUENCE CHARACTERISTICS:
        (A) LENGTH: 48 amino acids
        (B) TYPE: amino acid
        (D) TOPOLOGY: unknown (ii) MOLECULE TYPE: peptide (xi) SEQUENCE DESCRIPTION: SEQ ID NO:33:

```
Tyr Thr Ser Val Ile Thr Ile Glu Leu Ser Asn Ile Lys Glu Asn Lys
 1               5                  10                  15
Cys Asn Gly Thr Asp Ala Lys Val Lys Leu Ile Lys Gln Glu Leu Asp
                20                  25                  30
Lys Tyr Lys Asn Ala Val Thr Glu Leu Gln Leu Leu Met Gln Ser Thr
            35                  40                  45
```

(2) INFORMATION FOR SEQ ID NO:34:

(i) SEQUENCE CHARACTERISTICS:
        (A) LENGTH: 53 amino acids (B) TYPE: amino acid
        (D) TOPOLOGY: unknown (ii) MOLECULE TYPE: peptide (xi) SEQUENCE DESCRIPTION: SEQ ID NO:34:

Gly Glu Pro Ile Ile Asn Phe Tyr Asp Pro Leu Val Phe Pro Ser Asp
1               5                  10                  15

Glu Phe Asp Ala Ser Ile Ser Gln Val Asn Glu Lys Ile Asn Gln Ser
            20                  25                  30

Leu Ala Phe Ile Arg Lys Ser Asp Glu Leu Leu His Asn Val Asn Ala
        35                  40                  45

Gly Lys Ser Thr Thr
    50

(2) INFORMATION FOR SEQ ID NO:35:

(i) SEQUENCE CHARACTERISTICS:
        (A) LENGTH: 56 amino acids
        (B) TYPE: amino acid
        (D) TOPOLOGY: unknown (ii) MOLECULE TYPE: peptide (xi) SEQUENCE DESCRIPTION: SEQ ID NO:35:

Tyr Thr Pro Asn Asp Ile Thr Leu Asn Asn Ser Val Ala Leu Asp Pro
1               5                  10                  15

Ile Asp Ile Ser Ile Glu Leu Asn Lys Ala Lys Ser Asp Leu Glu Glu
            20                  25                  30

Ser Lys Glu Trp Ile Arg Arg Ser Asn Gln Lys Leu Asp Ser Ile Gly
        35                  40                  45

Asn Trp His Gln Ser Ser Thr Thr
    50              55

(2) INFORMATION FOR SEQ ID NO:36:

(i) SEQUENCE CHARACTERISTICS:
        (A) LENGTH: 70 amino acids
        (B) TYPE: amino acid
        (D) TOPOLOGY: unknown (ii) MOLECULE TYPE: peptide (xi) SEQUENCE DESCRIPTION: SEQ ID NO:36:

Gly Thr Ile Ala Leu Gly Val Ala Thr Ser Ala Gln Ile Thr Ala Ala
1               5                  10                  15

Val Ala Leu Val Glu Ala Lys Gln Ala Arg Ser Asp Ile Glu Lys Leu
            20                  25                  30

Lys Glu Ala Ile Arg Asp Thr Asn Lys Ala Val Gln Ser Val Gln Ser
        35                  40                  45

Ser Ile Gly Asn Leu Ile Val Ala Ile Lys Ser Val Gln Asp Tyr Val
    50                  55                  60

Asn Lys Glu Ile Val Pro
65              70

(2) INFORMATION FOR SEQ ID NO:37:

(i) SEQUENCE CHARACTERISTICS:
        (A) LENGTH: 4 amino acids
        (B) TYPE: amino acid
        (C) STRANDEDNESS:
        (D) TOPOLOGY: unknown

```
        (ii) MOLECULE TYPE: peptide (ix) FEATURE:
             (A) NAME/KEY: Modified-site
             (B) LOCATION: 1
             (D) OTHER INFORMATION: /label= A
                 /note= "Preceeding this amino acid, there may be an
                 amino group, an acetyl group, a 9-fluorenylmethoxy-
                 carbonyl group, a hydrophobic group or a macromolecular
                 carrier group."

(ix) FEATURE:
             (A) NAME/KEY: Modified-site
             (B) LOCATION: 4
             (D) OTHER INFORMATION: /label= B
                 /note= "Following this amino acid, there may be a
                 carboxyl group, an amido group, a hydrophobic group,
                 or a macromolecular carrier group."

(xi) SEQUENCE DESCRIPTION: SEQ ID NO:37:

Phe Tyr Asp Pro
 1

(2) INFORMATION FOR SEQ ID NO:38:

(i) SEQUENCE CHARACTERISTICS:
            (A) LENGTH: 5 amino acids
            (B) TYPE: amino acid
            (C) STRANDEDNESS:
            (D) TOPOLOGY: unknown (ii) MOLECULE TYPE: peptide (ix) FEATURE:
             (A) NAME/KEY: Modified-site
             (B) LOCATION: 1
             (D) OTHER INFORMATION: /label= A
                 /note= "Preceeding this amino acid, there may be an
                 amino group, an acetyl group, a 9-fluorenylmethoxy-
                 carbonyl group, a hydrophobic group or a macromolecular
                 carrier group."

(ix) FEATURE:
             (A) NAME/KEY: Modified-site
             (B) LOCATION: 5
             (D) OTHER INFORMATION: /label= B
                 /note= "Following this amino acid, there may be a
                 carboxyl group, an amido group, a hydrophobic group,
                 or a macromolecular carrier group."

(xi) SEQUENCE DESCRIPTION: SEQ ID NO:38:

Phe Tyr Asp Pro Leu
 1               5

(2) INFORMATION FOR SEQ ID NO:39:

(i) SEQUENCE CHARACTERISTICS:
            (A) LENGTH: 6 amino acids
            (B) TYPE: amino acid
            (C) STRANDEDNESS:
            (D) TOPOLOGY: unknown (ii) MOLECULE TYPE: peptide (ix) FEATURE:
             (A) NAME/KEY: Modified-site
             (B) LOCATION: 1
             (D) OTHER INFORMATION: /label= A
                 /note= "Preceeding this amino acid, there may be an
                 amino group, an acetyl group, a 9-fluorenylmethoxy-
                 carbonyl group, a hydrophobic group or a macromolecular
                 carrier group."

(ix) FEATURE:
             (A) NAME/KEY: Modified-site
```

(B) LOCATION: 6
            (D) OTHER INFORMATION: /label= B
                /note= "Following this amino acid, there may be a
                carboxyl group, an amido group, a hydrophobic group,
                or a macromolecular carrier group."

(xi) SEQUENCE DESCRIPTION: SEQ ID NO:39:

Phe Tyr Asp Pro Leu Val
 1               5

(2) INFORMATION FOR SEQ ID NO:40:

(i) SEQUENCE CHARACTERISTICS:
        (A) LENGTH: 7 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 7
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:40:

Phe Tyr Asp Pro Leu Val Phe
 1               5

(2) INFORMATION FOR SEQ ID NO:41:

(i) SEQUENCE CHARACTERISTICS:
        (A) LENGTH: 8 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 8
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:41:

Phe Tyr Asp Pro Leu Val Phe Pro
 1               5

(2) INFORMATION FOR SEQ ID NO:42:

(i) SEQUENCE CHARACTERISTICS:
            (A) LENGTH: 9 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= A
                /note= "Preceeding this amino acid, there may be an
                amino group, an acetyl group, a 9-fluorenylmethoxy-
                carbonyl group, a hydrophobic group or a macromolecular
                carrier group."

(ix) FEATURE:
            (A) NAME/KEY: Modified-site
            (B) LOCATION: 9
            (D) OTHER INFORMATION: /label= B
                /note= "Following this amino acid, there may be a
                carboxyl group, an amido group, a hydrophobic group,
                or a macromolecular carrier group."

(xi) SEQUENCE DESCRIPTION: SEQ ID NO:42:

Phe Tyr Asp Pro Leu Val Phe Pro Ser
 1               5

(2) INFORMATION FOR SEQ ID NO:43:

(i) SEQUENCE CHARACTERISTICS:
            (A) LENGTH: 10 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= A
                /note= "Preceeding this amino acid, there may be an
                amino group, an acetyl group, a 9-fluorenylmethoxy-
                carbonyl group, a hydrophobic group or a macromolecular
                carrier group."

(ix) FEATURE:
            (A) NAME/KEY: Modified-site
            (B) LOCATION: 10
            (D) OTHER INFORMATION: /label= B
                /note= "Following this amino acid, there may be a
                carboxyl group, an amido group, a hydrophobic group,
                or a macromolecular carrier group."

(xi) SEQUENCE DESCRIPTION: SEQ ID NO:43:

Phe Tyr Asp Pro Leu Val Phe Pro Ser Asp
 1               5                  10

(2) INFORMATION FOR SEQ ID NO:44:

(i) SEQUENCE CHARACTERISTICS:
            (A) LENGTH: 11 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= A

```
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 11
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:44:

Phe Tyr Asp Pro Leu Val Phe Pro Ser Asp Glu
 1               5                  10

(2) INFORMATION FOR SEQ ID NO:45:

(i) SEQUENCE CHARACTERISTICS:
        (A) LENGTH: 12 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 12
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:45:

Phe Tyr Asp Pro Leu Val Phe Pro Ser Asp Glu Phe
 1               5                  10

(2) INFORMATION FOR SEQ ID NO:46:

(i) SEQUENCE CHARACTERISTICS:
        (A) LENGTH: 13 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 13
        (D) OTHER INFORMATION: /label= B
            /note= "Following this amino acid, there may be a
            carboxyl group, an amido group, a hydrophobic group,
            or a macromolecular carrier group."
```

(xi) SEQUENCE DESCRIPTION: SEQ ID NO:46:

Phe Tyr Asp Pro Leu Val Phe Pro Ser Asp Glu Phe Asp
1               5                   10

(2) INFORMATION FOR SEQ ID NO:47:

(i) SEQUENCE CHARACTERISTICS:
        (A) LENGTH: 14 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 14
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:47:

Phe Tyr Asp Pro Leu Val Phe Pro Ser Asp Glu Phe Asp Ala
1               5                   10

(2) INFORMATION FOR SEQ ID NO:48:

(i) SEQUENCE CHARACTERISTICS:
        (A) LENGTH: 15 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 15
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:48:

Phe Tyr Asp Pro Leu Val Phe Pro Ser Asp Glu Phe Asp Ala Ser
1               5                   10                  15

(2) INFORMATION FOR SEQ ID NO:49:

(i) SEQUENCE CHARACTERISTICS:
        (A) LENGTH: 16 amino acids
        (B) TYPE: amino acid
        (C) STRANDEDNESS:
        (D) TOPOLOGY: unknown

```
       (ii) MOLECULE TYPE: peptide (ix) FEATURE:
            (A) NAME/KEY: Modified-site
            (B) LOCATION: 1
            (D) OTHER INFORMATION: /label= A
                /note= "Preceeding this amino acid, there may be an
                amino group, an acetyl group, a 9-fluorenylmethoxy-
                carbonyl group, a hydrophobic group or a macromolecular
                carrier group."

(ix) FEATURE:
            (A) NAME/KEY: Modified-site
            (B) LOCATION: 16
            (D) OTHER INFORMATION: /label= B
                /note= "Following this amino acid, there may be a
                carboxyl group, an amido group, a hydrophobic group,
                or a macromolecular carrier group."

(xi) SEQUENCE DESCRIPTION: SEQ ID NO:49:

Phe Tyr Asp Pro Leu Val Phe Pro Ser Asp Glu Phe Asp Ala Ser Ile
  1               5                  10                  15

(2) INFORMATION FOR SEQ ID NO:50:

(i) SEQUENCE CHARACTERISTICS:
            (A) LENGTH: 17 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= A
                /note= "Preceeding this amino acid, there may be an
                amino group, an acetyl group, a 9-fluorenylmethoxy-
                carbonyl group, a hydrophobic group or a macromolecular
                carrier group."

(ix) FEATURE:
            (A) NAME/KEY: Modified-site
            (B) LOCATION: 17
            (D) OTHER INFORMATION: /label= B
                /note= "Following this amino acid, there may be a
                carboxyl group, an amido group, a hydrophobic group,
                or a macromolecular carrier group."

(xi) SEQUENCE DESCRIPTION: SEQ ID NO:50:

Phe Tyr Asp Pro Leu Val Phe Pro Ser Asp Glu Phe Asp Ala Ser Ile
  1               5                  10                  15
Ser (2) INFORMATION FOR SEQ ID NO:51:

(i) SEQUENCE CHARACTERISTICS:
            (A) LENGTH: 18 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= A
                /note= "Preceeding this amino acid, there may be an
                amino group, an acetyl group, a 9-fluorenylmethoxy-
                carbonyl group, a hydrophobic group or a macromolecular
                carrier group."
```

```
    (ix) FEATURE:
         (A) NAME/KEY: Modified-site
         (B) LOCATION: 18
         (D) OTHER INFORMATION: /label= B
             /note= "Following this amino acid, there may be a
             carboxyl group, an amido group, a hydrophobic group,
             or a macromolecular carrier group."

(xi) SEQUENCE DESCRIPTION: SEQ ID NO:51:

Phe Tyr Asp Pro Leu Val Phe Pro Ser Asp Glu Phe Asp Ala Ser Ile
1               5                   10                  15

Ser Gln (2) INFORMATION FOR SEQ ID NO:52:

(i) SEQUENCE CHARACTERISTICS:
        (A) LENGTH: 19 amino acids
        (B) TYPE: amino acid
        (C) STRANDEDNESS:
        (D) TOPOLOGY: unknown (ii) MOLECULE TYPE: peptide (ix) FEATURE:
         (A) NAME/KEY: Modified-site
         (B) LOCATION: 1
         (D) OTHER INFORMATION: /label= A
             /note= "Preceeding this amino acid, there may be an
             amino group, an acetyl group, a 9-fluorenylmethoxy-
             carbonyl group, a hydrophobic group or a macromolecular
             carrier group."

(ix) FEATURE:
         (A) NAME/KEY: Modified-site
         (B) LOCATION: 19
         (D) OTHER INFORMATION: /label= B
             /note= "Following this amino acid, there may be a
             carboxyl group, an amido group, a hydrophobic group,
             or a macromolecular carrier group."

(xi) SEQUENCE DESCRIPTION: SEQ ID NO:52:

Phe Tyr Asp Pro Leu Val Phe Pro Ser Asp Glu Phe Asp Ala Ser Ile
1               5                   10                  15

Ser Gln Val (2) INFORMATION FOR SEQ ID NO:53:

(i) SEQUENCE CHARACTERISTICS:
        (A) LENGTH: 20 amino acids
        (B) TYPE: amino acid
        (C) STRANDEDNESS:
        (D) TOPOLOGY: unknown (ii) MOLECULE TYPE: peptide (ix) FEATURE:
         (A) NAME/KEY: Modified-site
         (B) LOCATION: 1
         (D) OTHER INFORMATION: /label= A
             /note= "Preceeding this amino acid, there may be an
             amino group, an acetyl group, a 9-fluorenylmethoxy-
             carbonyl group, a hydrophobic group or a macromolecular
             carrier group."

(ix) FEATURE:
         (A) NAME/KEY: Modified-site
         (B) LOCATION: 20
         (D) OTHER INFORMATION: /label= B
             /note= "Following this amino acid, there may be a
             carboxyl group, an amido group, a hydrophobic group,
             or a macromolecular carrier group."
```

(xi) SEQUENCE DESCRIPTION: SEQ ID NO:53:

Phe Tyr Asp Pro Leu Val Phe Pro Ser Asp Glu Phe Asp Ala Ser Ile
 1               5                  10                  15

Ser Gln Val Asn
            20

(2) INFORMATION FOR SEQ ID NO:54:

(i) SEQUENCE CHARACTERISTICS:
        (A) LENGTH: 21 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 21
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:54:

Phe Tyr Asp Pro Leu Val Phe Pro Ser Asp Glu Phe Asp Ala Ser Ile
 1               5                  10                  15

Ser Gln Val Asn Glu
            20

(2) INFORMATION FOR SEQ ID NO:55:

(i) SEQUENCE CHARACTERISTICS:
        (A) LENGTH: 22 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 22
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:55:

Phe Tyr Asp Pro Leu Val Phe Pro Ser Asp Glu Phe Asp Ala Ser Ile
 1               5                  10                  15

Ser Gln Val Asn Glu Lys
            20

(2) INFORMATION FOR SEQ ID NO:56:

(i) SEQUENCE CHARACTERISTICS:
        (A) LENGTH: 23 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 23
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:56:

```
Phe Tyr Asp Pro Leu Val Phe Pro Ser Asp Glu Phe Asp Ala Ser Ile
 1               5                  10                  15
Ser Gln Val Asn Glu Lys Ile
            20
```

(2) INFORMATION FOR SEQ ID NO:57:

(i) SEQUENCE CHARACTERISTICS:
        (A) LENGTH: 24 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 24
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:57:

```
Phe Tyr Asp Pro Leu Val Phe Pro Ser Asp Glu Phe Asp Ala Ser Ile
 1               5                  10                  15
Ser Gln Val Asn Glu Lys Ile Asn
            20
```

(2) INFORMATION FOR SEQ ID NO:58:

(i) SEQUENCE CHARACTERISTICS:
        (A) LENGTH: 25 amino acids
        (B) TYPE: amino acid (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= A
                /note= "Preceeding this amino acid, there may be an
                amino group, an acetyl group, a 9-fluorenylmethoxy-
                carbonyl group, a hydrophobic group or a macromolecular
                carrier group."

(ix) FEATURE:
            (A) NAME/KEY: Modified-site
            (B) LOCATION: 25
            (D) OTHER INFORMATION: /label= B
                /note= "Following this amino acid, there may be a
                carboxyl group, an amido group, a hydrophobic group,
                or a macromolecular carrier group."

(xi) SEQUENCE DESCRIPTION: SEQ ID NO:58:

Phe Tyr Asp Pro Leu Val Phe Pro Ser Asp Glu Phe Asp Ala Ser Ile
1               5                   10                  15

Ser Gln Val Asn Glu Lys Ile Asn Gln
            20                  25

(2) INFORMATION FOR SEQ ID NO:59:

(i) SEQUENCE CHARACTERISTICS:
            (A) LENGTH: 26 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= A
                /note= "Preceeding this amino acid, there may be an
                amino group, an acetyl group, a 9-fluorenylmethoxy-
                carbonyl group, a hydrophobic group or a macromolecular
                carrier group."

(ix) FEATURE:
            (A) NAME/KEY: Modified-site
            (B) LOCATION: 26
            (D) OTHER INFORMATION: /label= B
                /note= "Following this amino acid, there may be a
                carboxyl group, an amido group, a hydrophobic group,
                or a macromolecular carrier group."

(xi) SEQUENCE DESCRIPTION: SEQ ID NO:59:

Phe Tyr Asp Pro Leu Val Phe Pro Ser Asp Glu Phe Asp Ala Ser Ile
1               5                   10                  15

Ser Gln Val Asn Glu Lys Ile Asn Gln Ser
            20                  25

(2) INFORMATION FOR SEQ ID NO:60:

(i) SEQUENCE CHARACTERISTICS:
            (A) LENGTH: 27 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site

```
            (B) LOCATION: 1
            (D) OTHER INFORMATION: /label= A
                /note= "Preceeding this amino acid, there may be an
                amino group, an acetyl group, a 9-fluorenylmethoxy-
                carbonyl group, a hydrophobic group or a macromolecular
                carrier group."

(ix) FEATURE:
            (A) NAME/KEY: Modified-site
            (B) LOCATION: 27
            (D) OTHER INFORMATION: /label= B
                /note= "Following this amino acid, there may be a
                carboxyl group, an amido group, a hydrophobic group,
                or a macromolecular carrier group."

(xi) SEQUENCE DESCRIPTION: SEQ ID NO:60:

Phe Tyr Asp Pro Leu Val Phe Pro Ser Asp Glu Phe Asp Ala Ser Ile
 1               5                  10                  15

Ser Gln Val Asn Glu Lys Ile Asn Gln Ser Leu
            20                  25

(2) INFORMATION FOR SEQ ID NO:61:

(i) SEQUENCE CHARACTERISTICS:
            (A) LENGTH: 28 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= A
                /note= "Preceeding this amino acid, there may be an
                amino group, an acetyl group, a 9-fluorenylmethoxy-
                carbonyl group, a hydrophobic group or a macromolecular
                carrier group."

(ix) FEATURE:
            (A) NAME/KEY: Modified-site
            (B) LOCATION: 28
            (D) OTHER INFORMATION: /label= B
                /note= "Following this amino acid, there may be a
                carboxyl group, an amido group, a hydrophobic group,
                or a macromolecular carrier group."

(xi) SEQUENCE DESCRIPTION: SEQ ID NO:61:

Phe Tyr Asp Pro Leu Val Phe Pro Ser Asp Glu Phe Asp Ala Ser Ile
 1               5                  10                  15

Ser Gln Val Asn Glu Lys Ile Asn Gln Ser Leu Ala
            20                  25

(2) INFORMATION FOR SEQ ID NO:62:

(i) SEQUENCE CHARACTERISTICS:
            (A) LENGTH: 29 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= A
                /note= "Preceeding this amino acid, there may be an
                amino group, an acetyl group, a 9-fluorenylmethoxy-
                carbonyl group, a hydrophobic group or a macromolecular
                carrier group."
```

```
    (ix) FEATURE:
         (A) NAME/KEY: Modified-site
         (B) LOCATION: 29
         (D) OTHER INFORMATION: /label= B
             /note= "Following this amino acid, there may be a
             carboxyl group, an amido group, a hydrophobic group,
             or a macromolecular carrier group."

(xi) SEQUENCE DESCRIPTION: SEQ ID NO:62:

Phe Tyr Asp Pro Leu Val Phe Pro Ser Asp Glu Phe Asp Ala Ser Ile
 1               5                  10                  15

Ser Gln Val Asn Glu Lys Ile Asn Gln Ser Leu Ala Phe
             20                  25

(2) INFORMATION FOR SEQ ID NO:63:

(i) SEQUENCE CHARACTERISTICS:
         (A) LENGTH: 30 amino acids
         (B) TYPE: amino acid
         (C) STRANDEDNESS:
         (D) TOPOLOGY: unknown (ii) MOLECULE TYPE: peptide (ix) FEATURE:
         (A) NAME/KEY: Modified-site
         (B) LOCATION: 1
         (D) OTHER INFORMATION: /label= A
             /note= "Preceeding this amino acid, there may be an
             amino group, an acetyl group, a 9-fluorenylmethoxy-
             carbonyl group, a hydrophobic group or a macromolecular
             carrier group."

(ix) FEATURE:
         (A) NAME/KEY: Modified-site
         (B) LOCATION: 30
         (D) OTHER INFORMATION: /label= B
             /note= "Following this amino acid, there may be a
             carboxyl group, an amido group, a hydrophobic group,
             or a macromolecular carrier group."

(xi) SEQUENCE DESCRIPTION: SEQ ID NO:63:

Phe Tyr Asp Pro Leu Val Phe Pro Ser Asp Glu Phe Asp Ala Ser Ile
 1               5                  10                  15

Ser Gln Val Asn Glu Lys Ile Asn Gln Ser Leu Ala Phe Ile
             20                  25                  30

(2) INFORMATION FOR SEQ ID NO:64:

(i) SEQUENCE CHARACTERISTICS:
         (A) LENGTH: 31 amino acids
         (B) TYPE: amino acid
         (C) STRANDEDNESS:
         (D) TOPOLOGY: unknown (ii) MOLECULE TYPE: peptide (ix) FEATURE:
         (A) NAME/KEY: Modified-site
         (B) LOCATION: 1
         (D) OTHER INFORMATION: /label= A
             /note= "Preceeding this amino acid, there may be an
             amino group, an acetyl group, a 9-fluorenylmethoxy-
             carbonyl group, a hydrophobic group or a macromolecular
             carrier group."

(ix) FEATURE:
         (A) NAME/KEY: Modified-site
         (B) LOCATION: 31
         (D) OTHER INFORMATION: /label= B
             /note= "Following this amino acid, there may be a
             carboxyl group, an amido group, a hydrophobic group,
             or a macromolecular carrier group."
```

(xi) SEQUENCE DESCRIPTION: SEQ ID NO:64:

Phe Tyr Asp Pro Leu Val Phe Pro Ser Asp Glu Phe Asp Ala Ser Ile
1               5                   10                  15

Ser Gln Val Asn Glu Lys Ile Asn Gln Ser Leu Ala Phe Ile Arg
            20                  25                  30

(2) INFORMATION FOR SEQ ID NO:65:

(i) SEQUENCE CHARACTERISTICS:
        (A) LENGTH: 32 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic
            group or a macromolecular carrier group."

(ix) FEATURE:
        (A) NAME/KEY: Modified-site
        (B) LOCATION: 32
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:65:

Phe Tyr Asp Pro Leu Val Phe Pro Ser Asp Glu Phe Asp Ala Ser Ile
1               5                   10                  15

Ser Gln Val Asn Glu Lys Ile Asn Gln Ser Leu Ala Phe Ile Arg Lys
            20                  25                  30

(2) INFORMATION FOR SEQ ID NO:66:

(i) SEQUENCE CHARACTERISTICS:
        (A) LENGTH: 33 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 33
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:66:

Phe Tyr Asp Pro Leu Val Phe Pro Ser Asp Glu Phe Asp Ala Ser Ile
1               5                   10                  15

Ser Gln Val Asn Glu Lys Ile Asn Gln Ser Leu Ala Phe Ile Arg Lys

```
              20                  25                  30
Ser
```

(2) INFORMATION FOR SEQ ID NO:67:

(i) SEQUENCE CHARACTERISTICS:
        (A) LENGTH: 34 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 34
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:67:

```
Phe Tyr Asp Pro Leu Val Phe Pro Ser Asp Glu Phe Asp Ala Ser Ile
1               5                   10                  15
Ser Gln Val Asn Glu Lys Ile Asn Gln Ser Leu Ala Phe Ile Arg Lys
            20                  25                  30
Ser Asp
```

(2) INFORMATION FOR SEQ ID NO:68:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 35
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:68:

```
Phe Tyr Asp Pro Leu Val Phe Pro Ser Asp Glu Phe Asp Ala Ser Ile
1               5                   10                  15
Ser Gln Val Asn Glu Lys Ile Asn Gln Ser Leu Ala Phe Ile Arg Lys
            20                  25                  30
Ser Asp Glu
```

35

(2) INFORMATION FOR SEQ ID NO:69:

(i) SEQUENCE CHARACTERISTICS:
        (A) LENGTH: 36 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 36
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:69:

```
Phe Tyr Asp Pro Leu Val Phe Pro Ser Asp Glu Phe Asp Ala Ser Ile
 1               5                  10                  15

Ser Gln Val Asn Glu Lys Ile Asn Gln Ser Leu Ala Phe Ile Arg Lys
            20                  25                  30

Ser Asp Glu Leu
            35
```

(2) INFORMATION FOR SEQ ID NO:70:

(i) SEQUENCE CHARACTERISTICS:
        (A) LENGTH: 4 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 4
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:70:

```
Asp Glu Leu Leu
 1
```

(2) INFORMATION FOR SEQ ID NO:71:

(i) SEQUENCE CHARACTERISTICS:
        (A) LENGTH: 5 amino acids

```
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= A
                /note= "Preceeding this amino acid, there may be an
                amino group, an acetyl group, a 9-fluorenylmethoxy-
                carbonyl group, a hydrophobic group or a macromolecular
                carrier group."

(ix) FEATURE:
            (A) NAME/KEY: Modified-site
            (B) LOCATION: 5
            (D) OTHER INFORMATION: /label= B
                /note= "Following this amino acid, there may be a
                carboxyl group, an amido group, a hydrophobic group,
                or a macromolecular carrier group."

(xi) SEQUENCE DESCRIPTION: SEQ ID NO:71:

Ser Asp Glu Leu Leu
1               5

(2) INFORMATION FOR SEQ ID NO:72:

(i) SEQUENCE CHARACTERISTICS:
            (A) LENGTH: 6 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= A
                /note= "Preceeding this amino acid, there may be an
                amino group, an acetyl group, a 9-fluorenylmethoxy-
                carbonyl group, a hydrophobic group or a macromolecular
                carrier group."

(ix) FEATURE:
            (A) NAME/KEY: Modified-site
            (B) LOCATION: 6
            (D) OTHER INFORMATION: /label= B
                /note= "Following this amino acid, there may be a
                carboxyl group, an amido group, a hydrophobic group,
                or a macromolecular carrier group."

(xi) SEQUENCE DESCRIPTION: SEQ ID NO:72:

Lys Ser Asp Glu Leu Leu
1               5

(2) INFORMATION FOR SEQ ID NO:73:

(i) SEQUENCE CHARACTERISTICS:
            (A) LENGTH: 7 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= A
                /note= "Preceeding this amino acid, there may be an
                amino group, an acetyl group, a 9-fluorenylmethoxy-
                carbonyl group, a hydrophobic group or a macromolecular
```

```
            carrier group."

(ix) FEATURE:
        (A) NAME/KEY: Modified-site
        (B) LOCATION: 7
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:73:

Arg Lys Ser Asp Glu Leu Leu
 1               5

(2) INFORMATION FOR SEQ ID NO:74:

(i) SEQUENCE CHARACTERISTICS:
        (A) LENGTH: 8 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 8
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:74:

Ile Arg Lys Ser Asp Glu Leu Leu
 1               5

(2) INFORMATION FOR SEQ ID NO:75:

(i) SEQUENCE CHARACTERISTICS:
        (A) LENGTH: 9 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 9
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:75:

Phe Ile Arg Lys Ser Asp Glu Leu Leu
```

(2) INFORMATION FOR SEQ ID NO:76:

(i) SEQUENCE CHARACTERISTICS:
       (A) LENGTH: 10 amino acids
       (B) TYPE: amino acid
       (C) STRANDEDNESS:
       (D) TOPOLOGY: unknown (ii) MOLECULE TYPE: peptide (ix) FEATURE:
       (A) NAME/KEY: Modified-site
       (B) LOCATION: 1
       (D) OTHER INFORMATION: /label= A
           /note= "Preceeding this amino acid, there may be an
           amino group, an acetyl group, a 9-fluorenylmethoxy-
           carbonyl group, a hydrophobic group or a macromolecular
           carrier group."

(ix) FEATURE:
       (A) NAME/KEY: Modified-site
       (B) LOCATION: 10
       (D) OTHER INFORMATION: /label= B
           /note= "Following this amino acid, there may be a
           carboxyl group, an amido group, a hydrophobic group,
           or a macromolecular carrier group."

(xi) SEQUENCE DESCRIPTION: SEQ ID NO:76:

Ala Phe Ile Arg Lys Ser Asp Glu Leu Leu
1               5                   10

(2) INFORMATION FOR SEQ ID NO:77:

(i) SEQUENCE CHARACTERISTICS:
       (A) LENGTH: 11 amino acids
       (B) TYPE: amino acid
       (C) STRANDEDNESS:
       (D) TOPOLOGY: unknown (ii) MOLECULE TYPE: peptide (ix) FEATURE:
       (A) NAME/KEY: Modified-site
       (B) LOCATION: 1
       (D) OTHER INFORMATION: /label= A
           /note= "Preceeding this amino acid, there may be an
           amino group, an acetyl group, a 9-fluorenylmethoxy-
           carbonyl group, a hydrophobic group or a macromolecular
           carrier group."

(ix) FEATURE:
       (A) NAME/KEY: Modified-site
       (B) LOCATION: 11
       (D) OTHER INFORMATION: /label= B
           /note= "Following this amino acid, there may be a
           carboxyl group, an amido group, a hydrophobic group,
           or a macromolecular carrier group."

(xi) SEQUENCE DESCRIPTION: SEQ ID NO:77:

Leu Ala Phe Ile Arg Lys Ser Asp Glu Leu Leu
1               5                   10

(2) INFORMATION FOR SEQ ID NO:78:

(i) SEQUENCE CHARACTERISTICS:
       (A) LENGTH: 12 amino acids
       (B) TYPE: amino acid
       (C) STRANDEDNESS:
       (D) TOPOLOGY: unknown (ii) MOLECULE TYPE: peptide

```
    (ix) FEATURE:
          (A) NAME/KEY: Modified-site
          (B) LOCATION: 1
          (D) OTHER INFORMATION: /label= A
              /note= "Preceeding this amino acid, there may be an
              amino group, an acetyl group, a 9-fluorenylmethoxy-
              carbonyl group, a hydrophobic group or a macromolecular
              carrier group."

(ix) FEATURE:
          (A) NAME/KEY: Modified-site
          (B) LOCATION: 12
          (D) OTHER INFORMATION: /label= B
              /note= "Following this amino acid, there may be a
              carboxyl group, an amido group, a hydrophobic group,
              or a macromolecular carrier group."

(xi) SEQUENCE DESCRIPTION: SEQ ID NO:78:

Ser Leu Ala Phe Ile Arg Lys Ser Asp Glu Leu Leu
1               5                   10

(2) INFORMATION FOR SEQ ID NO:79:

(i) SEQUENCE CHARACTERISTICS:
          (A) LENGTH: 13 amino acids
          (B) TYPE: amino acid
          (C) STRANDEDNESS:
          (D) TOPOLOGY: unknown (ii) MOLECULE TYPE: peptide (ix) FEATURE:
          (A) NAME/KEY: Modified-site
          (B) LOCATION: 1
          (D) OTHER INFORMATION: /label= A
              /note= "Preceeding this amino acid, there may be an
              amino group, an acetyl group, a 9-fluorenylmethoxy-
              carbonyl group, a hydrophobic group or a macromolecular
              carrier group."

(ix) FEATURE:
          (A) NAME/KEY: Modified-site
          (B) LOCATION: 13
          (D) OTHER INFORMATION: /label= B
              /note= "Following this amino acid, there may be a
              carboxyl group, an amido group, a hydrophobic group,
              or a macromolecular carrier group."

(xi) SEQUENCE DESCRIPTION: SEQ ID NO:79:

Gln Ser Leu Ala Phe Ile Arg Lys Ser Asp Glu Leu Leu
1               5                   10

(2) INFORMATION FOR SEQ ID NO:80:

(i) SEQUENCE CHARACTERISTICS:
          (A) LENGTH: 14 amino acids
          (B) TYPE: amino acid
          (C) STRANDEDNESS:
          (D) TOPOLOGY: unknown (ii) MOLECULE TYPE: peptide (ix) FEATURE:
          (A) NAME/KEY: Modified-site
          (B) LOCATION: 1
          (D) OTHER INFORMATION: /label= A
              /note= "Preceeding this amino acid, there may be an
              amino group, an acetyl group, a 9-fluorenylmethoxy-
              carbonyl group, a hydrophobic group or a macromolecular
              carrier group."

(ix) FEATURE:
          (A) NAME/KEY: Modified-site
          (B) LOCATION: 14
          (D) OTHER INFORMATION: /label= B
```

/note= "Following this amino acid, there may be a
carboxyl group, an amido group, a hydrophobic group, or
a macromolecular carrier group."

(xi) SEQUENCE DESCRIPTION: SEQ ID NO:80:

Asn Gln Ser Leu Ala Phe Ile Arg Lys Ser Asp Glu Leu Leu
1               5                   10

(2) INFORMATION FOR SEQ ID NO:81:

(i) SEQUENCE CHARACTERISTICS:
      (A) LENGTH: 15 amino acids
      (B) TYPE: amino acid
      (C) STRANDEDNESS:
      (D) TOPOLOGY: unknown (ii) MOLECULE TYPE: peptide (ix) FEATURE:
      (A) NAME/KEY: Modified-site
      (B) LOCATION: 1
      (D) OTHER INFORMATION: /label= A
/note= "Preceeding this amino acid, there may be an
amino group, an acetyl group, a 9-fluorenylmethoxy-
carbonyl group, a hydrophobic group or a macromolecular
carrier group."

(ix) FEATURE:
      (A) NAME/KEY: Modified-site
      (B) LOCATION: 15
      (D) OTHER INFORMATION: /label= B
/note= "Following this amino acid, there may be a
carboxyl group, an amido group, a hydrophobic group,
or a macromolecular carrier group."

(xi) SEQUENCE DESCRIPTION: SEQ ID NO:81:

Ile Asn Gln Ser Leu Ala Phe Ile Arg Lys Ser Asp Glu Leu Leu
1               5                   10                  15

(2) INFORMATION FOR SEQ ID NO:82:

(i) SEQUENCE CHARACTERISTICS:
      (A) LENGTH: 16 amino acids
      (B) TYPE: amino acid
      (C) STRANDEDNESS:
      (D) TOPOLOGY: unknown (ii) MOLECULE TYPE: peptide (ix) FEATURE:
      (A) NAME/KEY: Modified-site
      (B) LOCATION: 1
      (D) OTHER INFORMATION: /label= A
/note= "Preceeding this amino acid, there may be an
amino group, an acetyl group, a 9-fluorenylmethoxy-
carbonyl group, a hydrophobic group or a macromolecular
carrier group."

(ix) FEATURE:
      (A) NAME/KEY: Modified-site
      (B) LOCATION: 16
      (D) OTHER INFORMATION: /label= B
/note= "Following this amino acid, there may be a
carboxyl group, an amido group, a hydrophobic group,
or a macromolecular carrier group."

(xi) SEQUENCE DESCRIPTION: SEQ ID NO:82:

Lys Ile Asn Gln Ser Leu Ala Phe Ile Arg Lys Ser Asp Glu Leu Leu
1               5                   10                  15

(2) INFORMATION FOR SEQ ID NO:83:

(i) SEQUENCE CHARACTERISTICS:

```
            (A) LENGTH: 17 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= A
                /note= "Preceeding this amino acid, there may be an
                amino group, an acetyl group, a 9-fluorenylmethoxy-
                carbonyl group, a hydrophobic group or a macromolecular
                carrier group."

(ix) FEATURE:
            (A) NAME/KEY: Modified-site
            (B) LOCATION: 17
            (D) OTHER INFORMATION: /label= B
                /note= "Following this amino acid, there may be a
                carboxyl group, an amido group, a hydrophobic group,
                or a macromolecular carrier group."

(xi) SEQUENCE DESCRIPTION: SEQ ID NO:83:

Glu Lys Ile Asn Gln Ser Leu Ala Phe Ile Arg Lys Ser Asp Glu Leu
 1               5                  10                  15

Leu (2) INFORMATION FOR SEQ ID NO:84:

(i) SEQUENCE CHARACTERISTICS:
            (A) LENGTH: 18 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= A
                /note= "Preceeding this amino acid, there may be an
                amino group, an acetyl group, a 9-fluorenylmethoxy-
                carbonyl group, a hydrophobic group or a macromolecular
                carrier group."

(ix) FEATURE:
            (A) NAME/KEY: Modified-site
            (B) LOCATION: 18
            (D) OTHER INFORMATION: /label= B
                /note= "Following this amino acid, there may be a
                carboxyl group, an amido group, a hydrophobic group,
                or a macromolecular carrier group."

(xi) SEQUENCE DESCRIPTION: SEQ ID NO:84:

Asn Glu Lys Ile Asn Gln Ser Leu Ala Phe Ile Arg Lys Ser Asp Glu
 1               5                  10                  15

Leu Leu (2) INFORMATION FOR SEQ ID NO:85:

(i) SEQUENCE CHARACTERISTICS:
            (A) LENGTH: 19 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
```

(B) LOCATION: 1
                (D) OTHER INFORMATION: /label= A
                    /note= "Preceeding this amino acid, there may be an
                    amino group, an acetyl group, a 9-fluorenylmethoxy-
                    carbonyl group, a hydrophobic group or a macromolecular
                    carrier group."

(ix) FEATURE:
                (A) NAME/KEY: Modified-site
                (B) LOCATION: 19
                (D) OTHER INFORMATION: /label= B
                    /note= "Following this amino acid, there may be a
                    carboxyl group, an amido group, a hydrophobic group,
                    or a macromolecular carrier group."

(xi) SEQUENCE DESCRIPTION: SEQ ID NO:85:

Val Asn Glu Lys Ile Asn Gln Ser Leu Ala Phe Ile Arg Lys Ser Asp
1               5                   10                  15

Glu Leu Leu (2) INFORMATION FOR SEQ ID NO:86:

(i) SEQUENCE CHARACTERISTICS:
                (A) LENGTH: 20 amino acids
                (B) TYPE: amino acid
                (C) STRANDEDNESS:
                (D) TOPOLOGY: unknown (ii) MOLECULE TYPE: peptide (ix) FEATURE:
                (A) NAME/KEY: Modified-site
                (B) LOCATION: 1
                (D) OTHER INFORMATION: /label= A
                    /note= "Preceeding this amino acid, there may be an
                    amino group, an acetyl group, a 9-fluorenylmethoxy-
                    carbonyl group, a hydrophobic group or a macromolecular
                    carrier group."

(ix) FEATURE:
                (A) NAME/KEY: Modified-site
                (B) LOCATION: 20
                (D) OTHER INFORMATION: /label= B
                    /note= "Following this amino acid, there may be a
                    carboxyl group, an amido group, a hydrophobic group,
                    or a macromolecular carrier group."

(xi) SEQUENCE DESCRIPTION: SEQ ID NO:86:

Gln Val Asn Glu Lys Ile Asn Gln Ser Leu Ala Phe Ile Arg Lys Ser
1               5                   10                  15

Asp Glu Leu Leu
            20

(2) INFORMATION FOR SEQ ID NO:87:

(i) SEQUENCE CHARACTERISTICS:
                (A) LENGTH: 21 amino acids
                (B) TYPE: amino acid
                (C) STRANDEDNESS:
                (D) TOPOLOGY: unknown (ii) MOLECULE TYPE: peptide (ix) FEATURE:
                (A) NAME/KEY: Modified-site
                (B) LOCATION: 1
                (D) OTHER INFORMATION: /label= A
                    /note= "Preceeding this amino acid, there may be an
                    amino group, an acetyl group, a 9-fluorenylmethoxy-
                    carbonyl group, a hydrophobic group or a macromolecular
                    carrier group."

(ix) FEATURE:

(A) NAME/KEY: Modified-site
(B) LOCATION: 21
(D) OTHER INFORMATION: /label= B
    /note= "Following this amino acid, there may be a
    carboxyl group, an amido group, a hydrophobic group,
    or a macromolecular carrier group."

(xi) SEQUENCE DESCRIPTION: SEQ ID NO:87:

```
Ser Gln Val Asn Glu Lys Ile Asn Gln Ser Leu Ala Phe Ile Arg Lys
 1               5                  10                  15

Ser Asp Glu Leu Leu
        20
```

(2) INFORMATION FOR SEQ ID NO:88:

(i) SEQUENCE CHARACTERISTICS:
      (A) LENGTH: 22 amino acids
      (B) TYPE: amino acid
      (C) STRANDEDNESS:
      (D) TOPOLOGY: unknown (ii) MOLECULE TYPE: peptide (ix) FEATURE:
      (A) NAME/KEY: Modified-site
      (B) LOCATION: 1
      (D) OTHER INFORMATION: /label= A
          /note= "Preceeding this amino acid, there may be an
          amino group, an acetyl group, a 9-fluorenylmethoxy-
          carbonyl group, a hydrophobic group or a macromolecular
          carrier group."

(ix) FEATURE:
      (A) NAME/KEY: Modified-site
      (B) LOCATION: 22
      (D) OTHER INFORMATION: /label= B
          /note= "Following this amino acid, there may be a
          carboxyl group, an amido group, a hydrophobic group,
          or a macromolecular carrier group."

(xi) SEQUENCE DESCRIPTION: SEQ ID NO:88:

```
Ile Ser Gln Val Asn Glu Lys Ile Asn Gln Ser Leu Ala Phe Ile Arg
 1               5                  10                  15

Lys Ser Asp Glu Leu Leu
        20
```

(2) INFORMATION FOR SEQ ID NO:89:

(i) SEQUENCE CHARACTERISTICS:
      (A) LENGTH: 23 amino acids
      (B) TYPE: amino acid
      (C) STRANDEDNESS:
      (D) TOPOLOGY: unknown (ii) MOLECULE TYPE: peptide (ix) FEATURE:
      (A) NAME/KEY: Modified-site
      (B) LOCATION: 1
      (D) OTHER INFORMATION: /label= A
          /note= "Preceeding this amino acid, there may be an
          amino group, an acetyl group, a 9-fluorenylmethoxy-
          carbonyl group, a hydrophobic group or a macromolecular
          carrier group."

(ix) FEATURE:
      (A) NAME/KEY: Modified-site
      (B) LOCATION: 23
      (D) OTHER INFORMATION: /label= B
          /note= "Following this amino acid, there may be a
          carboxyl group, an amido group, a hydrophobic group,
          or a macromolecular carrier group."

(xi) SEQUENCE DESCRIPTION: SEQ ID NO:89:

Ser Ile Ser Gln Val Asn Glu Lys Ile Asn Gln Ser Leu Ala Phe Ile
1               5                   10                  15

Arg Lys Ser Asp Glu Leu Leu
            20

(2) INFORMATION FOR SEQ ID NO:90:

(i) SEQUENCE CHARACTERISTICS:
      (A) LENGTH: 24 amino acids
      (B) TYPE: amino acid
      (C) STRANDEDNESS:
      (D) TOPOLOGY: unknown (ii) MOLECULE TYPE: peptide (ix) FEATURE:
      (A) NAME/KEY: Modified-site
      (B) LOCATION: 1
      (D) OTHER INFORMATION: /label= A
        /note= "Preceeding this amino acid, there may be an
        amino group, an acetyl group, a 9-fluorenylmethoxy-
        carbonyl group, a hydrophobic group or a macromolecular
        carrier group."

(ix) FEATURE:
      (A) NAME/KEY: Modified-site
      (B) LOCATION: 24
      (D) OTHER INFORMATION: /label= B
        /note= "Following this amino acid, there may be a
        carboxyl group, an amido group, a hydrophobic group,
        or a macromolecular carrier group."

(xi) SEQUENCE DESCRIPTION: SEQ ID NO:90:

Ala Ser Ile Ser Gln Val Asn Glu Lys Ile Asn Gln Ser Leu Ala Phe
1               5                   10                  15

Ile Arg Lys Ser Asp Glu Leu Leu
                20

(2) INFORMATION FOR SEQ ID NO:91:

(i) SEQUENCE CHARACTERISTICS:
      (A) LENGTH: 25 amino acids
      (B) TYPE: amino acid
      (C) STRANDEDNESS:
      (D) TOPOLOGY: unknown (ii) MOLECULE TYPE: peptide (ix) FEATURE:
      (A) NAME/KEY: Modified-site
      (B) LOCATION: 1
      (D) OTHER INFORMATION: /label= A
        /note= "Preceeding this amino acid, there may be an
        amino group, an acetyl group, a 9-fluorenylmethoxy-
        carbonyl group, a hydrophobic group or a macromolecular
        carrier group."

(ix) FEATURE:
      (A) NAME/KEY: Modified-site
      (B) LOCATION: 25
      (D) OTHER INFORMATION: /label= B
        /note= "Following this amino acid, there may be a
        carboxyl group, an amido group, a hydrophobic group,
        or a macromolecular carrier group."

(xi) SEQUENCE DESCRIPTION: SEQ ID NO:91:

Asp Ala Ser Ile Ser Gln Val Asn Glu Lys Ile Asn Gln Ser Leu Ala
1               5                   10                  15

Phe Ile Arg Lys Ser Asp Glu Leu Leu
                20                  25

(2) INFORMATION FOR SEQ ID NO:92:

(i) SEQUENCE CHARACTERISTICS:
        (A) LENGTH: 26 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 26
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:92:

```
Phe Asp Ala Ser Ile Ser Gln Val Asn Glu Lys Ile Asn Gln Ser Leu
 1               5                  10                  15
Ala Phe Ile Arg Lys Ser Asp Glu Leu Leu
            20                  25
```

(2) INFORMATION FOR SEQ ID NO:93:

(i) SEQUENCE CHARACTERISTICS:
        (A) LENGTH: 27 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 27
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:93:

```
Glu Phe Asp Ala Ser Ile Ser Gln Val Asn Glu Lys Ile Asn Gln Ser
 1               5                  10                  15
Leu Ala Phe Ile Arg Lys Ser Asp Glu Leu Leu
            20                  25
```

(2) INFORMATION FOR SEQ ID NO:94:

(i) SEQUENCE CHARACTERISTICS:
        (A) LENGTH: 28 amino acids
        (B) TYPE: amino acid

```
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= A
                /note= "Preceeding this amino acid, there may be an
                amino group, an acetyl group, a 9-fluorenylmethoxy-
                carbonyl group, a hydrophobic group or a macromolecular
                carrier group."

(ix) FEATURE:
            (A) NAME/KEY: Modified-site
            (B) LOCATION: 28
            (D) OTHER INFORMATION: /label= B
                /note= "Following this amino acid, there may be a
                carboxyl group, an amido group, a hydrophobic group,
                or a macromolecular carrier group."

(xi) SEQUENCE DESCRIPTION: SEQ ID NO:94:

Asp Glu Phe Asp Ala Ser Ile Ser Gln Val Asn Glu Lys Ile Asn Gln
 1               5                  10                  15

Ser Leu Ala Phe Ile Arg Lys Ser Asp Glu Leu Leu
            20                  25

(2) INFORMATION FOR SEQ ID NO:95:

(i) SEQUENCE CHARACTERISTICS:
            (A) LENGTH: 29 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= A
                /note= "Preceeding this amino acid, there may be an
                amino group, an acetyl group, a 9-fluorenylmethoxy-
                carbonyl group, a hydrophobic group or a macromolecular
                carrier group."

(ix) FEATURE:
            (A) NAME/KEY: Modified-site
            (B) LOCATION: 29
            (D) OTHER INFORMATION: /label= B
                /note= "Following this amino acid, there may be a
                carboxyl group, an amido group, a hydrophobic group,
                or a macromolecular carrier group."

(xi) SEQUENCE DESCRIPTION: SEQ ID NO:95:

Ser Asp Glu Phe Asp Ala Ser Ile Ser Gln Val Asn Glu Lys Ile Asn
 1               5                  10                  15

Gln Ser Leu Ala Phe Ile Arg Lys Ser Asp Glu Leu Leu
            20                  25

(2) INFORMATION FOR SEQ ID NO:96:

(i) SEQUENCE CHARACTERISTICS:
            (A) LENGTH: 30 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
```

(B) LOCATION: 1
            (D) OTHER INFORMATION: /label= A
                /note= "Preceeding this amino acid, there may be an
                amino group, an acetyl group, a 9-fluorenylmethoxy-
                carbonyl group, a hydrophobic group or a macromolecular
                carrier group."

(ix) FEATURE:
            (A) NAME/KEY: Modified-site
            (B) LOCATION: 30
            (D) OTHER INFORMATION: /label= B
                /note= "Following this amino acid, there may be a
                carboxyl group, an amido group, a hydrophobic group,
                or a macromolecular carrier group."

(xi) SEQUENCE DESCRIPTION: SEQ ID NO:96:

```
Pro Ser Asp Glu Phe Asp Ala Ser Ile Ser Gln Val Asn Glu Lys Ile
1               5                   10                  15

Asn Gln Ser Leu Ala Phe Ile Arg Lys Ser Asp Glu Leu Leu
            20                  25                  30
```

(2) INFORMATION FOR SEQ ID NO:97:

(i) SEQUENCE CHARACTERISTICS:
            (A) LENGTH: 31 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= A
                /note= "Preceeding this amino acid, there may be an
                amino group, an acetyl group, a 9-fluorenylmethoxy-
                carbonyl group, a hydrophobic group or a macromolecular
                carrier group."

(ix) FEATURE:
            (A) NAME/KEY: Modified-site
            (B) LOCATION: 31
            (D) OTHER INFORMATION: /label= B
                /note= "Following this amino acid, there may be a
                carboxyl group, an amido group, a hydrophobic group,
                or a macromolecular carrier group."

(xi) SEQUENCE DESCRIPTION: SEQ ID NO:97:

```
Phe Pro Ser Asp Glu Phe Asp Ala Ser Ile Ser Gln Val Asn Glu Lys
1               5                   10                  15

Ile Asn Gln Ser Leu Ala Phe Ile Arg Lys Ser Asp Glu Leu Leu
            20                  25                  30
```

(2) INFORMATION FOR SEQ ID NO:98:

(i) SEQUENCE CHARACTERISTICS:
            (A) LENGTH: 32 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= A
                /note= "Preceeding this amino acid, there may be an
                amino group, an acetyl group, a 9-fluorenylmethoxy-
                carbonyl group, a hydrophobic group or a macromolecular
                carrier group."

```
    (ix) FEATURE:
         (A) NAME/KEY: Modified-site
         (B) LOCATION: 32
         (D) OTHER INFORMATION: /label= B
             /note= "Following this amino acid, there may be a
             carboxyl group, an amido group, a hydrophobic group,
             or a macromolecular carrier group."

(xi) SEQUENCE DESCRIPTION: SEQ ID NO:98:

Val Phe Pro Ser Asp Glu Phe Asp Ala Ser Ile Ser Gln Val Asn Glu
 1               5                  10                  15

Lys Ile Asn Gln Ser Leu Ala Phe Ile Arg Lys Ser Asp Glu Leu Leu
                20                  25                  30

(2) INFORMATION FOR SEQ ID NO:99:

(i) SEQUENCE CHARACTERISTICS:
        (A) LENGTH: 33 amino acids
        (B) TYPE: amino acid
        (C) STRANDEDNESS:
        (D) TOPOLOGY: unknown (ii) MOLECULE TYPE: peptide (ix) FEATURE:
         (A) NAME/KEY: Modified-site
         (B) LOCATION: 1
         (D) OTHER INFORMATION: /label= A
             /note= "Preceeding this amino acid, there may be an
             amino group, an acetyl group, a 9-fluorenylmethoxy-
             carbonyl group, a hydrophobic group or a macromolecular
             carrier group."

(ix) FEATURE:
         (A) NAME/KEY: Modified-site
         (B) LOCATION: 33
         (D) OTHER INFORMATION: /label= B
             /note= "Following this amino acid, there may be a
             carboxyl group, an amido group, a hydrophobic group,
             or a macromolecular carrier group."

(xi) SEQUENCE DESCRIPTION: SEQ ID NO:99:

Leu Val Phe Pro Ser Asp Glu Phe Asp Ala Ser Ile Ser Gln Val Asn
 1               5                  10                  15

Glu Lys Ile Asn Gln Ser Leu Ala Phe Ile Arg Lys Ser Asp Glu Leu
                20                  25                  30

Leu (2) INFORMATION FOR SEQ ID NO:100:

(i) SEQUENCE CHARACTERISTICS:
        (A) LENGTH: 34 amino acids
        (B) TYPE: amino acid
        (C) STRANDEDNESS:
        (D) TOPOLOGY: unknown (ii) MOLECULE TYPE: peptide (ix) FEATURE:
         (A) NAME/KEY: Modified-site
         (B) LOCATION: 1
         (D) OTHER INFORMATION: /label= A
             /note= "Preceeding this amino acid, there may be an
             amino group, an acetyl group, a 9-fluorenylmethoxy-
             carbonyl group, a hydrophobic group or a macromolecular
             carrier group."

(ix) FEATURE:
         (A) NAME/KEY: Modified-site
         (B) LOCATION: 34
         (D) OTHER INFORMATION: /label= B
             /note= "Following this amino acid, there may be a
``` carboxyl group, an amido group, a hydrophobic group,
or a macromolecular carrier group."

(xi) SEQUENCE DESCRIPTION: SEQ ID NO:100:

Pro Leu Val Phe Pro Ser Asp Glu Phe Asp Ala Ser Ile Ser Gln Val
 1               5                  10                  15

Asn Glu Lys Ile Asn Gln Ser Leu Ala Phe Ile Arg Lys Ser Asp Glu
            20                  25                  30

Leu Leu (2) INFORMATION FOR SEQ ID NO:101:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 35
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:101:

Asp Pro Leu Val Phe Pro Ser Asp Glu Phe Asp Ala Ser Ile Ser Gln
 1               5                  10                  15

Val Asn Glu Lys Ile Asn Gln Ser Leu Ala Phe Ile Arg Lys Ser Asp
            20                  25                  30

Glu Leu Leu
        35

(2) INFORMATION FOR SEQ ID NO:102:

(i) SEQUENCE CHARACTERISTICS:
        (A) LENGTH: 36 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 36
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:102:

Tyr Asp Pro Leu Val Phe Pro Ser Asp Glu Phe Asp Ala Ser Ile Ser
1               5                   10                  15

Gln Val Asn Glu Lys Ile Asn Gln Ser Leu Ala Phe Ile Arg Lys Ser
            20                  25                  30

Asp Glu Leu Leu
        35

(2) INFORMATION FOR SEQ ID NO:103:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 35
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:103:

Tyr Asp Pro Leu Val Phe Pro Ser Asp Glu Phe Asp Ala Ser Ile Ser
1               5                   10                  15

Gln Val Asn Glu Lys Ile Asn Gln Ser Leu Ala Phe Ile Arg Lys Ser
            20                  25                  30

Asp Glu Leu
        35

(2) INFORMATION FOR SEQ ID NO:104:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."
    (ix) FEATURE:
        (A) NAME/KEY: Modified-site
        (B) LOCATION: 35
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:104:

```
Leu Val Phe Pro Ser Asp Glu Phe Asp Ala Ser Ile Ser Gln Val Asn
 1               5                  10                  15

Glu Lys Ile Asn Gln Ser Leu Ala Phe Ile Arg Lys Ser Asp Glu Leu
            20                  25                  30

Leu His Asn
         35
```

(2) INFORMATION FOR SEQ ID NO:105:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 35
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:105:

```
Val Phe Pro Ser Asp Glu Phe Asp Ala Ser Ile Ser Gln Val Asn Glu
 1               5                  10                  15

Lys Ile Asn Gln Ser Leu Ala Phe Ile Arg Lys Ser Asp Glu Leu Leu
            20                  25                  30

His Asn Val
         35
```

(2) INFORMATION FOR SEQ ID NO:106:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 35
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:106:

```
Phe Pro Ser Asp Glu Phe Asp Ala Ser Ile Ser Gln Val Asn Glu Lys
 1               5                  10                  15

Ile Asn Gln Ser Leu Ala Phe Ile Arg Lys Ser Asp Glu Leu Leu His
                20                  25                  30

Asn Val Asn
        35
```

(2) INFORMATION FOR SEQ ID NO:107:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 35
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:107:

```
Pro Ser Asp Glu Phe Asp Ala Ser Ile Ser Gln Val Asn Glu Lys Ile
 1               5                  10                  15

Asn Gln Ser Leu Ala Phe Ile Arg Lys Ser Asp Glu Leu Leu His Asn
                20                  25                  30

Val Asn Ala
        35
```

(2) INFORMATION FOR SEQ ID NO:108:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 35
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:108:

```
Ser Asp Glu Phe Asp Ala Ser Ile Ser Gln Val Asn Glu Lys Ile Asn
```

```
          1               5              10              15
Gln Ser Leu Ala Phe Ile Arg Lys Ser Asp Glu Leu Leu His Asn Val
               20              25              30
Asn Ala Gly
         35
```

(2) INFORMATION FOR SEQ ID NO:109:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 35
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:109:

```
Asp Glu Phe Asp Ala Ser Ile Ser Gln Val Asn Glu Lys Ile Asn Gln
 1               5              10              15
Ser Leu Ala Phe Ile Arg Lys Ser Asp Glu Leu Leu His Asn Val Asn
               20              25              30
Ala Gly Lys
         35
```

(2) INFORMATION FOR SEQ ID NO:110:

(i) SEQUENCE CHARACTERISTICS:
        (A) LENGTH: 35 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= A
            /note= "Preceeding this amino acid, there may be an
            amino group, an acetyl group, a 9-fluorenylmethoxy-
            carbonyl group, a hydrophobic group or a macromolecular
            carrier group."

(ix) FEATURE:
        (A) NAME/KEY: Modified-site
        (B) LOCATION: 35
        (D) OTHER INFORMATION: /label= B
            /note= "Following this amino acid, there may be a
            carboxyl group, an amido group, a hydrophobic group,
            or a macromolecular carrier group."

(xi) SEQUENCE DESCRIPTION: SEQ ID NO:110:

```
Phe Asp Ala Ser Ile Ser Gln Val Asn Glu Lys Ile Asn Gln Ser Leu
 1               5              10              15
```

```
Ala Phe Ile Arg Lys Ser Asp Glu Leu Leu His Asn Val Asn Ala Gly
            20                  25                  30

Lys Ser Thr
        35

(2) INFORMATION FOR SEQ ID NO:111:

(i) SEQUENCE CHARACTERISTICS:
         (A) LENGTH: 35 amino acids
         (B) TYPE: amino acid
         (C) STRANDEDNESS:
         (D) TOPOLOGY: unknown (ii) MOLECULE TYPE: peptide (ix) FEATURE:
         (A) NAME/KEY: Modified-site
         (B) LOCATION: 1
         (D) OTHER INFORMATION: /label= A
             /note= "Preceeding this amino acid, there may be an
             amino group, an acetyl group, a 9-fluorenylmethoxy-
             carbonyl group, a hydrophobic group or a macromolecular
             carrier group."

(ix) FEATURE:
         (A) NAME/KEY: Modified-site
         (B) LOCATION: 35
         (D) OTHER INFORMATION: /label= B
             /note= "Following this amino acid, there may be a
             carboxyl group, an amido group, a hydrophobic group,
             or a macromolecular carrier group."

(xi) SEQUENCE DESCRIPTION: SEQ ID NO:111:

Asp Ala Ser Ile Ser Gln Val Asn Glu Lys Ile Asn Gln Ser Leu Ala
1               5                   10                  15

Phe Ile Arg Lys Ser Asp Glu Leu Leu His Asn Val Asn Ala Gly Lys
            20                  25                  30

Ser Thr Thr
        35
```

US 6,440,656 B1

METHODS FOR THE INHIBITION OF RESPIRATORY SYNCYTIAL VIRUS TRANSMISSION

This is protease, and drugs are being developed which inhibit this protease (Erickson, J., 1990, Science 249:527–533). The clinical outcome of these candidate drugs is still in question.

Attention is also being given to the development of vaccines for the treatment of HIV infection. The HIV-1 envelope proteins (gp160, gp120, gp41) have been shown to be the major antigens for anti-HIV antibodies present in AIDS patients (Barin, et al., 1985, Science 228:1094–1096). Thus far, therefore, these proteins seem to be the most promising candidates to act as antigens for anti-HIV vaccine development. To this end, several groups have begun to use various portions of gp160, gp120, and/or gp41 as immunogenic targets for the host immune system. See for example, Ivanoff, L. et al., U.S. Pat. No. 5,141,867; Saith, G. et al., WO 92/22,654; Shafferman, A., WO 91/09,872; Formoso, C. et al., WO 90/07,119. Clinical results concerning these candidate vaccines, however, still remain far in the future.

Thus, although a great deal of effort is being directed to the design and testing of anti-retroviral drugs, a truly effective, non-toxic treatment is still needed.

3. SUMMARY OF THE INVENTION

The present invention relates to DP-178 (SEQ ID:1), a 36-amino acid synthetic peptide corresponding to amino acids 638 to 673 of the transmembrane protein (TM) gp41 from the HIV-1 isolate LAI, which exhibits potent anti-HIV-1 activity. As evidenced by the example presented below, in Section 6, the DP-178 (SEQ ID:1) anti-viral activity is so high that, on a weight basis, no other known anti-HIV agent is effective at concentrations as low as those at which DP-178 (SEQ ID:1) exhibits its inhibitory effects. The invention further relates to those portions, analogs, and homologs of DP-178 which also show such antiviral activity. The antiviral activity of such DP-178 portions, analogs, and homologs, includes, but is not limited to the inhibition of HIV transmission to uninfected CD-4$^+$ cells. The invention relates to the use of DP-178 (SEQ ID:1) and DP-178 fragments and/or analogs or homologs. Such uses may include, but are not limited to, the use of the peptides as inhibitors of human and non-human retroviral, especially HIV, transmission to uninfected cells, and as type and/or subtype-specific diagnostic tools.

An embodiment of the invention is demonstrated below wherein an extremely low concentration of DP-178 (SEQ ID:1), and very low concentrations of a DP-178 homolog (SEQ ID:3) are shown to be potent inhibitors of HIV-1 mediated CD-4$^+$ cell-cell fusion (i.e., syncytial formation) and infection of CD-4$^+$ cells by cell-free virus. Further, it is shown that DP-178 (SEQ ID:1) is not toxic to cells, even at concentrations 3 logs higher than the inhibitory DP-178 (SEQ ID:1) concentration.

The invention also relates to analogous DP178 peptides in other enveloped viruses that demonstrate similar antiviral properties.

The invention further relates to peptides analogous to DP-107 (SEQ ID NO:25), a peptide corresponding to amino acids 558–595 of the HIV-1$_{LAI}$ transmembrane protein (TM) of gp41, that are present in other enveloped viruses, and demonstrate antiviral properties. The present invention is based, in part, on the surprising discovery that the DP-107 and DP-108 domains of the gp41 protein non-covalently complex with each other, and that their interaction is necessary for the normal activity of the virus. The invention, therefore, further relates to methods for identifying antiviral compounds that disrupt the interaction between DP-107 and DP-178, and/or between DP-107-like and DP-178-like peptides.

Embodiments of the invention are demonstrated, below, wherein peptides having structural and/or similarity to DP-107 and DP-178 are identified.

3.1. Definitions

Peptides are defined herein as organic compounds comprising two or more amino acids covalently joined by peptide bonds. Peptides may be referred to with respect to the number of constituent amino acids, i.e., a dipeptide contains two amino acid residues, a tripeptide contains three, etc. Peptides containing ten or fewer amino acids may be referred to as oligopeptides, while those with more than ten amino acid residues are polypeptides.

Peptide sequences defined herein are represented by one-letter symbols for amino acid residues as follows:

A (alanine)
R (arginine)
N (asparagine)
D (aspartic acid)
C (cysteine)
Q (glutamine)
E (glutamic acid)
G (glycine)
H (histidine)
I (isoleucine)
L (leucine)
K (lysine)
M (methionine)
F (phenylalanine)
P (proline)
S (serine)
T (threonine)
W (tryptophan)
Y (tyrosine)
V (valine)

4. BRIEF DESCRIPTION OF THE FIGURES

FIG. 1. Amino acid sequence of DP-178 (SEQ ID:1) derived from HIV$_{LAI}$; DP-178 homologs derived from HIV-1$_{SF2}$ (DP-185; SEQ ID:3), HIV-1$_{RF}$ (SEQ ID:4), and HIV-1$_{MN}$ (SEQ ID:5); DP-178 homologs derived from amino acid sequences of two prototypic HIV-2 isolates, namely, HIV-2$_{rod}$ (SEQ ID:6) and HIV-2$_{NIHZ}$ (SEQ ID:7); control peptides: DP-180 (SEQ ID:2), a peptide incorporating the amino acid residues of DP-178 in a scrambled sequence; DP-118 (SEQ ID:10) unrelated to DP-178, which inhibits HIV-1 cell free virus infection; DP-125 (SEQ ID:8), unrelated to DP-178, was also previously shown to-inhibit HIV-1 cell free virus infection (Wild et al., 1992, Proc. Natl. Acad. Sci USA 89:10,537–10,541); DP-116 (SEQ ID:9), unrelated to DP-178 had previously been shown to be negative for inhibition of HIV-1 infection using the cell-free virus infection assay (Wild, et al., 1992, Proc. Natl. Acad. Sci USA 89:10,537–10,541). Throughout the figures, the one letter amino acid code is used.

FIG. 2. Inhibition of HIV-1 cell-free virus infection by synthetic peptides. IC50 refers to the concentration of peptide that inhibits RT production from infected cells by 50% compared to the untreated control. Control: the level of RT produced by untreated cell cultures infected with the same level of virus as treated cultures.

Figure 3:
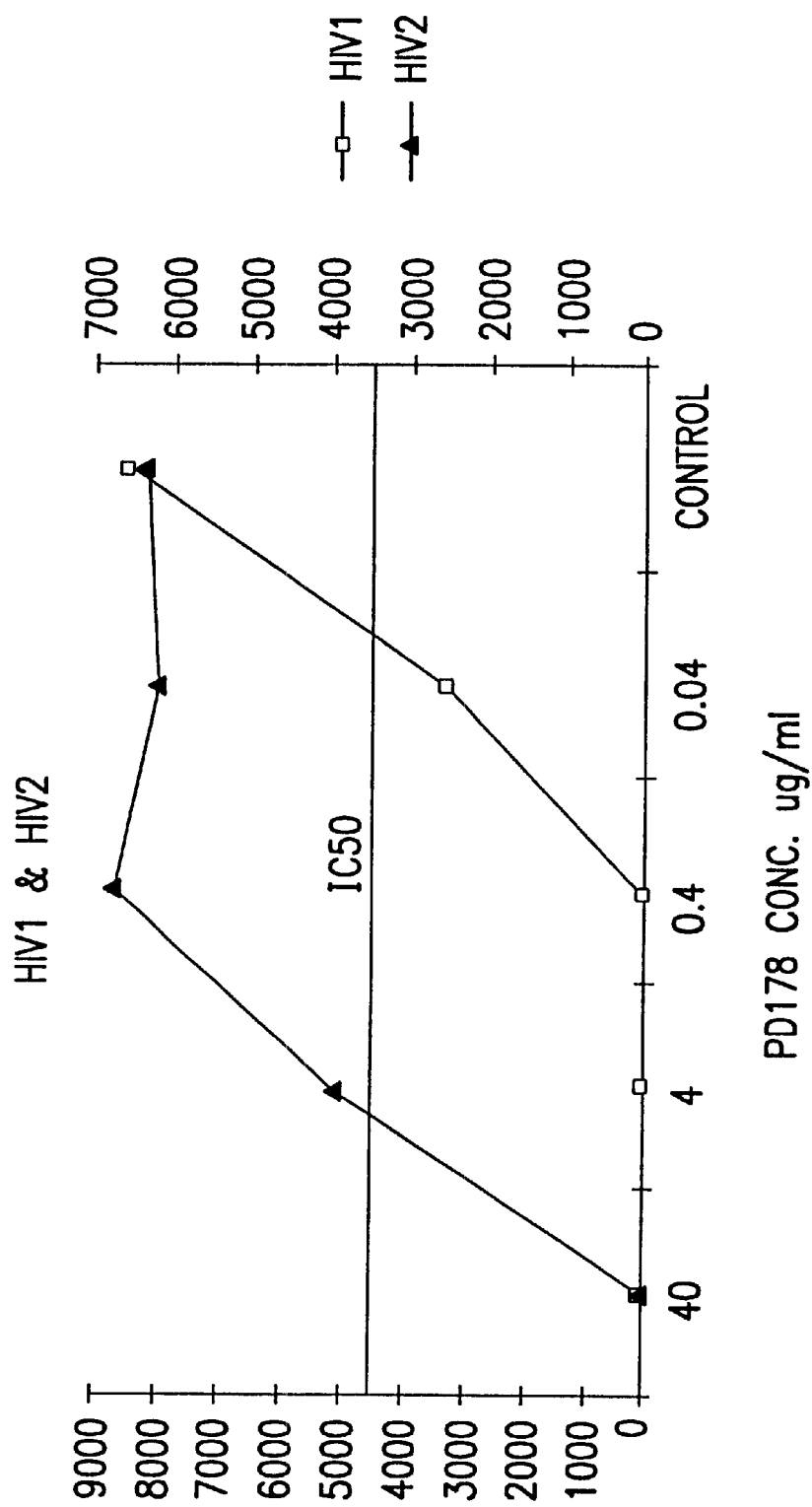

FIG. 3. Inhibition of HIV-1 and HIV-2 cell-free virus infection by the synthetic peptide DP-178 (SEQ ID:1). IC50:

concentration of peptide that inhibits RT production by 50% compared to the untreated control. Control: Level of RT produced by untreated cell cultures infected with the same level of virus as treated cultures.

FIG. 4A. Fusion Inhibition Assay. DP-178 (SEQ ID:1) inhibition of HIV-1 prototypic isolate-mediated syncytia formation. Data represents the number of virus-induced syncytia per cell.

FIG. 4B. Fusion Inhibition Assay. DP-180 (SEQ ID:2): scrambled control peptide. DP-185 (SEQ ID:3): DP-178 homolog derived from HIV-1$_{SF2}$ isolate. Control: number of syncytia produced in the absence of peptide.

FIG. 5. Fusion inhibition assay: HIV-1 vs. HIV-2. Data represents the number of virus-induced syncytia per well. ND: not done.

Figure 6:
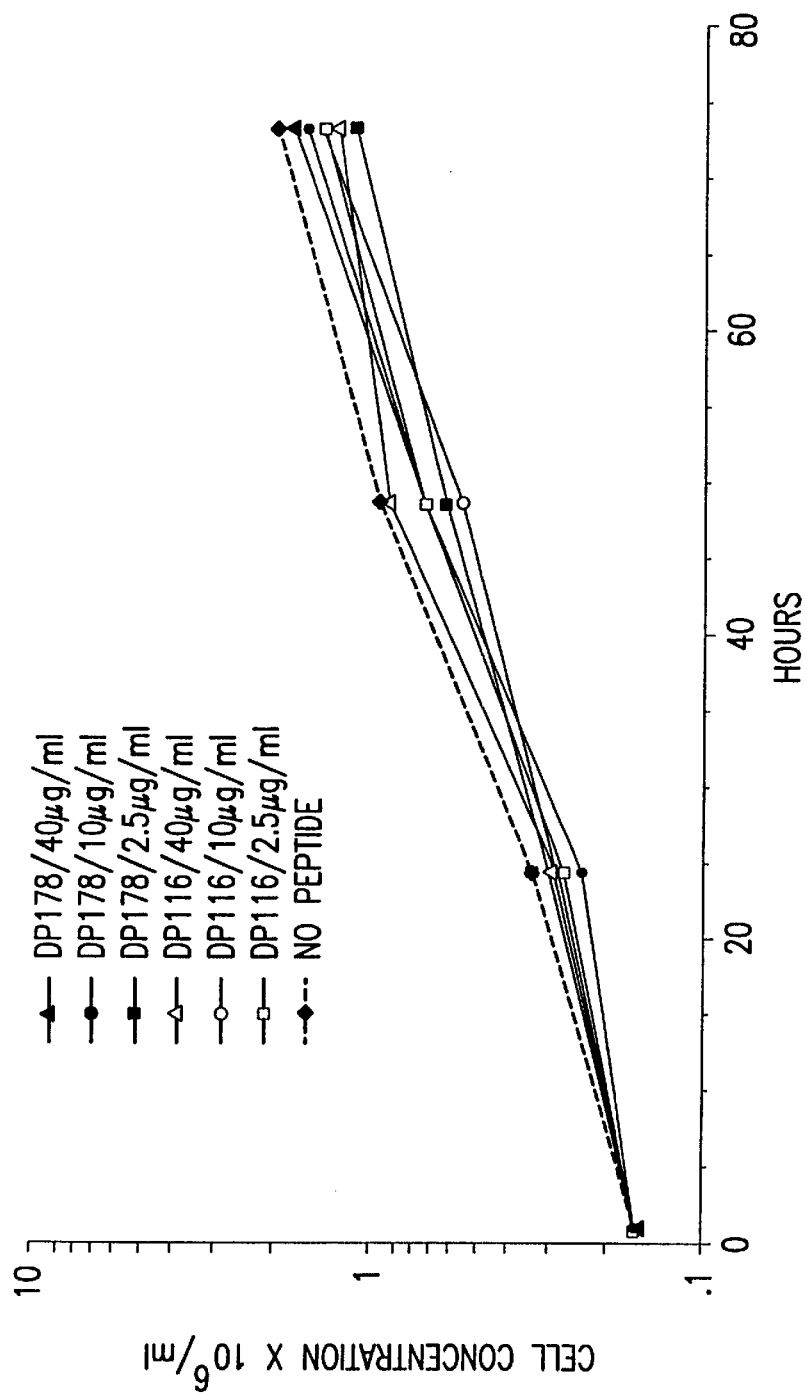

FIG. 6. Cytotoxicity study of DP-178 (SEQ ID:1) and DP-116 (SEQ ID:9) on CEM cells. Cell proliferation data is shown.

Figure 7:
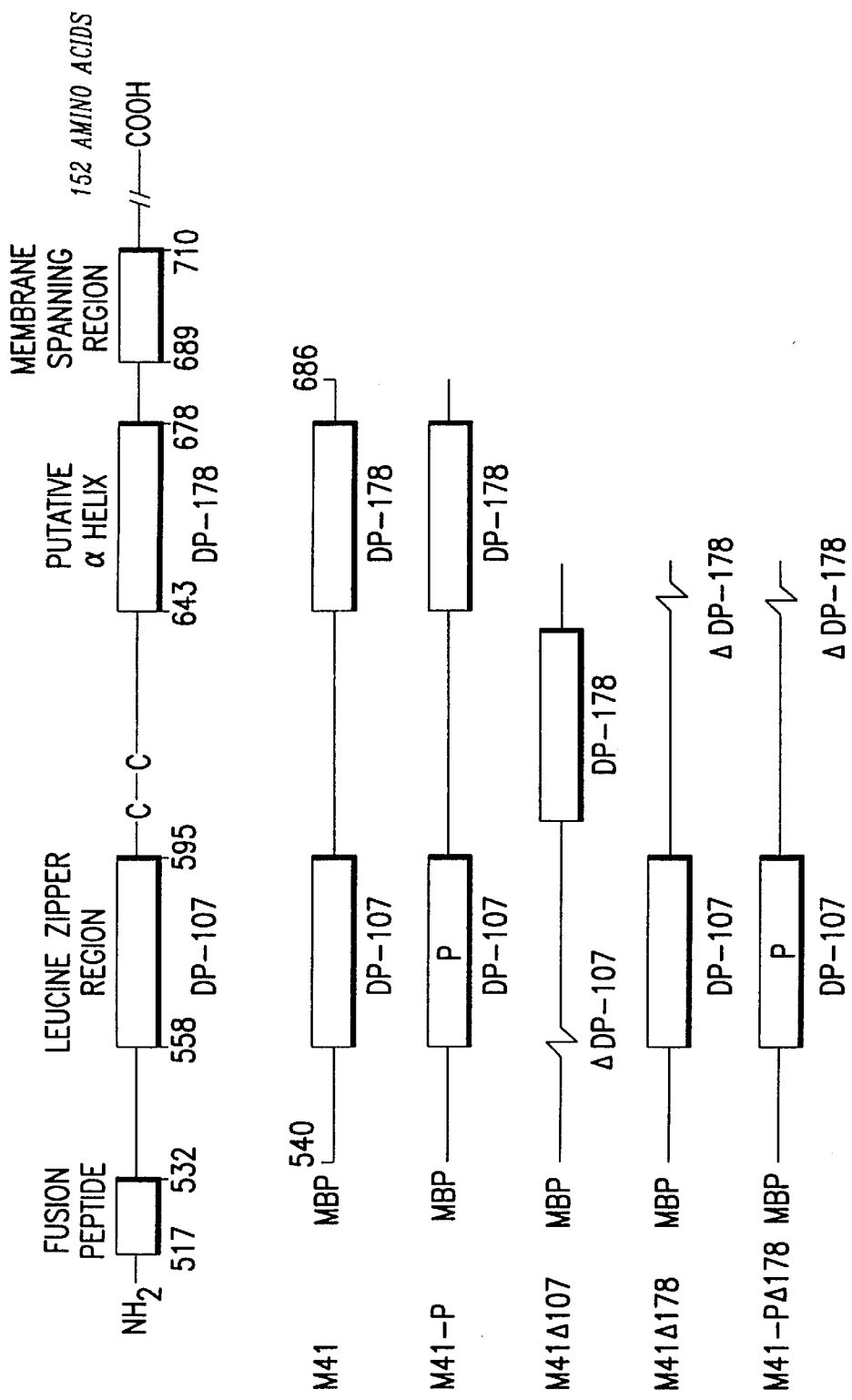

FIG. 7. Schematic representation of HIV-gp41 and maltose binding protein (MBP)-gp41 fusion proteins. DP107 and DP178 are synthetic peptides based on the two putative helices of gp41. The letter P in the DP107 boxes denotes an Ile to Pro mutation at amino acid number 578. Amino acid residues are numbered according to Meyers et al., Human Retroviruses and AIDS, 1991, Theoret. Biol. and Biophys. Group, Los Alamos Natl. Lab., Los Alamos, N.Mex.

Figure 8:
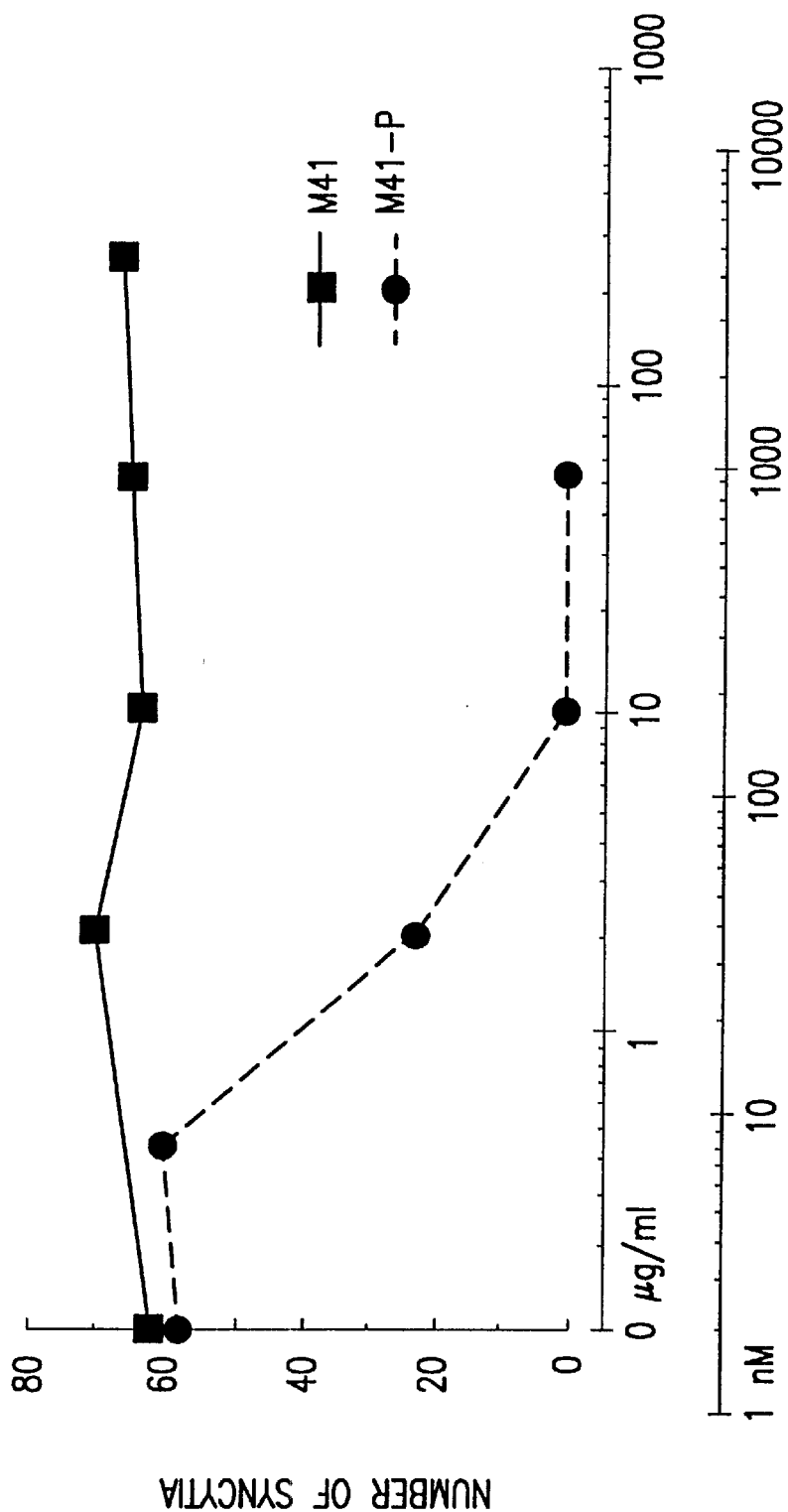

FIG. 8. A point mutation alters the conformation and anti-HIV activity of M41.

Figure 9:
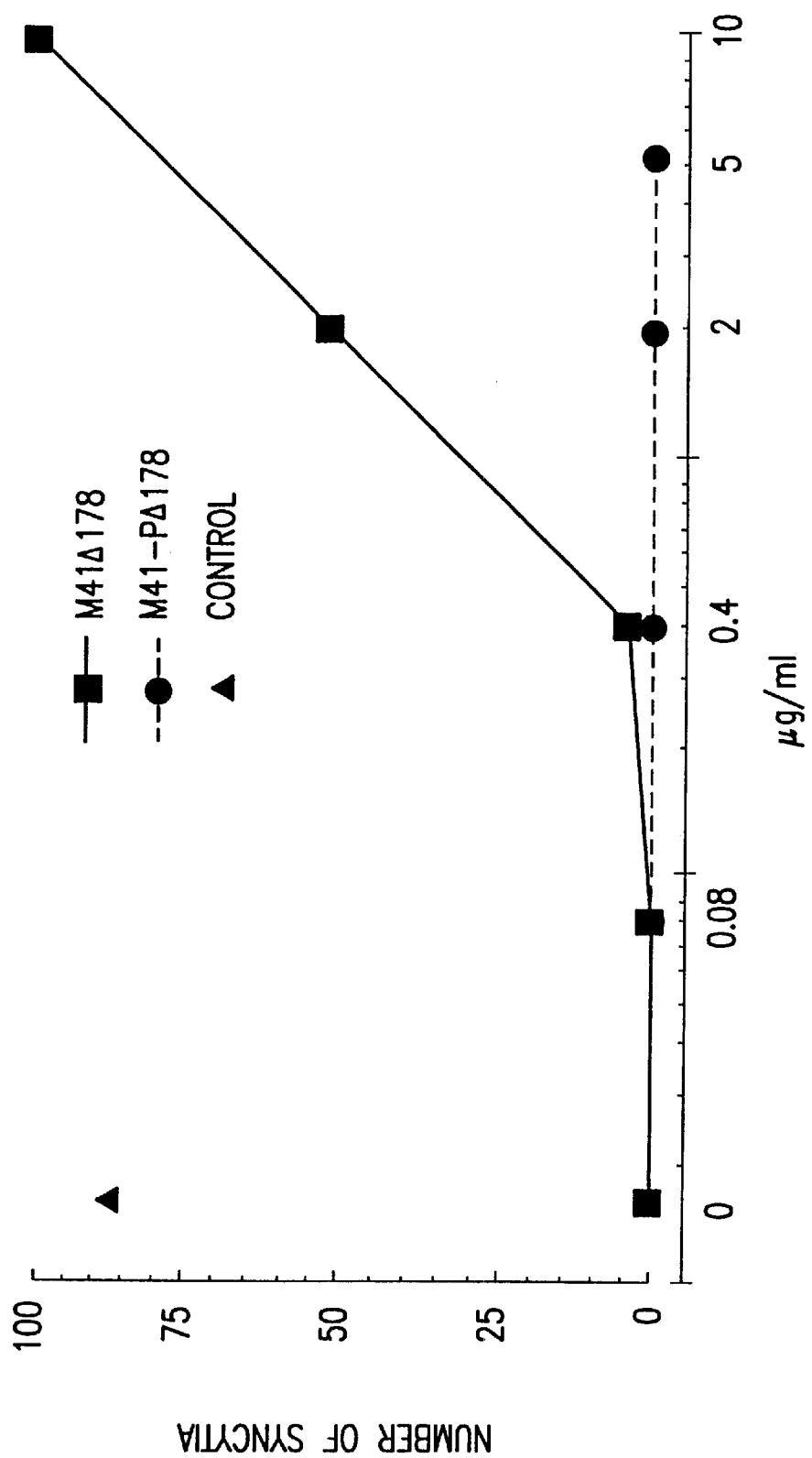

FIG. 9. Abrogation of DP178 anti-HIV activity. Cell fusion assays were carried out in the presence of 10 nM DP178 and various concentrations of M41Δ178 or M41PΔ178.

Figure 10:
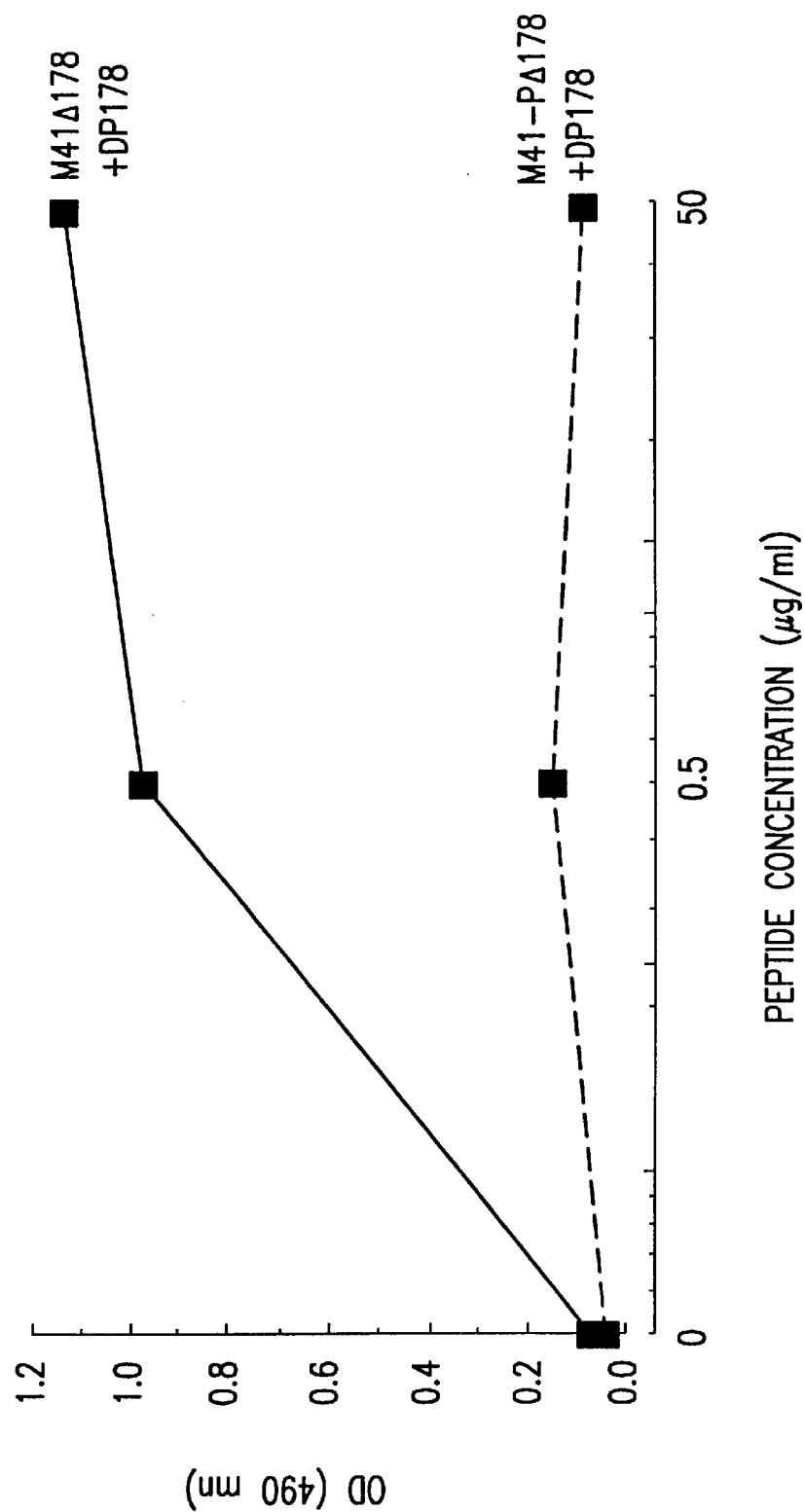

FIG. 10. Binding of DP178 to leucine zipper of gp41 analyzed by ELISA.

Figure 11A:
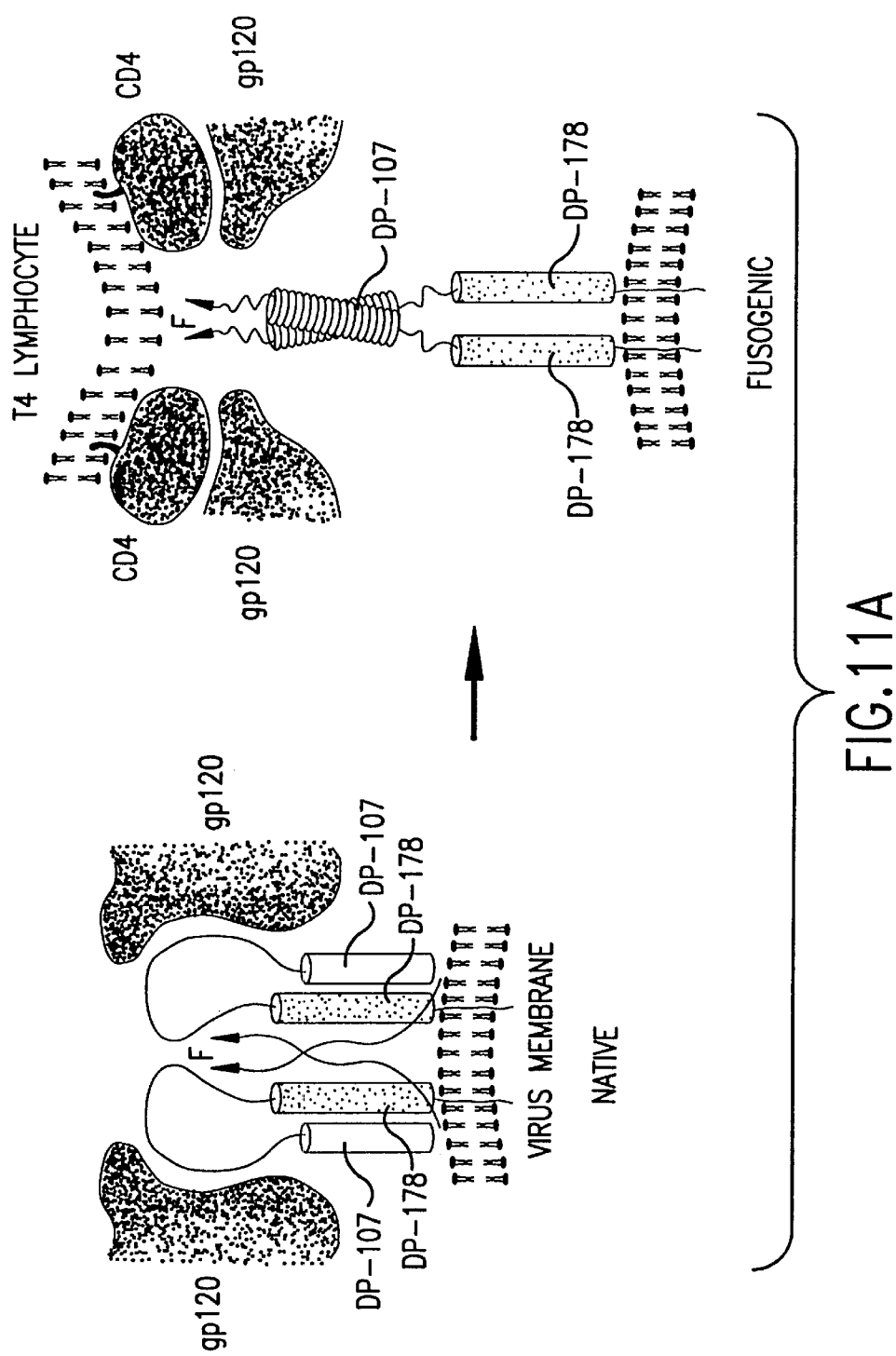
Figure 11B:
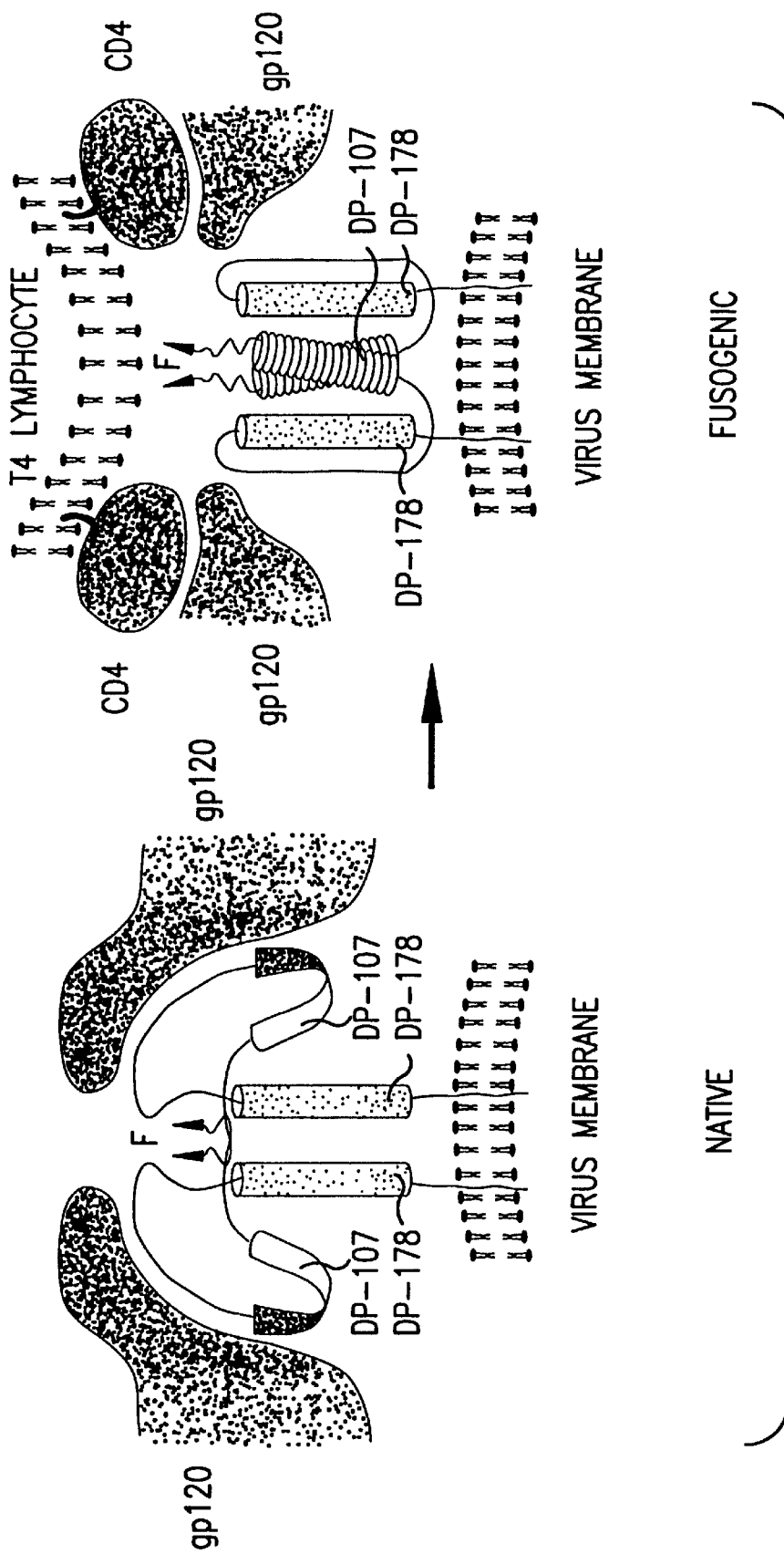

FIGS. 11A–B. Models for a structural transition in the HIV-1 TM protein. Two models are proposed which indicate a structural transition from a native oligomer to a fusogenic state following a trigger event (possibly gp120 binding to CD4). Common features of both models include (1) the native state is held together by noncovalent protein-protein interactions to form the heterodimer of gp120/41 and other interactions, principally though gp41 interactive sites, to form homo-oligomers on the virus surface of the gp120/41 complexes; (2) shielding of the hydrophobic fusogenic peptide at the N-terminus (F) in the native state; and (3) the leucine zipper domain (DP107) exists as a homo-oligomer coiled coil only in the fusogenic state. The major differences in the two models include the structural state (native or fusogenic) in which the DP107 and DP178 domains are complexed to each other. In the first model (A; FIG. 11A) this interaction occurs in the native state and in B during the fusogenic state. When triggered, the fusion complex in the model depicted in (A) is generated through formation of coiled-coil interactions in homologous DP107 domains resulting in an extended α-helix. This conformational change positions the fusion peptide for interaction with the cell membrane. In the second model (B; FIG. 11B), the fusogenic complex is stabilized by the association of the DP178 domain with the DP107 coiled-coil.

FIG. 12. Motif design using heptad repeat positioning of amino acids of known coiled-coils.

FIG. 13. Motif design using proposed heptad repeat positioning of amino acids of DP-107 and DP-178.

FIG. 14. Hybrid motif design crossing GCN4 and DP-107.

FIG. 15. Hybrid motif design crossing GCN4 and DP-178.

FIG. 16. Hybrid motif design 107×178×4, crossing DP-107 and DP-178. This motif was found to be the most consistent at identifying relevant DP-107-like and DP-178-like peptide regions.

FIG. 17. Hybrid motif design ALLMOTI5, crossing GCN4, DP-107, and DP-178.

FIG. 18. Hybrid motif design crossing GCN4, DP-107, DP-178, c-Fos c-Jun, c-Myc, and Flu Loop 36.

FIG. 19. Motifs designed to identify N-terminal proline-leucine zipper motifs.

FIG. 20. Search results (SEQ ID NO:26) for HIV-1 (BRU isolate) envelope protein gp41. Sequence search motif designations: Spades (♠): 107×178×4; Hearts (♥) ALLMOTI5; Clubs (♣): PLZIP; Diamonds (♦): transmembrane region (the putative transmembrane domains were identified using a PC/Gene program designed to search for such peptide regions). Asterisk (*): Lupas method. The amino acid sequences identified by each motif are bracketed by the respective characters. Representative sequences chosen based on all searches are underlined and in bold. DP-107 and DP-178 sequences are marked, and additionally double-underlined and italicized.

FIG. 21. Search results (SEQ ID NO:27) for human respiratory syncytial virus (RSV) strain A2 fusion glycoprotein F1. Sequence search motif designations are as in FIG. 20.

FIG. 22. Search results (SEQ ID NO:28) for simian immunodeficiency virus (SIV) envelope protein gp41 (AGM3 isolate). Sequence search motif designations are as in FIG. 20.

FIG. 23. Search results (SEQ ID NO:29) for canine distemper virus (strain Onderstepoort) fusion glycoprotein 1. Sequence search motif designations are as in FIG. 20.

FIG. 24. Search results (SEQ ID NO:30) for newcastle disease virus (strain Australia-Victoria/32) fusion glycoprotein F1. Sequence search motif designations are as in FIG. 20.

FIG. 25. Search results (SEQ ID NO:31) for human parainfluenza 3 virus (strain NIH 47885) fusion glycoprotein F1. Sequence search motif designations are as in FIG. 20.

FIG. 26. Search results (SEQ ID NO:32) for influenza A virus (strain A/AICHI/2/68) hemagglutinin precursor HA2. Sequence search designations are as in FIG. 20.

FIG. 27. Coiled-coil structural similarity and anti-RSV antiviral activity of 35-mer peptides synthesized utilizing the sequence of a 48-amino acid RSV F2 peptide (SEQ ID NO:33) which spans sequences identified utilizing the computer-assisted searches described herein. For the exact location and motifs utilized, see FIG. 21. "+" symbols are relative indicators of either structural similarity or antiviral activity, with a greater number of "+" symbols indicating a higher relative similarity or antiviral activity.

FIG. 28. Coiled-coil structural similarity and anti-RSV antiviral activity of 35-mer peptides synthesized utilizing the sequence of a 53-amino acid RSV F1 peptide (SEQ ID NO:34) which spans sequences identified utilizing the computer-assisted searches described herein. See FIG. 21 for the exact location and motifs used. "+" symbols are as described for FIG. 27.

FIG. 29. Coiled-coil structural similarity and anti-human parainfluenza 3 virus (HPF3) antiviral activity of 35-mer peptides synthesized utilizing the sequence of a 56-amino acid HPF3 peptide (SEQ ID NO:35) which spans sequences identified utilizing computer-assisted searches described herein. For the exact location and motifs utilized, see FIG. 25. "+" symbols are as described in FIG. 27.

FIG. 30. Coiled-coil structural similarity and anti-HPF3 antiviral activity of 35-mer peptides synthesized utilizing the sequence of a 70-amino acid HPF3 peptide (SEQ ID NO:36) which spans sequences identified utilizing the computer-assisted searches described herein. For the exact location and motifs utilized, see FIG. 25. "+" symbols are as described in FIG. 27.

5. DETAILED DESCRIPTION OF THE INVENTION

Described herein are peptides that exhibit potent antiviral activity. These peptides include DP-178 (SEQ ID:1), a gp41-derived 36 amino acid peptide, fragments and/or analogs of DP-178, and peptides which are homologous to DP-178. In addition, these peptides may include peptides exhibiting anti-viral activity which are analogous to DP-107, a 38 amino acid peptide corresponding to residues 558 to 595 of the HIV-1$_{LAI}$ transmembrane (TM) gp41 protein, and which are present in other enveloped viral proteins. Also described here are assays for testing the antiviral activities of such peptides. The present invention is based, in part, of the surprising discovery that the DP-107 and DP-178 domains of the gp41 protein complex with each other via non-covalent protein-protein interactions which are necessary for normal activity of the virus. As such, methods are described for the identification of antiviral compounds that disrupt the interaction between DP-107 and DP-178 peptides, and between DP-107-like and DP-178-like peptides. Finally, the use of the peptides of the invention as inhibitors of non-human and human viral and retroviral, especially HIV, transmission are detailed, as is the use of the peptides as diagnostic indicators of the presence of specific, viruses, especially retroviruses.

While not limited to any theory of operation, the following model is proposed to explain the potent anti-HIV activity of DP178, based, in part, on the experiments described in the working examples, infra. In the viral protein, gp41, DP178 corresponds to a putative α-helix region located in the C-terminal end of the gp41 ectodomain, and appears to associate with a distal site on gp41 whose interactive structure is influenced by the leucine zipper motif, a coiled-coil structure, referred to as DP107. The association of these two domains may reflect a molecular linkage or "molecular clasp" intimately involved in the fusion process. It is of interest that mutations in the C-terminal α-helix motif of gp41 (i.e., the D178 domain) tend to enhance the fusion ability of gp41, whereas mutations in the leucine zipper region (i.e., the DP107 domain) decrease or abolish the fusion ability of the viral protein. It may be that the leucine zipper motif is involved in membrane fusion while the C-terminal α-helix motif serves as a molecular safety to regulate the availability of the leucine zipper during virus-induced membrane fusion.

On the basis of the foregoing, two models are proposed of gp41-mediated membrane fusion which are schematically shown in FIG. 11A–B. The reason for proposing two models is that the temporal nature of the interaction between the regions defined by DP 107 and DP178 cannot, as yet, be pinpointed. Each model envisions two conformations for gp41-one in a "native" state as it might be found on a resting virion. The other in a "fusogenic" state to reflect conformational changes triggered following binding of gp120 to CD4 and just prior to fusion with the target cell membrane. The strong binding affinity between gp120 and CD4 may actually represent the trigger for the fusion process obviating the need for a pH change such as occurs for viruses that fuse within intracellular vesicles. The two major features of both models are: (1) the leucine zipper sequences (DP107) in each chain of oligomeric envelope are held apart in the native state and are only allowed access to one another in the fusogenic state so as to form the extremely stable coiled-coils, and (2) association of the DP178 and DP107 sites as they exist in gp41 occur either in the native or fusogenic state. FIG. 11A depicts DP178/DP107 interaction in the native state as a molecular class. On the other hand, if one assumes that the most stable form of the envelope occurs in the fusogenic state, the model in FIG. 11B can be considered.

When synthesized as peptides, both DP107 and DP178 are potent inhibitors of HIV infection and fusion, probably by virtue of their ability to form complexes with viral gp41 and interfere with its fusogenic process; e.g., during the structural transition of the viral protein from the native structure to the fusogenic state, the DP178 and DP107 peptides may gain access to their respective binding sites on the viral gp41, and exert a disruptive influence. DP107 peptides which demonstrate anti-HIV activity are described in-Applicants' co-pending application Ser. No. 07/927,532, filed Aug. 7, 1992, which is incorporated by reference herein in its entirety.

As shown in the working examples, infra, a truncated recombinant gp41 protein corresponding the ectodomain of gp41 containing both DP107 and DP178 domains (excluding the fusion peptide, transmembrane region and cytoplasmic domain of gp41) did not inhibit HIV-1 induced fusion. However, when a single mutation was introduced to disrupt the coiled-coil structure of the DP107 domain—a mutation which results in a total loss of biological activity of DP107 peptides—the inactive recombinant protein was transformed to an active inhibitor of HIV-1 induced fusion. This transformation may result from liberation of the potent DP178 domain from a molecular clasp with the leucine zipper, DP107 domain.

For clarity of discussion, the invention will be described for DP178 peptide inhibitors of HIV. However, the principles may be analogously applied to other fusogenic enveloped viruses, including but not limited to those viruses containing the peptides listed in Tables V through X, below.

5.1. DP-178 and DP-178-like Peptides

The peptide DP-178 (SEQ ID:1) of the invention corresponds to amino acid residues 638 to 673 of the transmembrane protein gp41 from the HIV-1$_{LAI}$ isolate, and has the 36 amino acid sequence (reading from amino to carboxy terminus):

NH$_2$-YTSLIHSLIEESQNQQEKNEQELLELDKWASLWN-WF-COOH (SEQ ID: 1)

In addition to the full-length DP-178 (SEQ ID:1) 36-mer, the peptides of the invention may include truncations of the DP-178 (SEQ ID:1) peptide which exhibit antiviral activity. Such truncated DP-178 (SEQ ID:1) peptides may comprise peptides of between 3 and 36 amino acid residues (i.e., peptides ranging in size from a tripeptide to a 36-mer polypeptide), and may include but are not limited to those listed in Tables I and II, below. Peptide sequences in these tables-are listed from amino (left) to carboxy (right) terminus. "X" may represent an amino group (—NH$_2$) and "Z"

may represent a carboxyl (—COOH) group. Alternatively, as described below, "X" and/or "Z" may represent a hydrophobic group, an acetyl group, a FMOC group, an amido group, or a covalently attached macromolecule.

TABLE I

DP-178 (SEQ ID:1) CARBOXY TRUNCATIONS

X-YTS-Z
X-YTSL-Z
X-YTSLI-Z
X-YTSLIH-Z
X-YTSLIHS-Z
X-YTSLIHSL-Z
X-YTSLIHSLI-Z
X-YTSLIHSLIE-Z
X-YTSLIHSLIEE-Z
X-YTSLIHSLIEES-Z
X-YTSLIHSLIEESQ-Z
X-YTSLIHSLIEESQN-Z
X-YTSLIHSLIEESQNQ-Z
X-YTSLIHSLIEESQNQQ-Z
X-YTSLIHSLIEESQNQQE-Z
X-YTSLIHSLIEESQNQQEK-Z
X-YTSLIHSLIEESQNQQEKN-Z
X-YTSLIHSLIEESQNQQEKNE-Z
X-YTSLIHSLIEESQNQQEKNEQ-Z
X-YTSLIHSLIEESQNQQEKNEQE-Z
X-YTSLIHSLIEESQNQQEKNEQEL-Z
X-YTSLIHSLIEESQNQQEKNEQELL-Z
X-YTSLIHSLIEESQNQQEKNEQELLE-Z
X-YTSLIHSLIEESQNQQEKNEQELLEL-Z
X-YTSLIHSLIEESQNQQEKNEQELLELD-Z
X-YTSLIHSLIEESQNQQEKNEQELLELDK-Z
X-YTSLIHSLIEESQNQQEKNEQELLELDKW-Z
X-YTSLIHSLIEESQNQQEKNEQELLELDKWA-Z
X-YTSLIHSLIEESQNQQEKNEQELLELDKWAS-Z
X-YTSLIHSLIEESQNQQEKNEQELLELDKWASL-Z
X-YTSLIHSLIEESQNQQEKNEQELLELDKWASLW-Z
X-YTSLIHSLIEESQNQQEKNEQELLELDKWASLWN-Z
X-YTSLIHSLIEESQNQQEKNEQELLELDKWASLWNW-Z
X-YTSLIHSLIEESQNQQEKNEQELLELDKWASLWNWF-Z

The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethoxy-carbonyl (FMOC) group; a macromolecular carrier group including but not limited to lipid-fatty acid conjugates, polyethylene glycol, or carbohydrates.
"Z" may represent a carboxyl group; an amido group; a T-butyloxycarbonyl group; a macromolecular carrier group including but not limited to lipid-fatty acid conjugates, polyethylene glycol, or carbohydrates.

TABLE II

DP-178 (SEQ ID:1) AMINO TRUNCATIONS

X-NWF-Z
X-WNWF-Z
X-LWNWF-Z
X-SLWNWF-Z
X-ASLWNWF-Z
X-WASLWNWF-Z
X-KWASLWNWF-Z
X-DKWASLWNWF-Z
X-LDKWASLWNWF-Z
X-ELDKWASLWNWF-Z
X-LELDKWASLWNWF-Z
X-LLELDKWASLWNWF-Z
X-ELLELDKWASLWNWF-Z
X-QELLELDKWASLWNWF-Z
X-EQELLELDKWASLWNWF-Z
X-NEQELLELDKWASLWNWF-Z
X-KNEQELLELDKWASLWNWF-Z

TABLE II-continued

DP-178 (SEQ ID:1) AMINO TRUNCATIONS

X-EKNEQELLELDKWASLWNWF-Z
X-QEKNEQELLELDKWASLWNWF-Z
X-QQEKNEQELLELDKWASLWNWF-Z
X-NQQEKNEQELLELDKWASLWNWF-Z
X-QNQQEKNEQELLELDKWASLWNWF-Z
X-SQNQQEKNEQELLELDKWASLWNWF-Z
X-ESQNQQEKNEQELLELDKWASLWNWF-Z
X-EESQNQQEKNEQELLELDKWASLWNWF-Z
X-IEESQNQQEKNEQELLELDKWASLWNWF-Z
X-LIEESQNQQEKNEQELLELDKWASLWNWF-Z
X-SLIEESQNQQEKNEQELLELDKWASLWNWF-Z
X-HSLIEESQNQQEKNEQELLELDKWASLWNWF-Z
X-IHSLIEESQNQQEKNEQELLELDKWASLWNWF-Z
X-LIHSLIEESQNQQEKNEQELLELDKWASLWNWF-Z
X-SLIHSLIEESQNQQEKNEQELLELDKWASLWNWF-Z
X-TSLIHSLIEESQNQQEKNEQELLELDKWASLWNWF-Z
X-YTSLIHSLIEESQNQQEKNEQELLELDKWASLWNWF-Z

The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethoxy-carbonyl group; a macromolecular carrier group including but not limited to lipid-fatty acid conjugates, polyethylene glycol, or carbohydrates.
"Z" may represent a carboxyl group; an amido group; a T-butyloxycarbonyl group; a macromolecular carrier group including but not limited to lipid-fatty acid conjugates, polyethylene glycol, or carbohydrates.

The antiviral peptides of the invention also include analogs of DP-178 and/or DP-178 truncations which may include, but are not limited to, peptides comprising the DP-178 (SEQ ID:1) sequence, or DP-178 truncated sequence, containing one or more amino acid substitutions, insertions and/or deletions. Analogs of DP-178 homologs, described below, are also within the scope of the invention. The DP-178 analogs of the invention exhibit antiviral activity, and may, further, possess additional advantageous features, such as, for example, increased bioavailability, and/or stability, or reduced host immune recognition.

HIV-1 and HIV-2 envelope proteins are structurally distinct, but there exists a striking amino acid conservation within the DP-178-corresponding regions of HIV-1 and HIV-2. The amino acid conservation is of a periodic nature, suggesting some conservation of structure and/or function. Therefore, one possible class of amino acid substitutions would include those amino acid changes which are predicted to stabilize the structure of the DP-178 peptides of the invention.

Amino acid substitutions may be of a conserved or non-conserved nature. Conserved amino acid substitutions consist of replacing one or more amino acids of the DP-178 (SEQ ID:1) peptide sequence with amino acids of similar charge, size, and/or hydrophobicity characteristics, such as, for example, a glutamic acid (E) to aspartic acid (D) amino acid substitution. When only conserved substitutions are made, the resulting peptide is functionally equivalent to DP-178 (SEQ ID:1) or the DP-178 peptide from which it is derived. Non-conserved substitutions consist of replacing one or more amino acids of the DP-178 (SEQ ID:1) peptide sequence with amino acids possessing dissimilar charge, size, and/or hydrophobicity characteristics, such as, for example, a glutamic acid (E) to valine (V) substitution.

Amino acid insertions may consist of single amino acid residues or stretches of residues ranging from 2 to 15 amino acids in length. One or more insertions may be introduced into DP-178 (SEQ ID:1), DP-178 fragments, analogs and/or DP-178 homologs (described below).

Deletions of DP-178 (SEQ ID:1), DP-178 fragments, analogs, and/or DP-178 homologs (described below) are also within the scope of the invention. Such deletions consist of the removal of one or more amino acids from the DP-178 or DP-178-like peptide sequence, with the lower limit length of the resulting peptide sequence being 4 to 6 amino acids. Such deletions may involve a single contiguous or greater than one discrete portion of the peptide sequences.

The peptides of the invention may further include homologs of DP-178 (SEQ ID:1) and/or DP-178 truncations which exhibit antiviral activity. Such DP-178 homologs are peptides whose amino acid sequences are comprised of the amino acid sequences of peptide regions of other (i.e., other than HIV-1$_{LAI}$) viruses that correspond to the gp41 peptide region from which DP-178 (SEQ ID:1) was derived. Such viruses may include, but are not limited to, other HIV-1 isolates and HIV-2 isolates. DP-178 homologs derived from the corresponding gp41 peptide region of other (i.e., non HIV-1$_{LAI}$) HIV-1 isolates may include, for example, peptide sequences as shown below.

NH$_2$-YT<u>NTI</u>YTL
LEESQNQQEKNEQELLELDKWASLWNWF-COOH
(DP-185; SEQ ID:3);

NH$_2$-YT<u>GII</u>YNL
LEESQNQQEKNEQELLELDKWA<u>N</u>LWNWF-COOH
(SEQ ID:4);

NH$_2$-YTSL<u>IYSL</u>LE
KSQIQQEKNEQELLELDKWASLWNWF-COOH
(SEQ ID:5).

SEQ ID:3 (DP-185), SEQ ID:4, and SEQ ID:5 are derived from-HIV-1$_{SF2}$, HIV-1$_{RF}$, and HIV-1$_{MN}$ isolates, respectively. Underlined amino acid residues refer to those residues that differ from the corresponding position in the DP-178 (SEQ ID:1) peptide. One such DP-178 homolog, DP-185 (SEQ ID:3), is described in the Working Example presented in Section 6, below, where it is demonstrated that DP-185 (SEQ ID:3) exhibits antiviral activity. The DP-178 homologs of the invention may also include truncations, amino acid substitutions, insertions, and/or deletions, as described above.

In addition, striking similarities, as shown in FIG. 1, exist within the regions of HIV-1 and HIV-2 isolates which correspond to the DP-178 sequence. A DP-178 homolog derived from the HIV-2$_{NIHZ}$ isolate has the 36 amino acid sequence (reading from amino to carboxy terminus):

NH$_2$-
LEANISQSLEQAQIQQEKNMYELQKLNSWDVFTN-
WL-COOH (SEQ ID:7)

Table III and Table IV show some possible truncations of the HIV-2$_{NIHZ}$ DP-178 homolog, which may comprise peptides of between 3 and 36 amino acid residues (i.e., peptides ranging in size from a tripeptide to a 36-mer polypeptide). Peptide sequences in these tables are listed from amino (left) to carboxy (right) terminus. "X" may represent an amino group (—NH$_2$) and "Z" may represent a carboxyl (—COOH) group. Alternatively, as described below, "X" and/or "Z" may represent a hydrophobic group, an acetyl group, a FMOC group, an amido group, or a covalently attached macromolecule, as described below.

TABLE III

HIV-2$_{NIHZ}$ DP-178 homolog carboxy truncations.

X-LEA-Z
X-LEAN-Z
X-LEANI-Z
X-LEANIS-Z
X-LEANISQ-Z
X-LEANISQS-Z
X-LEANISQSL-Z
X-LEANISQSLE-Z
X-LEANISQSLEQ-Z
X-LEANISQSLEQA-Z
X-LEANISQSLEQAQ-Z
X-LEANISQSLEQAQI-Z
X-LEANISQSLEQAQIQ-Z
X-LEANISQSLEQAQIQQ-Z
X-LEANISQSLEQAQIQQE-Z
X-LEANISQSLEQAQIQQEK-Z
X-LEANISQSLEQAQIQQEKN-Z
X-LEANISQSLEQAQIQQEKNM-Z
X-LEANISQSLEQAQIQQEKNMY-Z
X-LEANISQSLEQAQIQQEKNMYE-Z
X-LEANISQSLEQAQIQQEKNMYEL-Z
X-LEANISQSLEQAQIQQEKNMYELQ-Z
X-LEANISQSLEQAQIQQEKNMYELQK-Z
X-LEANISQSLEQAQIQQEKNMYELQKL-Z
X-LEANISQSLEQAQIQQEKNMYELQKLN-Z
X-LEANISQSLEQAQIQQEKNMYELQKLNS-Z
X-LEANISQSLEQAQIQQEKNMYELQKLNSW-Z
X-LEANISQSLEQAQIQQEKNMYELQKLNSWD-Z
X-LEANISQSLEQAQIQQEKNMYELQKLNSWDV-Z
X-LEANISQSLEQAQIQQEKNMYELQKLNSWDVF-Z
X-LEANISQSLEQAQIQQEKNMYELQKLNSWDVFT-Z
X-LEANISQSLEQAQIQQEKNMYELQKLNSWDVFTN-Z
X-LEANISQSLEQAQIQQEKNMYELQKLNSWDVFTNW-Z
X-LEANISQSLEQAQIQQEKNMYELQKLNSWDVFTNWL-Z

The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethoxy-carbonyl (FMOC) group; a macromolecular carrier group including but not limited to lipid-fatty acid conjugates, polyethylene glycol, or carbohydrates.
"Z" may represent a carboxyl group; an amido group; a T-butyloxycarbonyl group; a macromolecular carrier group including but not limited to lipid-fatty acid conjugates, polyethylene glycol, or carbohydrates.

TABLE IV

HIV-2$_{NIHZ}$ DP-178 homolog amino truncations.

X-NWL-Z
X-TNWL-Z
X-FTNWL-Z
X-VFTNWL-Z
X-DVFTNWL-Z
X-WDVFTNWL-Z
X-SWDVFTNWL-Z
X-NSWDVFTNWL-Z
X-LNSWDVFTNWL-Z
X-KLNSWDVFTNWL-Z
X-QKLNSWDVFTNWL-Z
X-LQKLNSWDVFTNWL-Z
X-ELQKLNSWDVFTNWL-Z
X-YELQKLNSWDVFTNWL-Z
X-MYELQKLNSWDVFTNWL-Z
X-NMYELQKLNSWDVFTNWL-Z
X-KNMYELQKLNSWDVFTNWL-Z
X-EKNMYELQKLNSWDVFTNWL-Z
X-QEKNMYELQKLNSWDVFTNWL-Z
X-QQEKNMYELQKLNSWDVFTNWL-Z
X-IQQEKNMYELQKLNSWDVFTNWL-Z
X-QIQQEKNMYELQKLNSWDVFTNWL-Z

TABLE IV-continued

HIV-2$_{NIHZ}$ DP-178 homolog amino truncations.

```
        X-AQIQQEKNMYELQKLNSWDVFTNWL-Z
        X-QAQIQQEKNMYELQKLNSWDVFTNWL-Z
        X-EQAQIQQEKNMYELQKLNSWDVFTNWL-Z
        X-LEQAQIQQEKNMYELQKLNSWDVFTNWL-Z
        X-SLEQAQIQQEKNMYELQKLNSWDVFTNWL-Z
        X-QSLEQAQIQQEKNMYELQKLNSWDVFTNWL-Z
        X-SQSLEQAQIQQEKNMYELQKLNSWDVFTNWL-Z
        X-ISQSLEQAQIQQEKNMYELQKLNSWDVFTNWL-Z
        X-NISQSLEQAQIQQEKNMYELQKLNSWDVFTNWL-Z
       X-ANISQSLEQAQIQQEKNMYELQKLNSWDVFTNWL-Z
      X-EANISQSLEQAQIQQEKNMYELQKLNSWDVFTNWL-Z
     X-LEANISQSLEQAQIQQEKNMYELQKLNSWDVFTNWL-Z
```

The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethoxy-carbonyl (FMOC) group; a macromolecular carrier group including but not limited to lipid-fatty acid conjugates, polyethylene glycol, or carbohydrates.
"Z" may represent a carboxyl group; an amido group; a T-butyloxycarbonyl group; a macromolecular carrier group including but not limited to lipid-fatty acid conjugates, polyethylene glycol, or carbohydrates.

5.2. DP-107 and DP-178 Analogous Antiviral Peptides

Peptide sequences functionally corresponding, and thus analogous to, the DP-178 sequences of the invention, described, above, in Section 5.1 may be found in other, non-HIV-1 envelope viruses. Further, peptide sequences functionally corresponding, and thus analogous to, DP-107, an HIV-1-derived antiviral peptide, may also be found in other, non-HIV-1 envelope viruses. DP-107 is a 38 amino acid peptide corresponding to residues 558 to 595 of HIV-1$_{LAI}$ transmembrane (TM) gp41 protein, which exhibits potent anti-viral activity. DP-107 is more fully described in Applicant's co-pending U.S. patent application Ser. No. 07/927,532. These DP-107-like and DP-178-like analogous peptides and present in TM proteins of envelope viruses and preferably exhibit antiviral activity, most preferably antiviral activity which is specific to the virus in which their native sequences are found.

DP-107-like and DP-178-like peptides may be identified, for example, by utilizing a computer-assisted search strategy such as that described and demonstrated, below, in the Examples presented in Sections 9 through 16. The search strategy identifies regions in other viruses that are similar in predicted secondary structure to DP-107 and DP-178.

This search strategy is described fully, below, in the Example presented in Section 9. While this search strategy is based, in part, on a primary amino acid motif deduced from DP-107 and DP-178, it is not based solely on searching for primary amino acid sequence homologies, as such protein sequence homologies exist within, but not between major groups of viruses. For example, primary amino acid sequence homology is high within the TM protein of different strains of HIV-1 or within the TM protein of different isolates of simian immunodeficiency virus (SIV). Primary amino acid sequence homology between HIV-1 and SIV, however, is low enough so as not to be useful. It is not possible, therefore, to find DP-107 or DP-178-like peptides within other viruses, whether structurally, or otherwise, based on primary sequence homology, alone.

Further, while it would be potentially useful to identify primary sequence arrangements of amino acids based on the physical chemical characteristics of different classes of amino acids rather than based on the specific amino acids themselves, for instance, a by concentrating on the coiled-coil nature of the peptide sequence, a computer algorithm designed by Lupas et al. to identify such coiled-coil propensities of regions within proteins (Lupas, A., et al., 1991 Science 252:1162–1164) is inadequate for identifying protein regions analogous to DP-107 or DP-178.

Specifically, analysis of HIV-1 gp160(containing both gp120 and gp41) using the Lupas algorithm does not identify the coiled-coil region within DP-107. It does, however, identify a region within DP-178 beginning eight amino acids N-terminal to the start of DP-178 and ending eight amino acids from the C-terminus. The DP-107 peptide has been shown experimentally to form a stable coiled coil. A search based on the Lupas search algorithm, therefore, would not have identified the DP-107 coiled-coil region. Conversely, the Lupas algorithm identified the DP-178 region a a potential coiled-coil motif. However, the peptide DP-178 derived from this region failed to form a coiled coil in solution. A possible explanation for the inability of the Lupas search algorithm to accurately identify coiled-coil sequences within the HIV-1 TM, is that the Lupas algorithm is based on the structure of coiled coils from proteins that are not structurally or functionally similar to the TM proteins of viruses, antiviral peptides (e.g. DP-107 and DP-178) of which are an object of this invention.

The computer search strategy of the invention, as demonstrated in the Examples presented below, in Sections 9 through 16, successfully identifies regions of viral TM proteins similar to DP-107 or DP-178. This search strategy was designed to be used with a commercially-available sequence database packages, preferably PC/Gene. A series of motifs were designed and engineered to range in stringency from very strict to very broad, as discussed in Section 9.

Among the protein sequence search motifs which may be utilized in such a computer-assisted DP-107-like and DP-178-like antiviral peptide search are the 107×178×4 motif, the ALLMOTI5 motif, and the PLZIP series of motifs, each of which is described in the Example presented in Section 9, below, with 107×178×4 being preferred.

Coiled-coiled sequences are thought to consist of heptad amino acid repeats. For ease of description, the amino acid positions within the heptad repeats are sometimes referred to as A through G, with the first position being A, the second B, etc. The motifs used to identify DP-107-like and DP-178-like sequences herein are designed to specifically search for and identify such heptad repeats. In the descriptions of each of the motifs described, below, amino acids enclosed by brackets, i.e., [ ], designate the only amino acid residues that are acceptable at the given position, while amino acids enclosed by braces, i.e., { }, designate the only amino acids which are unacceptable at the given heptad position. When a set of bracketed or braced amino acids is followed by a number in parentheses i.e., ( ), it refers to the number of subsequent amino acid positions for which the designated set of amino acids hold, e.g., a (2) means "for the next two heptad amino acid positions".

The ALLMOTI5 is written as follows:

{CDGHP]-{CFP} (2)-{CDGHP}-{CFP} (3)-
{CDGHP]-{CFP} (2)-{CDGHP}-{CFP} (3)-
{CDGHP]-{CFP}(2)-{CDGHP} -{CFP}(3)-
{CDGHP]-{CFP} (2)-{CDGHP}-{CFP} (3)-
{CDGHP]-{CFP} (2)-{CDGHP}-{CFP} (3)-

Translating this motif, it would read: "at the first (A) position of the heptad, any amino acid residue except C, D, G, H, or P is acceptable, at the next two (B,C) amino acid positions, any amino acid residue except C, F, or P is acceptable, at the fourth heptad position (D), any amino acid residue except C, D, G, H, or P is acceptable, at the next three (E, F, G) amino acid positions, any amino acid residue except C, F, or P is acceptable". This motif is designed to search for five consecutive heptad repeats (thus the repeat of the first line five times), meaning that it searches for 35-mer sized peptides. It may also be designed to search for 28-mers, by only repeating the initial motif four times. With respect to the ALLMOTI5 motif, a 35-mer search is preferred. Those viral sequences identified via such an ALLMOTI5 motif are listed in Table V, below, at the end of this Section. The viral sequences listed in Table V potentially exhibit antiviral activity, may be useful in the identification of antiviral compounds, and are intended to be within the scope of the invention.

The 107×178×4 motif is written as follows:

[EFIKLNQSTVWY]-{CFMP} (2)-[EFIKLNQSTVWY]-{CFMP} (3)-

[EFIKLNQSTVWY]-{CFMP} (2)-[EFIKLNQSTVWY]-{CFMP} (3)-

[EFIKLNQSTVWY]-{CFMP} (2)-[EFIKLNQSTVWY]-{CFMP} (3)-

[EFIKLNQSTVWY]-{CFMP} (2)-[EFIKLNQSTVWY]-{CFMP} (3)-

Translating this mofif, it would read: "at the first (A) position of the heptad, any amino acid residue except E, F, I, K, L, N, Q, S, T, V, W, or Y is acceptable, at the next two (B,C) amino acid positions, any amino acid residue except C, F, M or P is accepatble, at the fourth position (D), any amino acid residue except E, F, I, K, L, N, Q, S, T, V, W, or Y is acceptable, at the next three (E, F, G) amino acid positions, any amino acid residue except C, F, M or P is acceptable". This motif is designed to search for four consecutive heptad repeats (thus the repeat of the first line four times), meaning that it searches for 28-mer sized peptides. It may also be designed to search for 35-mers, by repeating the initial motif five times. With respect to the 107×178×4 motif, a 28-mer search is preferred. Those viral sequences identified via such a 107×178×4 motif are listed in Table V, below, at the end of this is Section. The viral sequences listed in Table V potentially exhibit antiviral activity, may be useful in the the identification of antiviral compounds, and are intended to be within the scope of the invention.

The PLZIP series of motifs are as listed in FIG. 19. These motifs are designed to identify leucine zipper coiled-coil like heptads wherein at least one proline residue is present at some predefined distance N-terminal to the repeat. These PLZIP motifs find regions of proteins with similarities to HIV-1 DP-178 generally located just N-terminal to the transmembrane anchor. These motifs may be translated according to the same convention described above. Each line depicted in FIG. 19 represents a single, complete search motif. "X" in these motifs refers to any amino acid residue. In instances wherein a motif contains two numbers within parentheses, this refers to a variable number of amino acid residues. For example, X (1,12)is translated to "the next one to twelve amino acid residues, inclusive, may be any amino acid".

Tables VI through X, below, at the end of this Section, list hits from such PLZIP motifs. The viral sequences listed in Table VI through X potentially exhibit antiviral activity, may be useful in the the identification of antiviral compounds, and are intended to be within the scope of the invention.

The Examples presented in Sections 17 and 18, below, demonstrate that respiratory syncytial virus and parainfluenza virus sequences identified via such a computer search exhibit antiviral and/or structural characteristics similar to those of DP-107 or DP-178.

The DP-107-like and DP-178-like analogous peptides may, further, contain any of the additional groups described for DP-178, above, in Section 5.1. For example, these peptides may include any of the additional amino-terminal groups which "X"of Tables I through IV may represent, and may also include any of the carboxy-terminal groups which "Z" of Tables I through IV may represent.

Additionally, such DP-107-like and DP-178-like peptides may further include DP-107-like or DP-178-like peptides, such as those listed in Tables V through X, above, containing one or more amino acid substitutions, insertions, and/or deletions. Also, analogs of such DP-107-like and DP-178-like peptides are intended to be within the scope of the invention. Such analogs of the invention may exhibit increased antiviral activity, and may, further, posses increased bioavailability, and/or stability, or reduced immune recognition.

The DP-107-like and DP-178-like amino acid substitutions, insertions and deletions, are as described for DP-178, above, in Section 5.1. Analog modifications are as described, below, in Section 5.3.

TABLE V

Search Results Summary for 107 × 178 × 4 and ALLMOTI5 Motifs

| 107 × 178 × 4 LIBRARY FILE | | | | ALLMOTI5 LIBRARY FILE | | | | |
|---|---|---|---|---|---|---|---|---|
| PENV_AVIRE | 420–468 | | | PENV1_FRSFV | 341–375 | | | |
| PENV_AVISN | 426–474 | | | FENV2_FRSPV | 341–378 | | | |
| PENV_BAEVM | 395–452 | | | PENV_AVIRE | 420–472 | | | |
| PENV_BIV06 | 544–603 | 631–695 | | PENV_AVISN | 426–478 | | | |
| PENV_BIV27 | 573–632 | 660–724 | | PENV_BAEVM | 390–456 | | | |
| PENV_BLVAF | 304–377 | | | PENV_BIV06 | 530–610 | 635–695 | | |
| PENV_BLVAU | 304–377 | | | PENV_BIV27 | 559–639 | 664–724 | | |
| PENV_BLVAV | 304–377 | | | PENV_BLVAF | 304–379 | | | |
| PENV_BLVB2 | 311–377 | | | PENV_BLVAU | 304–379 | | | |
| PENV_BLVB5 | 304–377 | | | PENV_BLVAV | 304–379 | | | |
| PENV_BLVJ | 304–377 | | | PENV_BLVB2 | 304–379 | | | |
| PENV_CAEVG | 165–192 | | | PENV_BLVB5 | 304–379 | | | |
| PENV_EIAV1 | 688–712 | | | PENV_BLVJ | 304–379 | | | |
| PENV_EIAV2 | 668–695 | | | PENV_CAEVC | 157–196 | 615–720 | 751–785 | 847–895 |
| PENV_EIAV3 | 668–712 | | | PENV_CAEVG | 154–193 | 613–718 | 749–783 | 845–893 |
| PENV_EIAV5 | 669–696 | | | PENV_EIAV1 | 436–525 | 559–593 | 668–716 | |
| PENV_EIAV9 | 668–712 | | | PENV_EIAV2 | 436–525 | 559–593 | 658–692 | |
| PENV_EIAVC | 668–712 | | | PENV_EIAV3 | 436–525 | 559–593 | 658–716 | |
| PENV_EIAVW | 668–712 | | | PENV_EIAV5 | 437–526 | 560–594 | 659–693 | |
| PENV_EIAVY | 668–712 | | | PENV_EIAV9 | 436–525 | 559–593 | 658–716 | |
| PENV_FENV1 | 517–544 | | | PENV_EIAVC | 436–525 | 559–593 | 658–716 | |
| PENV_FIVPE | 650–680 | 722–749. | | PENV_EIAVW | 436–525 | 559–593 | 658–716 | |
| PENV_FIVSD | 639–668 | 720–747 | | PENV_EIAVY | 436–525 | 559–593 | 658–716 | |
| PENV_FIVT2 | 640–679 | 721–748 | | PENV_FENV1 | 503–555 | 567–604 | | |
| PENV_FLVC6 | 509–538 | | | PENV_FIVPE | 610–690 | 715–756 | | |
| PENV_FLVGL | 490–519 | | | PENV_FIV8D | 601–688 | 713–754 | | |
| PENV_FLVLB | 510–539 | | | PENV_FIVT2 | 609–689 | 714–755 | | |
| PENV_FLVSA | 487–516 | | | PENV_FLVC6 | 497–549 | 661–595 | | |
| PENV_FOAMV | 318–355 | 866–893 | | PENV_FLVGL | 478–530 | 542–576 | | |
| PENV_FSVGA | 510–539 | | | PENV_FLVLB | 498–550 | 562–598 | | |
| PENV_FSVGB | 490–519 | | | PENV_FLVSA | 475–527 | 539–573 | | |
| PENV_FSVSM | 493–522 | | | PENV_FOAMV | 321–355 | 563–693 | 866–903 | |
| PENV_GALV | 523–564 | | | PENV_FRSFB | 318–354 | | | |
| PENV_HTL1A | 342–376 | | | PENV_FSVGA | 498–550 | 562–596 | | |
| PENV_HTL1C | 342–376 | | | PENV_FSVGB | 476–530 | 542–576 | | |
| PENV_HTL1M | 342–376 | | | PENV_FSVSM | 481–524 | 545–579 | | |
| PENV_HTLV2 | 336–370 | | | PENV_FSVST | 498–532 | | | |
| PENV_HV1A2 | 544–592 | 630–682 | 790–825 | PENV_GALV | 523–575 | 587–621 | | |
| PENV_HV1B1 | 545–594 | 631–683 | 791–818 | PENV_HTL1A | 321–383 | | | |
| PENV_HV1B8 | 540–589 | 626–678 | 786–813 | PENV_HTL1C | 316–383 | | | |
| PENV_HV1BN | 582–590 | 628–679 | 787–815 | PENV_HTL1M | 321–383 | | | |
| PENV_HV1BR | 550–599 | 636–688 | 798–823 | PENV_HTLV2 | 317–377 | | | |
| PENV_HV1C4 | 557–608 | 643–695 | 803–835 | PENV_HV1A2 | 497–593 | 612–711 | 766–845 | |
| PENV_HV1EL | 543–591 | 628–680 | | PENV_HV1B1 | 509–594 | 610–712 | 767–843 | |
| PENV_HV1H2 | 545–594 | 631–683 | 791–818 | PENV_HV1B8 | 500–589 | 605–707 | 762–838 | |

TABLE V-continued

Search Results Summary for 107 × 178 × 4 and ALLMOT15 Motifs

| 107 × 178 × 4 LIBRARY FILE | | | | ALLMOT15 LIBRARY FILE | | | |
|---|---|---|---|---|---|---|---|
| PENV_HV1H3 | 545–594 | | 631–683 | 791–818 | PENV_HV1BN | 501–590 | 609–708 | 783–831 |
| PENV_HV1J3 | 556–605 | | 642–694 | 802–829 | PENV_HV1BR | 510–599 | 615–717 | 772–841 |
| PENV_HV1JR | | | 637–677 | 783–811 | PENV_HV1C4 | 510–806 | 626–724 | 779–855 |
| PENV_HV1KB | 555–596 | | 633–707 | 776–824 | PENV_HV1EL | 502–591 | 607–709 | 768–829 |
| PENV_HV1MA | 547–595 | | 629–681 | 794–826 | PENV_HV1H2 | 505–594 | 610–712 | 767–836 |
| PENV_HV1MF | 543–592 | | 632–684 | 789–816 | PENV_HV1H3 | 505–594 | 610–712 | 767–843 |
| PENV_HV1MN | 567–595 | | 621–673 | 791–819 | PENV_HV1J3 | 517–605 | 622–723 | 778–843 |
| PENV_HV1ND | 536–583 | | 630–704 | 783–813 | PENV_HV1JR | 497–586 | 603–704 | 759–835 |
| PENV_HV1OY | 544–593 | | 631–683 | 789–820 | PENV_HV1KB | 511–545 | 585–599 | 618–718 772–848 |
| PENV_HV1PV | 545–594 | | 640–692 | 791–818 | PENV_HV1MA | 507–596 | 617–714 | 770–825 |
| PENV_HV1RH | 554–602 | | 622–674 | 800–832 | PENV_HV1MF | 503–592 | 622–710 | 765–841 |
| PENV_HV181 | 536–585 | | 627–679 | 782–809 | PENV_HV1MN | 506–595 | 617–713 | 774–841 |
| PENV_HV183 | 541–589 | | | 787–815 | PENV_HV1ND | 495–584 | 801–702 | 757–825 |
| PENV_HV18C | 545–593 | | 631–683 | | PENV_HV1OY | 497–593 | 610–711 | 766–842 |
| PENV_HV1W1 | 545–593 | | 631–683 | 791–818 | PENV_HV1PV | 605–594 | 610–712 | 767–843 |
| PENV_HV1W2 | 538–584 | | 622–674 | 782–809 | PENV_HV1RH | 507–603 | 619–721 | 776–852 |
| PENV_HV1Z2 | 542–591 | | 628–680 | 790–820 | PENV_HV1S1 | 496–585 | 602–703 | 758–830 |
| PENV_HV1Z6 | 545–593 | | 630–682 | 792–622 | PENV_HV1S3 | 494–590 | 607–708 | 763–837 |
| PENV_HV1Z8 | 573–601 | | 634–678 | 797–828 | PENV_HV1SC | 498–594 | 611–712 | 767–834 |
| PENV_HV1ZH | 545–594 | | 627–666 | 791–823 | PENV_HV1W1 | 498–594 | 611–712 | 767–836 |
| PENV_HV2BE | 532–594 | | 621–648 | 653–697 | PENV_HV1W2 | 489–584 | 602–703 | 758–827 |
| PENV_HV2CA | 534–593 | | 623–650 | 655–699 | PENV_HV1Z2 | 502–591 | 607–709 | 764–831 |
| PENV_HV2D1 | 523–550 | | 555–582 | 644–688 | PENV_HV1Z6 | 504–593 | 609–711 | 766–840 |
| PENV_HV2G1 | 524–551 | | 555–583 | 613–640 645–693 | PENV_HV1Z8 | 512–601 | 617–675 | 682–719 |
| PENV_HV2NZ | 524–551 | | 556–583 | 613–640 662–889 | PENV_HV1ZH | 522–594 | 612–712 | 774–831 777–839 |
| PENV_HV2RO | 533–592 | | 622–698 | | PENV_HV2BE | 510–595 | 617–680 | |
| PENV_HV2S2 | 527–554 | | 559–586 | 648–682 | PENV_HV2CA | 512–597 | 619–709 | |
| PENV_HV2SB | 557–584 | | 614–673 | | PENV_HV2D1 | 501–586 | 608–698 | |
| PENV_HV2ST | 527–554 | | 559–586 | 648–692 | PENV_HV2G1 | 502–587 | 609–699 | |
| PENV_MCFF | 473–612 | | | | PENV_HV2NZ | 488–587 | 609–699 | |
| PENV_MCFF3 | 488–515 | | | | PENV_HV2RO | 511–596 | 616–708 | |
| PENV_MLVAV | 517–544 | | | | PENV_HV2S2 | 505–590 | 612–702 | |
| PENV_MLVCB | 510–539 | | | | PENV_HV2SB | 526–588 | 614–700 | |
| PENV_MLVF5 | 523–553 | | | | PENV_HV2ST | 505–590 | 612–702 | |
| PENV_MLVFF | 523–553 | | | | PENV_IPMAE | 367–422 | 465–527 | |
| PENV_MLVFP | 523–553 | | | | PENV_JSRV | 403–455 | 571–605 | |
| PENV_MLVHO | 510–540 | | | | PENV_MCFF | 473–525 | 537–571 | |
| PENV_MLVKI | 40–81 | | | | PENV_MCFF3 | 474–526 | 538–572 | |
| PENV_MLVMO | 502–543 | | | | PENV_MLVAV | 503–555 | 567–601 | |
| PENV_MLVRD | 497–538 | | | | PENV_MLVCB | 498–550 | 562–596 | |
| PENV_MLVRK | 497–538 | | | | PENV_MLVF5 | 520–564 | 576–610 | |
| PENV_MMTVB | 458–485 | | 562–589 | | PENV_MLVFF | 520–564 | 576–610 | |
| PENV_MMTVG | 458–465 | | 562–589 | | PENV_MLVFP | 520–564 | 576–610 | |
| PENV_MPMV | 422–470 | | | | PENV_MLVHO | 504–551 | 563–597 | |
| PENV_MSVFB | 57–84 | | | | PENV_MLVKI | 40–92 | 104–138 | |
| PENV_OMVVS | 42–69 | | 196–223 | 780–807 | PENV_MLVMO | 502–554 | 566–600 | |

TABLE V-continued

Search Results Summary for 107 × 178 × 4 and ALLMOTI5 Motifs

| 107 × 178 × 4 LIBRARY FILE | | | | | ALLMOTI5 LIBRARY FILE | | | | | | | |
|---|---|---|---|---|---|---|---|---|---|---|---|---|
| PENV_RMCFV | 487–517 | | | | PENV_MLVRD | 497–549 | 551–595 | | | | | |
| PENV_SFV1 | 14–41 | 866–901 | | | PENV_MLVRK | 497–549 | 561–598 | | | | | |
| PENV_SFV3L | 18–45 | 319–357 | 673–700 | 863–898 | PENV_MMTVB | 477–539 | 556–612 | | | | | |
| PENV_SIVA1 | 661–588 | 592–619 | 652–679 | 697–724 | PENV_MMTVG | 477–539 | 556–612 | | | | | |
| PENV_SIVAG | 566–593 | 597–624 | 658–685 | 703–730 | PENV_MPMV | 408–474 | | | | | | |
| PENV_SIVAI | 548–603 | 634–708 | | | PENV_MSVFB | 43–95 | 107–141 | | | | | |
| PENV_SIVAT | 590–617 | 651–678 | | | PENV_OMVVS | 22–64 | 185–223 | 664–746 | 780–816 | | | |
| PENV_SIVCZ | 526–584 | 627–654 | | | PENV_RMCFV | 484–528 | 540–574 | | | | | |
| PENV_SIVGB | 589–650 | 784–816 | | | PENV_RSFFV | 342–376 | | | | | | |
| PENV_SIVM1 | 550–609 | 671–715 | | | PENV_SFV1 | 1–41 | 101–140 | 154–205 | 321–355 | 563–651 | 658–693 | 866–904 |
| PENV_SIVM2 | 156–215 | 277–289 | | | PENV_SFV3L | 5–46 | 158–209 | 319–357 | 560–706 | 863–901 | | |
| PENV_SIVMK | 553–608 | | | | PENV_SIVA1 | 269–310 | 551–823 | 643–693 | | | | |
| PENV_SIVML | 549–608 | | | | PENV_SIVAG | 558–628 | 651–899 | 808–852 | | | | |
| PENV_SIVS4 | 553–612 | 642–669 | 691–718 | | PENV_SIVAI | 257–291 | 336–370 | 535–607 | 627–684 | 792–840 | | |
| PENV_SIVSP | 554–595 | 646–722 | | | PENV_SIVAT | 264–298 | 549–621 | 644–692 | 796–833 | | | |
| PENV_SMRVH | 400–462 | | | | PENV_SIVCZ | 283–291 | 330–365 | 512–584 | 669–703 | 803–837 | | |
| PENV_SRV1 | 409–471 | | | | PENV_SIVGB | 586–654 | 677–725 | | | | | |
| PENV_VILV | 773–800 | | | | PENV_SIVM1 | 114–151 | 465–506 | 528–613 | 635–725 | 809–864 | | |
| PENV_VILV1 | 780–807 | | | | PENV_SIVM2 | 71–116 | 134–219 | 245–331 | | | | |
| PENV_VILV2 | 782–809 | | | | PENV_SIVMK | 464–505 | 540–812 | 638–724 | | | | |
| PHEMA_CVBLY | 208–242 | | | | PENV_SIVML | 464–505 | 540–612 | 638–724 | | | | |
| PHEMA_CVBM | 208–242 | | | | PENV_SIVS4 | 466–509 | 517–616 | 638–728 | 812–853 | | | |
| PHEMA_CVBQ | 208–242 | | | | PENV_SIVSP | 470–513 | 521–620 | 642–732 | 811–848 | | | |
| PHEMA_CVHOC | 208–242 | | | | PENV_SMRVH | 400–466 | | | | | | |
| PHEMA_IAAIC | 387–453 | | | | PENV_SRV1 | 409–475 | | | | | | |
| PHEMA_IABAN | 371–437 | | | | PENV_VILV | 21–62 | 184–222 | 637–740 | 773–809 | | | |
| PHEMA_IABUD | 381–451 | | | | PENV_VILV1 | 21–62 | 184–222 | 643–746 | 780–816 | | | |
| PHEMA_IACKA | 381–451 | | | | PENV_VILV2 | 21–62 | 184–222 | 645–748 | 782–818 | | | |
| PHEMA_IACKG | 382–441 | 494–528 | | | PHEMA_CVBLY | 208–242 | | | | | | |
| PHEMA_IACKP | 396–426 | | | | PHEMA_CVBM | 208–242 | | | | | | |
| PHEMA_IACKG | 396–426 | | | | PHEMA_CVBQ | 208–242 | | | | | | |
| PHEMA_IACKV | 384–443 | | | | PHEMA_CVHOC | 208–242 | | | | | | |
| PHEMA_IADA1 | 381–451 | | | | PHEMA_IAAIC | 380–458 | | | | | | |
| PHEMA_IADA2 | 423–453 | 499–543 | | | PHEMA_IABAN | 364–440 | | | | | | |
| PHEMA_IADA3 | 387–453 | | | | PHEMA_IABUD | 378–454 | | | | | | |
| PHEMA_IADA4 | 418–478 | | | | PHEMA_IACKA | 378–454 | | | | | | |
| PHEMA_IADCZ | 381–451 | | | | PHEMA_IACKG | 108–142 | 375–475 | 494–528 | | | | |
| PHEMA_IADE1 | 402–453 | 506–533 | | | PHEMA_IACKP | 360–452 | 487–532 | | | | | |
| PHEMA_IADH1 | 371–437 | | | | PHEMA_IACKQ | 360–452 | 487–532 | | | | | |
| PHEMA_IADH2 | 371–437 | | | | PHEMA_IACKS | 377–469 | 504–549 | | | | | |
| PHEMA_IADH3 | 371–437 | | | | PHEMA_IACKV | 112–146 | 377–469 | | | | | |
| PHEMA_IADH4 | 371–437 | | | | PHEMA_IADA1 | 377–454 | | | | | | |
| PHEMA_IADH5 | 371–437 | | | | PHEMA_IADA2 | 377–476 | 495–547 | | | | | |
| PHEMA_IADH6 | 371–437 | | | | PHEMA_IADA3 | 380–453 | | | | | | |
| PHEMA_IADH7 | 371–437 | | | | PHEMA_IADA4 | 379–478 | 506–548 | | | | | |
| PHEMA_IADIR | 415–446 | | | | PHEMA_IADCZ | 378–454 | | | | | | |

TABLE V-continued

Search Results Summary for 107 × 178 × 4 and ALLMOTI5 Motifs

| 107 × 178 × 4 LIBRARY FILE | | ALLMOTI5 LIBRARY FILE | | |
|---|---|---|---|---|
| PHEMA_IADM2 | 387–453 | PHEMA_IADE1 | 21–55 | 377–472 |
| PHEMA_IADNZ | 381–451 | PHEMA_IADH1 | 364–440 | |
| PHEMA_IADU3 | 387–453 | PHEMA_IADH2 | 364–440 | |
| PHEMA_IAEN7 | 387–453 | PHEMA_IADH3 | 364–440 | |
| PHEMA_IAFPR | 384–442 | PHEMA_IADH4 | 364–440 | |
| PHEMA_IAGRE | 381–451 | PHEMA_IADH5 | 364–440 | |
| PHEMA_IAGU2 | 505–532 | PHEMA_IADH6 | 364–440 | |
| PHEMA_IAGUA | 504–531 | PHEMA_IADH7 | 364–440 | |
| PHEMA_IAHAL | 386–452 | PHEMA_IADIR | 379–471 | |
| PHEMA_IAHC6 | 388–457 | PHEMA_IADM1 | 21–55 | 506–551 |
| PHEMA_IAHC7 | 388–457 | PHEMA_IADM2 | 380–456 | |
| PHEMA_IAHCD | 388–457 | PHEMA_IADNY | 21–55 | |
| PHEMA_IAHDE | 388–457 | PHEMA_IADNZ | 378–454 | |
| PHEMA_IAHFO | 386–452 | PHEMA_IADU1 | 21–55 | |
| PHEMA_IAHK6 | 386–452 | PHEMA_IADU3 | 380–456 | |
| PHEMA_IAHK7 | 388–457 | PHEMA_IAEN7 | 380–456 | |
| PHEMA_IAHLE | 388–457 | PHEMA_IAFPR | 377–477 | |
| PHEMA_IAHLO | 388–457 | PHEMA_IAGRE | 378–454 | |
| PHEMA_IAHMI | 386–452 | PHEMA_IAGU2 | 378–473 | |
| PHEMA_IAHNM | 386–452 | PHEMA_IAGUA | 377–476 | |
| PHEMA_IAHNN | 388–457 | PHEMA_IAHAL | 379–455 | |
| PHEMA_IAHPR | 388–457 | PHEMA_IAHC6 | 112–146 | 360–484 | 503–537 |
| PHEMA_IAHRO | 386–452 | PHEMA_IAHC7 | 112–146 | 360–484 | 503–537 |
| PHEMA_IAHSA | 386–452 | PHEMA_IAHCD | 360–484 | 503–537 |
| PHEMA_IAHSP | 388–457 | PHEMA_IAHDE | 360–484 | 503–537 |
| PHEMA_IAHSW | 388–457 | PHEMA_IAHFO | 379–455 | |
| PHEMA_IAHTE | 386–452 | PHEMA_IAHK6 | 379–455 | |
| PHEMA_IAHTO | 386–455 | PHEMA_IAHK7 | 379–455 | |
| PHEMA_IAHUR | 386–452 | PHEMA_IAHLE | 112–146 | 360–484 | 503–537 |
| PHEMA_IAKIE | 425–478 | PHEMA_IAHLO | 112–146 | 360–484 | 503–537 |
| PHEMA_IALEN | 425–478 | PHEMA_IAHMI | 379–455 | |
| PHEMA_IAMAA | 380–450 | PHEMA_IAHNM | 379–455 | |
| PHEMA_IAMAB | 385–455 | PHEMA_IAHNN | 112–146 | 360–484 | 503–537 |
| PHEMA_IAMAO | 387–453 | PHEMA_IAHPR | 112–146 | 360–484 | 503–537 |
| PHEMA_IAME1 | 387–453 | PHEMA_IAHRO | 379–455 | |
| PHEMA_IAME2 | 387–453 | PHEMA_IAHSA | 379–455 | |
| PHEMA_IAME6 | 371–437 | PHEMA_IAHSP | 112–146 | 360–484 | 503–537 |
| PHEMA_IAMIN | 382–441 | PHEMA_IAHSW | 112–146 | 360–484 | 503–537 |
| PHEMA_IANT6 | 387–453 | PHEMA_IAHTE | 379–455 | |
| PHEMA_IAPIL | 505–534 | PHEMA_IAHTO | 379–455 | |
| PHEMA_IAPUE | 425–478 | PHEMA_IAHUR | 379–455 | |
| PHEMA_IARUD | 351–451 | PHEMA_IAJAP | 375–467 | 502–547 |
| PHEMA_IASE2 | 381–451 | PHEMA_IAKIE | 376–478 | 506–541 |
| PHEMA_IASH2 | 506–547 | PHEMA_IALEN | 376–478 | 506–548 |
| PHEMA_IASTA | 384–443 | PHEMA_IAMAA | 377–453 | |
| PHEMA_IATKI | 415–445 | PHEMA_IAMAB | 382–458 | |

TABLE V-continued

Search Results Summary for 107 × 178 × 4 and ALLMOT5 Motifs

| 107 × 178 × 4 LIBRARY FILE | | ALLMOT5 LIBRARY FILE | |
|---|---|---|---|
| PHEMA_IATKM | 381–451 | PHEMA_IAMAO | 380–456 |
| PHEMA_IATKO | 507–534 | PHEMA_IAME1 | 380–456 |
| PHEMA_IATKP | 424–454 493–539 | PHEMA_IAME2 | 380–456 |
| PHEMA_IATKR | 381–422 | PHEMA_IAME6 | 384–440 |
| PHEMA_IATKW | 419–449 600–538 | PHEMA_IAMIN | 108–142 375–475 |
| PHEMA_IAUDO | 387–453 | PHEMA_IANT6 | 380–456 |
| PHEMA_IAUSS | 425–478 | PHEMA_IAPIL | 378–477 496–534 |
| PHEMA_IAVI7 | 388–454 | PHEMA_IAPUE | 376–478 506–548 |
| PHEMA_IAWIL | 424–477 | PHEMA_IARUD | 378–454 |
| PHEMA_IAZCO | 387–453 | PHEMA_IASE2 | 378–454 |
| PHEMA_IAZH2 | 371–437 | PHEMA_IASH2 | 379–474 506–552 |
| PHEMA_IAZH3 | 371–437 | PHEMA_IASTA | 112–148 377–469 |
| PHEMA_IAZIN | 418–478 506–547 | PHEMA_IATKI | 379–471 508–551 |
| PHEMA_IAZNJ | 418–478 506–547 | PHEMA_IATKM | 378–454 |
| PHEMA_IAZUK | 387–453 | PHEMA_IATKO | 392–470 504–548 |
| PHEMA_INBBE | 400–431 439–463 | PHEMA_IATKP | 378–454 493–540 |
| PHEMA_INBBO | 390–421 429–473 | PHEMA_IATKR | 30–84 374–474 |
| PHEMA_INBEN | 398–429 437–481 | PHEMA_IATKW | 373–472 487–539 |
| PHEMA_INBHK | 391–418 429–473 | PHEMA_IATRA | 21–55 |
| PHEMA_INBLE | 399–430 438–482 | PHEMA_IAUDO | 387–458 |
| PHEMA_INBMD | 389–420 428–472 | PHEMA_IAUSS | 376–478 608–548 |
| PHEMA_INBME | 393–424 432–476 | PHEMA_IAVI7 | 381–457 |
| PHEMA_INBOR | 398–429 437–481 | PHEMA_IAWIL | 375–477 605–547 |
| PHEMA_INBSI | 399–429 437–481 | PHEMA_IAZCO | 380–456 |
| PHEMA_INBUS | 391–422 430–474 | PHEMA_IAZH2 | 364–440 |
| PHEMA_INBVI | 393–424 432–476 | PHEMA_IAZH3 | 364–440 |
| PHEMA_INBVK | 400–431 439–483 | PHEMA_IAZIN | 379–478 506–548 |
| PHEMA_INCCA | 495–571 | PHEMA_IAZNJ | 379–478 506–548 |
| PHEMA_INCEN | 483–559 | PHEMA_IAZUK | 380–456 |
| PHEMA_INCGL | 483–559 | PHEMA_INBBE | 388–473 |
| PHEMA_INCHY | 482–558 | PHEMA_INBBO | 378–463 |
| PHEMA_INCJH | 496–572 | PHEMA_INBEN | 386–471 |
| PHEMA_INCKV | 482–558 | PHEMA_INBHK | 381–463 |
| PHEMA_INCMI | 482–559 | PHEMA_INBLE | 387–472 |
| PHEMA_INCNA | 482–558 | PHEMA_INBMD | 377–462 |
| PHEMA_INCP1 | 483–559 | PHEMA_INBME | 381–468 |
| PHEMA_INCP2 | 483–559 | PHEMA_INBOR | 386–471 |
| PHEMA_INCP3 | 483–559 | PHEMA_INBSI | 386–471 |
| PHEMA_INCTA | 483–559 | PHEMA_INBUS | 379–464 |
| PHEMA_INCYA | 483–559 | PHEMA_INBVI | 381–466 |
| PHEMA_NDVA | 64–91 | PHEMA_INBVK | 388–473 |
| PHEMA_NDVB | 64–91 | PHEMA_INCCA | 483–571 |
| PHEMA_NDVD | 64–91 | PHEMA_INCEN | 471–559 |
| PHEMA_NDVH | 64–91 | PHEMA_INCGL | 471–559 |
| PHEMA_NDVI | 64–91 | PHEMA_INCHY | 470–558 |
| PHEMA_NDVM | 64–91 | PHEMA_INCJH | 484–572 |

TABLE V-continued

Search Results Summary for 107 × 178 × 4 and ALLMOTI5 Motifs

| 107 × 178 × 4 LIBRARY FILE | | ALLMOTI5 LIBRARY FILE | | |
|---|---|---|---|---|
| PHEMA_NDVQ | 64–91 | PHEMA_INCKY | 470–558 | |
| PHEMA_NDVTG | 64–91 | PHEMA_INCMI | 470–558 | |
| PHEMA_NDVU | 64–91 | PHEMA_INCNA | 470–558 | |
| PHEMA_PHODV | 39–66 | PHEMA_INCP1 | 471–559 | |
| PHEMA_PI1HW | 79–110 | PHEMA_INCP2 | 471–559 | |
| PHEMA_PI3B | 66–93 | PHEMA_INCP3 | 471–559 | |
| PHEMA_PI3H4 | 27–61 | PHEMA_INCTA | 471–559 | |
| PHEMA_PI3HA | 27–61 | PHEMA_INCYA | 471–559 | |
| PHEMA_PI3HT | 27–76 | PHEMA_MEASE | 46–90 | |
| PHEMA_PI3HU | 23–70 | PHEMA_MEASH | 46–90 | |
| PHEMA_PI3HV | 27–61 | PHEMA_MEASI | 46–87 | |
| PHEMA_PI3HW | 27–61 | PHEMA_MEASY | 46–87 | |
| PHEMA_PI3HX | 27–61 | PHEMA_MUMPM | 34–99 | |
| PHEMA_RACVI | 166–214 | PHEMA_MUMPR | 34–99 | |
| PHEMA_SEND5 | 79–106 | PHEMA_MUMPS | 34–99 | |
| PHEMA_SENDF | 79–106 | PHEMA_NDVA | 8–52 | 477–529 |
| PHEMA_SENDH | 79–106 | PHEMA_NDVB | 1–49 | |
| PHEMA_SENDJ | 79–106 | PHEMA_NDVD | 1–49 | |
| PHEMA_SENDZ | 79–106 | PHEMA_NDVM | 1–49 | |
| PHEMA_SV41 | 22–52 | PHEMA_NDVQ | 1–49 | |
| PHEMA_VACCC | 119–146 | PHEMA_NDVTG | 1–49 | |
| PHEMA_VACCI | 109–146 | PHEMA_NDVU | 1–49 | |
| PHEMA_VACCT | 119–146 | PHEMA_PHODV | 39–73 | |
| PHEMA_VACCV | 109–146 | PHEMA_PI1HW | 66–110 | |
| PVENV_DHVI1 | 318–366 | PHEMA_PI2H | 247–281 | |
| PVENV_EAV | 120–147 | PHEMA_PI2HT | 247–281 | |
| PVENV_THOGV | 313–347 | PHEMA_PI3B | 38–93 | |
| PVF03_VACCC | 71–110 | PHEMA_PI3H4 | 13–110 | 394–428 |
| PVF03_VACCP | 71–110 | PHEMA_PI3HA | 20–110 | 394–428 |
| PVF05_VACCP | 33–60 | PHEMA_PI3HT | 13–110 | 394–428 |
| PVF05_VACCV | 33–60 | PHEMA_PI3HU | 13–110 | 394–428 |
| PVF11_VACCP | 274–321 | PHEMA_PI3HV | 13–110 | 394–428 |
| PVF11_VACCV | 270–317 | PHEMA_PI3HW | 13–110 | 394–428 |
| PVF12_VACCC | 10–37 | PHEMA_PI3HX | 13–110 | 394–428 |
| PVF12_VACCP | 10–37 | PHEMA_PI4HA | 54–88 | |
| PVF16_VACCC | 35–62 | PHEMA_RACVI | 166–214 | 256–290 |
| PVF16_VACCP | 152–179 | PHEMA_RINDK | 46–87 | |
| PVFP4_FOWPV | 146–173 | PHEMA_RINDL | 46–87 | 191–225 |
| PVFU8_ORFNZ | 59–86 | PHEMA_SEND5 | 57–110 | |
| PVFU8_VACCC | 37–64 | PHEMA_SENDF | 57–110 | |
| PVFU8_VACCV | 37–64 | PHEMA_SENDH | 57–110 | |
| PVG01_VACCC | 225–252 | PHEMA_SENDJ | 57–110 | |
| PVG01_VACCV | 164–191 | PHEMA_SENDZ | 57–110 | |
| PVG01_VARV | 225–252 | PHEMA_SV41 | 18–52 | 387–421 |
| PVG02_VACCV | 96–123 | PHEMA_SV5 | 27–82 | |
| PVG02_VARV | 96–123 | PHEMA_SV5LN | 27–82 | |

TABLE V-continued

Search Results Summary for 107 × 178 × 4 and ALLMOTI5 Motifs

| 107 × 178 × 4 LIBRARY FILE | | | | | ALLMOTI5 LIBRARY FILE | | | | | |
|---|---|---|---|---|---|---|---|---|---|---|
| PVG03_HSVEB | 146–176 | | | | PVENV_BEV | 195–229 | | | | |
| PVG03_HSVEK | 146–176 | | | | PVENV_DHVI1 | 318–366 | | | | |
| PVG05_VACCC | 48–75 | 131–161 | 225–289 | 355–389 | PVENV_MCV1 | 252–286 | | | | |
| PVG05_VARV | 48–75 | 124–161 | 255–289 | 355–389 | PVENV_MCV2 | 252–286 | | | | |
| PVG07_HSVI1 | 71–98 | | | | PVENV_THOGV | 313–354 | | | | |
| PVG09_VACCC | 308–338 | | | | PVENV_VACCC | 257–295 | | | | |
| PVG09_VACCV | 271–301 | | | | PVENV_VACCI | 257–295 | | | | |
| PVG09_VARV | 308–338 | | | | PVENV_VACCP | 257–295 | | | | |
| PVG12_SFV1R | 11–45 | | | | PVENV_VACCV | 257–295 | | | | |
| PVG17_HSVI1 | 177–204 | | | | PVF01_VACCC | 46–80 | 124–158 | | | |
| PVG18_HSVI1 | 174–208 | | | | PVF01_VACCV | 46–80 | 124–158 | | | |
| PVG1_SPV1R | 260–287 | | | | PVF03_VACCC | 71–110 | | | | |
| PVG1_SPV4 | 287–314 | 383–410 | | | PVF03_VACCV | 71–110 | | | | |
| PVG22_HSVI1 | 373–400 | 581–622 | 668–705 | 766–824 | PVF05_VACCC | 81–129 | 282–320 | | | |
| PVG24_HSVI1 | 31–58 | | | | PVF05_VACCP | 81–129 | 282–320 | | | |
| PVG28_HSVI1 | 253–290 | 497–528 | | | PVF05_VACCV | 81–129 | 293–321 | | | |
| PVG2R_AMEPV | 33–64 | 91–118 | | | PVF11_VACCC | 217–258 | 269–315 | | | |
| PVG2_SPV1R | 285–326 | | | | PVF11_VACCP | 213–254 | 265–311 | | | |
| PVG2_SPV4 | 146–173 | 175–205 | 262–310 | | PVF12_VACCC | 1–67 | 102–143 | 199–236 | 350–388 | 544–581 |
| PVG34_HSVI1 | 95–122 | | | | PVF12_VACCP | 1–67 | 102–143 | 199–236 | 350–388 | 544–581 |
| PVG37_HSVI1 | 442–469 | | | | PVF16_VACCC | 155–194 | | | | |
| PVG39_HSVI1 | 651–678 | 1088–1115 | | | PVF16_VACCP | 155–194 | | | | |
| PVG3L_AMEPV | 2–29 | | | | PVFP3_FOWPV | 1–43 | | | | |
| PVG3_SPV1R | 15–49 | | | | PVFP4_FOWPV | 139–173 | 239–273 | | | |
| PVG3_SPV4 | 18–52 | 87–148 | | | PVFP7_FOWPV | 23–57 | | | | |
| PVG45_HSVSA | 138–165 | | | | PVFPL_FOWP1 | 77–111 | | | | |
| PVG46_HSVI1 | 142–169 | 346–373 | 897–924 | 973–1007 | PVFUS_VACCC | 30–64 | | | | |
| PVG48_HSVSA | 360–394 | | | | PVFUS_VACCV | 30–64 | | | | |
| PVG4R_AMEPV | 4–31 | | | | PVG01_BPP22 | 94–135 | 400–468 | 475–513 | 608–659 | |
| PVG4_SPV1R | 116–146 | | | | PVG01_HSVI1 | 271–306 | 512–563 | 591–647 | 730–764 | |
| PVG51_HSVI1 | 34–61 | 87–114 | | | PVG01_VACCC | 301–339 | | | | |
| PVG52_HSVSA | 47–74 | | | | PVG01_VACCV | 240–276 | | | | |
| PVG56_HSVI1 | 582–609 | | | | PVG01_VARV | 301–339 | | | | |
| PVG5_SPV1R | 65–92 | | | | PVG03_HSVEB | 143–177 | | | | |
| PVG5_SPV4 | 56–83 | | | | PVG03_HSVEK | 143–177 | | | | |
| PVG63_HSVI1 | 550–584 | | | | PVG03_VARV | 64–98 | | | | |
| PVG64_HSVI1 | 477–504 | | | | PVG05_VACCC | 117–168 | 255–289 | 355–389 | | |
| PVG65_HSVI1 | 1213–1254 | | | | PVG05_VARV | 117–158 | 255–289 | 355–389 | | |
| PVG66_HSVI1 | 362–406 | | | | PVG06_HSVI1 | 61–109 | | | | |
| PVG67_HSVI1 | 1342–1369 | | | | PVG07_HSVI1 | 69–103 | | | | |
| PVG68_HSVI1 | 261–288 | | | | PVG07_VACCC | 114–175 | 324–358 | | | |
| PVG72_HSVI1 | 447–481 | | | | PVG07_VARV | 114–175 | 324–358 | | | |
| PVG75_HSVI1 | 388–422 | | | | PVG09_VACCC | 304–338 | | | | |
| PVG76_HSVI1 | 200–227 | | | | PVG09_VACCV | 267–301 | | | | |
| PVG7_SPV4 | 14–44 | | | | PVG09_VARV | 304–338 | | | | |
| PVGF1_IBVB | 1230–1260 | 2408–2435 | | | PVG10_HSVI1 | 63–97 | | | | |

TABLE V-continued

Search Results Summary for 107 × 178 × 4 and ALLMOT5 Motifs

| 107 × 178 × 4 LIBRARY FILE | | | | | ALLMOT5 LIBRARY FILE | | | | |
|---|---|---|---|---|---|---|---|---|---|
| PVGL2_CVBF | 399–426 | | | | PVGL2_SPV1R | 11–45 | | | |
| PVGL2_CVBL9 | 399–426 | 642–676 | 1022–1084 | 1278–1305 | PVGL2_HSVSA | 58–95 | | | |
| PVGL2_CVBLY | 399–426 | 642–676 | 1022–1084 | 1278–1305 | PVGL2_HSVI1 | 92–129 | 177–211 | | |
| PVGL2_CVBM | 399–426 | 642–676 | 1022–1084 | 1278–1305 | PVGL2_HSVI1 | 174–208 | 215–256 | | |
| PVGL2_CVBQ | 399–426 | 642–676 | 1022–1084 | 1278–1305 | PVGL1_AMEPV | 407–441 | | | |
| PVGL2_CVBV | 399–426 | 642–676 | 1022–1084 | 1278–1305 | PVGL1_SPV1R | 136–170 | 256–297 | | |
| PVGL2_CVH22 | 770–797 | 809–875 | 1056–1112 | | PVGL1_SPV4 | 287–321 | | | |
| PVGL2_CVM4 | 643–684 | 1030–1092 | | | PVGL2_HSVI1 | 117–158 | 437–629 | 320–357 | |
| PVGL2_CVMA6 | 36–63 | 591–632 | 978–1040 | | PVGL2_HSVI1 | 7–72 | 74–108 | 660–892 | 899–1056 |
| PVGL2_CVMJH | 502–543 | 889–951 | | | PVGL2_HSVI1 | 164–219 | | | |
| PVGL2_CVPFS | 69–110 | 692–733 | 1072–1145 | 1353–1389 | PVGL2_HSVI1 | 253–290 | | | |
| PVGL2_CVPPU | 69–107 | 690–731 | 1067–1143 | 1351–1387 | PVG2R_AMEPV | 29–63 | 184–218 | | |
| PVGL2_CVPR8 | 468–509 | 845–921 | 1129–1165 | | PVG2_SPV1R | 222–256 | 285–328 | | |
| PVGL2_CVPRM | 468–509 | 845–921 | 1129–1165 | | PVGL2_SPV4 | 255–310 | | | |
| PVGL2_EBV | 68–102 | | | | PVG33_HSVI1 | 149–183 | | | |
| PVGL2_FIPV | 189–233 | 454–481 | 709–736 | | PVG34_HSVI1 | 345–379 | | 1356–1392 | |
| PVGL2_IBV6 | 809–836 | 876–903 | 1057–1091 | | PVG35_HSVI1 | 17–90 | | | |
| PVGL2_IBVB | 808–836 | 875–902 | 1056–1090 | 1072–1148 | PVG37_HSVI1 | 435–472 | | | |
| PVGL2_IBVD2 | 809–836 | 876–903 | 1057–1091 | | PVG38_HSVI1 | 84–118 | | | |
| PVGL2_IBVK | 808–836 | 875–902 | 1056–1090 | | PVG39_HSVI1 | 124–158 | 266–300 | 203–244 | |
| PVGL2_IBVM | 808–835 | 875–902 | 1056–1090 | | PVG3_SPV1R | 8–49 | 162–196 | 87–121 | |
| PVGLB_EBV | 95–122 | 631–658 | | | PVG3_SPV4 | 6–54 | | | |
| PVGLB_HCMVA | 25–88 | 397–424 | 440–467 | 851–878 | PVG43_HSVI1 | 116–150 | 282–296 | 394–361 | 643–677 |
| PVGLB_HCMVT | 50–88 | 397–424 | 435–462 | 852–879 | PVG45_HSVSA | 121–162 | | | |
| PVGLB_HSVB1 | 427–454 | | | | PVG46_HSVI1 | 45–88 | 939–1078 | 1251–1321 | |
| PVGLB_HSVB2 | 447–474 | | | | PVG48_HSVI1 | 169–207 | 611–866 | 733–787 | |
| PVGLB_HSVBC | 426–453 | | | | PVG48_HSVSA | 360–417 | | | |
| PVGLB_HSVE1 | 443–470 | 934–961 | | | PVG49_HSVSA | 68–102 | | | |
| PVGLB_HSVE4 | 486–513 | 616–643 | | | PVG4R_AMEPV | 4–38 | | | |
| PVGLB_HSVEA | 443–470 | 934–961 | | | PVG4_SPV4 | 89–130 | | | |
| PVGLB_HSVEB | 443–470 | 934–961 | | | PVG51_HSVI1 | 34–73 | 89–123 | 162–196 | |
| PVGLB_HSVEL | 443–470 | 933–960 | | | PVG51_HSVSA | 29–70 | 123–157 | | |
| PVGLB_HSVMD | 93–120 | 352–379 | | | PVG53_HSVSA | 67–127 | | | |
| PVGLB_HSVMG | 381–408 | 441–475 | | | PVG54_HSVI1 | 355–396 | | | |
| PVGLB_HSVMM | 469–510 | | | | PVG55_HSVI1 | 101–135 | | | |
| PVGLB_MCMVS | 469–510 | | | | PVG56_HSVSA | 126–178 | | | |
| PVGLC_HSVI1 | 124–151 | 154–202 | 216–243 | 442–469 | PVG58_HSVI1 | 151–192 | 578–612 | 644–678 | 750–784 | 846–880 | 1111–1145 |
| PVGLC_HSVIK | 63–97 | | | | PVG59_HSVI1 | 10–72 | 89–123 | | |
| PVGLC_HSVMB | 62–96 | | | | PVG59_HSVSA | 169–209 | | | |
| PVGLC_HSVMG | 63–97 | | | | PVG5_SPV1R | 65–103 | | | |
| PVGLC_HSVMM | 295–322 | | | | PVG61_HSVI1 | 265–299 | | | |
| PVGLC_VZVD | 295–322 | | | | PVG63_HSVI1 | 546–584 | | | |
| PVGLC_VZVS | 111–148 | | | | PVG85_HSVI1 | 805–839 | 1213–1254 | | |
| PVGLF_HSV2 | 38–65 | 154–202 | 216–243 | 486–531 | PVG66_HSVI1 | 154–188 | 328–410 | | |
| PVGLF_BRSVA | 38–65 | 154–202 | 216–243 | 488–533 | PVG67_HSVI1 | 379–413 | 501–546 | 1321–1369 | 1476–1541 |
| PVGLF_BRSVC | 38–65 | 154–202 | 216–243 | 488–533 | PVG68_HSVI1 | 245–288 | | | |
| PVGLF_BRSVR | | | | | | | | | |

TABLE V-continued

Search Results Summary for 107 × 178 × 4 and ALLMOTI5 Motifs

| 107 × 178 × 4 LIBRARY FILE | | | | ALLMOTI5 LIBRARY FILE | | | | | |
|---|---|---|---|---|---|---|---|---|---|
| PVGLF_CDVO | 262–293 | 340–387 | | PVG72_HSVI1 | 447–484 | 723–767 | 912–949 | | |
| PVGLF_HRSV1 | 38–65 | 154–203 | 442–471 | PVG75_HSVI1 | 271–305 | 388–422 | | | |
| PVGLF_HRSVA | 38–65 | 154–202 | 213–243 | PVG8_SPV1R | 5–51 | | | | |
| PVGLF_HRSVL | 38–65 | 154–202 | 216–243 | 488–515 | PVGF1_IBVB | 142–179 | 1233–1267 | 2119–2156 | 3388–3424 | 3475–3513 | 3517–3556 | 3761–3795 |
| PVGLF_HRSVR | 38–65 | 154–202 | 213–243 | 488–518 | PVGH3_HCMVA | 10–44 | | | |
| PVGLF_MEASE | 228–262 | | 442–471 | PVGL2_CVBF | 642–676 | 850–885 | 993–1088 | | |
| PVGLF_MEASI | 231–265 | | | PVGL2_CVBL9 | 850–885 | 993–1109 | 1263–1305 | | |
| PVGLF_MEASY | 228–262 | | | PVGL2_CVBLY | 642–676 | 850–885 | 1263–1305 | | |
| PVGLF_MUMPM | 20–54 | 447–488 | | PVGL2_CVBM | 642–676 | 858–885 | 993–1109 | 1263–1305 | |
| PVGLF_MUMPR | 20–54 | 447–488 | | PVGL2_CVBQ | 642–676 | 850–885 | 993–1109 | 1263–1305 | |
| PVGLF_MUNP8 | 151–178 | 426–511 | | PVGL2_CVBV | 642–676 | 850–885 | 993–1109 | 1263–1305 | |
| PVGLF_NDVA | 151–178 | 426–512 | | PVGL2_CVH22 | 770–916 | 1055–1112 | 1270–1315 | | |
| PVGLF_NDVB | 151–178 | 426–512 | | PVGL2_CVM4 | 643–684 | 1001–1117 | 1217–1283 | | |
| PVGLF_NDVI | 151–178 | 426–512 | | PVGL2_CVMA5 | 591–632 | 949–1079 | 1129–1174 | | |
| PVGLF_NDVM | 151–178 | 426–512 | | PVGL2_CVMJH | 502–543 | 860–976 | 692–733 | 889–923 | 1040–1166 | 1352–1380 |
| PVGLF_NDVT | 151–178 | 426–512 | | PVGL2_CVPFS | 69–110 | 448–482 | 690–731 | 667–921 | 1038–1184 | 1351–1387 |
| PVGLF_NDVTG | 151–178 | 428–512 | | PVGL2_CVPPU | 69–110 | 446–480 | 665–899 | 816–892 | 1120–1185 | |
| PVGLF_NDVU | 151–178 | 428–512 | | PVGL2_CVPR8 | 224–258 | 468–509 | 665–899 | 818–962 | 1128–1165 | |
| PVGLF_PHODV | 36–83 | 221–262 | 309–336 | PVGL2_CVPRM | 224–258 | 468–509 | | | |
| PVGLF_PI1HC | 147–174 | 210–266 | | PVGL2_EBV | 68–102 | | | | |
| PVGLF_PI2H | 90–117 | 141–175 | 238–266 | 463–528 | PVGL2_FIPV | 169–245 | 451–486 | 695–736 | 892–926 | 1043–1189 | 1355–1392 |
| PVGLF_PI2HG | 90–117 | 141–175 | 238–266 | 483–528 | PVGL2_IBV6 | 791–905 | 1057–1091 | | |
| PVGLF_PI2HT | 90–117 | 141–176 | 238–266 | 483–528 | PVGL2_IBVB | 437–478 | 772–904 | 1056–1090 | | |
| PVGLF_PI3B | 115–182 | 207–241 | 459–497 | PVGL2_IBVD2 | 773–905 | 1057–1091 | | | |
| PVGLF_PI3H4 | 115–182 | 207–241 | 457–497 | PVGL2_IBVK | 437–478 | 772–904 | 1056–1090 | | |
| PVGLF_RINDK | 224–265 | 458–485 | | PVGL2_IBVM | 437–478 | 772–904 | 1056–1090 | | |
| PVGLF_RINDL | 224–265 | 458–506 | 480–507 | PVGLB_HCMVA | 43–88 | 128–162 | 436–484 | 844–878 | | |
| PVGLF_SEND6 | 211–245 | | 480–507 | PVGLB_HCMVT | 22–88 | 128–162 | 437–485 | 845–879 | | |
| PVGLF_SENDF | 122–149 | 211–245 | 480–507 | PVGLB_HSVI1 | 828–890 | 827–889 | | | |
| PVGLF_SENDH | 122–149 | 211–245 | 480–507 | PVGLB_HSV1F | 827–889 | | | | |
| PVGLF_SENDI | 122–149 | 211–245 | 480–507 | PVGLB_HSV1K | 827–889 | | | | |
| PVGLF_SENDJ | 122–149 | 211–245 | 480–507 | PVGLB_HSV1P | 828–890 | | | | |
| PVGLF_SENDZ | 122–149 | 241–269 | 459–496 | PVGLB_HSV23 | 828–890 | | | | |
| PVGLF_SV41 | 144–185 | 417–444 | | PVGLB_HSV2H | 828–890 | | | | |
| PVGLF_SV5 | 137–171 | 193–200 | 457–484 | PVGLB_HSV2S | 817–871 | | | | |
| PVGLF_TRITV | 124–161 | | | PVGLB_HSV6U | 37–71 | 165–223 | | | |
| PVGLG_BRSVC | 523–557 | | | PVGLB_HSVB1 | 859–913 | | | | |
| PVGLG_HRSV1 | 92–123 | | | PVGLB_HSVB2 | 440–474 | 848–902 | | | |
| PVGLG_HRSV4 | 63–93 | | | PVGLB_HSVBC | 863–900 | | | | |
| PVGLG_HRSV5 | 66–107 | | | PVGLB_HSVE1 | 642–678 | 911–961 | | | |
| PVGLG_HRSV8 | 243–273 | | | PVGLB_HSVE4 | 474–515 | 847–900 | | | |
| PVGLG_HSVE4 | 66–93 | | | PVGLB_HSVEA | 542–676 | 911–961 | | | |
| PVGLG_HSVEB | 271–298 | | | PVGLB_HSVEB | 542–676 | 911–961 | | | |
| PVGLG_RABVT | 383–410 | | | PVGLB_HSVEL | 642–678 | 910–960 | | | |
| PVGLG_VSVIG | 489–519 | | | PVGLB_HSVMD | 390–435 | 649–683 | 787–845 | | |
| PVGLH_EBV | 649–676 | 619–648 | | PVGLB_HSVSA | 240–288 | 406–447 | | | |

TABLE V-continued

Search Results Summary for 107 × 178 × 4 and ALLMOT15 Motifs

| 107 × 178 × 4 LIBRARY FILE | | ALLMOT15 LIBRARY FILE | | | | |
|---|---|---|---|---|---|---|
| PVGLH_HCMVA | 107–136 | 270–297 | | PVGLB_MCMV6 | 208–260 | 427–476 | 693–778 | 860–894 |
| PVGLH_HCMVT | 106–135 | | | PVGLB_PRVIF | 847–881 | | | |
| PVGLH_HSV6G | 82–89 | 360–403 | | PVGLC_HSV11 | 92–133 | 596–630 | 809–867 | |
| PVGLH_HSVSA | 388–416 | | | PVGLC_HSV1K | 469–510 | | | |
| PVGL1_HCMVA | 47–111 | | | PVGLC_HSV2 | 469–510 | | | |
| PVGLM_BUNGE | 512–546 | 914–941 | 1128–1255 | PVGLC_HSV23 | 442–476 | | | |
| PVGLM_BUNL7 | 913–950 | | | PVGLC_HSVBC | 443–477 | | | |
| PVGLM_BUNYW | 340–374 | 504–535 | 662–709 | PVGLC_HSVEB | 235–269 | | | |
| PVGLM_DUGBV | 945–972 | | | PVGLC_HSVMB | 182–218 | | | |
| PVGLM_HANTB | 73–100 | 693–720 | | PVGLC_HSVMG | 63–97 | | | |
| PVGLM_HANTH | 75–102 | | | PVGLC_HSVMM | 62–96 | | | |
| PVGLM_HANTL | 75–102 | | | PVGLC_PRVIF | 63–97 | | | |
| PVGLM_HANTV | 75–102 | | | PVGLC_VZVD | 183–235 | | | |
| PVGLM_PHV | 69–96 | | | PVGLC_VZVS | 280–321 | | | |
| PVGLM_PUUMH | 72–110 | | | PVGLD_HSVEA | 280–321 | | | |
| PVGLM_PUUMS | 72–110 | | | PVGLD_HSVEB | 89–123 | | | |
| PVGLM_SEOUR | 73–100 | 513–540 | 694–721 | PVGLD_HSVEK | 139–173 | | | |
| PVGLM_SEOUS | 73–100 | 513–540 | 894–721 | PVGLE_HSV11 | 139–173 | | | |
| PVGLN_BEFV | 523–584 | | | PVGLE_HSV2 | 111–145 | | | |
| PVGLP_BEV | 48–82 | 1145–1179 | 1184–1211 | PVGLF_BRSVA | 111–159 | | | |
| PVGLX_HSVEB | 17–44 | 413–444 | 1505–1532 | PVGLF_BRSVC | 146–202 | 804–545 | 506–547 | |
| PVGLX_PRVRI | 427–481 | | | PVGLF_BRSVR | 146–202 | 267–302 | 505–554 | |
| PVGLY_JUNIN | 14–41 | | | PVGLF_CDVO | 146–202 | 267–302 | 568–602 | |
| PVGLY_LASSG | 86–113 | | | PVGLF_HRSV1 | 228–297 | 340–381 | | |
| PVGLY_MOPEI | 86–113 | 316–346 | | PVGLF_HRSVA | 118–203 | 267–302 | 506–549 | |
| PVGLY_PIARV | 334–375 | | | PVGLF_HRSVL | 116–202 | 267–302 | 506–549 | |
| PVGLV_TACV | 109–138 | 315–350 | | PVGLF_HRSVR | 116–202 | 267–302 | 506–547 | |
| PVGLY_TACV5 | 303–338 | | | PVGLF_MEASE | 116–202 | 228–269 | 506–549 | |
| PVGLY_TACV7 | 302–337 | | | PVGLF_MEASI | 116–184 | 231–272 | 452–500 | |
| PVGLY_TACVT | 303–338 | | | PVGLF_MEASY | 119–187 | 231–272 | 455–503 | |
| PVGLZ_HSVEK | 17–44 | | | PVOLF_MUMPM | 116–184 | 228–269 | 452–500 | |
| PVGNM_BPMV | 403–430 | | | PVGLF_MUMPR | 20–54 | 103–179 | 235–272 | 447–502 |
| PVGNM_CPSMV | 192–221 | | | PVGLF_MUMPS | 20–54 | 103–179 | 235–272 | 447–502 |
| PVGP8_EBV | 104–149 | | | PVGLF_NDVA | 20–54 | 103–179 | 235–272 | 447–502 |
| PVM1_REOVL | 290–317 | | | PVGLF_NDVS | 117–182 | 231–272 | 426–512 | |
| PVM21_REOVD | 625–662 | | | PVGLF_NDVI | 122–182 | 231–272 | 426–517 | |
| PVM22_REOVD | 624–661 | | | PVGLF_NDVM | 133–182 | 236–272 | 426–517 | |
| PVM2_REOVJ | 624–881 | | | PVGLF_NDVT | 117–182 | 231–272 | 426–512 | |
| PVM3_REOVD | 169–186 | 343–370 | 450–483 | 631–690 | PVGLF_NDVTG | 117–182 | 231–272 | 426–517 | |
| PVMA2_BRSVA | 124–152 | | | PVGLF_NDVU | 122–182 | 231–272 | 425–517 | |
| PVMA2_HRSVA | 124–151 | | | PVGLF_PHODV | 122–182 | 231–272 | 426–512 | 533–581 |
| PVMAT_BRSVA | 219–248 | | | PVGLF_PI1HC | 29–63 | 197–266 | 309–350 | |
| PVMAT_HRSVA | 219–248 | | | PVGLF_PI2H | 123–174 | 207–267 | 459–503 | |
| PVMAT_INCIJ | 151–185 | | | PVGLF_PI2HG | 93–183 | 477–528 | | |
| PVMAT_NDVA | 247–274 | | | PVGLF_PI2HT | 93–183 | 477–528 | | |
| PVMAT_PI2HT | 96–123 | | | PVGLF_PI2HT | 93–185 | 477–528 | | |

TABLE V-continued

Search Results Summary for 107 × 178 × 4 and ALLMOTI5 Motifs

| 107 × 178 × 4 LIBRARY FILE | | | | ALLMOTI5 LIBRARY FILE | | | | |
|---|---|---|---|---|---|---|---|---|
| PVMAT_PI3B | 201–231 | | | PVGLF_PI3B | 117–182 | 207–241 | 456–518 | |
| PVMAT_PI3H4 | 201–231 | | | PVGLF_PI3H4 | 117–182 | 207–241 | 462–532 | |
| PVMAT_SV41 | 323–353 | | | PVGLF_RINDK | 112–180 | 224–265 | 448–493 | |
| PVME1_CVBM | 175–209 | | | PVGLF_RINDL | 112–180 | 224–265 | 448–508 | |
| PVME1_CVTKE | 175–209 | | | PVGLF_SEND5 | 127–188 | 211–271 | 463–533 | |
| PVME1_IBV6 | 21–48 | 184–218 | | PVGLF_SENDF | 127–188 | 211–271 | 463–533 | |
| PVME1_IBVB | 21–48 | 184–218 | | PVGLF_SENDH | 127–188 | 218–271 | 463–533 | |
| PVME1_IBVB2 | 21–48 | 184–218 | | PVGLF_SENDJ | 127–188 | 211–271 | 463–533 | |
| PVME1_IBVK | | 184–218 | | PVGLF_SENDZ | 127–188 | 211–271 | 463–533 | |
| PVMP_CAMVC | | 220–254 | 273–324 | PVGLF_SV41 | 96–188 | 454–508 | | |
| PVMP_CAMVD | 29–56 | 220–254 | 273–324 | PVGLF_SV5 | 103–171 | 241–275 | 451–487 | |
| PVMP_CAMVE | | 227–254 | 273–324 | PVGLF_TRTV | 105–161 | 190–224 | 457–498 | |
| PVMP_CAMVN | | 220–254 | 273–324 | PVGLG_BEFV | 506–812 | | | |
| PVMP_CAMVS | | 220–254 | 273–324 | PVGLG_BRSVC | 30–70 | 104–138 | | |
| PVMP_CAMVW | | 220–254 | 273–324 | PVGLG_HRSV1 | 30–81 | | | |
| PVMP_CERV | 26–53 | 100–127 | | PVGLG_HRSV2 | 30–85 | | | |
| PVMP_SOCMV | 4–31 | 78–118 | | PVGLG_HRSV3 | 30–85 | | | |
| PVMSA_HPBHE | 294–328 | | | PVGLG_HRSV4 | 30–107 | | | |
| PVMT1_DHVI1 | 38–65 | 237–284 | | PVGLG_HRSV5 | 30–85 | | | |
| PVMT8_MYXVL | 163–190 | | | PVGLG_HRSV6 | 30–85 | | | |
| PVMT9_MYXVL | 465–492 | | | PVGLG_HRSV7 | 30–85 | | | |
| | | | | PVGLG_HRSV8 | 30–81 | | | |
| | | | | PVGLG_HRSVA | 30–67 | | | |
| | | | | PVGLG_HRSVL | 25–85 | | | |
| | | | | PVGLG_HSVE4 | 271–306 | | | |
| | | | | PVGLG_SIGMA | 344–381 | 484–498 | | |
| | | | | PVGLG_SYNV | 488–523 | | | |
| | | | | PVGLG_VHSVO | 363–397 | | | |
| | | | | PVGLG_VSVIG | 476–510 | | | |
| | | | | PVGLH_EBV | 53–87 | 160–201 | 336–380 | 653–694 |
| | | | | PVGLH_HCMVA | 103–137 | 270–311 | 893–741 | |
| | | | | PVGLH_HCMVT | 102–136 | 692–740 | | |
| | | | | PVGLH_HSV11 | 447–481 | | | |
| | | | | PVGLH_HSV1E | 447–481 | | | |
| | | | | PVGLH_HSVBG | 357–406 | | | |
| | | | | PVGLH_HSVBC | 364–416 | | | |
| | | | | PVGLH_HSVE4 | 334–379 | 414–455 | | |
| | | | | PVGLH_HSVEB | 327–372 | 407–448 | | |
| | | | | PVGLH_HSVSA | 32–88 | 374–453 | 664–712 | |
| | | | | PVGLH_MCMVS | 440–474 | | | |
| | | | | PVGLH_PRVKA | 226–260 | | | |
| | | | | PVGLH_PRVN3 | 226–260 | | | |
| | | | | PVGLH_PRVRI | 226–260 | | | |
| | | | | PVGLH_VZVD | 455–506 | | | |
| | | | | PVGLI_HCMVA | 47–111 | 323–359 | | |
| | | | | PVGLM_BUNGE | 512–567 | 685–737 | 1228–1262 | |

TABLE V-continued

Search Results Summary for 107 × 178 × 4 and ALLMOT15 Motifs

| 107 × 178 × 4 LIBRARY FILE | ALLMOT15 LIBRARY FILE | | | |
|---|---|---|---|---|
| | PVGLM_BUNL7 | 643–677 | 916–950 | |
| | PVGLM_BUNSH | 643–677 | | |
| | PVGLM_BUNYW | 340–374 | 504–563 | 905–939 |
| | PVGLM_DUGBV | 937–989 | 1239–1300 | |
| | PVGLM_HANTB | 693–727 | | |
| | PVGLM_HANTH | 72–106 | | |
| | PVGLM_HANTL | 72–106 | | |
| | PVGLM_HANTV | 72–108 | | |
| | PVGLM_PHV | 73–111 | | |
| | PVGLM_PTPV | 149–251 | | |
| | PVGLM_SEOUR | 694–728 | | |
| | PVGLM_SEOUS | 693–730 | | |
| | PVGLN_BEFV | 377–414 | 513–569 | |
| | PVGLP_BEV | 43–82 | 90–124 | 622–856 |
| | PVGLX_HSVEB | 177–262 | | |
| | PVGLX_PRVRI | 420–461 | | |
| | PVGLY_JUNIN | 301–349 | | |
| | PVGLY_LASSG | 317–360 | 388–422 | |
| | PVGLY_LASSJ | 316–361 | 389–423 | |
| | PVGLY_LYCVA | 333–367 | 395–432 | |
| | PVGLY_LYCVW | 124–158 | 333–367 | 395–432 |
| | PVGLY_MOPEI | 316–359 | | |
| | PVGLY_PIARV | 334–375 | | |
| | PVGLY_TACV | 315–363 | | |
| | PVGLY_TACV5 | 303–351 | 382–416 | |
| | PVGLY_TACV7 | 302–350 | 381–415 | |
| | PVGLY_TACVT | 303–351 | 382–416 | |
| | PVGNB_CPMV | 835–869 | 403–437 | |
| | PVGNM_BPMV | 143–177 | | |
| | PVGNM_CPMV | 160–201 | | |
| | PVGNM_CPSMV | 192–226 | 758–792 | 674–915 |
| | PVGNM_RCMV | 837–871 | 912–946 | |
| | PVGP8_EBV | 94–149 | | |
| | PVM01_VACCC | 5–56 | | |
| | PVM1_REOVL | 287–321 | | |
| | PVM21_REOVD | 416–450 | 619–663 | |
| | PVM22_REOVD | 416–450 | 618–662 | |
| | PVM2_REOVJ | 416–450 | 618–662 | |
| | PVM2_REOVL | 135–190 | 618–662 | |
| | PVM3_REOVD | 42–90 | 337–371 | 623–558 | 618–690 |
| | PVMA2_BRSVA | 42–90 | | |
| | PVMA2_HRSVA | 193–234 | | |
| | PVMAT_CDVO | 73–114 | 151–208 | |
| | PVMAT_INCJ | 310–359 | | |
| | PVMAT_NDVA | 324–358 | | |
| | PVMAT_NDVB | | | |

TABLE V-continued

Search Results Summary for 107 × 178 × 4 and ALLMOT15 Motifs

| 107 × 178 × 4 LIBRARY FILE | ALLMOT15 LIBRARY FILE | | |
|---|---|---|---|
| | PVMAT_PI3B | 99–133 | 204–252 |
| | PVMAT_PI3H4 | 99–133 | 204–252 |
| | PVMAT_RABVA | 69–103 | |
| | PVMAT_RABVC | 69–103 | |
| | PVMAT_RABVE | 69–103 | |
| | PVMAT_RABVN | 69–103 | |
| | PVMAT_RABVP | 69–103 | |
| | PVMAT_RASVS | 69–103 | |
| | PVMAT_SYNV | 246–280 | |
| | PVMAT_VSVIG | 198–232 | |
| | PVME1_CVBM | 175–209 | |
| | PVME1_CVPFS | 98–140 | 212–267 |
| | PVME1_CVPPU | 212–257 | |
| | PVME1_CVPRM | 212–257 | |
| | PVME1_CVTKE | 28–62 | 175–209 |
| | PVME1_FIPV | 212–267 | |
| | PVME1_IBV6 | 21–55 | 177–218 |
| | PVME1_IBVB | 21–55 | 177–218 |
| | PVME1_IBVB2 | 21–55 | 177–218 |
| | PVME1_IBVK | 36–94 | |
| | PVMP_CAMVC | 187–254 | 270–324 |
| | PVMP_CAMVD | 187–254 | 270–324 |
| | PVMP_CAMVE | 187–254 | 270–324 |
| | PVMP_CAMVN | 187–254 | 270–324 |
| | PVMP_CAMVS | 187–254 | 270–324 |
| | PVMP_CAMVW | 187–254 | 270–324 |
| | PVMP_CERV | 212–246 | |
| | PVMP_FMVD | 217–251 | |
| | PVMP_SOCMV | 76–118 | |
| | PVMSA_HPBDB | 272–313 | 324–361 |
| | PVMSA_HPBOC | 271–312 | 323–360 |
| | PVMSA_HPBDU | 234–275 | 289–323 |
| | PVMSA_HPBOW | 272–313 | 324–361 |
| | PVMSA_HPBGS | 210–244 | |
| | PVMSA_HPBHE | 294–328 | |
| | PVMSA_WHV1 | 208–242 | |
| | PVMSA_WHV59 | 213–247 | |
| | PVMSA_WHV7 | 213–247 | |
| | PVMSA_WHVBI | 213–247 | |
| | PVMT1_DHV1 | 201–235 | |
| | PVMT1_IAANN | 92–126 | 174–222 |
| | PVMT1_IABAN | 92–126 | 174–222 |
| | PVMT1_IACAO | 31–79 | |

TABLE V-continued

Search Results Summary for 107 × 178 × 4 and ALLMOTI5 Motifs

| 107 × 178 × 4 LIBRARY FILE | ALLMOTI5 LIBRARY FILE | | |
|---|---|---|---|
| | PVMT1_IAFOW | 92–126 | 174–222 |
| | PVMT1_IAFPR | 92–126 | 174–222 |
| | PVMT1_IAFPW | 92–126 | 174–222 |
| | PVMT1_IALE1 | 92–126 | 174–222 |
| | PVMT1_IALE2 | 92–126 | 174–222 |
| | PVMT1_IAMAN | 92–126 | 174–222 |
| | PVMT1_IAPOC | 92–126 | 174–222 |
| | PVMT1_IAPUE | 92–126 | 174–222 |
| | PVMT1_IAUDO | 92–126 | 174–222 |
| | PVMT1_IAWIL | 92–126 | 174–222 |
| | PVMT1_IAZI1 | 92–126 | |
| | PVMT1_INBAC | 175–209 | |
| | PVMT1_INBLE | 175–209 | |
| | PVMT1_INBSI | 175–209 | |
| | PVMT2_INBAC | 132–184 | |
| | PVMT2_INBAD | 132–184 | |
| | PVMT2_INBLE | 132–184 | |
| | PVMT2_INBSI | 46–80 | |
| | PVMT8_MTXVL | | 145–197 |

TABLE VI

Search Results Summary for PCTLZIP, P1CTLZIP, and P2CTLZIP Motifs

| PCTLZIP LIBRARY FILE | | P1CTLZIP LIBRARY FILE | | | P2CTLZIP LIBRARY FILE | | |
|---|---|---|---|---|---|---|---|
| PENV_FOAMV | 481–496 | PENV_BIVO6 | 434–450 | | PENV_BIVO6 | 526–542 | |
| PENV_HV1MA | 438–453 | PENV_BIV27 | 463–479 | | PENV_BIV27 | 554–571 | |
| PENV_HV1MP | 163–188 | PENV_FOAMV | 481–496 | 864–880 | PENV_FENV1 | 30–47 | 630–647 |
| PENV_HVIRH | 445–480 | PENV_HV1KB | 762–788 | | PENV_FIVPE | 781–798 | |
| PEMV_HV18C | 188–201 | PENV_HV1MA | 437–453 | | PENV_FIVSD | 779–798 | |
| PENV_HVIZ2 | 123–138 | PENV_HV1MP | 183–199 | | PENV_FIVT2 | 780–797 | |
| PENV_HVIZH | 438–453 | PENV_HV1RH | 444–460 | | PENV_FRVC6 | 38–55 | 824–841 |
| PENV_HV28E | 750–785 | PENV_HV1S1 | 738–754 | | PENV_FLVGL | 806–822 | |
| PENV_HV2D1 | 741–758 | PENV_HVISC | 168–201 | | PENV_FLVLB | 825–842 | |
| PENV_HV231 | 741–758 | PENV_HV1Z2 | 123–138 | | PENV_FLVSA | 802–619 | |
| PENV_HV2NZ | 742–757 | PENV_HV1Z3 | 117–133 | | PENV_FOAMV | 710–727 | 967–974 |
| PENV_HV2RO | 751–766 | PENV_HVIZH | 437–453 | | PENV_FSVGA | 825–642 | |
| PENV_HV2S8 | 743–758 | PENV_HV2BE | 750–765 | | PENV_FSVGB | 806–822 | |
| PENV_HV2ST | 745–780 | PENV_HV2D1 | 741–758 | | PENV_FBVSM | 608–625 | |
| PENV_JSRV | 104–119 | PENV_HV2G1 | 741–758 | | PENV_HV1OY | 123–140 | |
| PENV_MMTVB | 618–633 | PENV_HV2NZ | 742–767 | | PENV_HV1Z2 | 410–427 | |
| PENV_MMTVG | 618–633 | PENV_HV2RO | 751–788 | | PENV_HV1Z3 | 154–171 | |
| PENV_SIVMK | 139–154 | PENV_HV2S8 | 743–758 | | PENV_HV2CA | 750–787 | |
| PENV_SIVML | 139–154 | PENV_HV2ST | 745–760 | | PENV_MCFF | 600–617 | |
| PHEMA_CVBLY | 391–408 | PENV_JSRV | 104–119 | 541–567 | PENV_MCFF3 | 601–618 | |
| PHEMA_CVBM | 391–408 | PENV_MCFF | 397–413 | | PENV_MLVAV | 630–647 | |
| PHEMA_CVSQ | 391–408 | PENV_MCFF3 | 397–413 | | PENV_MLVCB | 626–642 | |
| PHEMA_CVHOC | 391–408 | PENV_MLVAV | 427–443 | | PENV_MLVF5 | 639–656 | |
| PHEMA_CVMA5 | 402–417 | PENV_MLVCB | 423–438 | | PENV_MLVFF | 639–656 | |
| PHEMA_CVMS | 403–418 | PENV_MLVHO | 424–440 | | PENV_MLVFP | 639–656 | |
| PHEMA_INBAA | 295–310 | PENV_MLVMO | 426–442 | | PENV_MLVNO | 626–643 | |
| PHEMA_INBBE | 303–318 | PENV_MLVRD | 424–440 | | PENV_MLVKI | 167–164 | |
| PHEMA_INBBO | 293–309 | PENV_MLVRK | 424–440 | | PENV_MLVMO | 629–646 | |
| PHEMA_INBEN | 301–318 | PENV_MMTVB | 816–833 | | PENV_MLVRD | 624–641 | |
| PHEMA_INBFU | 288–301 | PENV_MMTVG | 618–633 | | PENV_MLVRK | 624–641 | |
| PHEMA_INBGL | 286–311 | PENV_SFV1 | 884–880 | | PENV_MSVFB | 170–187 | |
| PHEMA_INBHK | 293–308 | PENV_SFV3L | 881–577 | | PENV_RMCFV | 603–620 | |
| PHEMA_INBIB | 266–303 | PENV_SIVGB | 93–109 | | PENV_SPV1 | 710–727 | 957–974 |
| PHEMA_INBID | 299–314 | PENV_SIVMK | 139–154 | 802–818 | PENV_SFV3L | 707–724 | 954–971 |
| PHEMA_INBLE | 302–317 | PENV_SIVML | 139–154 | 801–817 | PENV_SIVM1 | 766–783 | |
| PHEMA_INBMD | 292–307 | PENV_SIVS4 | 808–822 | | PENV_SIVMK | 765–782 | |
| PHEMA_INBME | 298–311 | PENV_SIVBP | 810–826 | | PENV_SWML | 764–781 | |
| PHEMA_INBNA | 288–303 | PHEMA_CDVO | 38–62 | | PENV_SIVS4 | 769–786 | |
| PHEMA_INBOR | 301–318 | PHEMA_CVBLY | 391–408 | | PENV_SIVSP | 773–790 | |
| PHEMA_INBSI | 301–318 | PHEMA_CVBM | 391–408 | | PENV_SMRVH | 638–553 | |
| PHEMA_INSBJ | 299–313 | PHEMA_CVBQ | 391–408 | | PENV_SMSAV | 42–69 | |
| PHEMA_INBUS | 294–309 | PHEMA_CVHOC | 391–408 | | PHEMA_CDVO | 38–53 | 200–217 |
| PHEMA_INBVI | 296–311 | PHEMA_CVMA6 | 402–417 | | PHEMA_CVBLV | 391–408 | |
| PHEMA_INBVK | 303–318 | PHEMA_CVMS | 403–418 | | PHEMA_CVSM | 391–408 | |
| PHEMA_INBYB | 286–301 | PHEMA_IAAIC | 237–253 | | PHEMA_CVBQ | 391–408 | |
| PHEMA_MUMPM | 133–148 | PHEMA_IABAN | 221–237 | | PHEMA_CVHOC | 391–408 | |

TABLE VI-continued

Search Results Summary for PCTLZIP, P1CTLZIP, and P2CTLZIP Motifs

| PCTLZIP LIBRARY FILE | | | P1CTLZIP LIBRARY FILE | | P2CTLZIP LIBRARY FILE | |
|---|---|---|---|---|---|---|
| PHEMA__MUMPR | 133–148 | | PHEMA__IABUD | 234–250 | PHEMA__IAAIC | 322–339 |
| PHEMA__MUMPS | 133–148 | | PHEMA__IACKA | 234–250 | PHEMA__IABAN | 320–323 |
| PHEMA__PIHW | 345–380 | | PHEMA__IACKG | 231–247 | PHEMA__IABUD | 320–337 |
| PHEMA__PI2N | 65–80 | | PHEMA__IACKV | 230–248 | PHEMA__IACKA | 320–337 |
| PHEMA__PI2HT | 65–80 | | PHEMA__IADA1 | 234–250 | PHEMA__IACKG | 316–333 |
| PHEMA__RINDK | 366–383 | | PHEMA__IADA3 | 237–253 | PHEMA__IACKP | 302–319 |
| PHEMA__SV5 | 7–94 | | PHEMA__IADCZ | 234–250 | PHEMA__IACKQ | 302–319 |
| PHEMA__SV5CM | 7–94 | | PHEMA__IADH1 | 221–237 | PHEMA__IACKS | 319–336 |
| PHEMA__SV5CP | 7–94 | | PHEMA__IADH2 | 221–237 | PHEMA__IACKV | 315–332 |
| PHEMA__SV5LN | 7–94 | | PHEMA__IADH3 | 221–237 | PHEMA__IADA1 | 320–337 |
| PVENV__DHVI1 | 42–57 | | PHEMA__IADH4 | 221–237 | PHEMA__IADA3 | 322–339 |
| PVFP7__CAPVK | 89–104 | | PHEMA__IADH5 | 221–237 | PHEMA__IADCZ | 320–337 |
| PVFUS__VACC6 | 72–87 | | PHEMA__IADH6 | 221–237 | PHEMA__IADH1 | 306–323 |
| PVGOI__BPP22 | 242–257 | | PHEMA__IADH7 | 221–237 | PHEMA__IADH2 | 306–323 |
| PVGO1__HSVEB | 169–184 | | PHEMA__IADM2 | 237–253 | PHEMA__IAOH3 | 306–323 |
| PVGQ1__HSVI1 | 210–226 | 317–332 | PHEMA__IADNZ | 234–250 | PHEMA__IADN4 | 306–323 |
| PV006__BPT4 | 184–199 | | PHEMA__IAEN6 | 221–237 | PHEMA__IADH6 | 306–323 |
| PVOD7__BPT4 | 885–900 | | PHEMA__IAEN7 | 237–253 | PHEMA__IADN7 | 306–323 |
| PVGOS__HSVI1 | 134–149 | | PHEMA__IAFPR | 230–248 | PHEMA__IADM2 | 322–339 |
| PVGIO__BPPH2 | 183–196 | | PHEMA__IAHAL | 236–252 | PHEMA__IADMZ | 320–337 |
| PVG1O__BPPZA | 183–196 | | PHEMA__IANAR | 235–251 | PHEMA__IADU3 | 322–339 |
| PVGIO__HSVSA | 109–124 | | PHEMA__IAHC8 | 230–246 | PHEMA__IAEN6 | 306–323 |
| PVG16__BPP1 | 81–96 | | PHEMA__IAHC7 | 230–246 | PHEMA__IAEN7 | 322–339 |
| PVG18__BPT4 | 463–483 | | PHEMA__IAHCD | 230–246 | PHEMA__IAFPR | 315–332 |
| PVG2S__BPT4 | 97–112 | | PHEMA__IAHDE | 230–246 | PHBMA__IAGRE | 320–337 |
| PVG29__HSVI1 | 20–35 | | PHEMA__IAHFO | 236–252 | PHEMA__IAGU2 | 320–337 |
| PVG3O__BPPH6 | 11–94 | | PHEMA__IAHK6 | 236–252 | PHEMA__IAGUA | 319–336 |
| PVG3O__BPOX2 | 22–37 | | PHEMA__IAHK7 | 236–252 | PHEMA__IAHAL | 321–338 |
| PVG36__NBVSA | 108–123 | | PHEMA__IAHLE | 230–246 | PHEMA__IAHC6 | 315–332 |
| PVG37__BPT2 | 1253–1268 | | PHEMA__IAHLO | 230–246 | PHEMA__IAHC7 | 315–332 |
| PVG37__HBVI1 | 284–299 | | PHEMA__IAHMI | 236–252 | PHEMA__IAHCD | 315–332 |
| PVG55__HSVI1 | 22–37 | 143–158 | PHEMA__IAHNM | 236–252 | PHEMA__IAHDE | 315–332 |
| PVGS6__HSVI1 | 268–283 | | PHEMA__IANRO | 236–252 | PHEMA__IAHFO | 321–338 |
| PVGS8__HSVI1 | 102–117 | | PHEMA__IAHSA | 236–252 | PHEMA__IAHK6 | 321–338 |
| PVG59__HSVI1 | 267–292 | | PHEMA__IAHSP | 230–246 | PHEMA__IAHK7 | 321–339 |
| PVG65__HSVI1 | 518–533 | | PHEMA__IAHSW | 230–246 | PHEMA__IAHLE | 315–332 |
| PVG9__BPPH2 | 234–279 | | PHEMA__IAHTE | 236–252 | PHEMA__IAHLO | 316–332 |
| PVG9__BPPZA | 234–279 | | PHEMA__IAHTO | 236–252 | PHEMA__IAHMI | 321–338 |
| PVG9__SPV1R | 57–72 | | PHEMA__IAHUR | 236–252 | PHEMA__IAHNM | 321–338 |
| PVGF__BPPHX | 234–249 | | PHEMA__IAKIE | 235–251 | PHEMA__IAHNN | 315–332 |
| PVGL2__CVBF | 264–279 | | PHEMA__IALEN | 235–251 | PHEMA__IANPR | 315–332 |
| PVGL2__CVBL9 | 264–279 | | PHEMA__IAMAA | 233–249 | PHEMA__IAHRO | 321–338 |
| PVGL2__CVBLY | 264–279 | | PHEMA__IAMAB | 236–254 | PHEMA__IANSA | 321–338 |
| PVGL2__CVBM | 264–279 | | PHEMA__IAMAO | 237–253 | PNEMA__IANSP | 315–332 |
| PVGL2__CVBQ | 264–279 | | PHEMA__IAME1 | 237–253 | PHEMA__IANSW | 315–332 |
| PVGL2__CVBV | 264–279 | | PHEMA__IAME2 | 237–253 | PHEMA__IANTE | 321–339 |
| PVGL2__CVPFS | 442–467 | | PHEMA__IAMEG | 221–237 | PHEMA__IAHTO | 321–339 |

TABLE VI-continued

Search Results Summary for PCTLZIP, P1CTLZIP, and P2CTLZIP Motifs

| PCTLZIP LIBRARY FILE | | P1CTLZIP LIBRARY FILE | | | P2CTLZIP LIBRARY FILE | |
|---|---|---|---|---|---|---|
| PVGL2_CVPPU | 440–465 | PHEMA_IAMIN | 85–101 | | PHEMA_IAHUR | 321–339 |
| PVGL2_CVPRB | 218–233 | PHEMA_IANT8 | 237–263 | | PHEMA_IAJAP | 317–334 |
| PVGL2_CVPRM | 218–233 | PHEMA_IAQU7 | 221–237 | | PHEMA_IAMAA | 319–338 |
| PVGL2_IBV8 | 1056–1071 | PHEMA_IARUD | 234–250 | | PHEMA_IAMAB | 324–341 |
| PVGL2_IBVB | 1055–1070 | PHEMA_IASE2 | 234–250 | | PHEMA_IAMAO | 322–339 |
| PVGL2_IBVD2 | 1058–1071 | PHEMA_IASH2 | 234–250 | | PHEMA_IAME1 | 322–339 |
| PVGL2_IBVK | 1055–1070 | PHEMA_IASTA | 230–246 | | PHEMA_IAME2 | 322–339 |
| PVGL2_IBVM | 1055–1070 | PHEMA_IATAI | 235–251 | | PH

TABLE VI-continued

Search Results Summary for PCTLZIP, P1CTLZIP, and P2CTLZIP Motifs

| PCTLZIP LIBRARY FILE | P1CTLZIP LIBRARY FILE | | | P2CTLZIP LIBRARY FILE | |
|---|---|---|---|---|---|
| PVMT2_LALE2 | 25–40 | PHEMA_PI3H4 | 324–340 | PHEMA_SV5 | 84–101 |
| PVMT2_IAMAN | 25–40 | PHEMA_PI3HA | 324–340 | PHEMA_SV5CM | 84–101 |
| PVMT2_IAPUE | 25–40 | PHEMA_PI3HT | 324–340 | PHEMA_SV5CP | 84–101 |
| PVMT2_IASIN | 25–40 | PHEMA_PI3HU | 324–340 | PHEMA_SV5LN | 84–101 |
| PVMT2_IAUDO | 25–40 | PHEMA_PI3HV | 324–340 | PVFDS_VACCC | 280–297 |
| PVMT2_IAWIL | 25–40 | PHEMA_PI3HW | 324–340 | PVVDB_VACCP | 280–297 |
| PVMT2_MYXVL | 228–241 | PHEMA_PI3HX | 324–340 | PVFOS_VACCV | 281–298 |
| | | PHEMA_RINDK | 380–383 | PVFO9_VACCV | 176–193 |
| | | PHEMA_BV5 | 7–94 | PVFD9_VACCV | 209–226 |
| | | PHEMA_SV5CM | 7–94 | PVG27_HSVSA | 173–190 |
| | | PHEMA_SV5CP | 7–94 | PVG2S_H8VI1 | 648–686 |
| | | PHEMA_SV5LH | 7–94 | PVG39_HSVI1 | 109–128 |
| | | PVENV_DHVI1 | 42–57 | PVG43_HSVI1 | 171–188 |
| | | PVENV_EAV | 25–41 | PVG87_HSVI1 | 1252–1289 |
| | | PVFP2_FOWPV | 88–104 | PVG72_HSVI1 | 3073–3090 |
| | | PVFP7_CAPVK | 89–104 | PVGF1_HBVB | 1094–1111 |
| | | PVFUS_VACC6 | 72–87 | PVGLB_IBV6 | 738–753 |
| | | PVGO1_HSVEB | 169–184 | PVGLB_HSVE1 | 675–892 |
| | | PVGO1_HSVI1 | 209–225 | PVGLB_HSVE4 | 738–753 |
| | | PVGO8_HSVI1 | 134–149 | PVGLB_HSVEA | 738–753 |
| | | PVG1O_HSVSA | 109–124 | PVGLB_HSVEB | 597–814 |
| | | PVG11_HSVI1 | 103–119 | PVGLB_HSVEL | 807–824 |
| | | PVG12_HSVI1 | 270–288 | PVGLB_I1TV6 | 807–824 |
| | | PVG1_SPV1R | 76–92 | PVGLB_I1TVS | 180–197 |
| | | PVG29_HSVI1 | 20–35 | PVGLB_I1TVT | 489–498 |
| | | PVG3B_BPOX2 | 22–37 | PVGLC_PRVIF | 401–418 |
| | | PVG3S_HSVSA | 108–123 | PVGLE_VZVD | 355–392 |
| | | PVG37_HSVI1 | 284–299 | PVGL_SV5 | 245–282 |
| | | PVG41_HSVI1 | 244–260 | PVGLH_HCMVA | 245–282 |
| | | PVVG46_HSVI1 | 1244–1260 | PVGLH_HCMVT | 43–80 | 603–820 |
| | | PVG55_HBVI1 | 22–37 | 143–158 | PVGLH_HSVI1 | 364–381 | 603–820 |
| | | PVG56_HSVI1 | 268–283 | | PVGLH_HSVI1E | 81–98 |
| | | PVG58_HSVI1 | 101–117 | | PVGLI_HSVI1 | 81–98 |
| | | PVG58_HSVSA | 130–148 | 330–348 | PVGLM_BUNL7 | 712–729 |
| | | PVG59_HSVI1 | 267–282 | | PVGLM_BUNSH | 712–729 |
| | | PVG65_HSVI1 | 362–378 | 518–533 | PVGLM_PUUMH | 344–381 |
| | | PVG71_HSVSA | 89–105 | | PVGLM_PUUMS | 344–381 |
| | | PVG9_BPPN2 | 234–249 | | PVGLM_RVFV | 12–94 |
| | | PVG9_BPPZA | 234–249 | | PVGLM_RVFVZ | 12–94 |
| | | PVG9_SPV1R | 57–72 | | PVGLV_LASSG | 12–94 |
| | | PVGF1_IBVB | 2210–2226 | | PVGLY_LASSJ | 12–94 |
| | | PVGL2_CVBF | 123–139 | 174–190 | 264–279 | PVGLY_LYCVA | 521–536 |
| | | PVGL2_CVBL9 | 123–139 | 174–190 | 264–279 | PVGLY_LYCVW | |
| | | PVGL2_CVBIY | 123–139 | 174–190 | 264–279 | PVGLY_MOPEI | |
| | | PVGL2_CVBM | 123–139 | 174–190 | 264–279 | PVM1_REOVD | 280–297 |
| | | PVGL2_CVBQ | 31–47 | 123–139 | 174–190 | PVM1_REOVL | 280–297 |
| | | PVGL2_CVBV | 123–139 | 174–190 | 264–279 | PVMAT_COVO | 148–185 |

TABLE VI-continued

Search Results Summary for PCTLZIP, P1CTLZIP, and P2CTLZIP Motifs

| PCTLZIP LIBRARY FILE | P1CTLZIP LIBRARY FILE | | | P2CTLZIP LIBRARY FILE | |
|---|---|---|---|---|---|
| PVGI2_CVM4 | 95–111 | 1267–1283 | | PVMAT_MEASI | 187–104 |
| PVGI2_CVMA5 | 95–111 | 1215–1231 | | PVMP_CAMVC | 147–164 |
| PVGI2_CVMJH | 95–111 | 1126–1142 | | PVMP_CAMVD | 147–164 |
| PVGI2_CVPFS | 442–457 | 800–816 | 1274–1290 | PVMP_CAMVE | 147–164 |
| PVGI2_CVPPU | 440–456 | 504–519 | 798–814 | PVMP_CAMVN | 147–164 |
| PVGI2_CVPR8 | 218–233 | 576–592 | 1050–1066 | PVMP_CAMVS | 147–164 |
| PVGI2_CVPRM | 218–233 | 576–592 | 1050–1066 | PVMP_CAMVW | 147–164 |
| PVGI2_FIPV | 803–819 | 1277–1293 | | PVMSA_HPBVO | 111–94 |
| PVGI2_IBV6 | 1056–1071 | | | PVMSA_HPBV2 | 185–202 |
| PVGI2_IBV8 | 1055–1070 | | | PVMSA_HPBV4 | 185–202 |
| PVGI2_IBVD2 | 1058–1071 | | | PVMSAHPBVA | 174–191 |
| PVGI2_IBVK | 1055–1070 | | | PVMSA_HPBVD | 11–94 |
| PVGI2_IBVM | 1055–1070 | | | PVMSA_PBV1 | 174–191 |
| PVGI.S_HSVSA | 701–718 | | | PVMSA_HPBVL | 174–197 |
| PVGI.S_PRVIF | 203–218 | | | PVMSA_HPBVN | 11–94 |
| PVGI.B_VZVD | 522–538 | | | PVMSA_HPBVO | 174–191 |
| PVGI.C_HSVBC | 475–490 | | | PVMSA_HPBVP | 185–202 |
| PVGI.C_HSVE4 | 444–459 | | | PVMSA_HPBVR | 185–202 |
| PVGI.C_HSVEB | 427–442 | | | PVMSA_HPBVS | 11–94 |
| PVGI.C_PRVIF | 446–461 | | | PVMBA_HPBVW | 174–191 |
| PVGI.C_VZVD | 150–165 | | | PVMSA_PSVZI | 174–191 |
| PVGI.C_VZVS | 150–168 | | | PVMT2_IAANN | 25–42 |
| PVGI.D_HSV11 | 79–94 | | | PVMT2_IABAN | 25–42 |
| PVGI.D_HSV2 | 79–94 | | | PVMT2_IAFOW | 25–42 |
| PVGI.E_PRVRI | 3–94 | | | PVMT2_IAFFR | 25–42 |
| PVGI.F_BRSVA | 205–221 | 265–280 | | PVMT2_IAFPW | 25–42 |
| PVGI.F_BRBVC | 205–221 | 265–280 | | PVMT2_IALEI | 25–42 |
| PVGI.F_BRSVR | 205–221 | 265–280 | | PVMT2_IALE2 | 25–42 |
| PVGI.F_CDVO | 398–414 | | | PVMT2_IAMAM | 25–42 |
| PVGI.F_HRSVI1 | 205–221 | 265–280 | | PVMT2_IAPUE | 25–42 |
| PVGI.F_HRSVA | 205–221 | 265–280 | | PVMT2_IASIN | 25–42 |
| PVGI.F_HRBVL | 205–221 | 265–280 | | PVMT2_IAUDO | 25–42 |
| PVGI.F_HRSVR | 205–221 | 265–280 | | PVMT2_IAWIL | 25–42 |
| PVGI.F_MEASE | 286–302 | | | | |
| PVGI.F_MEASI | 289–306 | | | | |
| PVGI.F_MEASY | 286–302 | | | | |
| PVGI.F_MUMPM | 276–292 | | | | |
| PVGI.F_MUMPR | 276–292 | 278–292 | | | |
| PVGI.F_MUMPS | 5–94 | | | | |
| PVGI.F_NDVA | 273–289 | | | | |
| PVGI.P_NDVS | 273–289 | | | | |
| PVGI.P_NDVM | 273–289 | | | | |
| PVGI.P_NDVT | 273–289 | | | | |
| PVGI.F_NDVTG | 273–289 | | | | |
| PVGI.F_NDVU | 273–289 | | | | |
| PVGI.P_PHODV | 269–285 | 387–383 | | | |
| PVGI.F_RINDK | 282–298 | | | | |

TABLE VI-continued

Search Results Summary for PCTLZIP, P1CTLZIP, and P2CTLZIP Motifs

| PCTLZIP LIBRARY FILE | P1CTLZIP LIBRARY FILE | | P2CTLZIP LIBRARY FILE |
|---|---|---|---|
| | PVGLF_RINDL | 282–298 | |
| | PVGLF_TRITV | 175–191 | |
| | PVGLI_VZVD | 276–293 | |
| | PVGLM_HANTB | 355–371 | 900–915 |
| | PVGLM_HANTH | 499–515 | |
| | PVGLM_HANTL | 499–515 | |
| | PVGLM_HANTV | 499–515 | |
| | PVGLM_PTPV | 743–758 | |
| | PVGLM_PUUMH | 509–525 | |
| | PVGLM_PUUMS | 509–525 | |
| | PVGLM_SEOUR | 355–371 | 901–916 |
| | PVGLM_SEOUS | 355–371 | 900–915 |
| | PVGLM_UUK | 826–842 | |
| | PVGLP_BEV | 669–886 | |
| | PVGLY_LASSG | 12–94 | 428–441 |
| | PVGLY_LASSJ | 12–94 | 427–442 |
| | PVGLY_LYCVA | 12–94 | |
| | PVGLY_LVCVW | 12–94 | |
| | PVGLY_MOPEI | 12–94 | 425–440 |
| | PVGLY_PIARV | 1021–1037 | |
| | PVGNM_CPMV | 521–530 | |
| | PVM3_REOVD | 191–207 | |
| | PVMAT_MUMPS | 135–151 | |
| | PVMAT_NDVA | 135–151 | |
| | PVMAT_NDVB | 189–206 | |
| | PVMAT_PI2HT | 189–206 | |
| | PVMAT_SV41 | 98–114 | 132–148 |
| | PVMAT_SV6 | 118–134 | |
| | PVMP_CAMVC | 118–134 | |
| | PVMP_CAMVD | 118–134 | |
| | PVMP_CAMVE | 118–134 | |
| | PVMP_CAMVN | 118–134 | |
| | PVMP_CAMVS | 118–134 | |
| | PVMP_CAMVW | 115–131 | |
| | PVMP_FMVD | 380–396 | |
| | PVMSA_HPBGS | 187–202 | |
| | PVMSA_HPBV9 | 378–393 | |
| | PVMSA_WHV1 | 383–398 | |
| | PVMSA_WHV59 | 383–398 | |
| | PVMSA_WHV7 | 383–398 | |
| | PVMSA_WHV8 | 383–398 | |
| | PVMSA_WHV8I | 234–249 | |
| | PVMSA_WHVW6 | | |

TABLE VI-continued

Search Results Summary for PCTLZIP, P1CTLZIP, and P2CTLZIP Motifs

| PCTLZIP LIBRARY FILE | P1CTLZIP LIBRARY FILE | | P2CTLZIP LIBRARY FILE |
|---|---|---|---|
| | PVMT2_IAANN | 25–40 | |
| | PVMT2_IABAN | 25–40 | |
| | PVMT2_IAFOW | 25–40 | |
| | PVMT2_IAFPR | 25–40 | |
| | PVMT2_IAFPW | 25–40 | |
| | PVMT2_IALE1 | 25–40 | |
| | PVMT2_IALE2 | 25–40 | |
| | PVMT2_IAMAN | 25–40 | |
| | PVMT2_IAPUE | 25–40 | |
| | PVMT2_IASIN | 25–40 | |
| | PVMT2_IAUDO | 25–40 | |
| | PVMT2_IAWIL | 25–40 | |
| | PVMT9_MYXVL | 226–241 | |

TABLE VII

Search Results Summary for P3CTLZIP, P4CTLZIP, P5CTLZIP, and P6CTLZIP Motifs

| P3CTLZIP LIBRARY FILE | | | P4CTLZIP LIBRARY FILE | | | P5CTLZIP LIBRARY FILE | | | P6CTLZIP LIBRARY FILE | | | |
|---|---|---|---|---|---|---|---|---|---|---|---|---|
| PENV_BIV27 | 147–165 | | PENV1_FRSFV | 380–399 | | PENV1_FRSFV | 380–400 | | PENV_BIV06 | 47–68 | 625–546 | |
| PENV_CAEVC | 810–828 | | PENV_AVISU | 98–117 | | PENV2_FRSFV | 380–400 | | PENV_BIV27 | 47–68 | 147–168 | 564–575 |
| PENV_CAEVG | 808–826 | | PENV_BIV27 | 147–166 | | PENV_BAEVM | 170–190 | | PENV_FENV1 | 225–246 | 630–651 | |
| PENV_HV2BE | 750–768 | | PENV_HV1ZH | 123–142 | | PENV_FIVPE | 781–801 | | PENV_FLVC6 | 624–645 | | |
| PENV_HV2D1 | 741–759 | | PENV_HV2D2 | 9–29 | | PENV_FIVSD | 779–799 | | PENV_FLVGL | 447–468 | 605–626 | |
| PENV_HV2G1 | 741–759 | | PENV_HV2SB | 778–797 | | PENV_FIVT2 | 780–800 | | PENV_FLVLB | 467–488 | 625–646 | |
| PENV_HV2NZ | 742–760 | | PENV_JSRV | 541–560 | | PENV_FLVGL | 9–29 | | PENV_FLVSA | 444–465 | 602–623 | |
| PENV_HV2RO | 751–769 | | PENV_RSVP | 533–552 | | PENV_FOAMV | 255–275 | 924–944 | PENV_FOAMV | 153–174 | 957–978 | |
| PENV_HV2SB | 743–761 | | PHEMA_VACCC | 173–192 | | PENV_FSVGA | 9–29 | | PENV_FSVGA | 467–488 | 625–646 | |
| PENV_HV2ST | 745–763 | | PHEMA_VACCI | 173–192 | | PENV_HV1C4 | 428–448 | | PENV_FSVGB | 447–468 | 605–626 | |
| PENV_JSRV | 376–394 | | PHEMA_VACCT | 173–192 | | PENV_HV2CA | 750–770 | | PENV_FSVSM | 450–471 | 608–629 | |
| PHEMA_PI2H | 118–136 | | PHEMA_VACCV | 173–192 | | PENV_MLVF5 | 400–420 | | PENV_FSVST | 467–488 | | |
| PHEMA_PI2HT | 118–136 | | PVENV_BEV | 62–81 | | PENV_MMTVB | 643–663 | | PENV_GALV | 52–73 | 519–540 | |
| PHEMA_6V41 | 55–73 | | PVENV_MCV1 | 61–80 | | PENV_MMTVG | 643–663 | | PENV_HV2BE | 750–771 | | |
| PVENV_THOGV | 473–491 | | PVENV_MCV2 | 61–80 | | PENV_OMVVS | 75–95 | | PENV_HV2G1 | 741–782 | | |
| PVG16_BPP22 | 83–101 | | PVFUS_ORFNZ | 29–48 | | PENV_RSVP | 42–62 | | PENV_HV2NZ | 742–763 | | |
| PVG24_BPT4 | 115–133 | | PVG01_HSVEB | 169–188 | | PENV_SFV1 | 924–944 | | PENV_HV2RO | 751–772 | | |
| PVG36_HSVSA | 344–362 | | PVG01_VACCC | 376–395 | | PENV_SFV3L | 921–941 | | PENV_HV2ST | 745–766 | | |
| PVG40_HSVI1 | 14–32 | | PVG01_VACCV | 315–334 | | PENV_SIVM1 | 766–786 | | PENV_MCFF | 600–621 | | |
| PVG50_HSVSA | 5–94 | | PVG01_VARV | 376–395 | | PENV_SIVMK | 765–785 | | PENV_MCFF3 | 601–622 | | |
| PVG51_BPT4 | 63–81 | | PVG06_BPT4 | 627–646 | | PENV_SIVML | 764–784 | | PENV_MLVAV | 630–651 | | |
| PVG51_HSVI1 | 84–102 | | PVG10_HSVI1 | 35–54 | | PENV_SIVS4 | 769–789 | | PENV_MLVCB | 625–646 | | |
| PVG65_HSVI1 | 165–173 | | PVG11_HSVI1 | 103–122 | 150–169 | PENV_SIVSP | 773–793 | | PENV_MLVF5 | 639–660 | | |
| PVGF1_IBVB | 2788–2806 | 3374–3392 | PVG1_BPPH2 | 31–50 | | PHEMA_CDVO | 493–513 | | PENV_MLVFF | 639–660 | | |
| PVGL2_CVH22 | 1053–1071 | | PVG1_SPV1R | 659–678 | | PHEMA_CVBLY | 391–411 | | PENV_MLVFP | 639–660 | | |
| PVGL2_IBV6 | 1056–1074 | | PVG20_BPT4 | 231–250 | | PHEMA_CVBM | 391–411 | | PENV_MLVHO | 626–647 | | |
| PVGL2_IBVB | 1055–1073 | | PVG32_VZVD | 90–109 | | PHEMA_CVBQ | 391–411 | | PENV_MLVKI | 167–188 | | |
| PVGL2_IBVD2 | 1056–1074 | | PVG36_BPK3 | 132–151 | | PHEMA_CVHOC | 391–411 | | PENV_MLVMO | 629–650 | | |
| PVGL2_IBVK | 1055–1073 | | PVG37_BPT2 | 19–38 | 629–648 | PHEMA_CVMA5 | 402–422 | | PENV_MLVRD | 624–645 | | |
| PVGL2_IBVM | 1055–1073 | | PVG37_BPT4 | 19–38 | 625–644 | PHEMA_IACKG | 81–101 | | PENV_MLVRK | 624–645 | | |
| PVGLB_HSVB1 | 560–578 | 689–707 | PVG39_HSVI1 | 1038–1057 | | PHEMA_IADMA | 81–101 | | PENV_MSVFB | 170–191 | | |
| PVGLB_HSVBC | 692–710 | | PVG41_HSVI1 | 62–81 | | PHEMA_MUMPM | 397–417 | | PENV_RMCFV | 603–624 | | |
| PVGLB_HSVSA | 584–602 | | PVG43_BPPF3 | 380–399 | | PHEMA_MUMPR | 397–417 | | PENV_SFV1 | 957–978 | | |
| PVGLB_ILTV6 | 740–758 | | PVG46_BPPF1 | 337–356 | | PHEMA_MUMPS | 397–417 | | PENV_SFV3L | 157–178 | 954–975 | |
| PVGLB_ILTVS | 750–768 | | PVG59_HSVI1 | 142–161 | | PHEMA_PHODV | 493–513 | | PENV_SIVAI | 437–458 | | |
| PVGLB_ILTVT | 750–768 | | PVG61_HSVI1 | 117–136 | | PHEMA_PI1HW | 322–342 | | PENV_SIVAG | 442–463 | | |
| PVGLC_VZVD | 431–449 | | PVG67_HSVI1 | 318–337 | 1072–1091 | PHEMA_PI2H | 13–33 | | PENV_SIVA1 | 421–442 | | |
| PVGLC_VZVS | 431–449 | | PVGF1_IBVB | 1587–1606 | 2108–2127 | PHEMA_PI2HT | 13–33 | | PENV_SIVAT | 435–456 | | |
| PVGLF_PI3H4 | 2–94 | | PVGL2_CVBF | 991–1010 | | PHEMA_RINDL | 497–517 | | PENV_SMSAV | 42–63 | | |
| PVGLH_HSV6G | 314–332 | | PVGL2_CVBL9 | 991–1010 | | PHEMA_SEND5 | 322–342 | | PHEMA_CVMA5 | 402–423 | | |
| PVGLH_HSVE4 | 814–832 | | PVGL2_CVBLY | 991–1010 | | PHEMA_SENDF | 322–342 | | PHEMA_IADE1 | 266–287 | | |
| PVGLH_HSVEB | 807–826 | | PVGL2_CVBM | 991–1010 | | PHEMA_SENDH | 322–342 | | PHEMA_MUMPM | 225–246 | | |
| PVGLI_HSV11 | 5–94 | | PVGL2_CVBQ | 991–1010 | | PHEMA_SENDJ | 322–342 | | PHEMA_MUMPR | 225–246 | | |
| PVGNM_BPMV | 678–696 | | PVGL2_CVBV | 991–1010 | | PHEMA_SENDZ | 322–342 | | PHEMA_MUMPS | 225–246 | | |
| PVM01_VACCC | 134–152 | 177–195 | PVGL2_CVH22 | 768–787 | 1115–1134 | PVENV_LELV | 27–47 | 148–168 | PHEMA_PHODV | 213–234 | | |

TABLE VII-continued

Search Results Summary for P3CTLZIP, P4CTLZIP, P5CTLZIP, and P6CTLZIP Motifs

| P3CTLZIP LIBRARY FILE | | P4CTLZIP LIBRARY FILE | | P5CTLZIP LIBRARY FILE | | P6CTLZIP LIBRARY FILE | |
|---|---|---|---|---|---|---|---|
| PVM01_VACCV | 83–101 | PVGL2_CVM4 | 999–1018 | PVENV_THOGV | 356–376 | PHEMA_PI2H | 13–34 |
| PVM1_REOVD | 227–245 | PVGL2_CVMA5 | 947–966 | PVG01_VACCC | 298–318 | PHEMA_PI2HT | 13–34 |
| PVM1_REOVL | 227–245 | PVGL2_CVMJH | 856–877 | PVG01_VACCV | 237–257 | PHEMA_SV5 | |
| PVMAT_HRSVA | 44–62 | PVGL2_CVPFS | 64–83 | PVG01_VARV | 298–318 | PHEMA_SV5CM | 379–400 |
| PVMAT_NDVA | 190–208 | PVGL2_CVPPU | 64–83 | PVG06_VACCV | 31–51 | PHEMA_SV5CP | 379–400 |
| PVMAT_NDVB | 190–208 | PVGL2_CVPR8 | 814–833 | PVG06_VARV | 31–51 | PHEMA_SV5LN | 379–400 |
| PVMP_CAMVC | 183–201 | PVGL2_CVPRM | 814–833 | PVG09_BPPF1 | 25–45 | PVG01_HSVEB | 169–190 |
| PVMP_CAMVD | 183–201 | PVGL2_FIPV | 1041–1060 | PVG12_HSVI1 | 151–171 | PVG01_HSVI1 | 589–610 |
| PVMP_CAMVE | 183–201 | PVGL2_IBV6 | 588–607 | PVG22_HSVI1 | 300–320 | PVG23_HSVI1 | 314–335 |
| PVMP_CAMVN | 183–201 | PVGL2_IBVB | 587–606 | PVG39_HSVI1 | 648–668 | PVG37_BPOX2 | 65–86 |
| PVMP_CAMVS | 183–201 | PVGL2_IBVD2 | 587–606 | PVG51_HSVI1 | 29–49 | PVG43_HSVI1 | 157–178 |
| PVMP_CAMVW | 183–201 | PVGL2_IBVK | 587–606 | PVG63_HSVI1 | 336–356 | PVG55_HSVI1 | 288–309 |
| PVMP_FMVD | 180–198 | PVGL2_IBVM | 587–606 | PVG65_HSVI1 | 117–137 | PVG55_HSVSA | 85–106 |
| | | PVGLB_HCMVA | 706–725 | PVG74_HSVSA | 124–144 | PVG56_HSVI1 | 1155–1176 |
| | | PVGLB_HCMVT | 707–726 | PVGL2_IBV6 | 328–348 | PVG58_HSVSA | 266–287 |
| | | PVGLB_HSV6U | 117–136 | PVGL2_IBVB | 327–347 | PVG60_HSVI1 | 30–51 |
| | | PVGLB_ILTV6 | 256–275 | PVGL2_IBVD2 | 328–346 | PVG63_HSVI1 | 238–259 |
| | | PVGLB_ILTVS | 266–285 | PVGL2_IBVD3 | 328–348 | PVGF1_IBVB | 1856–1877 |
| | | PVGLB_ILTVT | 266–285 | PVGL2_IBVK | 327–347 | PVGH3_HCMVA | 157–178 |
| | | PVGLC_HSV11 | 3–94 | PVGL2_IBVM | 327–347 | PVGL2_CVBF | 1259–1280 |
| | | PVGLC_HSV1K | 3–94 | PVGL2_IBVU2 | 310–330 | PVGL2_CVBL9 | 1259–1280 |
| | | PVGLC_HSVBC | 475–494 | PVGL2_EBV | 732–752 | PVGL2_CVBIY | 1259–1280 |
| | | PVGLG_CHAV | 436–455 | PVGLB_HCMVA | 750–770 | PVGL2_CVBM | 1259–1280 |
| | | PVGLG_RABVH | 372–391 | PVGLB_HCMVT | 751–771 | PVGL2_CVBQ | 1259–1280 |
| | | PVGLI_HSVEB | 44–63 | PVGLB_HSV23 | 79–99 | PVGL2_CVBV | 1259–1280 |
| | | PVGLI_VZVO | 278–297 | PVGLB_HSV2H | 79–99 | PVGL2_CVM4 | 1317–1338 |
| | | PVGLM_BUNGE | 117–136 | PVGLB_HSV2S | 65–85 | PVGL2_CVMA5 | 1265–1286 |
| | | PVGLM_PHV | 152–171 | PVGLB_HBV6U | 72–92 | PVGL2_CVMJH | 1176–1197 |
| | | PVGLM_PTPV | 997–1016 | PVGLB_HSVB2 | 279–299 | PVGLB_HSV11 | 83–104 |
| | | PVGLM_PUUMH | 155–174 | PVGLB_HSVSA | 63–83 | PVGLB_HSV1F | 82–103 |
| | | PVGLM_PUUMS | 155–174 | PVGLB_MCMVS | 738–758 | PVGLB_HSV1K | 82–103 |
| | | PVGLM_RVFV | 830–849 | PVGLF_PI3H4 | 283–303 | PVGLB_HBV1P | 83–104 |
| | | PVGLM_RVFVZ | 830–849 | PVGLG_RABVE | 454–474 | PVGLB_MCMVS | 135–156 |
| | | PVGLM_UUK | 655–674 | PVGLG_RABVH | 454–474 | PVGLC_PRVIF | 446–467 |
| | | PVGLY_LYCVW | 89–108 | PVGLG_RABVP | 454–474 | PVGLF_CDVO | 336–357 |
| | | PVGNB_CPMV | 1165–1184 | PVGLG_RABVS | 454–474 | PVGLF_MEASE | 224–245 |
| | | PVM3_REOVD | 521–540 | PVGLG_RABVT | 454–474 | PVGLF_MEASI | 227–248 |
| | | PVME1_CVBM | 171–190 | PVGLH_MCMVS | 670–690 | PVGLF_MEASY | 224–245 |
| | | PVME1_CVH22 | 136–155 | PVGLM_BUNL7 | 1325–1345 | PVGLF_MUMPM | 446–467 |
| | | PVME1_CVPFS | 174–193 | PVGLM_BUNSH | 1325–1345 | PVGLF_MUMPR | 446–467 |
| | | PVME1_CVPPU | 174–193 | PVGLM_BUNYW | 996–1016 | PVGLF_MUMPS | 446–467 |
| | | PVME1_CVPRM | 174–193 | PVGLM_HANTB | 999–1019 | PVGLF_PHODV | 305–326 |
| | | PVME1_CVTKE | 171–190 | PVGLM_HANTH | 1000–1020 | PVGLF_PI1HC | 456–477 |
| | | | | PVGLM_HANTL | 1001–1021 | PVGLF_PI2H | 450–471 |
| | | | | PVGLM_HANTV | 1001–1021 | PVGLF_PI2HG | 450–471 |
| | | | | PVGLM_RVFVZ | 1156–1176 | PVGLF_PI2HT | 450–471 |

126–144 1038–1057 970–990
1036–1055 378–398
771–790
770–789
771–790
770–789
770–789
467–486
467–486

TABLE VII-continued

Search Results Summary for P3CTLZIP, P4CTLZIP, P5CTLZIP, and P6CTLZIP Motifs

| P3CTLZIP LIBRARY FILE | P4CTLZIP LIBRARY FILE | P5CTLZIP LIBRARY FILE | | P6CTLZIP LIBRARY FILE | | |
|---|---|---|---|---|---|---|
| | | PVGLM_SEOUR | 1000–1020 | PVGLF_PI3B | 405–426 | 453–474 |
| | | PVGLM_SEOUS | 999–1019 | PVGLF_PI3H4 | 453–474 | |
| | | PVGLM_UUK | 925–945 | PVGLF_RINDK | 220–241 | |
| | | PVGLY_LYCVA | 12–32 | PVGLF_RINDL | 220–241 | |
| | | PVGLY_LYCVW | 12–32 | PVGLF_SEND5 | 460–481 | |
| | | PVGLY_PIARV | 12–32 | PVGLF_SENDF | 460–481 | |
| | | PVGNB_CPMV | 141–161 | PVGLF_SENDH | 460–481 | |
| | | PVMAT_MUMPS | 310–330 | PVGLF_SENDJ | 460–481 | |
| | | PVMAT_NDVA | 309–329 | PVGLF_SENDZ | 460–481 | |
| | | PVMAT_NDVB | 309–329 | PVGLF_SV41 | 453–474 | |
| | | PVMAT_PI2HT | 308–328 | PVGLF_SV5 | 446–467 | |
| | | PVMAT_PI4HA | 312–332 | PVGLH_HCMVA | 691–712 | |
| | | PVMAT_PI4HB | 312–332 | PVGLH_HCMVT | 690–711 | |
| | | PVMAT_SV41 | 308–328 | PVGLH_HSVE4 | 304–325 | |
| | | PVMAT_SV5 | 308–328 | PVGLH_HSVEB | 297–318 | |
| | | PVME1_IBV6 | 74–94 | PVGLH_HSVSA | 658–679 | |
| | | PVME1_IBVB | 74–94 | PVGL1_HSV2 | 2–23 | |
| | | PVME1_IBVB2 | 74–94 | PVGL1_HSV23 | 2–23 | |
| | | PVME1_IBVK | 74–94 | PVGLM_BUNGE | 197–218 | |
| | | PVMSA_HPBDB | 201–221 | PVGLM_BUNL7 | 190–211 | |
| | | PVMSA_HPBGS | 209–229 | PVGLM_BUNSH | 190–211 | |
| | | PVMSA_HPBHE | 293–313 | PVGLM_BUNYW | 193–214 | |
| | | PVMSA_WHV1 | 207–227 | PVGLY_LASSG | 237–258 | |
| | | PVMSA_WHV59 | 212–232 | PVGLY_LASSJ | 238–259 | |
| | | PVMSA_WHV7 | 212–232 | PVGP8_EBV | 67–88 | |
| | | PVMSA_WHV8 | 212–232 | PVM01_VACCC | 261–302 | |
| | | PVMSA_WHVBI | 212–232 | PVM01_VACCV | 230–251 | |
| | | PVMSA_WHVW6 | 63–83 | PVMAT_HRSVA | 139–160 | |
| | | | | PVMAT_RINDK | 200–221 | 239–260 |
| | | | | PVMAT_TRTV | 122–143 | |
| | | | | PVME1_CVHOC | 64–85 | |
| | | | | PVMSA_HPBDB | 201–222 | |
| | | | | PVMSA_HPBVO | 70–91 | |
| | | | | PVMSA_HPBV2 | 244–265 | |
| | | | | PVMSA_HPBV4 | 244–265 | |
| | | | | PVMSA_HPBV9 | 244–265 | |
| | | | | PVMSA_HPBVA | 233–254 | |
| | | | | PVMSA_HPBVD | 70–91 | |
| | | | | PVMSA_HPBVI | 233–254 | |
| | | | | PVMSA_HPBVJ | 233–254 | |
| | | | | PVMSA_HPBVL | 233–254 | |
| | | | | PVMSA_HPBVN | 70–91 | |
| | | | | PVMSA_HPBVO | 233–254 | |
| | | | | PVMSA_HPBVP | 244–265 | |
| | | | | PVMSA_HPBVR | 244–265 | |
| | | | | PVMSA_HPBVS | 70–91 | |

TABLE VII-continued

Search Results Summary for P3CTLZIP, P4CTLZIP, P5CTLZIP, and P6CTLZIP Motifs

| P3CTLZIP LIBRARY FILE | P4CTLZIP LIBRARY FILE | P5CTLZIP LIBRARY FILE | P6CTLZIP LIBRARY FILE | |
|---|---|---|---|---|
| | | | PVMSA_HPBVW | 233–254 |
| | | | PVMSA_HPBVY | 223–254 |
| | | | PVMSA_HPBVZ | 233–254 |
| | | | PVMT2_IAANN | 25–46 |
| | | | PVMT2_IABAN | 25–46 |
| | | | PVMT2_IAFOW | 25–46 |
| | | | PVMT2_IAFPR | 25–46 |
| | | | PVMT2_IAFPW | 25–46 |
| | | | PVMT2_IALE1 | 25–46 |
| | | | PVMT2_IALE2 | 25–46 |
| | | | PVMT2_IAMAN | 25–46 |
| | | | PVMT2_IAPUE | 25–46 |
| | | | PVMT2_IASIN | 25–46 |
| | | | PVMT2_IAUDO | 25–46 |
| | | | PVMT2_IAWIL | 25–46 |

TABLE VIII

Search Results Summary for P7CTLZIP, P8CTLZIP, and P9CTLZIP Motifs

| P7CTLZIP LIBRARY FILE | | | P8CTLZIP LIBRARY FILE | | | P9CTLZIP LIBRARY FILE | | |
|---|---|---|---|---|---|---|---|---|
| PEN_BAEVM | 202–224 | | PENV1_FRSFV | 380–403 | | PENV_BLVAF | 303–327 | |
| PENV_HV1B1 | 498–520 | | PNEV2_FRSFV | 380–403 | | PENV_BLVAU | 303–327 | |
| PENV_HV1B8 | 493–516 | | PENV_BIV06 | 178–201 | | PENV_BLVAV | 303–327 | |
| PENV_HV1BN | 494–516 | | PENv_BIV27 | 207–230 | | PENV_BLVB2 | 303–327 | |
| PENV_HV1BR | 503–526 | | PENV_FOAMV | 664–887 | | PENV_BLVB6 | 303–327 | |
| PENV_HV1EL | 495–517 | | PENV_HV1Z3 | 175–198 | | PENV_BLVJ | 303–327 | |
| PENV_HV1H2 | 498–520 | | PENV_HV2BE | 3–26 | 781–804 | PENV_FIVPE | 781–806 | |
| PENV_HV1H3 | 498–520 | | PENV_HV2CA | 750–773 | | PENV_FIVSD | 779–803 | |
| PENV_HV1J3 | 510–532 | | PENV_HV2D1 | 3–26 | 772–795 | PENV_FIVT2 | 780–804 | |
| PENV_HV1JR | 490–512 | | PENV_HV2G1 | 772–795 | | PHEMA_CVBLY | 391–415 | |
| PENV_HV1KB | 504–529 | | PENV_HV2NZ | 777–800 | | PHEMA_CVBM | 391–415 | |
| PENV_HV1MA | 500–522 | | PENV_JSRV | 541–564 | | PHEMA_CVBQ | 391–415 | |
| PENV_HV1MF | 496–518 | | PENV_SFV1 | 884–887 | | PHEMA_CHVOC | 391–415 | |
| PENV_HV1ND | 488–510 | | PENV_SFV3L | 861–804 | | PHEMA_INCCA | 442–446 | |
| PENV_HV1PV | 496–520 | | PENV_SIVM1 | 803–826 | | PHEMA_INCEN | 430–454 | |
| PENV_HV1S1 | 489–511 | | PENV_SIVMK | 802–825 | | PHEMA_INCGL | 430–454 | |
| PENV_HV1Z2 | 123–145 | 495–517 | PENV_SIVML | 801–824 | | PHEMA_INCHY | 429–453 | |
| PENV_HV1Z6 | 497–519 | | PENV_SIVS4 | 806–829 | | PHEMA_INCJH | 443–467 | |
| PENV_HV1Z8 | 505–527 | | PENV_SIVSP | 810–833 | | PHEMA_INCKY | 429–453 | |
| PENV_HV1ZH | 498–520 | | PHEMA_CDVO | 200–223 | | PHEMA_INCMI | 429–453 | |
| PENV_JSRV | 376–398 | | PHEMA_PI2H | 65–88 | | PHEMA_INCNA | 429–453 | |
| PENV_MPMV | 213–235 | | PHEMA_PI2HT | 65–88 | | PHEMA_INCP1 | 430–454 | |
| PENV_SRV1 | 213–235 | | PVF11_VACCC | 161–184 | | PHEMA_INCP2 | 430–454 | |
| PHEMA_IAAIC | 37–59 | | PVF15_VACCC | 25–48 | | PHEMA_INCP3 | 430–454 | |
| PHEMA_IABAN | 21–43 | | PVF15_VACCP | 3–26 | | PHEMA_INCTA | 430–454 | |
| PHEMA_IADA3 | 37–59 | | PVG1L_AMEPV | 313–336 | | PHEMA_INCYA | 430–454 | |
| PHEMA_IADH2 | 21–43 | | PVG28_HSVI1 | 491–514 | | PHEMA_MUMPM | 101–125 | |
| PHEMA_IADH3 | 21–43 | | PVG43_HSVI1 | 322–345 | | PHEMA_MUMPR | 101–125 | |
| PHEMA_IADH4 | 21–43 | | PVG52_HSVI1 | 229–252 | | PHEMA_MUMPS | 101–125 | |
| PHEMA_IADH5 | 21–43 | | PVG67_HSVI1 | 722–745 | | PHEMA_PI1HW | 29–53 | |
| PHEMA_IADH6 | 21–43 | | PVGL2_CVBF | 10–33 | | PVENV_BEV | 62–88 | |
| PHEMA_IADH7 | 21–43 | | PVGL2_CVBL9 | 651–674 | | PVF05_BACCC | 280–304 | |
| PHEMA_IADM2 | 37–59 | | PVGL2_CVBLY | 10–33 | | PVF05_VACCP | 380–304 | |
| PHEMA_IADMA | 28–50 | | PVGL2_CVM4 | 1267–1280 | | PVF05_VACCV | 281–305 | |
| PHEMA_IADU3 | 37–59 | | PVGL2_CVMA5 | 1215–1238 | | PVF09_VACCC | 176–200 | |
| PHEMA_IAEN6 | 21–43 | | PVGL2_CVMJH | 1126–1149 | | PVF09_VACCV | 176–200 | |
| PHEMA_IAEN7 | 37–59 | | PVGL2_CVPFS | 1274–1297 | | PVGO1_VZVD | 58–82 | |
| PHEMA_IAMAO | 37–59 | | PVGL2_CVPPU | 1272–1295 | | PVG10_HSVSA | 355–379 | |
| PHEMA_IAME1 | 37–59 | | PVGL2_CVPR8 | 1050–1073 | | PVG12_HSVSA | 68–92 | |
| PHEMA_IAME2 | 37–59 | | PVGL2_CVPRM | 1050–1073 | | PVG19_HSVI1 | 88–112 | |
| PHEMA_IAME6 | 21–43 | | PVGL2_FIPV | 1277–1300 | | PVG28_HSVI1 | 173–197 | |
| PHEMA_IANT6 | 37–59 | | PVGL2_IBV6 | 196–219 | | PVG43_HSVI1 | 109–133 | |
| PHEMA_IAQU7 | 21–43 | | PVGL2_IBVB | 95–218 | | PVG87_HSVI1 | 108–132 | 1005–1029 |
| PHEMA_IATKM | 33–55 | | PVGL2_IBVD2 | 196–219 | | PVG72_HSVI1 | 720–744 | |
| PHEMA_IAUDO | 37–59 | | PVGL2_IBVD3 | 196–219 | | PVGF1_IBVB | 3601–3826 | |
| PHEMA_IAVI7 | 38–60 | | PVGL2_IBVK | 195–218 | | PVGL8_HSVMD | 589–613 | |
| PHEMA_IAX31 | 37–59 | | PVGL2_IBVM | 195–218 | | PVGLB_ILTV8 | 597–621 | |
| PHEMA_IAZCO | 37–59 | | PVGL2_IBVU1 | 178–201 | | PVGLB_ILTV3 | 607–631 | |
| PHEMA_IAZH2 | 21–43 | | PVGL2_IBVU2 | 178–201 | | PVGLB_ILTVT | 607–631 | |
| PHEMA_IAZH3 | 21–43 | | PVGL2_IBVU3 | 178–201 | | PVGLE_HSVI1 | 413–437 | |
| PHEMA_IAZUK | 37–59 | | PVGLB_HCMVA | 525–558 | | PVGLE_VZVD | 489–493 | |
| PHEMA_PHODV | 36–58 | | PVGLB_HCMVT | 536–559 | | PVGLF_SVS | 401–425 | |
| PHEMA_PI2H | 65–87 | | PVGLS_HSVSA | 483–506 | | PVGLH_HCMVA | 574–599 | |
| PHEMA_PI2HT | 65–87 | | PVGLB_MCMV8 | 566–589 | | PVGLH_HCMVT | 573–597 | |
| PVFP7_CAFVK | 89–111 | | PVGLC_HSVI1 | 467–490 | | PVGLH_HSV11 | 443–467 | 803–827 |
| PVFUS_VACC6 | 72–94 | | PVGLC_HSV1K | 467–490 | | PVGLH_HSV1E | 443–467 | 803–827 |
| PVGO1_HSVI1 | 317–339 | | PVGLC_HSV2 | 435–458 | | PVGLM_BUNL7 | 31–55 | |
| PVGO3_VACCC | 50–72 | | PVGLC_HSV23 | 436–459 | | PVGLM_BUNSH | 31–55 | |
| PVGO3_VARV | 50–72 | | PVGLM_BUNL7 | 1387–1410 | | PVGLM_HANTH | 694–718 | |
| PVGO4_VACCC | 11–33 | | PVGLM_BUNSH | 1387–1410 | | PVGLM_RVFV | 344–368 | |
| PVGO4_VARV | 11–33 | | PVGLM_UUK | 966–989 | | PVGLM_RVFVZ | 344–368 | |
| PVG19_HSVI1 | 88–110 | | PVGLY_JUNIN | 12–35 | | PVGLM_UUK | 561–585 | |
| PVG28_HSVI1 | 173–195 | | PVGLY_LASSG | 12–35 | | PVGNM_CPMV | 311–335 | |
| PVG29_HSVI1 | 20–42 | | PVGLY_LASSJ | 12–35 | | PVGP2_EBV | 657–681 | |
| PVG46_HSVI1 | 134–156 | | PVGLY_LYCVA | 12–35 | | PVGP3_EBV | 854–878 | |
| PVG48_HSVSA | 71–93 | | PVGLY_LYCVW | 12–35 | | PVM1_REOVD | 380–304 | |
| PVG58_HSVSA | 266–288 | | PVGLY_MOPEI | 12–35 | | PVM1_REOVL | 280–304 | |
| PVG59_HSVI1 | 267–289 | | PVGLY_TACV | 12–35 | | PVM21_REOVD | 188–192 | |
| PVG5_SPV4 | 42–64 | | PVGLY_TACV5 | 12–35 | | PVM22_REOVD | 168–192 | |
| PVG60_HSVI1 | 53–75 | | PVGLY_TACV7 | 12–35 | | PVM2_REOVJ | 168–192 | |
| PVG85_HSVI1 | 1347–1369 | | PVGLY_TACVT | 12–35 | | PVM2_REOVL | 168–192 | |
| PVG6_SPV1R | 60–82 | | PVGNM_CPMV | 741–764 | | PVMAT_MEAS1 | 87–111 | |
| PVGL2_IBV6 | 1055–1078 | | PVM1_REOVD | 324–347 | 454–477 | PVMAT_SSPVB | 314–338 | |

TABLE VIII-continued

Search Results Summary for P7CTLZIP, P8CTLZIP, and P9CTLZIP Motifs

| P7CTLZIP LIBRARY FILE | | | P8CTLZIP LIBRARY FILE | | P9CTLZIP LIBRARY FILE | |
|---|---|---|---|---|---|---|
| PVGL2_IBVB | 1055–1077 | | PVM1_REOVL | 454–477 | PVME1_CVBM | 137–161 |
| PVGL2_IBVD2 | 1056–1078 | | PVMAT_MUMPS | 227–250 | PVME1_CVHOC | 137–161 |
| PVGL2_IBVK | 1055–1077 | | PVMSA_HPBDB | 269–292 | PVME1_CVTKE | 137–161 |
| PVGL2_IBVM | 1055–1077 | | PVMSA_HPBDC | 268–291 | PVME1_IBV6 | 74–98 |
| PVGLB_HSV6U | 117–139 | | PVMSA_HPBDU | 231–254 | PVME1_IBVB | 74–98 |
| PVGLV_HSVB2 | 745–767 | | PVSMA_HPBDW | 269–292 | PVME1_IBVB2 | 74–98 |
| PVGLC_HSVMB | 399–421 | | PVMSA_HPBHE | 236–259 | PVME1_IBVK | 74–98 |
| PVGLC_HSVMG | 398–420 | | | | PVMSA_HPBG8 | 271–295 |
| PVGLC_HSVMM | 399–421 | | | | PVMSA_WHV1 | 269–293 |
| PVGLF_BRSVA | 265–287 | 482–504 | | | PVMSA_WHV59 | 274–298 |
| PVGLF_BRSVC | 484–506 | | | | PVMSA_WHV7 | 274–298 |
| PVGLF_BRSVR | 484–506 | | | | PVMSA_WHV8 | 274–298 |
| PVGLF_HRSV1 | 484–506 | | | | PVMSA_WHV8I | 274–298 |
| PVGLF_HRSVA | 484–506 | | | | PVMSA_WHVW6 | 125–149 |
| PVGLF_HRSVL | 484–506 | | | | | |
| PVGLF_HRSVR | 484–506 | | | | | |
| PVGLF_TRTV | 452–474 | | | | | |
| PVGLG_IHNV | 77–99 | | | | | |
| PVGLG_VHSV0 | 406–428 | | | | | |
| PVGLH_H3VE4 | 814–836 | | | | | |
| PVGLH_HSVEB | 807–829 | | | | | |
| PVGLI_HCMVA | 158P14 180 | | | | | |
| PVGLM_PTPV | 743–765 | | | | | |
| PVGLP_BEV | 430–452 | 1546–1568 | | | | |
| PVGLY_LASSG | 428–448 | | | | | |
| PVGLY_LASSJ | 427–449 | | | | | |
| PVGLY_MOPEI | 425–447 | | | | | |
| PVGP2_EBV | 657–679 | | | | | |
| PVGP3_EBV | 854–878 | | | | | |
| PVM1_REOVD | 414–436 | | | | | |
| PVM1_REOVL | 414–438 | | | | | |
| PVM3_REOVD | 304–326 | | | | | |
| PVMAT_PI1HC | 195–217 | | | | | |
| PVMAT_PI2HT | 132–164 | | | | | |
| PVMAT_SENDF | 195–217 | | | | | |
| PVMAT_SENDH | 195–217 | | | | | |
| PVMAT_SENDZ | 195–217 | | | | | |
| PVMAT_SV41 | 132–154 | | | | | |
| PVMEM_EBV | 131–153 | | | | | |
| PVMP_CERV | 293–315 | | | | | |

TABLE IX

Search Results Summary for P12CTLZIP Motif

| P12LZIPC LIBRARY FILE | | | | | | | |
|---|---|---|---|---|---|---|---|
| PENV1_FRSFV | 380–407 | | | | | | |
| PENV2_FRSPV | 380–407 | | | | | | |
| PENV_AVISU | 98–117 | | | | | | |
| PENV_BAEVM | 202–224 | | | | | | |
| PENV_BIVO6 | 525–546 | | | | | | |
| PENV_BIV27 | 147–168 | 207–230 | 463–479 | 554–575 | | | |
| PENV_BLVAF | 303–327 | | | | | | |
| PENV_BLVAU | 303–327 | | | | | | |
| PENV_BLVAV | 303–327 | | | | | | |
| PENV_BLVB2 | 303–327 | | | | | | |
| PENV_BLVB6 | 303–327 | | | | | | |
| PENV_BLVJ | 303–327 | | | | | | |
| PENV_FENV1 | 30–47 | 225–246 | 630–651 | | | | |
| PENV_FLVC6 | 38–55 | 624–645 | | | | | |
| PENV_FLVGL | 9–29 | 447–468 | 606–626 | | | | |
| PENV_FLVLB | 467–488 | 613–646 | | | | | |
| PENV_FLVSA | 444–465 | 602–623 | | | | | |
| PENV_FOAMV | 153–174 | 255–275 | 300–325 | 481–496 | 710–727 | 864–887 | 924–951 | 957–978 |
| PENV_FSVGA | 9–29 | 467–488 | 625–646 | | | | |
| PENV_FSVGB | 447–468 | 605–626 | | | | | |
| PENV_FSVSM | 450–471 | 608–629 | | | | | |
| PENV_FSVST | 467–488 | | | | | | |
| PENV_GALV | 52–73 | 519–540 | | | | | |

TABLE IX-continued

Search Results Summary for P12CTLZIP Motif

| | | | | | | |
|---|---|---|---|---|---|---|
| PENV_HV181 | 498–520 | | | | | |
| PENV_HV188 | 493–515 | | | | | |
| PENV_HV18N | 494–516 | | | | | |
| PENV_HV18R | 503–525 | | | | | |
| FENV_HV1C4 | 428–448 | | | | | |
| PENV_HV1EL | 495–517 | | | | | |
| PENV_HV1H2 | 498–520 | | | | | |
| PENV_HV1H3 | 498–520 | | | | | |
| PENV_HV1J3 | 510–532 | | | | | |
| PENV_HV1JR | 490–512 | | | | | |
| PENV_HV1KB | 604–626 | 552–579 | 752–768 | | | |
| PENV_HV1MA | 438–453 | 500–522 | | | | |
| PENV_HV1MF | 496–518 | | | | | |
| PENV_HV1ND | 488–510 | | | | | |
| PENV_HV1OY | 123–140 | | | | | |
| PENV_HV1PV | 498–520 | | | | | |
| PENV_HV1RH | 445–460 | | | | | |
| PENV_HV1S1 | 489–511 | 7380–754 | | | | |
| PENV_HV1Z2 | 123–145 | 410–427 | 495–517 | | | |
| PENV_HV1Z3 | 117–133 | 175–198 | | | | |
| PENV_WV1Z6 | 497–519 | | | | | |
| PENV_HV1Z8 | 505–527 | | | | | |
| PENV_HV1ZH | 123–142 | 438–453 | 498–520 | | | |
| PENV_HV2BE | 3–26 | 750–775 | 781–804 | | | |
| PENV_HV2CA | 750–777 | | | | | |
| PENV_HV2D1 | 3–26 | 741–766 | 772–795 | | | |
| PENV_HV2D2 | 9–28 | | | | | |
| PENV_HV2G1 | 741–766 | 772–795 | | | | |
| PENV_HV2NZ | 742–767 | 777–800 | | | | |
| PENV_HV2RO | 751–776 | | | | | |
| PENV_HV2SB | 743–768 | 778–804 | | | | |
| PENV_HV2ST | 745–770 | | | | | |
| PENV_JSRV | 104–119 | 299–325 | 376–398 | 541–564 | | |
| PENV_MCFF | 600–621 | | | | | |
| PENV_MCFF3 | 601–622 | | | | | |
| PENV_MLVAV | 630–651 | | | | | |
| PENV_MLVCB | 625–646 | | | | | |
| PENV_MLVF5 | 639–660 | | | | | |
| PENV_MLVFF | 639–660 | | | | | |
| PENV_MLVFP | 639–660 | | | | | |
| PENV_MLVHO | 626–647 | | | | | |
| PENV_MLVKI | 187–188 | | | | | |
| PENV_MLVMO | 629–650 | | | | | |
| PENV_MLVRD | 624–645 | | | | | |
| PENV_MLVRK | 624–645 | | | | | |
| PENV_MMTVB | 643–663 | | | | | |
| PENV_MMTVG | 643–663 | | | | | |
| PENV_MPMV | 213–235 | | | | | |
| PENV_MSVFB | 170–191 | | | | | |
| PENV_OMVVS | 75–100 | 658–683 | | | | |
| PENV_RMCFV | 603–624 | | | | | |
| PENV_RSVP | 42–69 | 533–552 | | | | |
| PENV_SFV1 | 300–325 | 710–727 | 864–887 | 924–951 | 957–978 | |
| PENV_SFV3L | 157–178 | 304–329 | 707–724 | 861–884 | 921–948 | 954–975 |
| PENV_SIVA1 | 437–458 | | | | | |
| PENV_SIVAG | 442–463 | | | | | |
| PENV_SIVAI | 421–442 | | | | | |
| PENV_SIVAT | 435–456 | | | | | |
| PENV_SIVGB | 93–109 | | | | | |
| PENV_SIVM1 | 766–793 | 803–826 | | | | |
| PENV_SIVM2 | 139–154 | 765–792 | 802–825 | | | |
| PENV_SIVMK | 139–154 | 764–791 | 801–824 | | | |
| PENV_SIVML | 769–789 | 806–829 | | | | |
| PENV_SIVS4 | 773–793 | 810–833 | | | | |
| PENV_SMSAV | 42–63 | | | | | |
| PENV_SRV1 | 213–235 | | | | | |
| PHEMA_CDVO | 36–53 | 200–223 | | | | |
| PHEMA_CVBLY | 391–415 | | | | | |
| PHEMA_CVBM | 391–415 | | | | | |
| PHEMA_CVBQ | 391–415 | | | | | |
| PHEMA_CYNOC | 391–415 | | | | | |
| PHEMA_CVMA5 | 402–123 | | | | | |
| PHEMA_CVMS | 403–418 | | | | | |
| PHEMA_IAAIC | 37–59 | 322–339 | | | | |
| PHEMA_IABAN | 21–43 | 306–323 | | | | |
| PHEMA_IABUD | 320–337 | | | | | |
| PHEMA_IACKA | 320–337 | | | | | |

TABLE IX-continued

Search Results Summary for P12CTLZIP Motif

| | | | |
|---|---|---|---|
| PHEMA_IACKG | 81–101 | 316–333 | |
| PHEMA_IACKP | 302–319 | | |
| PHEMA_IACKQ | 302–319 | | |
| PHEMA_IACKS | 319–336 | | |
| PHEMA_IACKV | 230–246 | 315–332 | |
| PHEMA_IADA1 | 320–337 | | |
| PHEMA_IADA2 | 319–336 | | |
| PHEMA_IADA3 | 37–59 | 322–339 | |
| PHEMA_IADCZ | 320–337 | | |
| PHEMA_IADE1 | 266–287 | | |
| PHEMA_IADH1 | 306–323 | | |
| PHEMA_IADH2 | 21–43 | 306–323 | |
| PHEMA_IADH3 | 21–43 | 306–323 | |
| PHEMA_IADH4 | 21–43 | 306–323 | |
| PHEMA_IADH5 | 21–43 | | |
| PHEMA_IADH6 | 21–43 | 306–323 | |
| PHEMA_IADH7 | 21–43 | 306–323 | |
| PHEMA_IADM2 | 37–59 | 322–339 | |
| PHEMA_IADMA | 26–50 | 81–101 | |
| PHEMA_IADNZ | 320–337 | | |
| PHEMA_IADU3 | 37–59 | 322–339 | |
| PHEMA_IAEN6 | 21–43 | 306–323 | |
| PHEMA_IAEN7 | 37–59 | 322–339 | |
| PHEMA_IAFPR | 230–246 | 315–332 | |
| PHEMA_IAGRE | 320–337 | | |
| PHEMA_IAGU2 | 320–337 | | |
| PHEMA_IAGUA | 319–336 | | |
| PHEMA_IAHAL | 321–338 | | |
| PHEMA_IAHAR | 230–246 | 315–332 | |
| PHEMA_IAHC6 | 230–246 | 315–332 | |
| PHEMA_IAHC7 | 230–246 | 315–332 | |
| PHEMA_IAHCD | 230–246 | 315–332 | |
| PHEMA_IAHDE | 230–246 | 315–332 | |
| PHEMA_IAHFO | 236–252 | 321–338 | |
| PHEMA_IAHK6 | 321–338 | | |
| PHEMA_IAHK7 | 236–252 | 321–338 | |
| PHEMA_IAHLE | 230–246 | 315–332 | |
| PHEMA_IAHLO | 230–246 | 315–332 | |
| PHEMA_IAHMI | 236–252 | 321–338 | |
| PHEMA_IAHNM | 236–252 | 321–338 | |
| PHEMA_IAHNN | 315–332 | | |
| PHEMA_IAHPR | 315–332 | | |
| PHEMA_IAHRO | 236–252 | 321–338 | |
| PHEMA_IAHSA | 236–252 | 321–338 | |
| PHEMA_IAHSP | 230–246 | 315–332 | |
| PHEMA_IAHSW | 230–246 | 315–332 | |
| PHEMA_IAHTE | 236–252 | 321–338 | |
| PHEMA_IAHTO | 236–252 | 321–338 | |
| PHEMA_IAHUR | 236–252 | 321–338 | |
| PHEMA_IAJAP | 317–334 | | |
| PHEMA_IAMAA | 197–223 | 319–336 | |
| PHEMA_IAMAB | 202–228 | 324–341 | |
| PHEMA_IAMAO | 37–59 | 322–339 | |
| PHEMA_IAME1 | 37–59 | 322–339 | |
| PHEMA_IAME2 | 37–59 | 322–339 | |
| PHEMA_IAME6 | 21–43 | | |
| PHEMA_IAMIN | 85–101 | 231–247 | 316–333 |
| PHEMA_IANT6 | 37–59 | 322–339 | |
| PHEMA_IAPIL | 320–337 | | |
| PHEMA_IAQU7 | 21–43 | 306–323 | |
| PHEMA_IARUD | 320–337 | | |
| PHEMA_IASE2 | 320–337 | | |
| PHEMA_IASH2 | 321–338 | | |
| PHEMA_IASTA | 230–246 | 315–332 | |
| PHEMA_IATAI | 33–55 | 320–337 | |
| PHEMA_IATKI | 233–249 | | |
| PHEMA_IATKR | 230–246 | | |
| PHEMA_IATKW | 229–245 | | |
| PHEMA_IAUDO | 37–59 | 322–339 | 380–397 |
| PHEMA_IAVI7 | 38–60 | 323–340 | |
| PHEMA_IAX31 | 37–59 | | |
| PHEMA_IAZCO | 37–59 | 322–339 | |
| PHEMA_IAZH2 | 21–43 | 306–323 | |
| PHEMA_IAZH3 | 21–43 | 306–323 | |
| PHEMA_IAZUK | 37–59 | 322–339 | |
| PHEMA_INBAA | 115–131 | 295–310 | |
| PHEMA_INBBE | 123–139 | 303–318 | |

TABLE IX-continued

Search Results Summary for P12CTLZIP Motif

| | | | | | |
|---|---|---|---|---|---|
| PHEMA_INBBO | 116–132 | 293–308 | | | |
| PHEMA_INBEN | 123–139 | 301–316 | | | |
| PHEMA_INBFU | 108–124 | 266–301 | | | |
| PHEMA_INBGL | 119–135 | 296–311 | | | |
| PHEMA_INBHK | 116–132 | 293–308 | | | |
| PHEMA_INBIB | 108–124 | 288–303 | | | |
| PHEMA_INBID | 120–136 | 299–314 | | | |
| PHEMA_INBLE | 123–139 | 302–317 | | | |
| PHEMA_INBMD | 113–129 | 292–307 | | | |
| PHEMA_INBME | 116–132 | 296–311 | | | |
| PHEMA_INBNA | 108–124 | 288–303 | | | |
| PHEMA_INBOR | 123–139 | 301–316 | | | |
| PHEMA_INBSI | 123–139 | 301–316 | | | |
| PHEMA_INBSJ | 119–135 | 298–313 | | | |
| PHEMA_INBUS | 116–132 | 294–309 | | | |
| PHEMA_INBVI | 116–132 | 296–311 | | | |
| PHEMA_INBVK | 123–139 | 303–318 | | | |
| PHEMA_INBYB | 108–124 | 288–301 | | | |
| PHEMA_INCCA | 442–466 | | | | |
| PHEMA_INCEN | 430–454 | | | | |
| PHEMA_INCGL | 430–454 | | | | |
| PHEMA_INCHY | 429–453 | | | | |
| PHEMA_INCJH | 443–467 | | | | |
| PHEMA_INCKY | 429–153 | | | | |
| PHEMA_INCMI | 429–153 | | | | |
| PHEMA_INCNA | 429–453 | | | | |
| PHEMA_INCP1 | 430–454 | | | | |
| PHEMA_INCP2 | 430–454 | | | | |
| PHEMA_INCP3 | 430–454 | | | | |
| PHEMA_INCTA | 430–454 | | | | |
| PHEMA_INCYA | 430–454 | | | | |
| PHEMA_MUMPM | 133–148 | 225–246 | 387–394 | 397–417 | |
| PHEMA_MUMPR | 101–125 | 133–148 | 225–246 | 397–417 | |
| PHEMA_MUMPS | 101–125 | 133–148 | 225–246 | 367–394 | 397–417 |
| PHEMA_NDVA | 93–110 | | | | |
| PHEMA_NDVB | 93–110 | | | | |
| PHEMA_NDVD | 93–110 | | | | |
| PHEMA_NDVH | 93–110 | | | | |
| PHEMA_NDVI | 93–110 | | | | |
| PHEMA_NDVM | 93–110 | | | | |
| PHEMA_NDVQ | 93–110 | | | | |
| PHEMA_NDVTG | 93–110 | | | | |
| PHEMA_NDVU | 93–110 | | | | |
| PHEMA_PHODV | 36–56 | 213–234 | 493–513 | | |
| PHEMA_PI1HW | 29–53 | 322–342 | 345–360 | 486–503 | |
| PHEMA_PI2H | 13–40 | 65–88 | 118–136 | | |
| PHEMA_PI2HT | 13–40 | 65–88 | 118–136 | | |
| PHEMA_PI3B | 111–128 | 272–299 | 324–340 | | |
| PHEMA_PI3H4 | 111–128 | 272–299 | 324–340 | | |
| PHEMA_PI3HA | 111–128 | 272–299 | 324–340 | | |
| PHEMA_PI3HT | 111–128 | 272–299 | 324–340 | | |
| PHEMA_PI3HU | 111–128 | 272–299 | 324–340 | | |
| PHEMA_PI3HV | 111–128 | 272–299 | 324–340 | | |
| PHEMA_PI3HW | 111–128 | 272–299 | 324–340 | | |
| PHEMA_PI3HX | 111–128 | 272–299 | 324–340 | | |
| PHEMA_PI4HA | 50–67 | | | | |
| PHEMA_RINDK | 368–383 | | | | |
| PHEMA_RINDL | 4–30 | | | | |
| PHEMA_SEND5 | 322–342 | | | | |
| PHEMA_SENDF | 322–342 | | | | |
| PHEMA_SENDH | 322–342 | | | | |
| PHEMA_SENDJ | 322–342 | | | | |
| PHEMA_SENDZ | 322–342 | | | | |
| PHEMA_SV41 | 55–73 | 85–102 | 107–132 | | |
| PHEMA_SV5 | 7–28 | 84–101 | 379–400 | | |
| PHEMA_SV5CM | 7–28 | 84–101 | 379–400 | | |
| PHEMA_SV5CP | 7–28 | 84–101 | 379–400 | | |
| PHEMA_SV5LN | 7–28 | 84–101 | 379–400 | | |
| PHEMA_VACCC | 173–192 | | | | |
| PHEMA_VACCI | 173–192 | | | | |
| PHEMA_VACCT | 173–192 | | | | |
| PHEMA_VACCV | 173–192 | | | | |
| PVENV_BEV | 62–86 | 87–114 | | | |
| PVENV_DNVI1 | 42–57 | 484–511 | | | |
| PVENV_EAV | 25–41 | | | | |
| PVENV_LELV | 27–47 | 148–168 | | | |
| PVENV_MCV1 | 61–80 | | | | |

TABLE IX-continued

Search Results Summary for P12CTLZIP Motif

| | | | | | | |
|---|---|---|---|---|---|---|
| PVENV_MCV2 | 61–80 | 306–333 | | | | |
| PVENV_THOGV | 196–221 | 356–383 | 473–491 | | | |
| PVFO5_VACCC | 280–305 | | | | | |
| PVFO5_VACCP | 280–305 | | | | | |
| PVFO5_VACCV | 280–305 | | | | | |
| PVFO9_VACCC | 176–200 | | | | | |
| PVFO9_VACCV | 176–200 | | | | | |
| PVF11_VACCC | 161–184 | | | | | |
| PVF15_VACCC | 25–48 | | | | | |
| PVF15_VACCP | 3–26 | | | | | |
| PVFP1_FOWPV | 297–323 | | | | | |
| PVFP2_FOWPV | 68–104 | | | | | |
| PVFP7_CAPVK | 89–111 | | | | | |
| PVFP7_FOWPV | 65–90 | | | | | |
| PVFP8_CAPVK | 51–76 | | | | | |
| PVFUS_ORFNZ | 29–48 | | | | | |
| PVFUS_VACC6 | 72–94 | | | | | |
| PVGO1_HSVEB | 169–195 | | | | | |
| PVGO1_HSVI1 | 210–225 | 317–339 | 589–616 | | | |
| PVGO1_VACCC | 298–318 | 376–395 | | | | |
| PVGO1_VACCV | 237–257 | 315–334 | | | | |
| PVGO1_VARV | 298–318 | 376–395 | | | | |
| PVGO1_VZVD | 58–82 | | | | | |
| PVGO3_VACCC | 50–72 | | | | | |
| PVGO3_VARV | 50–72 | | | | | |
| PVGO4_VACCC | 11–33 | | | | | |
| PVGO4_VARV | 11–33 | | | | | |
| PVGO6_VACCC | 31–51 | | | | | |
| PVGO6_VARV | 31–51 | | | | | |
| PVGO8_HSVI1 | 134–149 | 159–185 | | | | |
| PVG10_HSVI1 | 35–54 | | | | | |
| PVG10_HSVSA | 109–124 | 355–379 | | | | |
| PVG11_HSVI1 | 103–122 | 150–176 | | | | |
| PVG12_HSVI1 | 151–178 | 270–286 | | | | |
| PVG12_HSVSA | 68–92 | | | | | |
| PVG15_HSVEB | 194–209 | | | | | |
| PVG19_HSVI1 | 88–112 | | | | | |
| PVG1L_AMEPV | 313–336 | | | | | |
| PVG1_SPV1R | 76–92 | 359–676 | | | | |
| PVG22_HSVI1 | 300–327 | | | | | |
| PVG23_HSVI1 | 314–335 | | | | | |
| PVG27_HSVI1 | 158–184 | | | | | |
| PVG27_HSVSA | 209–226 | | | | | |
| PVG28_HSVI1 | 173–197 | 491–518 | | | | |
| PVG28_HSVSA | 14–40 | | | | | |
| PVG29_HSVI1 | 20–42 | | | | | |
| PVG30_HSVI1 | 166–191 | | | | | |
| PVG32_VZVD | 90–109 | | | | | |
| PVG36_HSVSA | 108–123 | 344–362 | | | | |
| PVG37_HSVI1 | 284–299 | | | | | |
| PVG39_HSVI1 | 646–675 | 970–990 | 1038–1065 | | | |
| PVG40_HSVI1 | 14–32 | | | | | |
| PVG41_HSVI1 | 11–38 | 62–81 | 244–260 | | | |
| PVG43_HSVI1 | 109–133 | 157–178 | 322–345 | 521–538 | | |
| PVG46_HSVI1 | 134–156 | 580–607 | 937–963 | 1244–1270 | | |
| PVG48_HSVSA | 71–93 | | | | | |
| PVG50_HSVI1 | 5–30 | 58–83 | | | | |
| PVG50_HSVSA | 63–81 | 95–117 | 206–233 | | | |
| PVG51_HSVI1 | 29–49 | 84–102 | | | | |
| PVG52_HSVI1 | 229–252 | | | | | |
| PVG55_HSVI1 | 22–37 | 143–168 | 288–309 | | | |
| PVG55_HSVSA | 85–106 | | | | | |
| PVG56_HSVI1 | 1155–1176 | | | | | |
| PVG58_HSVSA | 130–146 | 266–288 | 293–319 | 330–346 | | |
| PVG59_HSVI1 | 142–161 | 267–289 | | | | |
| PVG5_SPV4 | 42–84 | | | | | |
| PVG60_HSVI1 | 30–51 | 53–75 | | | | |
| PVG61_HSVI1 | 76–102 | 117–136 | | | | |
| PVG63_HSVI1 | 238–259 | 336–383 | | | | |
| PVG64_HSVI1 | 420–445 | | | | | |
| PVG65_HSVI1 | 117–137 | 155–173 | 362–378 | 518–533 | 1147–1174 | 1347–1369 |
| PVG67_HSVI1 | 108–132 | 171–188 | 318–344 | 722–745 | 1005–1029 | 1072–1091 | 1315–1341 |
| PVG6_SPV1R | 60–82 | | | | | |
| PVG70_HSVI1 | 184–209 | | | | | |
| PVG71_HSVSA | 69–105 | | | | | |
| PVG72_HSVI1 | 445–471 | 535–561 | 720–744 | 1252–1269 | | |
| PVG74_HSVSA | 124–151 | | | | | |

TABLE IX-continued

Search Results Summary for P12CTLZIP Motif

| | | | | | | | | | |
|---|---|---|---|---|---|---|---|---|---|
| PVG9_SPV1R | 57–72 | | | | | | | | |
| PVGF1_IBVB | 1587–1606 | 1856–1877 | 2108–2127 | 2210–2226 | 2788–2806 | 2973–2999 | 3073–3090 | 3374–3390 | 3601–3625 |
| PVGH3_HCMVA | 157–178 | | | | | | | | |
| PVGL2_CVBF | 10–33 | 123–139 | 174–190 | 264–279 | 991–1017 | 1259–1280 | | | |
| PVGL2_CVBL9 | 123–139 | 174–190 | 264–279 | 651–674 | 991–1017 | 1259–1280 | | | |
| PVGL2_CVBLY | 10–33 | 123–139 | 174–190 | 264–279 | 991–1017 | 1259–1280 | | | |
| PVGL2_CVBM | 123–139 | 174–190 | 264–279 | 991–1017 | 1259–1280 | | | | |
| PVGL2_CVBQ | 31–47 | 123–139 | 174–190 | 991–1017 | 1259–1280 | | | | |
| PVGL2_CVBV | 123–139 | 174–190 | 264–279 | 991–1017 | 1259–1280 | | | | |
| PVGL2_CVH22 | 768–794 | 1053–1071 | 1115–1134 | | | | | | |
| PVGL2_CVM4 | 95–111 | 999–1025 | 1267–1290 | 1317–1338 | | | | | |
| PVGL2_CVMA5 | 95–111 | 947–973 | 1215–1238 | 1265–1286 | | | | | |
| PVGL2_CVMJH | 95–111 | 858–884 | 1126–1149 | 1178–1197 | | | | | |
| PVGL2_CVPFS | 64–83 | 442–457 | 800–816 | 1038–1064 | 1274–1297 | | | | |
| PVGL2_CVPPU | 64–83 | 440–455 | 504–519 | 798–814 | 1036–1082 | 1272–1295 | | | |
| PVGL2_CVPR8 | 218–233 | 576–592 | 814–840 | 1050–1073 | | | | | |
| PVGL2_CVPRM | 218–233 | 576–592 | 814–840 | 1050–1073 | | | | | |
| PVGL2_FIPV | 803–819 | 1041–1067 | 1277–1300 | | | | | | |
| PVGL2_IBV6 | 196–219 | 588–607 | 771–797 | 1056–1081 | 1094–1111 | | | | |
| PVGL2_IBVb | 195–218 | 587–606 | 770–796 | 1055–1080 | | | | | |
| PVGL2_IBVD2 | 196–219 | 588–607 | 771–797 | 1056–1081 | | | | | |
| PVGL2_IBVD3 | 196–219 | | | | | | | | |
| PVGL2_IBVK | 195–218 | 587–606 | 770–796 | 1065–1080 | | | | | |
| PVGL2_IBVM | 195–218 | 378–398 | 587–606 | 770–795 | 1065–1080 | | | | |
| PVGL2_IBVU1 | 178–201 | | | | | | | | |
| PVGL2_IBVU2 | 178–201 | | | | | | | | |
| PVGL2_IBVU3 | 178–201 | | | | | | | | |
| PVGLB_EBV | 732–752 | | | | | | | | |
| PVGLB_HCMVA | 535–558 | 706–732 | 750–777 | | | | | | |
| PVGLB_HCMVT | 536–559 | 707–733 | 751–778 | | | | | | |
| PVGLB_HSV11 | 83–104 | | | | | | | | |
| PVGLB_HSV1F | 82–103 | | | | | | | | |
| PVGLB_HSV1K | 82–103 | | | | | | | | |
| PVGLB_HSV1P | 83–104 | | | | | | | | |
| PVGLB_HSV23 | 79–99 | | | | | | | | |
| PVGLB_HSV2H | 79–99 | | | | | | | | |
| PVGLB_HSV28 | 65–85 | | | | | | | | |
| PVGLB_HSV6U | 72–92 | 117–144 | | | | | | | |
| PVGLB_HSVB1 | 560–578 | 689–707 | | | | | | | |
| PVGLB_HSVB2 | 279–299 | 745–767 | | | | | | | |
| PVGLB_JSVBC | 692–710 | | | | | | | | |
| PVGLB_HSVE1 | 738–753 | | | | | | | | |
| PVGLB_HSVE4 | 675–692 | | | | | | | | |
| PVGLB_HSVEA | 736–753 | | | | | | | | |
| PVGLB_HSVEB | 736–753 | | | | | | | | |
| PVGLB_HSVEL | 736–753 | | | | | | | | |
| PVGLB_HSVMD | 589–613 | | | | | | | | |
| PVGLB_HSVSA | 483–506 | 584–602 | 701–716 | | | | | | |
| PVGLB_ILTV6 | 256–275 | 597–621 | 740–758 | | | | | | |
| PVGLB_ILTVS | 266–285 | 607–631 | 750–768 | | | | | | |
| PVGLB_ILTVT | 266–285 | 607–631 | 750–768 | | | | | | |
| PVGLB_MCMVS | 135–156 | 566–589 | 738–765 | | | | | | |
| PVGLB_PRVIF | 203–218 | | | | | | | | |
| PVGLB_VXVD | 522–538 | | | | | | | | |
| PVGLC_HSV11 | 467–493 | | | | | | | | |
| PVGLC_HSV1K | 3–22 | 467–493 | | | | | | | |
| PVGLC_HSV2 | 435–458 | | | | | | | | |
| PVGLC_HSV23 | 436–459 | | | | | | | | |
| PVGLC_HSVBC | 475–494 | | | | | | | | |
| PVGLC_HSVE4 | 444–459 | | | | | | | | |
| PVGLC_HSVEB | 427–442 | | | | | | | | |
| PVGLC_HSVMB | 399–421 | | | | | | | | |
| PVGLC_HSVMG | 398–420 | | | | | | | | |
| PVGLC_HSVMM | 399–421 | | | | | | | | |
| PVGLC_PRVIF | 180–197 | 446–472 | | | | | | | |
| PVGLC_VZVD | 431–449 | | | | | | | | |
| PVGLC_VZVS | 431–449 | | | | | | | | |
| PVGLD_HSV11 | 79–94 | | | | | | | | |
| PVGLD_HSV2 | 79–94 | | | | | | | | |
| PVGLE_HSV11 | 104–129 | 413–437 | | | | | | | |
| PVGLE_VZVD | 469–493 | | | | | | | | |
| PVGLF_BRSVA | 205–221 | 265–287 | 482–504 | | | | | | |
| PVGLF_BRSVC | 205–221 | 265–287 | 484–506 | | | | | | |
| PVGLF_BRSVR | 205–221 | 265–287 | 484–508 | | | | | | |
| PVGLF_CDVO | 336–361 | 398–414 | 583–589 | | | | | | |
| PVGLF_HRSV1 | 205–221 | 265–287 | 484–506 | | | | | | |

TABLE IX-continued

| Search Results Summary for P12CTLZIP Motif | | | | | |
|---|---|---|---|---|---|
| PVGLF_HRSVA | 205–221 | 265–287 | 484–506 | | |
| PVGLF_HRSVL | 205–221 | 265–287 | 484–506 | | |
| PVGLF_HRSVR | 205–221 | 265–287 | 484–506 | | |
| PVGLF_MEASE | 224–245 | 286–302 | 451–477 | | |
| PVGLF_MEASI | 277–248 | 289–305 | 454–480 | | |
| PVGLF_MEASY | 224–245 | 286–302 | 451–477 | | |
| PVGLF_MUMPM | 276–292 | 446–467 | | | |
| PVGLF_MUMPR | 276–292 | 446–467 | | | |
| PVGLF_MUMPS | 5–20 | 276–292 | 446–467 | | |
| PVGLF_NDVA | 273–289 | | | | |
| PVGLF_NDVB | 273–289 | | | | |
| PVGLF_NDVM | 273–289 | | | | |
| PVGLF_NDVT | 273–289 | | | | |
| PVGLF_NDVTG | 273–289 | | | | |
| PVGLF_NDVU | 273–289 | | | | |
| PVGLF_PHODV | 269–285 | 305–326 | 367–383 | 531–558 | |
| PVGLF_PI1HC | 456–477 | | | | |
| PVGLF_PI2H | 450–471 | | | | |
| PVGLF_PI2HG | 450–471 | | | | |
| PVGLF_PI2HT | 450–471 | | | | |
| PVGLF_PI3B | 283–310 | 405–426 | 453–474 | | |
| PVGLF_PI3H4 | 2–20 | 283–310 | 453–474 | | |
| PVGLF_RINDK | 220–241 | 282–298 | 447–473 | | |
| PVGLF_RINDL | 220–241 | 282–298 | 447–473 | | |
| PVGLF_SEND5 | 460–481 | | | | |
| PVGLF_SENDF | 460–481 | | | | |
| PVGLF_SENDH | 460–481 | | | | |
| PVGLF_SENDJ | 460–481 | | | | |
| PVGLF_SENDZ | 460–481 | | | | |
| PVGLF_SV41 | 453–474 | | | | |
| PVGLF_SV5 | 401–425 | 446–467 | | | |
| PVGLF_TRTV | 175–191 | 452–474 | | | |
| PVGLG_IHNV | 77–99 | | | | |
| PVGLG_RABVE | 454–474 | | | | |
| PVGLG_RABVH | 372–391 | 454–474 | | | |
| PVGLG_RABVP | 454–474 | | | | |
| PVGLG_RABVS | 454–474 | | | | |
| PVGLG_RABVT | 454–474 | | | | |
| PVGLG_VHSV0 | 406–428 | | | | |
| PVGLH_HCMVA | 211–237 | 365–382 | 574–598 | 691–712 | |
| PVGLH_HCMVT | 210–236 | 364–381 | 573–597 | 690–711 | |
| PVGLH_HSV11 | 245–262 | 443–467 | 803–827 | | |
| PVGLH_HSV1E | 245–262 | 443–467 | 803–827 | | |
| PVGLH_HSV6G | 314–332 | | | | |
| PVGLH_HSVE4 | 304–325 | 814–836 | | | |
| PVGLH_HSVEB | 297–318 | 807–832 | | | |
| PVGLH_HSVSA | 454–479 | 656–679 | | | |
| PVGLH_MCMVS | 670–890 | | | | |
| PVGLI_HCMVA | 168–160 | | | | |
| PVGLI_HSV11 | 43–60 | | | | |
| PVGLI_HSVEB | 44–63 | | | | |
| PVGLI_VZVD | 278–297 | | | | |
| PVGLM_BUNGE | 117–136 | 197–222 | | | |
| PVGLM_BUNL7 | 31–55 | 81–98 | 190–211 | 1325–1345 | 1387–1410 |
| PVGLM_BUNSH | 31–55 | 81–98 | 190–211 | 1325–1345 | 1387–1410 |
| PVGLM_BUNYW | 193–216 | 1379–1404 | | | |
| PVGLM_HANTB | 355–371 | 692–717 | 900–915 | 999–1019 | |
| PVGLM_HANTH | 499–515 | 694–718 | 1000–1020 | | |
| PVGLM_HANTL | 499–515 | 694–718 | 1001–1021 | | |
| PVGLM_HANTV | 499–515 | 694–718 | 1001–1021 | | |
| PVGLM_PHV | 152–171 | | | | |
| PVGLM_PTPV | 743–765 | 997–1016 | 1275–1302 | | |
| PVGLM_PUUMH | 155–174 | 509–525 | 712–729 | | |
| PVGLM_PUUMS | 155–174 | 509–525 | 712–729 | 1092–1117 | |
| PVGLM_RVFV | 53–80 | 344–368 | 830–858 | | |
| PVGLM_RVFVZ | 53–80 | 344–366 | 830–858 | 1156–1176 | |
| PVGLM_SEOUR | 355–371 | 693–718 | 901–916 | 1000–1020 | |
| PVGLM_SEOUS | 355–371 | 692–717 | 900–915 | 999–1019 | |
| PVGLM_UUK | 581–585 | 855–874 | 826–842 | 925–952 | 966–989 |
| PVGLP_BEV | 430–452 | 889–885 | 1099–1124 | 1546–1588 | |
| PVGLX_PRVRI | 149–176 | | | | |
| PVGLY_JUNIN | 12–38 | | | | |
| PVGLY_LASSG | 12–38 | 237–258 | 426–448 | | |
| PVGLY_LASSJ | 12–38 | 238–259 | 427–449 | | |
| PVGLY_LYCVA | 12–38 | | | | |
| PVGLY_LYCVW | 12–38 | 69–108 | | | |
| PVGLY_MOPEI | 12–38 | 425–447 | | | |

TABLE IX-continued

Search Results Summary for P12CTLZIP Motif

| | | | | | | |
|---|---|---|---|---|---|---|
| PVGLY_PIARV | 12–38 | 441–466 | | | | |
| PVGLY_TACV | 12–38 | | | | | |
| PVGLY_TACV5 | 12–38 | | | | | |
| PVGLY_TACV7 | 12–38 | | | | | |
| PVGLY_TACVT | 12–38 | | | | | |
| PVGNB_CPMV | 141–161 | 568–594 | 757–783 | 1110–1135 | 1165–1184 | |
| PVGNM_BPMV | 678–696 | | | | | |
| PVGNM_CPMV | 311–335 | 741–764 | 1021–1037 | | | |
| PVGP2_EBV | 657–681 | | | | | |
| PVGP3_EBV | 854–878 | | | | | |
| PVGP8_EBV | 67–88 | | | | | |
| PVMO1_VACCC | 134–159 | 177–195 | 281–302 | | | |
| PVMO1_VACCV | 83–108 | 126–144 | 230–251 | | | |
| PVM1_REOVD | 141–168 | 227–245 | 280–304 | 324–347 | 414–436 | 454–477 |
| PVM1_REOVL | 141–168 | 227–245 | 280–304 | 414–436 | 454–477 | |
| PVM21_REOVD | 168–192 | | | | | |
| PVM22_REOVD | 168–192 | | | | | |
| PVM2_REOVJ | 168–192 | | | | | |
| PVM2_REOVL | 168–192 | | | | | |
| PVM3_REOVD | 304–326 | 521–540 | | | | |
| PVMAT_BRSVA | 37–62 | | | | | |
| PVMAT_CDVO | 148–165 | 283–309 | | | | |
| PVMAT_HRSVA | 44–62 | 139–180 | | | | |
| PVMAT_LPMV | 311–338 | | | | | |
| PVMAT_MEASE | 283–309 | | | | | |
| PVMAT_MEASH | 283–309 | | | | | |
| PVMAT_MEASI | 87–111 | | | | | |
| PVMAT_MEASU | 283–309 | | | | | |
| PVMAT_MUMPS | 191–207 | 227–250 | 310–330 | | | |
| PVMAT_NDVA | 135–151 | 190–208 | 309–329 | | | |
| PVMAT_NDVB | 135–151 | 190–208 | 309–329 | | | |
| PVMAT_PI1HC | 195–217 | | | | | |
| PVMAT_PI2HT | 132–154 | 189–205 | 308–328 | | | |
| PVMAT_PI4HA | 312–332 | | | | | |
| PVMAT_PI4HB | 312–332 | | | | | |
| PVMAT_RINDK | 200–221 | 239–260 | 283–309 | | | |
| PVMAT_SENDF | 195–217 | | | | | |
| PVMAT_SENDH | 195–217 | | | | | |
| PVMAT_SENDZ | 195–217 | | | | | |
| PVMAT_SSPVB | 283–309 | 314–336 | | | | |
| PVMAT_SV41 | 132–154 | 189–205 | 308–328 | | | |
| PVMAT_SV5 | 98–114 | 132–148 | 308–335 | | | |
| PVMAT_SVCV | 141–167 | | | | | |
| PVMAT_TRTV | 122–143 | | | | | |
| PVME1_CVBM | 9–36 | 137–161 | 171–190 | | | |
| PVME1_CVH22 | 136–155 | | | | | |
| PVME1_CVHOC | 9–36 | 64–85 | 137–161 | | | |
| PVME1_CVMA5 | 10–37 | | | | | |
| PVME1_CVMJH | 10–37 | | | | | |
| PVME1_CVPFS | 174–193 | | | | | |
| PVME1_CVPPU | 174–193 | | | | | |
| PVME1_CVPRM | 174–193 | | | | | |
| PVME1_CVTKE | 9–36 | 137–161 | 171–190 | | | |
| PVME1_IBV6 | 74–98 | | | | | |
| PVME1_IBVB | 74–101 | | | | | |
| PVME1_IBVB2 | 74–101 | | | | | |
| PVME1_IBVK | 74–98 | | | | | |
| PVMEM_EBV | 131–157 | 178–203 | | | | |
| PVMP_CAMVC | 118–134 | 147–164 | 183–201 | | | |
| PVMP_CAMVD | 118–134 | 147–164 | 183–201 | | | |
| PVMP_CAMVE | 118–134 | 147–164 | 183–201 | | | |
| PVMP_CAMVN | 118–134 | 147–164 | 183–201 | | | |
| PVMP_CAMVS | 118–134 | 147–164 | 183–201 | | | |
| PVMP_CAMVW | 118–134 | 147–164 | 183–201 | | | |
| PVMP_CERV | 293–318 | | | | | |
| PVMP_FMVD | 115–131 | 180–198 | | | | |
| PVMP_SOCMV | 122–147 | 273–299 | | | | |
| PVMSA_HPBDB | 201–228 | 269–295 | | | | |
| PVMSA_HPBDC | 194–221 | 268–294 | | | | |
| PVMSA_HPBDU | 157–184 | 231–257 | | | | |
| PVMSA_HPBDW | 194–221 | 269–295 | | | | |
| PVMSA_HPBGS | 209–236 | 271–295 | 380–395 | | | |
| PVMSA_HPSHE | 236–262 | 293–320 | | | | |
| PVMSA_HPBV0 | 70–96 | | | | | |
| PVMSA_HPBV2 | 185–202 | 244–270 | | | | |
| PVMSA_HPBV4 | 185–202 | 244–270 | | | | |
| PVMSA_HPBV9 | 244–270 | | | | | |

TABLE IX-continued

Search Results Summary for P12CTLZIP Motif

| | | | |
|---|---|---|---|
| PVMSA_HPBVA | 174–191 | 233–259 | |
| PVMSA_HPBVD | 11–28 | 70–96 | |
| PVMSA_HPBVI | 233–259 | | |
| PVMSA_HPBVJ | 174–191 | 233–259 | |
| PVMSA_HPBVL | 174–191 | 233–259 | |
| PVMSA_HPBVN | 11–28 | 70–96 | |
| PVMSA_HPBVO | 174–191 | 233–259 | |
| PVMSA_HPBVP | 185–202 | 244–270 | |
| PVMSA_HPBVR | 185–202 | 244–270 | |
| PVMSA_HPBVS | 11–28 | 70–96 | |
| PVMSA_HPBVW | 174–191 | 233–259 | |
| PVMSA_HPBVY | 174–191 | 233–259 | |
| PVMSA_HPBVZ | 174–191 | 233–259 | |
| PVMSA_WHV1 | 207–234 | 269–293 | 378–393 |
| PVMSA_WHV59 | 212–239 | 274–298 | 383–398 |
| PVMSA_WHV7 | 212–239 | 274–298 | 383–398 |
| PVMSA_WHV8 | 212–239 | 274–298 | 383–398 |
| PVMSA_WHV8I | 212–239 | 274–298 | 383–398 |
| PVMSA_WHVW6 | 125–149 | 234–249 | |
| PVMT2_IAANN | 25–46 | | |
| PVMT2_IABAN | 25–46 | | |
| PVMT2_IAFOW | 25–46 | | |
| PVMT2_IAFPR | 25–46 | | |
| PVMT2_IAFPW | 25–46 | | |
| PVMT2_IALE1 | 25–46 | | |
| PVMT2_IALE2 | 25–46 | | |
| PVMT2_IAMAN | 25–46 | | |
| PVMT2_IAPUE | 25–46 | | |
| PVMT2_IASIN | 25–46 | | |
| PVMT2_IAUDO | 25–46 | | |
| PVMT2_IAWIL | 25–46 | | |
| PVMT9_MYXVL | 226–241 | | |

TABLE X

Search Results Summary for P23CTLZIP Motif

P23LZIPC
LIBRARY FILE

| | | | |
|---|---|---|---|
| PENV_AVISU | 98–136 | | |
| PENV_BAEVM | 202–240 | 526–564 | |
| PENV_BIV06 | 434–472 | 526–553 | 628–659 |
| PENV_BIV27 | 554–582 | 657–688 | |
| PENV_CAEVG | 44–78 | | |
| PENV_EIAV1 | 795–828 | | |
| PENV_EIAV2 | 795–828 | | |
| PENV_EIAV3 | 795–828 | | |
| PENV_EIAV6 | 796–829 | | |
| PENV_EIAV9 | 795–828 | | |
| PENV_EIAVC | 795–828 | | |
| PENV_EIAVW | 795–828 | | |
| PENV_EIAVY | 798–828 | | |
| PENV_FIVPE | 128–166 | | |
| PENV_FIVT2 | 46–74 | | |
| PENV_FLVGL | 447–475 | | |
| PENV_FLVLB | 487–495 | | |
| PENV_FLVBA | 444–472 | | |
| PENV_FOAMV | 44–78 | 481–519 | 552–584 |
| PENV_FRSFB | 315–350 | | |
| PENV_FSVGA | 467–495 | | |
| PENV_FSVGB | 447–475 | | |
| PENV_FSVSM | 450–478 | | |
| PENV_FSVST | 467–495 | | |
| PENV_GALV | 519–554 | | |
| PENV_HV1A2 | 729–762 | | |
| PENV_HV1B1 | 730–763 | | |
| PENV_HV1B8 | 725–758 | | |
| PENV_HV1BN | 743–781 | | |
| PENV_HV1BR | 735–768 | | |
| PENV_HV1C4 | 742–776 | | |
| PENV_HV1EL | 254–286 | 727–780 | |
| PENV_HV1H2 | 730–763 | | |
| PENV_HV1H3 | 730–763 | | |

TABLE X-continued

Search Results Summary for P23CTLZIP Motif

P23LZIPC
LIBRARY FILE

| | | |
|---|---|---|
| PENV_HV1J3 | 741–774 | |
| PENV_HV1JR | 722–755 | |
| PENV_HV1KB | 552–586 | 762–790 |
| PENV_HV1MA | 268–289 | 733–766 |
| PENV_HV1MF | 728–761 | |
| PENV_HV1MN | 392–430 | 731–764 |
| PENV_HV1ND | 248–279 | |
| PENV_HV1OY | 729–762 | |
| PENV_HV1PV | 730–763 | |
| PENV_HV1RH | 739–772 | |
| PENV_HV1SC | 730–763 | |
| PENV_HV1W1 | 730–763 | |
| PENV_HV1W2 | 721–754 | |
| PENV_HV1Z2 | 264–286 | 727–780 |
| PENV_HV1Z3 | 260–281 | |
| PENV_HV1Z6 | 255–286 | 729–762 |
| PENV_HV2BE | 781–811 | |
| PENV_HV2D1 | 772–802 | |
| PENV_HV2G1 | 772–802 | |
| PENV_HV2NZ | 777–814 | |
| PENV_HV2SB | 743–775 | |
| PENV_JSRV | 299–332 | 484–515 |
| PENV_MMTVB | 435–472 | |
| PENV_MMTVG | 435–472 | |
| PENV_RSVP | 533–570 | |
| PENV_SFV1 | 44–78 | 492–530 |
| PENV_SFV3L | 48–82 | 550–588 |
| PENV_SIVCZ | 745–776 | |
| PENV_SIVGB | 247–277 | 353–386 |
| PENV_SIVM1 | 788–800 | |
| PENV_SIVMK | 765–799 | |
| PENV_SIVML | 511–545 | 764–798 |
| PENV_SIVS4 | 468–486 | |
| PENV_SIVSP | 462–490 | 810–840 |
| PHEMA_CDVO | 200–234 | |
| PHEMA_IABUD | 23–55 | |
| PHEMA_IACKA | 23–56 | |
| PHEMA_IACKV | 517–547 | |
| PHEMA_IADA1 | 23–56 | |
| PHEMA_IADCZ | 23–55 | |
| PHEMA_IADH6 | 293–323 | |
| PHEMA_IADNZ | 23–55 | |
| PHEMA_IAFPR | 15–51 | |
| PHEMA_IAGRE | 23–55 | |
| PHEMA_IAMAA | 22–54 | |
| PHEMA_IAMAB | 27–59 | |
| PHEMA_IARUD | 23–55 | |
| PHEMA_IASE2 | 23–55 | |
| PHEMA_IASTA | 517–547 | |
| PHEMA_MUMPM | 19–52 | 101–132 |
| PHEMA_MUMPR | 19–52 | 101–132 |
| PHEMA_MUMPS | 19–52 | 101–132 |
| PHEMA_NDVA | 60–88 | |
| PHEMA_NDVB | 60–88 | |
| PHEMA_NDVD | 60–88 | |
| PHEMA_NDVH | 60–88 | |
| PHEMA_NDVI | 60–88 | |
| PHEMA_NDVM | 60–88 | |
| PHEMA_NDVQ | 60–88 | |
| PHEMA_NDVTG | 60–88 | |
| PHEMA_NDVU | 60–88 | |
| PHEMA_PI1HW | 29–60 | 196–233 |
| PHEMA_PI2H | 13–46 | 334–369 |
| PHEMA_PI2HT | 13–46 | 334–369 |
| PHEMA_PI3B | 194–231 | |
| PHEMA_PI3H4 | 194–231 | |
| PHEMA_PI3HA | 194–231 | |
| PHEMA_PI3HT | 194–231 | |
| PHEMA_PI3HU | 194–231 | |
| PHEMA_PI3HV | 194–231 | |
| PHEMA_PI3HW | 194–231 | |
| PHEMA_PI3HX | 194–231 | |
| PHEMA_PI4HA | 245–280 | 338–376 |
| PHEMA_RACVI | 255–293 | |

TABLE X-continued

Search Results Summary for P23CTLZIP Motif

P23LZIPC
LIBRARY FILE

| | | | |
|---|---|---|---|
| PHEMA_RINDL | 282–313 | | |
| PHEMA_SEND5 | 16–54 | 196–233 | |
| PHEMA_SENDF | 16–54 | 196–233 | |
| PHEMA_SENDH | 16–54 | 196–233 | |
| PHEMA_SENDJ | 16–54 | 196–233 | |
| PHEMA_SENDZ | 23–54 | 196–233 | |
| PHEMA_SV41 | 55–84 | 330–365 | |
| PHEMA_SV5 | 7–36 | | |
| PHEMA_SV5CM | 7–41 | | |
| PHEMA_SV5CP | 7–41 | | |
| PHEMA_SV5LN | 7–35 | | |
| PHEMA_VACCC | 258–294 | | |
| PHEMA_VACCI | 259–294 | | |
| PHEMA_VACCT | 258–294 | | |
| PHEMA_VACCV | 258–294 | | |
| PVENV_BEV | 16–51 | 87–117 | |
| PVENV_DHVI1 | 297–335 | | |
| PVENV_MCV1 | 203–236 | | |
| PVENV_MCV2 | 203–236 | | |
| PVENV_VACCC | 208–241 | | |
| PVENV_VACCI | 208–241 | | |
| PVENV_VACCP | 208–241 | | |
| PVENV_VACCV | 208–241 | | |
| PVF03_VACCC | 2–40 | 61–93 | |
| PVF03_VACCV | 2–40 | 61–93 | |
| PVFP1_FOWPV | 297–330 | | |
| PVFP4_FOWPV | 237–267 | | |
| PVFP7_CAPVK | 89–118 | | |
| PVFU8_VACCC | 28–61 | | |
| PVFU8_VACCV | 28–61 | | |
| PVG01_HSVI1 | 317–346 | | |
| PVG02_HSVEB | 163–196 | | |
| PVG02_VACCV | 92–120 | | |
| PVG02_VARV | 92–120 | | |
| PVG03_HSVI1 | 108–136 | | |
| PVG06_HSVI1 | 54–83 | | |
| PVG06_VACCC | 99–136 | | |
| PVG06_VARV | 99–136 | | |
| PVG07_VACCC | 113–145 | | |
| PVG07_VARV | 113–145 | | |
| PVG09_VACCC | 303–338 | | |
| PVG09_VACCV | 266–301 | | |
| PVG09_VARV | 303–338 | | |
| PVG11_HSVI1 | 150–183 | | |
| PVG12_HSV11 | 206–243 | | |
| PVG12_HSVSA | 68–106 | | |
| PVG1_SPV1R | 254–292 | 303–337 | 414–452 |
| PVG22_HSVI1 | 300–337 | 647–678 | |
| PVG23_HSVI1 | 70–108 | | |
| PVG26_HSVI1 | 94–125 | | |
| PVG27_HSVSA | 36–74 | | |
| PVG28_HSVI1 | 491–521 | | |
| PVG28_HSVSA | 7–40 | | |
| PVG2R_AMEPV | 180–217 | | |
| PVG2_SPV4 | 209–244 | | |
| PVG35_HSVI1 | 15–46 | 190–226 | |
| PVG36_HSVSA | 151–185 | | |
| PVG39_HSVI1 | 543–577 | 648–682 | |
| PVG40_HSVSA | 187–216 | | |
| PVG41_HSVI1 | 11–45 | 202–233 | |
| PVG42_HSVI1 | 91–125 | | |
| PVG43_HSVI1 | 109–140 | 157–185 | |
| PVG46_HSVI1 | 888–925 | | |
| PVG48_HSVSA | 329–357 | | |
| PVG50_HSVSA | 113–141 | | |
| PVG51_HSVI1 | 29–64 | 84–120 | |
| PVG52_HSVI1 | 96–134 | | |
| PVG55_HSVI1 | 100–129 | | |
| PVG56_HSVI1 | 631–667 | 1091–1126 | |
| PVG58_HSVI1 | 342–375 | 480–508 | |
| PVG58_HSVSA | 25–60 | 195–233 | |
| PVG59_HSVI1 | 82–118 | | |
| PVG61_HSVI1 | 76–109 | | |
| PVG64_HSVI1 | 55–89 | 363–401 | 420–452 |

TABLE X-continued

Search Results Summary for P23CTLZIP Motif

P23LZIPC
LIBRARY FILE

| | | | | |
|---|---|---|---|---|
| PVG65__HSVI1 | 801–836 | 1190–1326 | | |
| PVG67__HSVI1 | 150–188 | 1150–1185 | | |
| PVG6__SPV1R | 60–89 | | | |
| PVG71__HSVSA | 128–158 | | | |
| PVG72__HSVI1 | 445–478 | 720–751 | 1158–1189 | 1252–1285 |
| PVG75__HSVI1 | 263–291 | 387–422 | | |
| PVG78__H8VI1 | 187–221 | | | |
| PVG7__SPV1R | 18–46 | | | |
| PVGF1__IBVB | 1719–1747 | 1856–1891 | 2108–2146 | 3601–3633 |
| PVGH3__HCMVA | 80–115 | 157–185 | | |
| PVGL2__CVBF | 1259–1294 | | | |
| PVGL2__CVBL9 | 651–681 | 1259–1294 | | |
| PVGL2__CVBLY | | 1259–1294 | | |
| PVGL2__CVBM | | 1259–1294 | | |
| PVGL2__CVBQ | | 1259–1294 | | |
| PVGL2__CVBV | | 1259–1294 | | |
| PVGL2__CVH22 | 1053–1088 | | | |
| PVGL2__CVM4 | 1287–1304 | | | |
| PVGL2__CVMA5 | 1215–1252 | | | |
| PVGL2__CVMJH | 1128–1163 | | | |
| PVGL2__CVPFS | 632–665 | 736–764 | 1328–1383 | |
| PVGL2__CVPPU | 630–663 | 734–762 | 1326–1381 | |
| PVGL2__CVPR8 | 512–540 | 1104–1139 | | |
| PVGL2__CVPRM | 408–441 | 1104–1139 | | |
| PVGL2__FIPV | 635–668 | 739–767 | 1331–1366 | |
| PVGL2__IBVB | 153–188 | | | |
| PVGLB__HCMVA | 116–147 | 708–743 | | |
| PVGLB__HCMVT | 116–147 | 707–744 | | |
| PVGLB__HSVGU | 72–110 | | | |
| PVGLB__HSVB1 | 254–288 | | | |
| PVGLB__HSVB2 | 264–299 | 745–774 | | |
| PVGLB__HSVBC | 253–287 | | | |
| PVGLB__ILTV6 | 442–472 | | | |
| PVGLB__ILTV8 | 452–482 | | | |
| PVGLB__IVTVT | 452–482 | | | |
| PVGLB__MCMV8 | 135–163 | 738–776 | | |
| PVGLC__HSV11 | 487–500 | | | |
| PVGLC__HSV1K | 487–500 | | | |
| PVGLC__HSV2 | 435–465 | | | |
| PVGLC__HSV23 | 436–466 | | | |
| PVGLC__HSVBC | 475–507 | | | |
| PVGLC__VZVD | 351–388 | 513–548 | | |
| PVGLC__VZVS | 351–388 | 513–548 | | |
| PVGLD__HSVEA | 340–370 | | | |
| PVGLD__HSVEB | 41–70 | 390–420 | | |
| PVGLD__HSVEK | 41–70 | 390–420 | | |
| PVGLE__HSVE4 | 95–125 | | | |
| PVGLE__HSVEB | 63–100 | 390–420 | | |
| PVGLE__HSVEL | 63–100 | 392–422 | | |
| PVGLE__PRVRI | 332–369 | | | |
| PVGLF__BRSVA | 265–301 | 482–511 | | |
| PVGLF__BRSVC | 484–513 | | | |
| PVGLF__BRSVR | 484–513 | | | |
| PVGLF__CDVO | 562–596 | | | |
| PVGLF__HRSV1 | 484–513 | | | |
| PVGLF__HRSVA | 484–513 | | | |
| PVGLF__HRSVL | 484–513 | | | |
| PVGLF__HRSVR | 484–513 | | | |
| PVGLF__MEASE | 224–256 | 451–484 | | |
| PVGLF__MEASI | 227–259 | 454–487 | | |
| PVGLF__MEASY | 224–256 | 451–484 | | |
| PVGLF__MUMPM | 446–475 | | | |
| PVGLF__MUMPR | 446–474 | | | |
| PVGLF__MUMPS | 5–38 | 446–474 | | |
| PVGLF__NDVI | 132–165 | | | |
| PVGLF__PHODV | 531–565 | | | |
| PVGLF__PI1HC | 456–484 | | | |
| PVGLF__PI3B | 453–481 | | | |
| PVGLF__PI3H4 | 453–481 | | | |
| PVGLF__RINDK | 220–252 | 447–480 | | |
| PVGLF__RINDL | 220–252 | 447–480 | | |
| PVGLF__SEND5 | 460–488 | | | |
| PVGLF__SENDF | 460–488 | | | |
| PVGLF__SENDH | 460–488 | | | |

TABLE X-continued

Search Results Summary for P23CTLZIP Motif

P23LZIPC
LIBRARY FILE

| | | | | | |
|---|---|---|---|---|---|
| PVGLF_SENDJ | 460–488 | | | | |
| PVGLF_SENDZ | 460–488 | | | | |
| PVGLF_SV5 | 446–474 | | | | |
| PVGLF_TRTV | 452–481 | | | | |
| PVGLG_HSVEB | 327–364 | | | | |
| PVGLG_SYNV | 524–553 | | | | |
| PVGLG_VSVIG | 450–488 | | | | |
| PVGLG_VSVJO | 457–492 | | | | |
| PVGLG_VSVO | 450–488 | | | | |
| PVGLG_VSVSJ | 450–488 | | | | |
| PVGLH_HCMVA | 691–719 | | | | |
| PVGLH_HCMVT | 690–718 | | | | |
| PVGLH_HCV6G | 640–677 | | | | |
| PVGLH_HSVE4 | 814–850 | | | | |
| PVGLH_HSVEB | 807–843 | | | | |
| PVGLI_HCMVA | 158–194 | | | | |
| PVGLM_BUNGE | 197–227 | 438–468 | 982–1020 | 1049–1084 | |
| PVGLM_BUNL7 | 190–220 | | | | |
| PVGLM_BUNSH | 190–220 | 344–381 | | | |
| PVGLM_BUNYW | 193–228 | 434–472 | 823–854 | | |
| PVGLM_DUGBV | 244–273 | 637–672 | 888–915 | 935–965 | 1403–1441 |
| PVGLM_HANTB | 610–641 | 1081–1119 | | | |
| PVGLM_HANTH | 188–222 | 612–643 | 1082–1120 | | |
| PVGLM_HANTL | 188–222 | 612–643 | 1083–1121 | | |
| PVGLM_HANTV | 188–222 | 612–643 | 1083–1121 | | |
| PVGLM_PHV | 616–649 | 1088–1121 | | | |
| PVGLM_PTPV | 949–982 | 1275–1309 | | | |
| PVGLM_PUUMH | 620–653 | 1092–1125 | | | |
| PVGLM_PUUMS | 620–653 | 1092–1125 | | | |
| PVGLM_RVFV | 620–653 | 830–883 | | | |
| PVGLM_RVFVZ | 620–653 | 830–863 | 1156–1185 | | |
| PVGLM_SEOUR | 605–641 | 1082–1120 | | | |
| PVGLM_SEOUS | 610–641 | 1081–1119 | | | |
| PVGLM_UUK | 431–468 | 966–995 | | | |
| PVGLF_BEV | 1491–1526 | | | | |
| PVGLY_JUNIN | 12–45 | | | | |
| PVGLY_LASSG | 237–265 | | | | |
| PVGLY_LASSJ | 238–288 | | | | |
| PVGLY_PIARV | 12–50 | | | | |
| PVGLY_TACV | 12–50 | | | | |
| PVGLY_TACV5 | 12–50 | 89–124 | | | |
| PVGLY_TACV7 | 12–50 | 89–124 | | | |
| PVGLY_TACVT | 12–50 | 89–124 | | | |
| PVGNB_CPMV | 1527–1555 | | | | |
| PVGNM_BPMV | 137–167 | 280–327 | 837–888 | | |
| PVGNM_CPMV | 209–242 | 741–771 | | | |
| PVGNM_CPSMV | 60–88 | 479–515 | | | |
| PVGNM_RCMV | 766–799 | | | | |
| PVGP2_EBV | 78–111 | | | | |
| PVGP3_EBV | 78–111 | | | | |
| PVM1_REOVD | 280–318 | 324–361 | | | |
| PVM1_REOVL | 280–318 | | | | |
| PVM21_REOVD | 168–199 | | | | |
| PVM22_REOVD | 168–199 | | | | |
| PVM2_REOVJ | 168–199 | | | | |
| PVM2_REOVL | 168–199 | | | | |
| PVM3_REOVD | 333–364 | | | | |
| PVMAT_SV5 | 308–342 | | | | |
| PVMTA_TRTV | 122–150 | | | | |
| PVME1_CVBM | 64–102 | | | | |
| PVME1 CVHOC | 64–102 | | | | |
| PVME1_CVMA5 | 65–103 | | | | |
| PVME1_CVMJH | 65–103 | | | | |
| PVME1_CVTKE | 64–102 | | | | |
| PVMEM_EBV | 178–213 | | | | |
| PVMP_CERV | 93–126 | | | | |
| PVMP_SOCMV | 66–98 | 273–303 | | | |
| PVMSA_HPBDB | 201–238 | 269–302 | | | |
| PVMSA_HPBDC | 194–227 | 268–301 | | | |
| PVMSA_HPBDU | 157–190 | 231–264 | | | |
| PVMSA_HPBDW | 194–227 | 269–302 | | | |
| PVMSA_HPBGS | 209–243 | 271–307 | | | |
| PVMSA_HPBHE | 159–195 | 236–269 | | | |
| PVMSA_HPBV0 | 70–98 | | | | |

TABLE X-continued

Search Results Summary for P23CTLZIP Motif

P23LZIPC
LIBRARY FILE

| | | |
|---|---|---|
| PVMSA_HPVB2 | 244–272 | |
| PVMSA_HPVB4 | 244–272 | |
| PVMSA_HPBV9 | 244–272 | |
| PVMSA_HPBVA | 233–261 | |
| PVMSA_HPBVD | 70–98 | |
| PVMSA_HPBVI | 233–261 | |
| PVMSA_HPBVJ | 233–261 | |
| PVMSA_HPBVL | 233–261 | |
| PVMSA_HPBVN | 70–98 | |
| PVMSA_HPBVO | 233–261 | |
| PVMSA_HPBVP | 244–272 | |
| PVMSA_HPBVR | 244–272 | |
| PVMSA_HPBVS | 70–98 | |
| PVMSA_HPBVW | 233–261 | |
| PVMSA_HPBVY | 233–261 | |
| PVMSA_HPBVZ | 233–261 | |
| PVMSA_WHV1 | 207–241 | 269–305 |
| PVMSA_WHV59 | 212–246 | 274–310 |
| PVMSA_WHV7 | 212–246 | 274–310 |
| PVMSA_WHV8 | 212–246 | 274–310 |
| PVMSA_WHV81 | 212–246 | 274–310 |
| PVMSA_WHVW6 | 125–161 | |
| PVMT2_L IAZI1 | 10–44 | |
| PVMT8_MYXVL | 5–34 | 141–170 |
| PVMT9_MYXVL | 246–282 | |

5.3. Synthesis of Peptides

The peptides of the invention may be synthesized or prepared by techniques well known in the art. See, for example, Creighton, 1983, Proteins: Structures and Molecular Principles, W.H. Freeman and Co., NY, which is incorporated herein by reference in its entirety. Short peptides, for example, can be synthesized on a solid support or in solution. Longer peptides amy be made using recombinant DNA techniques. Here, the nucleotide sequences encoding the peptides of the invention may be synthesized, and/or cloned, and expressed according to techniques well known to those of ordinary skill in the art. See, for example, Sambrook, et al., 1989, Molecular Cloning, A Laboratory Manual, Vols. 1–3, Cold Spring Harbor Press, N.Y.

The peptides of the invention may alternatively be synthesized such that one or more of the bonds which link the amino acid residues of the peptides are non-peptide bonds. These alternative non-peptide bonds may be formed by utilizing reactions well known to those in the art, and may include, but are not limited to imino, ester, hydrazide, semicarbazide, and azo bonds, to name but a few. In yet another embodiment of the invention, peptides comprising the sequences described above may be synthesized with additional chemical groups present at their amino and/or carboxy termini, such that, for example, the stability, bioavailability, and/or inhibitory activity of the peptides is enhanced. For example, hydrophobic groups such as carbobenzoxyl, dansyl, or t-butyloxycarbonyl groups, may be added to the peptides' amino termini. Likewise, an acetyl group or a 9-fluorenylmethoxy-carbonyl group may be placed at the peptides' amino termini. (See "X" in Tables I to IV, above.) Additionally, the hydrophobic group, t-butyloxycarbonyl, or an amido group may be added to the peptides' carboxy termini. (See "Z" in Tables I to IV, above.) Further, the peptides of the invention may be synthesized such that their steric configuration is altered. For example, the D-isomer of one or more of the amino acid residues of the peptide may be used, rather than the usual L-isomer. Still further, at least one of the amino acid residues of the peptides of the invention may be substituted by one of the well known non-naturally occurring amino acid residues. Alterations such as these may serve to increase the stability, bioavailability and/or inhibitory action of the peptides of the invention.

Any of the peptides described above may, additionally, have a non-peptide macromolecular carrier group covalently attached to their amino and/or carboxy termini. Such macromolecular carrier groups may include, for example, lipid-fatty acid conjugates, polyethylene glycol, or carbohydrates. "X", in Tables I to IV, above, may therefore additionally represent any of the above macromolecular carrier groups covalently attached to the amino terminus of a peptide. Likewise, "Z", in Tables I to IV, may additionally represent any of the macromolecular carrier groups described above.

5.4. Assays for Antiviral Activity

The antiviral activity exhibited by the peptides of the invention may be measured, for example, by easily performed in vitro assays, such as those described below, which can test the peptides' ability to inhibit syncytia formation, or their ability to inhibit infection by cell-free virus. Using these assays, such parameters as the relative antiviral activity of the peptides, exhibit against a given strain of virus and/or the strain specific inhibitory activity of the peptide can be determined. A cell fusion assay may be utilized to test the peptides' ability to inhibit HIV-induced syncytia formation in vitro. Such an assay may comprise culturing uninfected CD-4$^+$ cells (such as Molt or CEM cells, for example) in the presence of chronically HIV-infected cells and a peptide to be assayed. For each peptide, a range of peptide concentrations may be tested. This range should include a control culture wherein no peptide has been added. Standard conditions for culturing, well known to those of ordinary skill in the art, are used. After incubation for an appropriate period (24 hours at 37° C., for example) the culture is examined microscopically for the presence of multinucleated giant cells, which are indicative of cell fusion and syncytia formation.

A reverse transcriptase (RT) assay may be utilized to test the peptides' ability to inhibit infection of CD-4+ cells by cell-free HIV. Such an assay may comprise culturing an appropriate concentration (i.e., $TCID_{50}$) of virus and CD-4+ cells in the presence of the peptide to be tested. Culture conditions well known to those in the art are used. As above, a range of peptide concentrations may be used, in addition to a control culture wherein no peptide has been added. After incubation for an appropriate period (e.g., 7 days) of culturing, a cell-free supernatant is prepared, using standard procedures, and tested for the present of RT activity as a measure of successful infection. The RT activity may be tested using standard techniques such as those described by, for example, Goff et al. (Goff, S. et al., 1981, J. Virol. 38:239–248) and/or Willey et al. (Willey, R. et al., 1988, J. Virol. 62:139–147). These references are incorporated herein by reference in their entirety.

Standard methods which are well-known to those of skill in the art may be utilized for assaying non-retroviral activity. See, for example, Pringle et al. (Pringle, C. R. et al., 1985, J. Medical Virology 17:377–386) for a discussion of respiratory syncytial virus and parainfluenza virus activity assay techniques. Further, see, for example, "Zinsser Microbiology", 1988, Joklik, W. K. et al., eds., Appleton & Lange, Norwalk, Conn., 19th ed., for a general review of such techniques. These references are incorporated by reference herein in its entirety.

5.5. Uses of the Peptides of the Invention

The DP-178 (SEQ ID:1) peptides of the invention, and DP-178 fragments, analogs, and homologs, exhibit potent antiviral activity. The DP-107-like and DP-178-like peptides of the invention preferably exhibit antiviral activity. As such, the peptides may be used as inhibitors of human and non-human viral and retroviral, especially HIV, transmission to uninfected cells.

The human retroviruses whose transmission may be inhibited by the peptides of the invention include, but are not limited to all strains of HIV-1 and HIV-2 and the human T-lymphocyte viruses (HTLV-I and II). The non-human retroviruses whose transmission may be inhibited by the peptides of the invention include, but are not limited to bovine leukosis virus, feline sarcoma and leukemia viruses, simian immunodeficiency, sarcoma and leukemia viruses, and sheep progress pneumonia viruses.

Non retroviral viruses whose transmission may be inhibited by the peptides of the invention include, but are not limited to human respiratory syncytial virus, canine distemper virus, newcastle disease virus, human parainfluenza virus, and influenza viruses. Further, any virus or retrovirus containing peptides listed in Tables V through X above, may be inhibited by the peptides of the invention.

As discussed more fully, below, in Section 5.5.1 and in the Example presented, below, in Section 8, DP-107 and DP-178, and DP-107-like and DP-178-like peptides form non-covalent protein-protein interactions which are required for normal activity of the virus. Thus, the peptides of the invention may also be utilized as components in assays for the identification of compounds that interfere with such protein-protein interactions and may, therefore, act as antiviral agents. These assays are discussed, below, in Section 5.5.1.

5.5.1. Antiviral Compound Screening Assays for Compounds that Interact with the PKD1 Gene Product As demonstrated in the Example presented in Section 8, below, DP-107 and DP-178 portions of the TM protein gp41 form non-covalent protein-protein intereactions. As also demonstrated, the maintenance of such interactions is necessary for normal viral infectivity. Thus, compounds which bind DP-107, bind DP-178, and/or act to disrupt normal DP-107/DP-178 protein-protein interactions may act as patent antiviral agents. Described below are assays for the identification of such compounds. Note that, while, for case and clarity of discussion, DP-107 and DP-178 peptides will be used as components of the assays described, but it is to be understood that any of the DP-107-like or DP-178-like peptides described, above, in Sections 5.1 and 5.2 may also be utilized as part of these screens for antiviral compounds.

Compounds which may be tested for an ability to bind DP-107, DP-178, and/or disrupt DP-107/DP-178 interactions, and which therefore, potentially represent antiviral compounds, include, but are not limited to, peptides made of D- and/or L-configuration amino acids (in, for example, the form of random peptide libraries; see Lam, K. S. et al., 1991, Nature 354:82–84), phosphopeptides (in, for example, the form of random or partially degenerate, directed phosphopeptide libraries; see, for example, Songyang, Z. et al., 1993, Cell 72:767–778), antibodies, and small organic or inorganic molecules. Synthetic compounds, natural products, and other sources of potentially effective materials may be screened in a variety of ways, as described in this Section. The compounds, antibodies, or other molecules identified may be tested for an ability to inhibit viral activity, utilizing, for example, viral assays such as those described, above, in Section 5.4.

Among the peptides which may be tested are soluble peptides comprising DP-107 and/or DP-178 domains, and peptides comprising DP-107 and/or DP-178 domains having one or more mutations within one or both of the domains, such as the M41-P peptide described, below, in the Example presented in Section 8, which contains a isoleucine to proline mutation within the DP-178 sequence.

In one embodiment of such screening methods is a method for identifying a compound to be tested for antiviral ability comprising:

(a) exposing at least one compound to a peptide comprising a DP-107 peptide for a time sufficient to allow binding of the compound to the DP-107 peptide;

(b) removing non-bound compounds; and (c) determining the presence of the compound bound to the DP-107 peptide, thereby identifying an agent to be tested for antiviral ability.

In a second embodiment of such screening methods is a method for identifying a compound to be tested for antiviral ability comprising:

(a) exposing at least one compound to a peptide comprising a DP-178 peptide for a time sufficient to allow binding of the compound to the DP-178 peptide;

(b) removing non-bound compounds; and (c) determining the presence of the compound bound to the DP-178 peptide, thereby identifying an agent to be tested for antiviral ability.

One method utilizing these types of approaches that may be pursued in the isolation of such DP-107-binding or DP-178-binding compounds is an assay which would include the attachment of either the DP-107 or the DP-178 peptide to a solid matrix, such as, for example, agarose or plastic beads, microtiter plate wells, petri dishes, or membranes composed of, for example, nylon or nitrocellulose. In such an assay system, either the DP-107 or DP-178 protein may be anchored onto a solid surface, and the compound, or test substance, which is not anchored, is labeled, either directly or indirectly. In practice, microtiter plates are conveniently utilized. The anchored component may be immobilized by non-covalent or covalent attachments. Non-covalent attachment may be accomplished simply by coating the solid surface with a solution of the protein and drying. Alternatively, an immobilized antibody, preferably a monoclonal antibody, specific for the protein may be used to anchor the protein to the solid surface. The surfaces may be prepared in advance and stored.

In order to conduct the assay, the labeled compound is added to the coated surface containing the anchored DP-107 or DP-178 peptide. After the reaction is complete, unreacted components are removed (e.g., by washing) under conditions such that any complexes formed will remain immobilized on the solid surface. The detection of complexes anchored on the solid surface can be accomplished in a number of ways. Where the compound is pre-labeled, the detection of label immobilized on the surface indicates that complexes were formed. Where the labeled component is not pre-labeled, an indirect label can be used to detect complexes anchored on the surface; e.g., using a labeled antibody specific for the compound (the antibody, in turn, may be directly labeled or indirectly labeled with a labeled anti-Ig antibody).

Alternatively, such an assay can be conducted in a liquid phase, the reaction products separated from unreacted components, and complexes detected; e.g., using an immobilized antibody specific for DP-107 or DP-178, whichever is appropriate for the given assay, or ab antibody specific for the compound, i.e., the test substance, in order to anchor any complexes formed in solution, and a labeled antibody specific for the other member of the complex to detect anchored complexes.

By utilizing procedures such as this, large numbers of types of molecules may be simultaneously screened for DP-107 or DP-178-binding capability, and thus potential antiviral activity.

Further, compounds may be screened for an ability to inhibit the formation of or, alternatively, disrupt DP-107/DP-178 complexes. Such compounds may then be tested for antiviral capability. For ease of description, DP-107 and DP-178 will be referred to as "binding partners." Compounds that disrupt such interactions may exhibit antiviral activity. Such compounds may include, but are not limited to molecules such as antibodies, peptides, and the like described above.

The basic principle of the assay systems used to identify compounds that interfere with the interaction between the DP-107 and DP-178 peptides involves preparing a reaction mixture containing peptides under conditions and for a time sufficient to allow the two peptides to interact and bind, thus forming a complex. In order to test a compound for disruptive activity, the reaction is conducted in the presence and absence of the test compound, i.e., the test compound may be initially included in the reaction mixture, or added at a time subsequent to the addition of one of the binding partners; controls are incubated without the test compound or with a placebo. The formation of any complexes between the binding partners is then detected. The formation of a complex in the control reaction, but not in the reaction mixture containing the test compound indicates that the compound interferes with the interaction of the DP-107 and DP-178 peptides.

The assay for compounds that interfere with the interaction of the binding partners can be conducted in a heterogeneous or homogeneous format. Heterogeneous assays involve anchoring one of the binding partners onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the binding partners, e.g., by competition, can be identified by conducting the reaction in the presence of the test substance; i.e., by adding the test substance to the reaction mixture prior to or simultaneously with the binding partners. On the other hand, test compounds that disrupt preformed complexes, e.g. compounds with higher binding constants that displace one of the binding partners from the complex, can be tested by adding the test compound to the reaction mixture after complexes have been formed. The various formats are described briefly below.

In a heterogeneous assay system, one binding partner, e.g., either the DP-107 or DP-178 peptide, is anchored onto a solid surface, and its binding partner, which is not anchored, is labeled, either directly or indirectly. In practice, microtiter plates are conveniently utilized. The anchored species may be immobilized by non-covalent or covalent attachments. Non-covalent attachment may be accomplished simply by coating the solid surface with a solution of the protein and drying. Alternatively, an immobilized antibody specific for the protein may be used to anchor the protein to the solid surface. The surfaces may be prepared in advance and stored.

In order to conduct the assay, the binding partner of the immobilized species is added to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the binding partner was pre-labeled, the detection of label immobilized on the surface indicates that complexes were formed. Where the binding partner is not pre-labeled, an indirect label can be used to detect complexes anchored on the surface; e.g., using a labeled antibody specific for the binding partner (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one binding partner to anchor any complexes formed in solution, and a labeled antibody specific for the other binding partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the DP-107 and DP-178 peptides is prepared in which one of the binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the

5.6 Pharmaceutical Formulations, Dosages and Modes of Administration

With respect to HIV, the peptides of the invention may be used as a therapeutic in the treatment of AIDS. The peptides of the invention may be administered using techniques well known to those in the art. Preferably, agents are formulated and administered systemically. Techniques for formulation and administration may be found in "Remington's Pharmaceutical Sciences", 18th ed., 1990, Mack Publishing Co., Easton, Pa. Suitable routes may include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few. Most preferably, administration is intravenous. For injection, the agents of the invention may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art.

In addition, the peptides may be used as a prophylactic measure in previously uninfected individuals after acute exposure to an HIV virus. Examples of such prophylactic use of the peptides may include, but are not limited to, prevention of virus transmission from mother to infant and other settings where the likelihood of HIV transmission exists, such as, for example, accidents in health care settings wherein workers are exposed to HIV-containing blood products. The peptides of the invention in such cases may serve the role of a prophylactic vaccine, wherein the host raises antibodies against the peptides of the invention, which then serve to neutralize HIV viruses by, for example, inhibiting further HIV infection. Administration of the peptides of the invention as a prophylactic vaccine, therefore, would comprise administering to a host a concentration of peptides effective in raising an immune response which is sufficient to neutralize HIV, by, for example, inhibiting HIV ability to infect cells. The exact concentration will depend upon the specific peptide to be administered, but may be determined by using standard techniques for assaying the development of an immune response which are well known to those of ordinary skill in the art. The peptides to be used as vaccines are usually administered intramuscularly.

The peptides may be formulated with a suitable adjuvant in order to enhance the immunological response. Such adjuvants may include, but are not limited to mineral gels such as aluminum hydroxide; surface active substances such as lysolecithin, pluronic polyols, polyanions; other peptides; oil emulsions; and potentially useful human adjuvants such as BCG and Corynebacterium parvum. Many methods may be used to introduce the vaccine formulations described here. These methods include but are not limited to oral, intradermal, intramuscular, intraperitoneal, intravenous, subcutaneous, and intranasal routes.

Alternatively, an effective concentration of polyclonal or monoclonal antibodies raised against the peptides of the invention may be administered to a host so that no uninfected cells become infected by HIV. The exact concentration of such antibodies will vary according to each specific antibody preparation, but may be determined using standard techniques well known to those of ordinary skill in the art. Administration of the antibodies may be accomplished using a variety of techniques, including, but not limited to those described in this section.

Effective dosages of the peptides of the invention to be administered may be determined through procedures well known to those in the art which address such parameters as biological half-life, bioavailability, and toxicity. Given the data presented below in Section 6, DP-178, for example, may prove efficacious in vivo at doses required achieve circulating levels of long per ml of peptide.

A therapeutically effective dose refers to that amount of the compound sufficient to result in amelioration of symptoms or a prolongation of survival in a patient. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. The data obtained from these cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal disruption of the PTK/adaptor protein complex, or a half-maximal inhibition of the cellular level and/or activity of a complex component) as determined in cell culture. Such information can be used to more accurately determine useful doses in humans. Levels in plasma may be measured, for example, by high performance liquid chromatography (HPLC).

The exact formulation, route of administration and dosage can be chosen by the individual physician in view of the patient's condition. (See e.g. Fingl et al., 1975, in "The Pharmacological Basis of Therapeutics", Ch. 1 p1).

It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The dose and perhaps dose frequency, will also vary according to the age, body weight, and response of the individual patient. A program comparable to that discussed above may be used in veterinary medicine.

As demonstrated in the Example presented below in Section 6, the antiviral activity of the peptides of the invention may show a pronounced type and subtype specificity, i.e., specific peptides may be effective in inhibiting the activity of only specific viruses. This feature of the invention presents many advantages. One such advantage, for example, lies in the field of diagnostics, wherein one can use the antiviral specificity of the peptide of the invention to ascertain the identity of a viral isolate. With respect to HIV, one may easily determine whether a viral isolate consists of an HIV-1 or HIV-2 strain. For example, uninfected CD-4+ cells may be co-infected with an isolate which has been identified as containing HIV the DP-178 (SEQ ID:1) peptide, after which the retroviral activity of cell supernatents may be assayed, using, for example, the techniques described above in Section 5.2. Those isolates whose retroviral activity is completely or nearly completely inhibited contain HIV-1. Those isolates whose viral activity is unchanged or only reduced by a small amount, may be considered to not contain HIV-1. Such an isolate may then be treated with one or more of the other DP-178 peptides of the invention, and subsequently be tested for its viral activity in order to determine the identify of the viral isolate.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

6. EXAMPLE

DP-178 (SEQ ID:1) is a Potent Inhibitor of HIV-1 Infection

In this example, DP-178 (SEQ ID:1) is shown to be a potent inhibitor of HIV-1 mediated CD-4+ cell-cell fusion and infection by cell free virus. In the fusion assay, this peptide completely blocks virus induced syncytia formation at concentrations of from 1–10 ng/ml. In the infectivity assay the inhibitory concentration is somewhat higher, blocking infection at 90 ng/ml. It is further shown that DP-178 (SEQ ID:1) shows that the antiviral activity of DP-178 (SEQ ID:1) is highly specific for HIV-1. Additionally, a synthetic peptide, DP-185 (SEQ ID:3), representing a HIV-1-derived DP-178 homolog is also found to block HIV-1-mediated syncytia formation.

6.1. Materials and Methods
6.1.1. Peptide Synthesis

Peptides were synthesized using Fast Moc chemistry on an Applied Biosystems Model 431A peptide synthesizer. Amidated peptides were prepared using Rink resin (Advanced Chemtech) while peptides containing free carboxy termini were synthesized on Wang (p-alkoxy-benzyl-alcohol) resin (Bachem). First residues were double coupled to the appropriate resin and subsequent residues were single coupled. Each coupling step was followed by acetic anhydride capping. Peptides were cleaved from the resin by treatment with trifluoracetic acid (TFA) (10 ml), $H_2O$ (0.5 ml), thioanisole (0.5 ml), ethanedithiol (0.25 ml), and crystalline phenol (0.75 g). Purification was carried out by reverse phase HPLC. Approximately 50 mg samples of crude peptide were chromatographed on a Waters Delta Pak C18 column (19mm×30 cm, 15μ spherical) with a linear gradient; $H_2O$/acetonitrile 0.1% TFA. Lyophilized peptides were stored desiccated and peptide solutions were made in water at about 1 mg/ml. Electrospray mass spectrometry yielded the following results: DP-178 (SEQ ID:1):4491.87 (calculated 4491.94); DP-180 (SEQ ID:2):4491.45 (calculated 4491.94); DP-185 (SEQ ID:3):not done (calculated 4546.97).

6.1.2. Virus

The HIV-1$_{LAI}$ virus was obtained from R. Gallo (Popovic, M. et al., 1984, Science 224:497–508) and propagated in CEM cells cultured in RPMI 1640 containing 10% fetal calf serum. Supernatant from the infected CEM cells was passed through a 0.2 μm filter and the infectious titer estimated in a microinfectivity assay using the AA5 cell line to support virus replication. For this purpose, 25 μl of serial diluted virus was added to 75 μl AA5 cells at a concentration of 2×10$^5$/ml in a 96-well microtitre plate. Each virus dilution was tested in triplicate. Cells were cultured for eight days by addition of fresh medium every other day. On day 8 post infection, supernatant samples were tested for virus replication as evidenced by reverse transcriptase activity released to the supernatant. The TCID$_{50}$ was calculated according to the Reed and Muench formula (Reed, L. J. et al., 1938, Am. J. Hyg. 27:493–497). The titer of the HIV-1$_{LAI}$ and HIV-1$_{MN}$ stocks used for these studies, as measured on the AA5 cell line, was approximately 1.4×106 and 3.8×10$^4$ TCID$_{50}$/ml, respectively.

6.1.3. Cell Fusion Assay

Approximately 7×10$^4$ Molt cells were incubated with 1×10$^4$ CEM cells chronically infected with the HIV-1$_{LAI}$ virus in 96-well plates (one-half area cluster plates; Costar, Cambridge, Mass.) in a final volume of 100 μl culture medium as previously described (Matthews, T. J. et al., 1987, Proc. Natl. Acad. Sci. USA 84: 5424–5428). Peptide inhibitors were added in a volume of 10 μl and the cell mixtures were incubated for 24 hr. at 37° C. At that time, multinucleated giant cells were estimated by microscopic examination at a 40× magnification which allowed visualization of the entire well in a single field.

6.1.4. Cell Free Virus Infection Assay

Synthetic peptides were incubated at 37° C. with either 247 TCID$_{50}$ (for experiment depicted in FIG. 2), or 62 TCID$_{50}$ (for experiment depicted in FIG. 3) units of HIV-1$_{LAI}$ virus or 25 TCID$_{50}$ units of HIV-2$_{NIH2}$ and CEM CD4$^+$ cells at peptide concentrations of 0, 0.04, 0.4, 4.0, and 40 μg/ml for 7 days. The resulting reverse transcriptase (RT) activity in counts per minute was determined using the assay described, below, in Section 6.1.5. See, Reed, L. J. et al., 1938, Am. J. Hyg. 27: 493–497 for an explanation of TCID$_{50}$ calculations.

6.1.5. Reverse Transcriptase Assay

The micro-reverse transcriptase (RT) assay was adapted from Goff et al. (Goff, S. et al., 1981, J. Virol. 38:239–248) and Willey et al. (Willey, R. et al., 1988, J. Virol. 62:139–147). Supertanants from virus/cell cultures are adjusted to 1% Triton-X100. A 10 μl sample of supernatant was added to 50 μl of RT cocktail in a 96-well U-bottom microtitre plate and the samples incubated at 37° C. for 90 min. The RT cocktail contained 75 mM KCl, 2 mM dithiothreitol, 5 mM MgCl$_2$, 5 μg/ml poly A (Pharmacia, cat. No. 27-4110-01), 0.25 units/ml oligo dT (Pharmacia, cat. No. 27-7858-01), 0.05% NP40, 50 mM Tris-HCl, pH 7.8, 0.5 μM non-radioactive dTTP, and 10 μCi/ml $^{32}$P-dTTP (Amersham, cat. No. PB.10167).

After the incubation period, 40 μl of reaction mixture was applied to a Schleicher and Schuell (S+S) NA45 membrane (or DE81 paper) saturated in 2×SSC buffer (0.3M NaCl and 0.003M sodium citrate) held in a S+S Minifold over one sheet of GB003 (S+S) filter paper, with partial vacuum applied. Each well of the minifold was washed four times with 200 μl 2×SSC, under full vacuum. The membrane was removed from the minifold and washed 2 more times in a pyrex dish with an excess of 2×SSC. Finally, the membrane was drained on absorbent paper, placed on Whatman #3 paper, covered with Saran wrap, and exposed to film overnight at −70° C.

6.2. Results

6.2.1. Peptide Inhibition of Infected Cell-induced Syncytia Formation

The initial screen for antiviral activity assayed peptides' ability to block syncytium formation induced by overnight co-cultivation of uninfected Molt4 cells with chronically HIV-1 infected CEM cells. The results of several such experiments are presented herein. In the first of these experiments, serial DP-178 (SEQ ID:1) peptide concentrations between 10 μg/ml and 12.5 ng/ml were tested for blockade of the cell fusion process. For these experiments, CEM cells chronically infected with either HIV-1$_{LAI}$, HIV-1$_{MN}$, HIV-1$_{RF}$, or HIV-1$_{SF2}$ virus were cocultivated overnight with uninfected Molt 4 cells. The results (FIG. 4) show that DP-178 (SEQ ID:1) afforded complete protection against each of the HIV-1 isolates down to the lowest concentration of DP-178 (SEQ ID:1) used. For HIV$_{LAI}$ inhibition, the lowest concentration tested was 12.5 ng/ml; for all other HIV-1 viruses, the lowest concentration of DP-178 (SEQ ID:1) used in this study was 100 ng/ml. A second peptide, DP-180 (SEQ ID:2), containing the same amino acid residues as DP-178 (SEQ ID:1) but arranged in a random order exhibited no evidence of anti-fusogenic activity even at the high concentration of 40 μg/ml (FIG. 4). These observations indicate that the inhibitory effect of DP-178 (SEQ ID:1) is primary sequence-specific and not related to non-specific peptide/protein interactions. The actual endpoint (i.e., the lowest effective inhibitory concentration) of DP-178 inhibitory action is within the range of 1–10 ng/ml.

The next series of experiments involved the preparation and testing of a DP-178 (SEQ ID:1) homolog for its ability to inhibit HIV-1-induced syncytia formation. As shown in FIG. 1, the sequence of DP-185 (SEQ ID:3) is slightly different from DP-178 (SEQ ID:1) in that its primary sequence is taken from the HIV-1$_{SF2}$ isolate and contains several amino acid differences relative to DP-178 (SEQ ID:1) near the N terminus. As shown in FIG. 4, DP-185 (SEQ ID:3), exhibits inhibitory activity even at 312.5 ng/ml, the lowest concentration tested.

The next series of experiments involved a comparison of DP-178 (SEQ ID:1) HIV-1 and HIV-2 inhibitory activity. As shown in FIG. 5, DP-178 (SEQ ID:1) blocked HIV-1-mediated syncytia formation at peptide concentrations below 1 ng/ml. DP-178 (SEQ ID:1) failed, however, to block HIV-2 mediated syncytia formation at concentrations as high as 10 μg/ml. This striking 4 log selectivity of DP-178 (SEQ ID:1) as an inhibitor of HIV-1-mediated cell fusion demonstrates an unexpected HIV-1 specificity in the action of DP-178 (SEQ ID:1). DP-178 (SEQ ID:1) inhibition of HIV-1-mediated cell fusion, but the peptide's inability to inhibit HIV-2 medicated cell fusion in the same cell type at the concentrations tested provides further evidence for the high degree of selectivity associated with the antiviral action of DP-178 (SEQ ID:1).

6.2.2. Peptide Inhigition of Infection by Cell-free Virus

DP-178 (SEQ ID:1) was next tested for its ability to block CD-4$^+$ CEM cell infection by cell free HIV-1 virus. The results, shown in FIG. 2, are from an experiment in which DP-178 (SEQ ID:1) was assayed for its ability to block infection of CEM cells by an HIV-1$_{LAI}$ isolate. Included in the experiment were three control peptides, DP-116 (SEQ ID:9), DP-125 (SEQ ID:8), and DP-118 (SEQ ID:10). DP-116 (SEQ ID:9) represents a peptide previously shown to be inactive using this assay, and DP-125 (SEQ ID:8; Wild, C. et al., 1992, Proc. Natl. Acad, Sci. USA 89:10,537) and DP-118 (SEQ ID:10) are peptides which have previously been shown to be active in this assay. Each concentration (0, 0.04, 0.4, 4, and 40 μg/ml) of peptide was incubated with 247 TCID$_{50}$ units of HIV-1$_{LAI}$ virus and CEM cells. After 7 days of culture, cell-free supernatant was tested for the presence of RT activity as a measure of successful infection. The results, shown in FIG. 2, demonstrate that DP-178 (SEQ ID:1) inhibited the de novo infection process mediated by the HIV-1 viral isolate at concentrations as low as 90 ng/ml (IC50=90 ng/ml). In contrast, the two positive control peptides, DP-125 (SEQ: ID:8) and DP-118 (SEQ ID:10), had over 60-fold higher IC50 concentrations of approximately 5 μg/ml.

In a separate experiment, the HIV-1 and HIV-2 inhibitory action of DP-178 (SEQ ID:1) was tested with CEM cells and either HIV-1$_{LAI}$ or HIV-2$_{NIHZ}$. 62 TCID$_{50}$ HIV-1$_{LAI}$ or 25 GCID$_{50}$ HIV-2$_{NIHZ}$ were used in these experiments, and were incubated for 7 days. As may be seen in FIG. 3, DP-178 (SEQ ID:1) inhibited HIV-1 infection with an IC50 of about 31 ng/ml. In contrast, DP-178 (SEQ ID:1) exhibited a much higher IC50 for HIV-2$_{NIHZ}$, thus making DP-178 (SEQ ID:1) two logs more potent as a HIV-1 inhibitor than a HIV-2 inhibitor. This finding is consistent with the results of the fusion inhibition assays described, above, in Section 6.2.1, and further supports a significant level of selectivity (i.e., for HIV-1 over HIV-2).

7. EXAMPLE

The HIV-1 Inhibitor, DP-178 SEQ ID NO:1, is Non-cytotoxic

In this Example, the 36 amino acid synthetic peptide inhibitor DP-178 (SEQ ID:1) is shown to be non-cytotoxic to cells in culture, even at the highest peptide concentrations (40 μg/ml) tested.

7.1. Materials and Methods

Cell proliferation and toxicity assay: Approximately 3.8× 10$^5$ CEM cells for each peptide concentration were incubated for 3 days at 37° C. in T25 flasks. Peptides tested were DP-178 (SEQ ID:1) and DP-116 (SEQ ID:9), as described in FIG. 1. The concentrations of each peptide used were 0, 2.5, 10, and 40 μg/ml. Cell counts were taken at incubation times of 0, 24, 48, and 72 hours.

7.2. Results

Whether the potent HIV-1 inhibitor DP-178 (SEQ ID:1) exhibited any cytotoxic effects was assessed by assaying the peptide's effects on the proliferation and viability of cells in culture. CEM cells were incubated in the presence of varying concentrations of DP-178 (SEQ ID:1), and DP-116 (SEQ ID:9), a peptide previously shown to be ineffective as a HIV inhibitor (Wild, C. et al., 1992, Proc. Natl. Acad. Sci. USA 89:10,537–10,541). Additionally, cells were incubated in the absence of either peptide.

The results of the cytotoxicity study demonstrate that DP-178 (SEQ ID: 1) exhibits no cytotoxic effects on cells in culture. As can be seen, below, in Table XI, even the proliferation and viability characteristics of cells cultured for 3 days in the presence of the highest concentration of DP-178 (SEQ ID:1) tested (40 μg/ml) do not significantly differ from the DP-116 (SEQ ID:9) or the no-peptide controls. The cell proliferation data is also represented in graphic form in FIG. 6. As was demonstrated in the Working Example presented above in Section 6, DP-178 (SEQ ID:1) completely inhibits HIV-1 mediated syncytia formation at peptide concentrations between 1 and 10 ng/ml, and completely inhibits cell-free viral infection at concentrations of at least 90 ng/ml. Thus, this study demonstrates that even at peptide concentrations greater than 3 log higher than the HIV inhibitory dose, DP-178 (SEQ ID:1) exhibits no cytotoxic effects.

TABLE XI

| Peptide | Peptide Concentration μg/ml | % Viability at time (hours) | | | |
|---|---|---|---|---|---|
| | | 0 | 24 | 48 | 72 |
| DP178 (SEQ ID:1) | 40 | 98 | 97 | 95 | 97 |
| | 10 | 98 | 97 | 98 | 98 |
| | 2.5 | 98 | 93 | 96 | 96 |
| DP116 (SEQ ID:9) | 40 | 98 | 95 | 98 | 97 |
| | 10 | 98 | 95 | 93 | 98 |
| | 2.5 | 98 | 96 | 98 | 99 |
| No Peptide | 0 | 98 | 97 | 99 | 98 |

8. EXAMPLE

The Interaction of DP178 and DP107

Soluble recombinant forms of gp41 used in the example described below provide evidence that the DP178 peptide associates with a distal site on gp41 whose interactive structure is influenced by the DP107 leucine zipper motif. A single mutation disrupting the coiled-coil structure of the leucine zipper domain transformed the soluble recombinant gp41 protein from an inactive to an active inhibitor of HIV-1 fusion. This transformation may result from liberation of the potent DP178 domain from a molecular clasp with the leucine zipper, DP107, determinant. The results also indicate that the anti-HIV activity of various gp41 derivatives (peptides and recombinant proteins) may be due to their ability to form complexes with viral gp41 and interfere with its fusogenic process.

8.1. Materials and Methods
8.1.1. Construction of Fusion Proteins and GP41 Mutants Construction of fusion proteins and mutants shown in FIG. 7 was accomplished as follows: the DNA sequence corresponding to the extracellular domain of gp41 (540–686) was cloned into the Xmn I site of the expression vector pMal-p2 (New England Biolab) to give M41. The gp41 sequence was amplified from pgtat (Malim et al., 1988, Nature 355: 181–183) by using polymerase chain reaction (PCR) with upstream primer 5'-ATGACGCTGACGGTACAGGCC-3' (primer A)(SEQ ID:11) and downstream primer 5'-TGACTAAGCTTAATACCACAGCCAATTTGTTAT-3' (primer B)(SEQ ID:12). M41-P was constructed by using the T7-Gen in vitro mutagenesis kit from United States Biochemicals (USB) following the supplier's instructions. The mutagenic primer (5'-GGAGCTGCTTGGGGCCCCAGAC-3') introduces (SEQ ID:13) an Ile to Pro mutation in M41 at position 578. M41Δ107 was made using a deletion mutagenic primer 5'-CCAAATCCCCAGGAGCTGCTCGAGCTGCACTAT-ACCAGAC-3' (primer C)(SEQ ID:14) following the USB T7-Gen mutagenesis protocol. M41Δ178 was made by cloning the DNA fragment corresponding to gp41 amino acids 540–642 into the Xmn I site of pMal-p2. Primer A and 5'-ATAGCTTCTAGATTAATTGTTAATTTCTCTGTCCC-3' (primer D)(SEQ ID:15) were used in the PCR with the template pgtat to generate the inserted DNA fragments. M41-P was used as the template with primer A and D in PCR to generate M41-PΔ178. All inserted sequences and mutated residues were checked by restriction enzyme analysis and confirmed by DNA sequencing.

8.1.2. Purification and Chatacterization of Fusion Proteins

The fusion proteins were purified according to the protocol described in the manufacturer's brochure of protein fusion and purification systems from New England Biolabs (NEB). Fusion proteins (10 ng) were analyzed by electrophoresis on 8% SDS polyacrylamide gels. Western blotting analysis was performed as described by Sambrook et al, 1989, Molecular Cloning: A Laboratory Manual, 2d Ed, Cold Spring Harbor Laboratory Press, Cold Spring Harbor, N.Y., Ch. 18, pp. 64–75. An HIV-1 positive serum diluted 1000-fold, or a human Fab derived from repertoire cloning was used to react with the fusion proteins. The second antibody was HRP-conjugated goat antihuman Fab. An ECL Western blotting detection system (Amersham) was used to detect the bound antibody. A detailed protocol for this detection system was provided by the manufacturer. Rainbow molecular weight marker (Amersham) were used to estimate the size of fusion proteins.

8.1.3. Cell Fusion Assays for Anti-HIV Activity

Cell fusion assays were performed as previously described (Matthews et al., 1987, Proc. Natl. Acad. Sci. USA 84: 5424–5481). CEM cells (7×10$^4$) were incubated with HIV-1$_{IIIB}$. chronically infected CEM cells (10$^4$) in 96-well flat-bottomed half-area plates (Costar) in 100 μl culture medium. Peptide and fusion proteins at various concentrations in 10 μl culture medium were incubated with the cell mixtures at 37° C. for 24 hours. Multinucleated syncytia were estimated with microscopic examination. Both M41 and M41-P did not show cytotoxicity at the concentrations tested and shown in FIG. 8.

Inhibition of HIV-1 induced cell-cell fusion activity was carried out in the presence of 10 nM DP178 and various concentrations of M41Δ178 or M41-PΔ178 as indicated in FIG. 9. There was no observable syncytia in the presence of 10 nM DP178. No peptide or fusion protein was added in the control samples.

8.1.4. ELISA Analysis of DP178 Binding to the Leucine Zipper Motif of GP41

The amino acid sequence of DP178 used is: YTSLIH-SLIEESQNQQEKNEQELLELDKWASLWNWF. For enzyme linked immunoassay (ELISA), M41Δ178 or M41-PΔ178 (5 μg/ml) in 0.1M NaHCO$_3$, pH 8.6, were coated on 96 wells Linbro ELISA plates (Flow Lab, Inc.) overnight. Each well was washed three times with distilled water then blocked with 3% bovine serum albumin (BSA) for 2 hours. After blocking, peptides with 0.5% BSA in TBST (40 mM Tris-HCl pH7.5, 150 mM NaCl, 0.05% Tween 20) were added to the ELISA plates and incubated at room temperature for 1 hour. After washing three times with TBST, Fab-d was added at a concentration of 10 ng/ml with 0.5% BSA in TBST. The plates were washed three times with TBST after incubation at room temperature for 1 hour. Horse radish peroxidase (HRP) conjugated goat antihuman Fab antiserum at a 2000 fold dilution in TBST with 0.5% BSA was added to each well and incubated at room temperature for 45 minutes. The plates were then washed four times with TBST. The peroxidase substrate o-phenylene diamine (2.5 mg/ml) and 0.15% H$_2$O$_2$ were added to develop the color. The reaction was stopped with an equal volume of 4.5 N H$_2$SO$_4$ after incubation at room temperature for 10 minutes. The optical density of the stopped reaction mixture was measured with a micro plate reader (Molecular Design) at 490 nm. Results are shown in FIG. 10.

8.2. Results 8.2.1. The Expression and Characterization of the Ectodomain of GP41

As a step toward understanding the roles of the two helical regions in gp41 structure and function, the ectodomain of gp41 was expressed as a maltose binding fusion protein (M41) (FIG. 7). The fusogenic peptide sequence at the N-terminal of gp41 was omitted from this recombinant protein and its derivatives to improve solubility. The maltose binding protein facilitated purification of the fusion proteins under relatively mild, non-denaturing conditions. Because the M41 soluble recombinant gp41 was not glycosylated, lacked several regions of the transmembrane protein (i.e., the fusion peptide, the membrane spanning, and the cytoplasmic domains), and was expressed in the absence of gp120, it was not expected to precisely reflect the structure of native gp41 on HIV-1 virions. Nevertheless, purified M41 folded in a manner that preserved certain discontinuous epitopes as evidenced by reactivity with human monoclonal antibodies, 98-6, 126-6, and 50-69, previously shown to bind conformational epitopes on native gp41 expressed in eukaryotic cells (Xu et al., 1991, J. Virol. 65: 4832–4838; Chen, 1994, J. Virol. 68:2002–2010). Thus, at least certain regions of native gp41 defined by these antibodies appear to be reproduced in the recombinant fusion protein M41. Furthermore, M41 reacted with a human recombinant Fab (Fab-d) that recognizes a conformational epitope on gp41 and binds HIV-1 virions as well as HIV-1 infected cells but not uninfected cells as analyzed by FACS. Deletion of either helix motif, i.e., DP107 or DP178, of the M41 fusion protein eliminated reactivity with Fab-d. These results indicate that both helical regions, separated by 60 amino acids in the primary sequence, are required to maintain the Fab-d epitope.

8.2.2. Anti-HIV Activity of the Recombinant Ectodomain of GP41

The wild type M41 fusion protein was tested for anti-HIV-1 activity. As explained, supra, synthetic peptides corresponding to the leucine zipper (DP107) and the C-terminal putative helix (DP178) show potent anti-HIV activity. Despite inclusion of both these regions, the recombinant M41 protein did not affect HIV-1 induced membrane fusion at concentrations as high as 50 AM (Table XII, below).

TABLE XII

DISRUPTION OF THE LEUCINE ZIPPER OF GP41 FREES THE ANTI-HIV MOTIF

| | DP107 | DP178 | M41 | M41-P | M41-PΔ178 |
|---|---|---|---|---|---|
| Cell fusion (IC$_{90}$) | 1 μM | 1 nM | >50 μM | 83 nM | >50 μM |
| Fab-D binding (k$_D$) | — | — | 3.5 × 10$^{-9}$ | 2.5 × 10$^{-8}$ | — |
| HIV infectivity (IC$_{90}$) | 1 μM | 80 nM | >16 μM | 66 nM | >8 μM |

1 The affinity constants of Fab-d binding to the fusion proteins were determined using a protocol described by B. Friguet et al., 1985, J. Immunol. Method. 77:305–319.
— = No detectable binding of Fab-d to the fusion proteins.

Antivirul Infectivity Assays. 20 μl of serially diluted virus stock was incubated for 60 minutes at ambient temperature with 20 μl of the indicated concentration of purified recombinant fusion protein in RPMI 1640 containing 10% fetal bovine serum and antibiotics in a 96-well microtiter plate. 20 µl of CEM4 cells at 6×10$^5$ cells/ml were added to each well, and cultures were incubated at 37° C in a humidified $CO_2$ incubator. Cells were cultured for 9 postinfection, supernatant samples were assayed for reverse transcriptase (RT) activity, as described below, to monitor viral replication. The 50% tissue culture infectious dose ($TCID_{50}$) was calculated for each condition according to the formula of Reed & Muench, 1937, Am. J. Hyg. 27:493–497. RT activity was determined by a modification of the published methods of Goff et al., 1981, J. Virol. 38:239–248 and Willey et al., 1988, J. Virol. 62:139–147 as described in Chen et al., 1993, AIDS Res. Human Retroviruses 9:1079–1086.

Surprisingly, a single amino acid substitution, proline in place of isoleucine in the middle of the leucine zipper motif, yielded a fusion protein (M41-P) which did exhibit antiviral activity (Table XII and FIG. 8). As seen in Table XII, M41-P blocked syncytia formation by 90% at approximately 85 nM and neutralized HIV-1$_{IIIB}$ infection by 90% at approximately 70 nM concentrations. The anti-HIV-1 activity of M41-P appeared to be mediated by the C-terminal helical sequence since deletion of that region from M41-P yielded an inactive fusion protein, M41-PΔ178 (Table XII). That interpretation was reinforced by experiments demonstrating that a truncated fusion protein lacking the DP178 sequence, M41Δ178, abrogated the potent anti-fusion activity of the DP178 peptide in a concentration-dependent manner (FIG. 9). The same truncated fusion protein containing the proline mutation disrupting the leucine zipper, M41-PΔ178, was not active in similar competition experiments (FIG. 9). The results indicate that the DP178 peptide associates with a second site on gp41 whose interactive structure is dependent on a wild type leucine zipper sequence. A similar interaction may occur within the wild type fusion protein, M41, and act to form an intramolecular clasp which sequesters the DP178 region, making it unavailable for anti-viral activity.

A specific association between these two domains is also indicated by other human monoclonal Fab-d studies. For example, Fab-d failed to bind either the DP178 peptide or the fusion protein M41Δ178, but its epitope was reconstituted by simply mixing these two reagents together (FIG. 10). Again, the proline mutation in the leucine zipper domain of the fusion protein, M41-PΔ178, failed to reconstitute the epitope in similar mixing experiments.

9. EXAMPLE

Method for Computer-Assisted Identification of DP-107-like and DP-178-like Sequences A number of known coiled-coil sequences have been well described in the literature and contain heptad repeat positioning for each amino acid. Coiled-coil nomenclature labels each of seven amino acids of a heptad repeat A through G, with amino acids A and D tending to be hydrophobic positions. Amino acids E and G tend to be charged. These four positions (A, D, E, and G) form the amphipathic backbone structure of a monomeric alpha-helix. The backbones of two or more amphipathic helices interact with each other to form di-, tri-, tetrameric, etc., coiled-coil structures. In order to begin to design computer search motifs, a series of well characterized coiled coils were chosen including yeast transcription factor GCN4 (SEQ ID:20), Influenza Virus hemagglutinin loop 36 (SEQ ID:24), and human proto-oncogenes c-Myc (SEQ ID:23), c-Fos (SEQ ID:21), and c-Jun (SEQ ID:22). For each peptide sequence, a strict homology for the A and D positions, and a list of the amino acids which could be excluded for the B, C, E, F, and G positions (because they are not observed in these positions) was determined. Motifs were tailored to the DP-107 and DP-178 sequences by deducing the most likely possibilities for heptad positioning of the amino acids of HIV-1 Bru DP-107, which is known to have coiled-coil structure, and HIV-1 Bru DP-178, which is still structurally undefined. The analysis of each of the sequences is contained in FIG. 12. For example, the motif for GCN4 was designed as follows:

1. The only amino acids (using standard single letter amino acid codes) found in the A or D positions of GCN4 were [LMNV].
2. All amino acids were found at B, C, E, F, and G positions except {CFGIMPTW}.
3. The PESEARCH motif would, therefore, be written as follows:
   [LMNV]-{CFGIMPTW} (2)-[LMNV]-{CFGIMPTW} (3)-
   [LMNV]-{CFGIMPTW} 2)-[LMNV]-{CFGIMPTW} 3)-
   [LMNV]-{CFGIMPTW} 2)-[LMNV]-{CFGIMPTW} 3)-
   [LMNV]-{CFGIMPTW} 2)-[LMNV]-{CFGIMPTW} 3)

Translating or reading the motif: "at the first A position either L, M, N, or V must occur; at positions B and C (the next two positions) accept everything except C, F, G, I, M, P, T, or W; at the D position either L, M, N, or V must occur; at positions E, F, and G (the next 3 positions) accept everything except C, F, G, I, M, P, T, or W." This statement is contained four times in a 28-mer motif and five times in a 35-mer motif. The basic motif key then would be: [LMNV]-{CFGIMPTW}. The motif keys for the remaining well described coiled-coil sequences are summarized in FIG. 12.

The motif design for DP-107 and DP-178 was slightly different than the 28-mer model sequences described above due to the fact that heptad repeat positions are not defined and the peptides are both longer than 28 residues. FIG. 13 illustrates several possible sequence alignments for both DP-107 and DP-178 and also includes motif designs based on 28-mer, 35$^{-mer}$, and full-length peptides. Notice that only slight differences occur in the motifs as the peptides are lengthened. Generally, lengthening the base peptide results in a less stringent motif. This is very useful in broadening the possibilities for identifying DP-107-or DP-178-like primary amino acid sequences referred to in this document as "hits".

In addition to making highly specific motifs for each type peptide sequence to be searched, it is also possible to make "hybrid" motifs. These motifs are made by "crossing" two or more very stringent motifs to make a new search algorithm which will find not only both "parent" motif sequences but also any peptide sequences which have similarities to one, the other, or both "parents". For example, in Table 3 the "parent" sequence of GCN4 is crossed with each of the possible "parent" motifs of DP-107. Now the hybrid motif must contain all of the amino acids found in the A and D positions of both parents, and exclude all of the amino acids not found in either parent at the other positions. The resulting hybrid from crossing GCN4 or [LMNV] {CFGIMPTW} and DP-107 (28-mer with the first L in the D position) or [ILQT] {CDFIMPST}, is [ILMNQTV] {CFIMPT}. Notice that now only two basic hybrid motifs exist which cover both framing possibilities, as well as all peptide lengths of the parent DP-107 molecule. FIG. 15 represents the hybridizations of GCN4 with DP-178. FIG. 16 represents the hybridizations of DP-107 and DP-178. It is important to keep in mind that the represented motifs, both parent and hybrid, are motif keys and not the depiction of the full-length motif needed to actually do the computer search.

Hybridizations can be performed on any combination of two or more motifs. Table 5 summarizes several three-motif hybridizations including GCN4, DP-107 (both frames), and DP-178 (also both frames). Notice that the resulting motifs are now becoming much more similar to each other. In fact, the first and third hybrid motifs are actually subsets of the second and fourth hybrid motifs respectively. This means that the first and third hybrid motifs are slightly more stringent than the second and fourth. It should also be noted that with only minor changes in these four motifs, or by hybridizing them, a single motif could be obtained which would find all of the sequences. However, it should be remembered that stringency is also reduced. Finally, the most broad-spectra and least-stringent hybrid motif is described in FIG. 18 which summarizes the hybridization of GCN4, DP-107 (both frames), DP-178 (both frames), c-Fos, c-Jun, c-Myc, and Flu loop 36.

A special set of motifs was designed based on the fact that DP-178 is located only approximately ten amino acids upstream of the transmembrane spanning region of gp41 and just C-terminal to a proline which separates DP-107 and DP-178. It has postulated that DP-178 may be an amphipathic helix when membrane associated, and that the proline might aid in the initiation of the helix formation. The same arrangement was observed in Respiratory Syncytial Virus; however, the DP-178-like region in this virus also had a leucine zipper just C-terminal to the proline. Therefore, designed N-terminal proline-leucine zipper motifs were designed to analyze whether any other viruses might contain this same pattern. The motifs are summarized in FIG. 19.

The PC/Gene protein database contains 5879 viral amino acid sequences (library file PVIRUSES; CD-ROM release 11.0). Of these, 1092 are viral envelope or glycoprotein sequences (library file PVIRUSE1). Tables V through X contain lists of protein sequence names and motif hit locations for all the motifs searched.

10. EXAMPLE

Computer-assisted Identification of DP-107 and DP-178-like Sequences in Human Immunodeficiency Virus FIG. 20 represents search results for HIV-1 BRU isolate gp41 (PC/Gene protein sequence PENV_HV1BR). Notice that the hybrid motif which crosses DP-107 and DP-178 (named 107×178×4; the same motif as found in FIG. 16 found three hits including amino acids 550–599, 636–688, and 796–823. These areas include DP-107 plus eight N-terminal and four C-terminal amino acids; DP-178 plus seven N-terminal and ten C-terminal amino acids; and an area inside the transmembrane region (cytoplasmic). FIG. 20 (SEQ ID:26) also contains the results obtained from searching with the motif named ALLMOTI5, for which the key is found in FIG. 17 ({CDGHP} {CFP}×5). This motif also found three hits including DP-107 (amino acids 510–599), DP-178 (615–717), and a cytoplasmic region (772–841). These hits overlap the hits found by the motif 107×178×4 with considerable additional sequences on both the amino and carboxy termini. This is not surprising in that 107×178×4 is a subset of the ALLMOTI5 hybrid motif. Importantly, even though the stringency of ALLMOTI5 is considerably less than 107×178×4, it still selectively identifies the DP-107 and DP-178 regions of gp41 shown to contain sequences for inhibitory peptides of HIV-1. The results of these two motif searches are summarized in Table V under the PC/Gene protein sequence name PENV_HV1BR. The proline-leucine zipper motifs also gave several hits in HIV-1 BRU including 503–525 which is at the very C-terminus of gp120, just upstream of the cleavage site (P7LZIPC and P12LZIPC); and 735–768 in the cytoplasmic domain of gp41 (P23LZIPC). These results are found in Tables VIII, IX, and X under the same sequence name as mentioned above. Notice that the only area of HIV-1 BRU which is predicted by the Lupas algorithm to contain a coiled-coil region, is from amino acids 635–670. This begins eight amino acids N-terminal to the start and ends eight amino acids N-terminal to the end of DP-178. DP-107, despite the fact that it is a known coiled coil, is not predicted to contain a coiled-coil region using the Lupas method.

11. EXAMPLE

Computer-assisted Identification of DP-107-like and DP-178-like Sequences in Human Respiratory Syncytial Virus FIG. 21 represents search results (SEQ ID:27) for Human Respiratory Syncytial Virus (RSV; Strain A2) fusion glycoprotein F1 (PC/Gene protein sequence name PVGLF_HRSVA). Motif 107×178×4 finds three hits including amino acids 152–202, 213–243, and 488–515. The arrangement of these hits is similar to what is found in HIV-1 except that the motif finds two regions with similarities to DP-178, one just downstream of what would be called the DP-107 region or amino acids 213–243, and one just upstream of the transmembrane region (also similar to DP-178) or amino acids 488–515. Motif ALLMOTI5 also finds three areas including amino acids 116–202, 267–302, and 506–549. The proline-leucine zipper motifs also gave several hits including amino acids 205–221 and 265–287 (P1LZIPC 265–280, P12LZIPC), and 484–513 (P7LZIPC and P12LZIPC 484–506, P23LZIPC). Notice that the PLZIP motifs also identify regions which share location similarities with DP-178 of HIV-1.

12. EXAMPLE

Computer-assisted Identification of DP-107-like and DP-178-like Sequences in Simian Immunodeficiency Virus Motif hits (SEQ ID:28) for Simian immunodeficiency Virus gp41 (AGM3 isolate; PC/Gene protein sequence name PENV_SIVAG) are shown in FIG. 22. Motif 107×178×4 finds three hits including amino acids 566–593, 597–624, and 703–730. The first two hits only have three amino acids between them and could probably be combined into one hit from 566–624 which would represent a DP-107-like hit. Amino acids 703 to 730 would then represent a DP-178-like hit. ALLMOTI5 also finds three hits including amino acids 556–628 (DP-107-like), 651–699 (DP-178-like), and 808–852 which represents the transmembrane spanning region. SIV also has one region from 655–692 with a high propensity to form a coiled coil as predicted by the Lupas algorithm. Both 107×178×4 and ALLMOTI5 motifs find the same region. SIV does not have any PLZIP motif hits in gp41.

13. EXAMPLE

Computer-assisted Identification of DP-107-like and DP-178 Like Sequences in Canine Distemper Virus Canine Distemper Virus (strain Onderstepoort) fusion glycoprotein F1 (PC/Gene Protein sequence name PVGLF_

CDVO) has regions similar to Human RSV which are predicted to be DP-107-like and DP-178-like (FIG. 23, SEQ ID:29). Motif 107×178×4 highlights one area just C-terminal to the fusion peptide at amino acids 252–293. Amino acids 252–286 are also predicted to be coiled coil using the Lupas algorithm. Almost 100 amino acids C-terminal to the first region is a DP-178-like area at residues 340–367. ALLMOTI5 highlights three areas of interest including: amino acids 228–297, which completely overlaps both the Lupas prediction and the DP-107-like 107×178×4 hit; residues 340–381, which overlaps the second 107×178×4 hit; and amino acids 568–602, which is DP178-like in that it is located just N-terminal to the transmembrane region. It also overlaps another region (residues 570–602) predicted by the Lupas method to have a high propensity to form a coiled coil. Several PLZIP motifs successfully identified areas of interest including P6 and P12LZIPC which highlight residues 336–357 and 336–361 respectively; P1 and P12LZIPC which find residues 398–414; and P12 and P23LZIPC which find residues 562–589 and 562–592 respectively.

14. EXAMPLE

Computer-assisted Identification of DP-107-like and DP-178-like Sequences in Newcastle Disease Virus FIG. 24 shows the motif hits (SEQ ID NO:30) found in Newcastle Disease Virus (strain Australia-Victoria/32; PC Gene protein sequence name PVGLF_NDVA). Motif 107× 178×4 finds two areas including a DP-107-like hit at amino acids 151–178 and a DP-178-like hit at residues 426–512. ALLMOTI5 finds three areas including residues 117–182, 231–272, and 426–512. The hits from 426–512 include a region which is predicted by the Lupas method to have a high coiled-coil propensity (460–503). The PLZIP motifs identify only one region of interest at amino acids 273–289 (P1 and 12LZIPC).

15. EXAMPLE

Computer-assisted Identification of DP-107-like and DP-178-like Sequences in Human Parainfluenza Virus Both motifs 107×178×4 and ALLMOTI5 exhibit DP-107-like hits in the same region, 115–182 and 117–182 respectively, of Human Parainfluenza Virus (strain NIH 47885; PC/Gene protein sequence name PVGLF_p13H4; (FIG. 25, SEQ ID NO:31). In addition, the two motifs have a DP-178-like hit just slightly C-terminal at amino acids 207–241. Both motifs also have DP-178-like hits nearer the transmembrane region including amino acids 457–497 and 462–512 respectively. Several PLZIP motif hits are also observed including 283–303 (P5LZIPC), 283–310 (P12LZIPC), 453–474 (P6LZIPC), and 453–481 (P23LZIPC). The Lupas algorithm predicts that amino acids 122–176 have a propensity to form a coiled-coil.

16. EXAMPLE

Computer-assisted Identification of DP-107-like and DP-178-like Sequences of Influenza A Virus FIG. 26 illustrates the Lupas prediction (SEQ ID NO:32) for a coiled coil in Influenza A Virus (strain A/Aichi/2/68) at residues 379–436, as well as the motif hits for 107×178×4 at amino acids 387–453, and for ALLMOTI5 at residues 380–456. Residues 383–471 (38–125 of HA2) were shown by Carr and Kim to be an extended coiled coil when under acidic pH (Carr and Kim, 1993, Cell 73: 823–832). The Lupas algorithyan predicts a coiled-coil at residues 379–436. All three methods successfully predicted the region shown to actually have coiled-coil structure; however, ALLMOTI5 predicted the greatest portion of the 88 residue stretch.

17. EXAMPLE

RSV Antiviral Compounds

In the Example presented herein, respiratory syncytial virus (RSV) peptide sequences identified by utilizing the computer-assisted coiled-coil peptide sequence searches described in Example 9, above, are shown to encode peptide domains that exhibit structural similarity to actual, known coiled-coil peptides, and are, additionally found to exhibit antiviral activity.

17.1 Materials and Methods

Structural analyses consisted of circular dichroism (CD) studies, which were conducted according to the methods described in the Applicants' co-pending U.S. patent application Ser. No 08/073,028.

Anti-RSV antiviral activity was assayed as described in Pringle, C. R. et al., 1985, J. Medical Vir. 17:377–386.

A 48 amino acid RSV F2 peptide (SEQ ID NO:33) and a 53 amino acid F1-178 (SEQ ID NO:34) peptide are utilized which span sequences that were identified via the computer assisted peptide sequence search strategies described in Example 9, above. See FIG. 21 for the exact position of these sequences and for the motifs utilized.

17.2 Results 35-mer oligopeptides were synthesized which constituted portions of the 48 amino acid RSV F2 peptide sequence (FIG. 27) and portions of the 53 amino acid F1-178 peptide sequence (FIG. 28). The oligopeptides were assayed, via CD analysis, for structural similarity to known coiled-coil structures, and for anti-RSV activity. As shown in FIGS. 27 and 28, a number of these oligopeptides exhibited substantial coiled-coil structural similarity and/or antiviral activity.

Thus, the computer assisted searches described, herein, in Example 9, for example, successfully identified viral peptide domains that represent highly promising anti-RSV antiviral compounds.

18. EXAMPLE

HPF3 Antiviral Compounds

In the Example presented herein, human parainfluenza virus 3 (HPF3) peptide sequences identified by utilizing the computer-assisted coiled-coil peptide sequence searches described in Example 9, above, are shown to encode peptide domains that exhibit structural similarity to actual, known coiled-coil peptides, and are, additionally found to exhibit antiviral activity.

18.1 Materials and Methods

Structural analyses consisted of circular dichroism (CD) studies, which were conducted according to the methods described in the Applicants' co-pending U.S. patent application Ser. No 08/073,028.

Anti-HPF3 antiviral activity was assayed as described in Pringle, C. R. et al., 1985, J. Medical Vir. 17:377–386.

A 56 amino acid and 70 amino acid HPF3 peptide are utilized which span sequences that were identified via the computer assisted peptide sequence search strategies described in Example 9, above. See FIG. 25 for the exact positions of these sequences and for the motifs utilized.

18.2 Results 35-mer oligopeptides were synthesized which constituted portions of the 56 amino acid (SEQ ID NO:35) sequence (FIG. 29) and portions of the 70 amino acid HPF3 peptide (SEQ ID NO:36) sequence (FIG. 30). The oligopeptides were assayed, via CD analysis, for structural similarity to known coiled-coil structures, and for anti-HPF3 activity. As shown in FIGS. 29 and 30, a number of these oligopeptides exhibited substantial coiled-coil structural similarity and/or antiviral activity.

Thus, the computer assisted searches described, herein, in Example 9, for example, successfully identified viral peptide domains that represent highly promising anti-HPF3 antiviral compounds.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method for the inhibition of transmission of a respiratory syncytial virus to a cell, comprising contacting the cell with an effective concentration of an isolated peptide consisting of an amino acid sequence of a 16 to 39 amino acid residue region of a respiratory syncytial virus protein for an effective period of time, wherein:
   (a) said region is recognized by an ALLMOTI5, 107× 178×4, or PLZIP sequence search motif;
   (b) said peptide further comprises an amino terminal X, and a carboxy terminal Z in which:
      X comprises an amino group, an acetyl group, a 9-fluorenylmethoxy-carbonyl group, a hydrophobic group, or a macromolecular carrier group; and
      Z comprises a carboxyl group, an amido group, a hydrophobic group, or a macromolecular carrier group; and
   (c) fusion of the virus to the cell is inhibited.

2. A method for the inhibition of transmission of a respiratory syncytial virus to a cell, comprising contacting the cell with an effective concentration of a peptide for an effective period of time, wherein the peptide has the formula:

X-FYDPLVFPSDEFDASISQVNEKINQSLAFIRKSDE-Z (SEQ ID NO:68);

X-DPLVFPSDEFDASISQVNEKINQSLAFIRKSDELL-Z (SEQ ID NO:101);

X-YDPLVFPSDEFDASISQVNEKINQSLAFIRKSDEL-Z (SEQ ID NO:103);

X-LVFPSDEFDASISQVNEKINQSLAFIRKSDELLHN-Z (SEQ ID NO:104);

X-VFPSDEFDASISQVNEKINQSLAFIRKSDELLHN-V-Z (SEQ ID NO:105);

X-FPSDEFDASISQVNEKINQSLAFIRKSDELLHNV-N-Z (SEQ ID NO:106);

X-PSDEFDASISQVNEKINQSLAFIRKSDELLHNVN-A-Z (SEQ ID NO:107);

X-SDEFDASISQVNEKINQSLAFIRKSDELLHNVNA-G-Z (SEQ ID NO:108);

X-DEFDASISQVNEKINQSLAFIRKSDELLHNVNA-GK-Z (SEQ ID NO:109);

X-FDASISQVNEKINQSLAFIRKSDELLHNVNAGK-ST-Z (SEQ ID NO:110); or

X-DASISQVNEKINQSLAFIRKSDELLHNVNAGKS-TT-Z (SEQ ID NO:111)

in which:
   amino acid residues are presented by the single-letter code;
   X comprises an amino group, an acetyl group, a 9-fluoromethyoxymethyl-carbonyl group, a hydrophobic group, or a macromolecular carrier group;

Z comprises a carboxyl group, an amido group, a hydrophobic group, or a macromolecular carrier group;

and wherein fusion of the virus to the cell is inhibited.

3. The method of claim 2, wherein the peptide has the formula:

X-DPLVFPSDEFDASISQVNEKINQSLAFIRKSDELL-Z (SEQ ID NO. 101).

4. The method of claim 2, wherein the peptide has the formula:

X-YDPLVFPSDEFDASISQVNEKINQSLAFIRKSDEL-Z (SEQ ID NO. 103).

5. The method of claim 2, wherein the peptide has the formula:

X-LVFPSDEFDASISQVNEKINQSLAFIRKSDELLHN-Z (SEQ ID NO. 104).

6. The method of claim 2, wherein the peptide has the formula:

X-VFPSDEFDASISQVNEKINQSLAFIRKSDELLHNV-Z (SEQ ID NO. 105).

7. The method of claim 2, wherein the peptide has the formula:

X-FPSDEFDASISQVNEKINQSLAFIRKSDELLHNV-N-Z (SEQ ID NO. 106).

8. The method of claim 2, wherein the peptide has the formula:

X-PSDEFDASISQVNEKINQSLAFIRKSDELLHNVN-A-Z (SEQ ID NO. 107).

9. The method of claim 2, wherein the peptide has the formula:

X-SDEFDASISQVNEKINQSLAFIRKSDELLHNVNA-G-Z (SEQ ID NO. 108).

10. The method of claim 2, wherein the peptide has the formula:

X-DEFDASISQVNEKINQSLAFIRKSDELLHNVNA-GK-Z (SEQ ID NO. 109).

11. The method of claim 2, wherein the peptide has the formula:

X-FDASISQVNEKINQSLAFIRKSDELLHNVNAGK-ST-Z (SEQ ID NO. 110).

12. The method of claim 2, wherein the peptide has the formula:

X-DASISQVNEKINQSLAFIRKSDELLHNVNAGKS-TT-Z (SEQ ID NO. 111).

13. The method of claim 2, wherein the peptide has the formula:

X-FYDPLVFPSDEFDASISQVNEKINQSLAFIRKSDE-Z (SEQ ID NO. 68).

* * * * *